(12) United States Patent
D'Agostino et al.

(10) Patent No.: US 12,186,011 B2
(45) Date of Patent: Jan. 7, 2025

(54) DEVICES, SYSTEMS, AND METHODS FOR PULSED ELECTRIC FIELD TREATMENT OF THE DUODENUM

(71) Applicant: ENDOGENEX, INC., Plymouth, MN (US)

(72) Inventors: Robert Anthony D'Agostino, Woodbury, MN (US); John Samuel Batchelder, Somers, NY (US); John Bernard Logan, Plymouth, MN (US); Alex Alden Peterson, Maple Grove, MN (US); Michael Patrick Brenzel, St. Paul, MN (US); Corey Addison Fanger, Victoria, MN (US); John Robert Ballard, Waconia, MN (US); Paul Hindrichs, Plymouth, MN (US); Matthew Heidner, Maple Grove, MN (US)

(73) Assignee: Endogenex, Inc., Plymouth, MN (US)

( * ) Notice: Subject to any disclaimer, the term of this patent is extended or adjusted under 35 U.S.C. 154(b) by 588 days.

(21) Appl. No.: 17/076,692

(22) Filed: Oct. 21, 2020

(65) Prior Publication Data
US 2021/0113265 A1    Apr. 22, 2021

Related U.S. Application Data

(60) Provisional application No. 63/029,275, filed on May 22, 2020, provisional application No. 62/924,100, filed on Oct. 21, 2019.

(51) Int. Cl.
*A61B 18/14* (2006.01)
*A61B 18/00* (2006.01)
(Continued)

(52) U.S. Cl.
CPC ........ *A61B 18/1492* (2013.01); *A61B 18/082* (2013.01); *A61B 18/1206* (2013.01);
(Continued)

(58) Field of Classification Search
CPC .............. A61B 18/082; A61B 18/1492; A61B 18/1206; A61B 18/14; A61B 2018/00214;
(Continued)

(56) References Cited

U.S. PATENT DOCUMENTS

| 1,953,819 A | 4/1934 | Payne |
| 3,245,408 A | 4/1966 | Gonser |

(Continued)

FOREIGN PATENT DOCUMENTS

| AU | 2014200616 A1 | 2/2014 |
| CN | 1647747 A | 8/2005 |

(Continued)

OTHER PUBLICATIONS

Final Office Action mailed on Feb. 19, 2021, for U.S. Appl. No. 15/766,604, filed Apr. 6, 2018, 18 pages.
(Continued)

*Primary Examiner* — Khadijeh A Vahdat
*Assistant Examiner* — Marina Delaney Templeton
(74) *Attorney, Agent, or Firm* — Cooley LLP

(57) ABSTRACT

Described here are devices, systems, and methods for applying pulsed or modulated electric fields to tissue. In some variations, a device may comprise a first elongate body comprising a lumen, a second elongate body at least partially positioned within the lumen, and an expandable member rolled about the second elongate body. The expandable member may comprise an inner end coupled to the second elongate body, an outer end coupled to the first elongate body, and an electrode array.

28 Claims, 87 Drawing Sheets
(45 of 87 Drawing Sheet(s) Filed in Color)

(51) Int. Cl.
*A61B 18/08* (2006.01)
*A61B 18/12* (2006.01)

(52) U.S. Cl.
CPC ............. *A61B 2018/00214* (2013.01); *A61B 2018/00494* (2013.01); *A61B 2018/00577* (2013.01); *A61B 2018/00791* (2013.01); *A61B 2018/00964* (2013.01); *A61B 2018/00982* (2013.01); *A61B 2018/1467* (2013.01)

(58) Field of Classification Search
CPC .. A61B 2018/00577; A61B 2018/1467; A61B 2018/1475; A61B 2018/1465; A61B 2018/0016; A61B 2018/1495; A61B 2018/00285; A61B 2018/0022; A61B 2018/00494; A61B 2018/00613; A61B 2018/00791; A61B 2018/00964; A61B 2018/00982; G03B 1/24
See application file for complete search history.

(56) References Cited

U.S. PATENT DOCUMENTS

| | | |
|---|---|---|
| 4,325,374 A | 4/1982 | Komiya |
| 4,676,228 A | 6/1987 | Krasner et al. |
| 4,969,885 A | 11/1990 | Farin |
| 4,979,948 A | 12/1990 | Geddes et al. |
| 5,019,034 A | 5/1991 | Weaver et al. |
| 5,084,044 A | 1/1992 | Quint |
| 5,117,828 A | 6/1992 | Metzger et al. |
| 5,122,137 A | 6/1992 | Lennox |
| 5,137,817 A | 8/1992 | Busta et al. |
| 5,190,540 A | 3/1993 | Lee |
| 5,282,785 A | 2/1994 | Shapland et al. |
| 5,286,254 A | 2/1994 | Shapland et al. |
| 5,383,917 A | 1/1995 | Desai et al. |
| 5,419,763 A | 5/1995 | Hildebrand |
| 5,427,118 A | 6/1995 | Nita et al. |
| 5,464,386 A | 11/1995 | Hofmann |
| 5,498,238 A | 3/1996 | Shapland et al. |
| 5,505,700 A | 4/1996 | Leone et al. |
| 5,507,724 A | 4/1996 | Hofmann et al. |
| 5,515,100 A | 5/1996 | Nogo |
| 5,549,603 A | 8/1996 | Feiring |
| 5,575,772 A | 11/1996 | Lennox |
| 5,674,267 A | 10/1997 | Mir et al. |
| 5,697,281 A | 12/1997 | Eggers et al. |
| 5,702,359 A | 12/1997 | Hofmann et al. |
| 5,704,908 A | 1/1998 | Hofmann et al. |
| 5,800,484 A | 9/1998 | Gough et al. |
| 5,807,306 A | 9/1998 | Shapland et al. |
| 5,810,762 A | 9/1998 | Hofmann |
| 5,879,349 A | 3/1999 | Edwards |
| 5,944,710 A | 8/1999 | Dev et al. |
| 5,964,753 A | 10/1999 | Edwards |
| 5,968,012 A | 10/1999 | Ren et al. |
| 6,027,488 A | 2/2000 | Hofmann et al. |
| 6,045,532 A | 4/2000 | Eggers et al. |
| 6,053,937 A | 4/2000 | Edwards et al. |
| 6,055,453 A | 4/2000 | Hofmann et al. |
| 6,056,744 A | 5/2000 | Edwards |
| 6,068,650 A | 5/2000 | Hofmann et al. |
| 6,086,581 A | 7/2000 | Reynolds et al. |
| 6,112,123 A | 8/2000 | Kelleher et al. |
| 6,120,493 A | 9/2000 | Hofmann |
| 6,162,237 A * | 12/2000 | Chan ............... A61F 2/95 606/198 |
| 6,216,034 B1 | 4/2001 | Hofmann et al. |
| 6,219,577 B1 | 4/2001 | Brown, II et al. |
| 6,233,482 B1 | 5/2001 | Hofmann et al. |
| 6,241,701 B1 | 6/2001 | Hofmann |
| 6,325,777 B1 | 12/2001 | Zadno-Azizi et al. |
| 6,326,177 B1 | 12/2001 | Schoenbach et al. |
| 6,389,314 B2 | 5/2002 | Feiring |
| 6,428,538 B1 * | 8/2002 | Blewett ............ A61B 18/1485 606/41 |
| 6,516,223 B2 | 2/2003 | Hofmann |
| 6,529,778 B2 | 3/2003 | Prutchi |
| 6,542,778 B1 | 4/2003 | Fuhr et al. |
| 6,582,423 B1 | 6/2003 | Thapliyal et al. |
| 6,675,809 B2 | 1/2004 | Stack et al. |
| 6,678,558 B1 | 1/2004 | Dimmer et al. |
| 6,697,669 B2 | 2/2004 | Dev et al. |
| 6,697,670 B2 | 2/2004 | Chomenky et al. |
| 6,714,861 B2 | 3/2004 | Okude et al. |
| 6,758,846 B2 | 7/2004 | Goble et al. |
| 6,795,728 B2 | 9/2004 | Chornenky et al. |
| 6,905,496 B1 | 6/2005 | Ellman et al. |
| 6,936,024 B1 * | 8/2005 | Houser ............ A61B 18/1492 604/22 |
| 6,978,172 B2 | 12/2005 | Mori et al. |
| 6,994,706 B2 | 2/2006 | Chornenky et al. |
| 7,004,941 B2 | 2/2006 | Tvinnereim et al. |
| 7,054,685 B2 | 5/2006 | Dimmer et al. |
| 7,150,745 B2 | 12/2006 | Stern et al. |
| 7,175,669 B2 | 2/2007 | Geitz |
| 7,220,284 B2 | 5/2007 | Kagan et al. |
| 7,272,050 B2 | 9/2007 | Han et al. |
| 7,285,117 B2 | 10/2007 | Krueger et al. |
| 7,326,207 B2 | 2/2008 | Edwards |
| 7,412,284 B2 | 8/2008 | Hofmann |
| 7,422,587 B2 | 9/2008 | Bek et al. |
| 7,458,378 B2 | 12/2008 | Utley et al. |
| 7,571,729 B2 | 8/2009 | Saadat et al. |
| 7,620,451 B2 | 11/2009 | Demarais et al. |
| 7,737,109 B2 | 6/2010 | Miller |
| 7,742,795 B2 | 6/2010 | Stone et al. |
| 7,758,623 B2 | 7/2010 | Dzeng et al. |
| 7,904,172 B2 | 3/2011 | Kon et al. |
| 7,909,755 B2 | 3/2011 | Itoi |
| 7,959,627 B2 | 6/2011 | Utley et al. |
| 8,032,207 B2 | 10/2011 | Lapanashvili et al. |
| 8,048,067 B2 | 11/2011 | Davalos et al. |
| 8,221,411 B2 | 7/2012 | Francischelli et al. |
| 8,251,986 B2 | 8/2012 | Chornenky et al. |
| 8,267,932 B2 | 9/2012 | Baxter et al. |
| 8,282,631 B2 | 10/2012 | Davalos et al. |
| 8,323,229 B2 | 12/2012 | Shin et al. |
| 8,355,799 B2 | 1/2013 | Marion et al. |
| 8,361,066 B2 | 1/2013 | Long et al. |
| 8,428,735 B2 | 4/2013 | Littlewood et al. |
| 8,473,051 B1 | 6/2013 | Wessels et al. |
| 8,529,612 B2 | 9/2013 | Singh |
| 8,562,588 B2 | 10/2013 | Hobbs et al. |
| 8,636,648 B2 | 1/2014 | Gazdzinski |
| 8,647,338 B2 | 2/2014 | Chornenky et al. |
| 8,740,894 B2 | 6/2014 | Edwards |
| 8,790,339 B2 | 7/2014 | Edwards et al. |
| 8,814,860 B2 | 8/2014 | Davalos et al. |
| 8,915,911 B2 | 12/2014 | Azure |
| 8,926,576 B2 | 1/2015 | Mikkaichi |
| 8,926,606 B2 | 1/2015 | Davalos et al. |
| 9,005,100 B2 | 4/2015 | Gnanashanmugam et al. |
| 9,005,189 B2 | 4/2015 | Davalos et al. |
| 9,011,431 B2 | 4/2015 | Long et al. |
| 9,078,665 B2 | 7/2015 | Moss et al. |
| 9,119,600 B2 | 9/2015 | Richardson et al. |
| 9,168,096 B2 | 10/2015 | Kreindel |
| 9,173,704 B2 | 11/2015 | Hobbs et al. |
| 9,179,970 B2 | 11/2015 | Utley et al. |
| 9,191,801 B2 | 11/2015 | Kwak |
| 9,198,733 B2 | 12/2015 | Neal, II et al. |
| 9,277,957 B2 | 3/2016 | Long et al. |
| 9,283,051 B2 | 3/2016 | Garcia et al. |
| 9,289,606 B2 | 3/2016 | Paul et al. |
| 9,308,043 B2 | 4/2016 | Zarins et al. |
| 9,314,620 B2 | 4/2016 | Long et al. |
| 9,345,538 B2 | 5/2016 | Deem et al. |
| 9,351,789 B2 | 5/2016 | Novichenok et al. |
| 9,351,790 B2 | 5/2016 | Zemel et al. |
| 9,358,020 B2 | 6/2016 | Smith |
| 9,462,960 B2 | 10/2016 | Kassab |
| 9,480,524 B2 | 11/2016 | Chornenky et al. |

(56) References Cited

U.S. PATENT DOCUMENTS

| | | |
|---|---|---|
| 9,555,020 B2 | 1/2017 | Pasricha et al. |
| 9,597,147 B2 | 3/2017 | Jackson et al. |
| 9,598,691 B2 | 3/2017 | Davalos |
| 9,737,360 B2 | 8/2017 | West et al. |
| 9,788,885 B2 | 10/2017 | Long et al. |
| 9,801,681 B2 | 10/2017 | Laske et al. |
| 9,827,041 B2 | 11/2017 | Zarins et al. |
| 9,861,435 B2 | 1/2018 | Richardson et al. |
| 9,867,652 B2 | 1/2018 | Sano et al. |
| 9,918,789 B2 | 3/2018 | Bagley et al. |
| 9,924,991 B2 | 3/2018 | West et al. |
| 9,937,344 B2 | 4/2018 | Starkebaum et al. |
| 9,988,885 B1 | 6/2018 | Shahinpour et al. |
| 9,993,281 B2 | 6/2018 | Kelly et al. |
| 9,993,297 B2 | 6/2018 | Ben-Oren et al. |
| 9,999,467 B2 | 6/2018 | Moss et al. |
| 10,004,558 B2 | 6/2018 | Long et al. |
| 10,010,666 B2 | 7/2018 | Rubinsky et al. |
| 10,016,232 B1 | 7/2018 | Bowers et al. |
| 10,039,596 B2 | 8/2018 | Zarins et al. |
| 10,064,697 B2 | 9/2018 | Sharma et al. |
| 10,070,914 B2 | 9/2018 | Schoenbach et al. |
| 10,117,701 B2 | 11/2018 | Davalos et al. |
| 10,154,874 B2 | 12/2018 | Davalos et al. |
| 10,154,876 B2 | 12/2018 | Callas et al. |
| 10,238,447 B2 | 3/2019 | Neal, II et al. |
| 10,245,098 B2 | 4/2019 | Davalos et al. |
| 10,245,105 B2 | 4/2019 | Davalos |
| 10,292,755 B2 | 5/2019 | Arena et al. |
| 10,299,857 B2 | 5/2019 | Rajagopalan et al. |
| 10,322,286 B2 | 6/2019 | Viswanathan et al. |
| 10,342,598 B2 | 7/2019 | Long et al. |
| 10,349,998 B2 | 7/2019 | Levin et al. |
| 10,350,004 B2 | 7/2019 | Gifford, III et al. |
| 10,368,944 B2 | 8/2019 | Schaer |
| 10,448,989 B2 | 10/2019 | Arena et al. |
| 10,463,426 B2 | 11/2019 | Chornenky et al. |
| 10,548,653 B2 | 2/2020 | Hoey et al. |
| 10,558,665 B2 | 2/2020 | Mazumder |
| 10,569,081 B2 | 2/2020 | Howard |
| 10,582,963 B2 | 3/2020 | Woloszko et al. |
| 10,610,663 B2 | 4/2020 | Rajagopalan et al. |
| 10,614,949 B2 | 4/2020 | Smith et al. |
| 10,722,302 B2 | 7/2020 | Sherman et al. |
| 10,722,305 B2 | 7/2020 | Moss et al. |
| 10,765,474 B2 | 9/2020 | Kadamus et al. |
| 10,842,668 B2 | 11/2020 | Singh |
| 10,856,926 B2 | 12/2020 | Azamian et al. |
| 10,869,178 B1 | 12/2020 | Snapp |
| 10,869,718 B2 | 12/2020 | Rajagopalan et al. |
| 10,881,455 B2 | 1/2021 | Schwartz et al. |
| 10,888,377 B2 | 1/2021 | Ben-Oren et al. |
| 10,898,263 B2 | 1/2021 | Bagley et al. |
| 10,912,609 B2 | 2/2021 | De La Rama et al. |
| 10,939,949 B2 | 3/2021 | Rubinsky et al. |
| 10,946,193 B2 | 3/2021 | Athos et al. |
| 10,953,241 B2 | 3/2021 | Luttrull et al. |
| 10,959,774 B2 | 3/2021 | Kadamus et al. |
| 10,973,561 B2 | 4/2021 | Caplan et al. |
| 10,987,149 B2 | 4/2021 | Rajagopalan et al. |
| 11,103,674 B2 | 8/2021 | Rajagopalan et al. |
| 11,185,367 B2 | 11/2021 | Rajagopalan et al. |
| 11,246,639 B2 | 2/2022 | Rajagopalan et al. |
| 11,254,926 B2 | 2/2022 | Neal, II et al. |
| 11,272,979 B2 | 3/2022 | Garcia et al. |
| 11,278,349 B2 | 3/2022 | Stewart et al. |
| 11,298,175 B2 | 4/2022 | Konings |
| 11,311,333 B2 | 4/2022 | Rajagopalan et al. |
| 11,337,749 B2 | 5/2022 | DeSimone et al. |
| 11,357,978 B2 | 6/2022 | Bowers et al. |
| 11,364,072 B2 | 6/2022 | Howard et al. |
| 11,376,064 B2 | 7/2022 | Rankin |
| 11,382,681 B2 | 7/2022 | Arena et al. |
| 11,389,171 B2 | 7/2022 | Goldsmith |
| 11,419,659 B2 | 8/2022 | Levin et al. |
| 11,439,457 B2 | 9/2022 | Caplan et al. |
| 11,453,873 B2 | 9/2022 | Davalos et al. |
| 11,464,968 B2 | 10/2022 | Howard |
| 11,471,208 B2 | 10/2022 | Waldstreicher et al. |
| 11,547,851 B2 | 1/2023 | Krimsky et al. |
| 11,596,474 B2 | 3/2023 | Van Der Weide et al. |
| 11,638,603 B2 | 5/2023 | Sano et al. |
| 11,638,819 B2 | 5/2023 | Gundert et al. |
| 11,655,466 B2 | 5/2023 | Neal, II et al. |
| 11,723,712 B2 | 8/2023 | Athos et al. |
| 11,779,395 B2 | 10/2023 | Moss et al. |
| 11,826,521 B2 | 11/2023 | Rajagopalan et al. |
| 11,878,128 B2 | 1/2024 | Rajagopalan et al. |
| 11,912,975 B2 | 2/2024 | Soden et al. |
| 2001/0044596 A1* | 11/2001 | Jaafar .................. A61N 1/327 604/103.01 |
| 2002/0087208 A1* | 7/2002 | Koblish ............ A61B 18/1492 606/41 |
| 2003/0055464 A1 | 3/2003 | Darvish et al. |
| 2003/0093072 A1 | 5/2003 | Friedman |
| 2003/0153905 A1 | 8/2003 | Edwards et al. |
| 2003/0181898 A1 | 9/2003 | Bowers |
| 2003/0236496 A1 | 12/2003 | Samson et al. |
| 2004/0095100 A1 | 5/2004 | Thompson |
| 2004/0215180 A1 | 10/2004 | Starkebaum et al. |
| 2004/0215296 A1 | 10/2004 | Ganz et al. |
| 2004/0220559 A1 | 11/2004 | Kramer et al. |
| 2004/0236376 A1 | 11/2004 | Miklavcic et al. |
| 2005/0090873 A1 | 4/2005 | Imran |
| 2005/0183732 A1 | 8/2005 | Edwards |
| 2005/0192652 A1 | 9/2005 | Cioanta et al. |
| 2005/0234293 A1 | 10/2005 | Yamamoto et al. |
| 2006/0084962 A1 | 4/2006 | Joye et al. |
| 2006/0095032 A1* | 5/2006 | Jackson ............ A61B 18/1492 606/41 |
| 2006/0135963 A1 | 6/2006 | Kick et al. |
| 2006/0217698 A1 | 9/2006 | Starkebaum et al. |
| 2006/0293730 A1 | 12/2006 | Rubinsky et al. |
| 2007/0016262 A1 | 1/2007 | Gross et al. |
| 2007/0043345 A1 | 2/2007 | Davalos et al. |
| 2007/0100355 A1 | 5/2007 | Bonde et al. |
| 2007/0225800 A1 | 9/2007 | Sahatjian et al. |
| 2008/0058786 A1 | 3/2008 | Boyden et al. |
| 2008/0058887 A1 | 3/2008 | Griffin et al. |
| 2008/0207994 A1 | 8/2008 | Gonon |
| 2008/0223380 A1 | 9/2008 | Chinn |
| 2008/0275445 A1 | 11/2008 | Kelly et al. |
| 2009/0012469 A1 | 1/2009 | Nita |
| 2009/0203995 A1 | 8/2009 | Matonick |
| 2009/0248012 A1 | 10/2009 | Maor et al. |
| 2009/0269317 A1 | 10/2009 | Davalos |
| 2009/0281477 A1 | 11/2009 | Mikus et al. |
| 2010/0023004 A1 | 1/2010 | Francischelli et al. |
| 2010/0023047 A1 | 1/2010 | Simpson |
| 2010/0114325 A1 | 5/2010 | Yang et al. |
| 2010/0179530 A1 | 7/2010 | Long et al. |
| 2010/0191235 A1 | 7/2010 | Moshe et al. |
| 2010/0204560 A1 | 8/2010 | Salahieh et al. |
| 2010/0210994 A1 | 8/2010 | Zarif |
| 2010/0222677 A1 | 9/2010 | Placek et al. |
| 2010/0249771 A1 | 9/2010 | Pearson et al. |
| 2010/0256630 A1 | 10/2010 | Hamilton et al. |
| 2011/0091564 A1 | 4/2011 | Chu |
| 2011/0106273 A1 | 5/2011 | Belhe et al. |
| 2011/0118732 A1 | 5/2011 | Rubinsky et al. |
| 2011/0144635 A1 | 6/2011 | Harper et al. |
| 2011/0160514 A1 | 6/2011 | Long et al. |
| 2011/0172659 A1 | 7/2011 | Brannan |
| 2011/0208175 A1 | 8/2011 | Sobotka et al. |
| 2011/0224768 A1 | 9/2011 | Edwards |
| 2011/0288543 A1 | 11/2011 | Cheng et al. |
| 2012/0010610 A1 | 1/2012 | Keppel |
| 2012/0041465 A1 | 2/2012 | Shalon |
| 2012/0059255 A1 | 3/2012 | Paul et al. |
| 2012/0109122 A1 | 5/2012 | Arena et al. |
| 2012/0116266 A1 | 5/2012 | Houser et al. |
| 2012/0191089 A1 | 7/2012 | Gonzalez et al. |
| 2012/0259269 A1 | 10/2012 | Meyer |
| 2013/0030430 A1 | 1/2013 | Stewart et al. |

(56) References Cited

U.S. PATENT DOCUMENTS

| | | |
|---|---|---|
| 2013/0184702 A1 | 7/2013 | Neal, II et al. |
| 2013/0190675 A1 | 7/2013 | Sandoski |
| 2013/0345670 A1 | 12/2013 | Rajagopalan et al. |
| 2014/0031810 A1 | 1/2014 | Mahvi et al. |
| 2014/0074077 A1 | 3/2014 | Lane |
| 2014/0088362 A1 | 3/2014 | Terliuc et al. |
| 2014/0088529 A1 | 3/2014 | Bengtson |
| 2014/0114304 A1* | 4/2014 | Wang ............... A61B 18/1492 606/41 |
| 2014/0121646 A1 | 5/2014 | Lodin et al. |
| 2014/0135606 A1* | 5/2014 | Yasui ............. G01N 35/00009 600/365 |
| 2014/0214026 A1* | 7/2014 | Degen ............... A61N 1/0514 606/41 |
| 2014/0371736 A1 | 12/2014 | Levin et al. |
| 2015/0141987 A1 | 5/2015 | Caplan et al. |
| 2015/0148738 A1 | 5/2015 | Caplan et al. |
| 2015/0164584 A1 | 6/2015 | Davalos et al. |
| 2015/0173824 A1 | 6/2015 | Davalos et al. |
| 2015/0182282 A1 | 7/2015 | Zemel et al. |
| 2015/0182735 A1 | 7/2015 | Chang et al. |
| 2015/0216592 A1 | 8/2015 | Gnanashanmugam et al. |
| 2015/0289923 A1 | 10/2015 | Davalos et al. |
| 2015/0327944 A1 | 11/2015 | Neal, II et al. |
| 2016/0051324 A1 | 2/2016 | Stewart et al. |
| 2016/0058493 A1 | 3/2016 | Neal, II et al. |
| 2016/0066977 A1 | 3/2016 | Neal, II et al. |
| 2016/0081745 A1 | 3/2016 | Rajagopalan et al. |
| 2016/0175582 A1 | 6/2016 | Serna et al. |
| 2016/0235470 A1 | 8/2016 | Callas et al. |
| 2016/0287314 A1 | 10/2016 | Arena et al. |
| 2016/0331441 A1 | 11/2016 | Konings |
| 2016/0338761 A1 | 11/2016 | Chornenky et al. |
| 2016/0354142 A1 | 12/2016 | Pearson et al. |
| 2016/0361109 A1 | 12/2016 | Weaver et al. |
| 2016/0367310 A1 | 12/2016 | Onik et al. |
| 2016/0374754 A1 | 12/2016 | Asirvatham et al. |
| 2017/0000559 A1 | 1/2017 | Rioux et al. |
| 2017/0014183 A1 | 1/2017 | Gifford, III et al. |
| 2017/0035501 A1 | 2/2017 | Chornenky et al. |
| 2017/0095290 A1 | 4/2017 | Sherman et al. |
| 2017/0105781 A1 | 4/2017 | Pasricha et al. |
| 2017/0112562 A1 | 4/2017 | Woloszko et al. |
| 2017/0203132 A1 | 7/2017 | Luttrull et al. |
| 2017/0232269 A1 | 8/2017 | Luttrull et al. |
| 2017/0245928 A1 | 8/2017 | Xiao et al. |
| 2017/0265929 A1 | 9/2017 | Callas et al. |
| 2017/0333122 A1 | 11/2017 | Rajagopalan et al. |
| 2017/0348049 A1 | 12/2017 | Vrba et al. |
| 2018/0021084 A1 | 1/2018 | Onik et al. |
| 2018/0028252 A1 | 2/2018 | Lalonde |
| 2018/0028264 A1 | 2/2018 | Onik et al. |
| 2018/0042661 A1 | 2/2018 | Long et al. |
| 2018/0043153 A1 | 2/2018 | Viswanathan et al. |
| 2018/0071014 A1 | 3/2018 | Neal et al. |
| 2018/0125575 A1 | 5/2018 | Schwartz et al. |
| 2018/0193082 A1 | 7/2018 | Rubinsky et al. |
| 2018/0193090 A1 | 7/2018 | de la Rama et al. |
| 2018/0193590 A1 | 7/2018 | Rajagopalan et al. |
| 2018/0214202 A1 | 8/2018 | Howard et al. |
| 2018/0221622 A1 | 8/2018 | Rajagopalan et al. |
| 2018/0250074 A1 | 9/2018 | Ben-Oren et al. |
| 2018/0250508 A1 | 9/2018 | Howard |
| 2018/0263694 A1 | 9/2018 | Moss et al. |
| 2018/0296264 A1* | 10/2018 | DeSimone ......... A61N 1/36007 |
| 2019/0069949 A1* | 3/2019 | Vrba .................... A61B 18/06 |
| 2019/0175248 A1 | 6/2019 | Neal, II et al. |
| 2019/0223938 A1 | 7/2019 | Arena et al. |
| 2019/0223948 A1* | 7/2019 | Stewart ............. A61B 18/1206 |
| 2019/0233809 A1 | 8/2019 | Neal, II et al. |
| 2019/0254740 A1 | 8/2019 | Koya et al. |
| 2019/0256839 A1 | 8/2019 | Neal, II et al. |
| 2019/0282294 A1 | 9/2019 | Davalos et al. |
| 2019/0328445 A1 | 10/2019 | Sano et al. |
| 2019/0344053 A1 | 11/2019 | Wang et al. |
| 2019/0376055 A1 | 12/2019 | Davalos et al. |
| 2020/0060758 A1 | 2/2020 | Rajagopalan et al. |
| 2020/0060942 A1 | 2/2020 | Rajagopalan et al. |
| 2020/0093541 A9 | 3/2020 | Neal, II et al. |
| 2020/0129230 A1 | 4/2020 | Forsyth et al. |
| 2020/0155217 A1 | 5/2020 | Morneau et al. |
| 2020/0268475 A1 | 8/2020 | Adler, Jr. et al. |
| 2020/0315700 A1* | 10/2020 | Petitpierre ......... A61B 18/1492 |
| 2020/0323576 A1 | 10/2020 | Neal et al. |
| 2021/0077183 A1 | 3/2021 | Basu et al. |
| 2021/0128335 A1 | 5/2021 | Thompson et al. |
| 2021/0161582 A1 | 6/2021 | Byrd et al. |
| 2021/0393327 A1 | 12/2021 | Eyster et al. |
| 2022/0022952 A1 | 1/2022 | Koop et al. |
| 2022/0054184 A9 | 2/2022 | Rajagopalan et al. |
| 2022/0071700 A1 | 3/2022 | DeSimone et al. |
| 2022/0117658 A1 | 4/2022 | Rajagopalan et al. |
| 2022/0265337 A1 | 8/2022 | Rajagopalan et al. |
| 2022/0331601 A1 | 10/2022 | D'Agostino et al. |
| 2022/0354571 A1 | 11/2022 | Caplan et al. |
| 2022/0387095 A1 | 12/2022 | Neal, II et al. |
| 2023/0000543 A1 | 1/2023 | Sano et al. |
| 2023/0123435 A1 | 4/2023 | Meadowcraft et al. |
| 2023/0149706 A1 | 5/2023 | Krimsky et al. |
| 2023/0165621 A1 | 6/2023 | Biasella et al. |
| 2023/0172650 A1 | 6/2023 | Castellvi et al. |
| 2023/0200883 A1 | 6/2023 | Caplan et al. |
| 2023/0233250 A1 | 7/2023 | Rajagopalan et al. |
| 2023/0310066 A1 | 10/2023 | Tegg et al. |
| 2023/0380897 A1 | 11/2023 | Liu et al. |
| 2023/0405313 A1 | 12/2023 | Pastori et al. |
| 2023/0414274 A1 | 12/2023 | Moss et al. |
| 2024/0016536 A1 | 1/2024 | Kato et al. |
| 2024/0156523 A1 | 5/2024 | D'Agostino et al. |
| 2024/0180613 A1 | 6/2024 | D'Agostino et al. |

FOREIGN PATENT DOCUMENTS

| | | |
|---|---|---|
| CN | 103517731 A | 1/2014 |
| EP | 2 865 349 A1 | 4/2015 |
| EP | 3 050 531 A1 | 8/2016 |
| EP | 3 316 813 A1 | 5/2018 |
| EP | 3 169 260 B1 | 9/2019 |
| JP | 2009-531157 A | 9/2009 |
| JP | 2012-515018 A | 7/2012 |
| JP | 2015013954 A | 2/2015 |
| JP | 2015097780 A | 5/2015 |
| JP | 2019516512 A | 6/2019 |
| WO | WO-91/16945 A1 | 11/1991 |
| WO | WO-9519735 A1 | 7/1995 |
| WO | WO-98/15318 A1 | 4/1998 |
| WO | WO-00/35349 A1 | 6/2000 |
| WO | WO-2001068015 | 9/2001 |
| WO | WO-2005/089433 A2 | 9/2005 |
| WO | WO-2005/089433 A3 | 9/2005 |
| WO | WO-2008137757 A1 | 11/2008 |
| WO | WO-2009009444 A1 | 1/2009 |
| WO | WO-2009132190 A2 | 10/2009 |
| WO | WO-2011/047387 A2 | 4/2011 |
| WO | WO-2011/047387 A3 | 4/2011 |
| WO | WO-2011/072221 A1 | 6/2011 |
| WO | WO-2012078522 A1 | 6/2012 |
| WO | WO-2012088149 A2 | 6/2012 |
| WO | WO-2012099974 A2 | 7/2012 |
| WO | WO-2012161875 A1 | 11/2012 |
| WO | WO-2013012892 A2 | 1/2013 |
| WO | WO-2013116822 A1 | 8/2013 |
| WO | WO-2013130655 A1 | 9/2013 |
| WO | WO-2014/026055 A1 | 2/2014 |
| WO | WO-2014022436 A1 | 2/2014 |
| WO | WO-2014055997 A1 | 4/2014 |
| WO | WO-2014/118782 A2 | 8/2014 |
| WO | WO-2014/118782 A3 | 8/2014 |
| WO | WO-2014118738 A1 | 8/2014 |
| WO | WO-2014121664 A1 | 8/2014 |
| WO | WO-2014/189887 A2 | 11/2014 |
| WO | WO-2014/189887 A3 | 11/2014 |
| WO | WO-2014197632 A2 | 12/2014 |
| WO | WO-2015148541 A1 | 10/2015 |

(56) References Cited

FOREIGN PATENT DOCUMENTS

| | | |
|---|---|---|
| WO | WO-2015159296 A1 | 10/2015 |
| WO | WO-2016011269 A1 | 1/2016 |
| WO | WO-2016115031 A2 | 7/2016 |
| WO | WO-2016/178697 A1 | 11/2016 |
| WO | WO-2017/004432 A1 | 1/2017 |
| WO | WO-2017/062753 A1 | 4/2017 |
| WO | WO-2017/203380 A1 | 11/2017 |
| WO | WO-2017/212257 A1 | 12/2017 |
| WO | WO-2018/050025 A1 | 3/2018 |
| WO | WO-2018/089773 A1 | 5/2018 |
| WO | WO-2018/140473 A1 | 8/2018 |
| WO | WO-2018/167451 A1 | 9/2018 |
| WO | WO-2019018362 A1 | 1/2019 |
| WO | WO-2019136240 A1 | 7/2019 |
| WO | WO-2021081131 A1 | 4/2021 |
| WO | WO-2022171141 A1 | 8/2022 |
| WO | WO-2022226113 A1 | 10/2022 |
| WO | WO-2022260723 A1 | 12/2022 |
| WO | WO-2023280822 A1 | 1/2023 |
| WO | WO-2023086537 A1 | 5/2023 |
| WO | WO-2023093514 A1 | 6/2023 |
| WO | WO-2023147319 A1 | 8/2023 |
| WO | WO-2023150215 A1 | 8/2023 |
| WO | WO-2023161492 A1 | 8/2023 |
| WO | WO-2023172773 A1 | 9/2023 |
| WO | WO-2023122100 A3 | 11/2023 |

OTHER PUBLICATIONS

International Search Report mailed on Apr. 14, 2021, for PCT Application No. PCT/US2020/056720, filed on Oct. 21, 2020, 7 pages.
Non-Final Office Action mailed on Jul. 2, 2021, for U.S. Appl. No. 15/766,604, filed Apr. 6, 2018, 14 pages.
Samihah Zura Mohd Nani (2015). "What is the best solvent for drugs?" 21 total pages.
Written Opinion of the International Searching Authority mailed on Apr. 14, 2021, for PCT Application No. PCT/US2020/056720, filed on Oct. 21, 2020, 13 pages.
International Search Report and Written Opinion in Intl. Application No. PCT/US2022/049653, mailed Mar. 27, 2023, 10 pages.
Non-Final Office Action for U.S. Appl. No. 17/529,037, dated Apr. 25, 2023, 10 pages.
Office Action for Australian Application No. AU20210240126 dated Apr. 5, 2023, 3 pages.
Office Action for Australian application No. AU20210240126, mailed on Oct. 10, 2022, 3 pages.
Office Action for European Application No. EP20160854413 dated Jul. 3, 2023, 5 pages.
Office Action for Israel Application No. IL20230300334, dated Aug. 9, 2023, 4 pages.
Office Action for Japanese Application No. JP20180517566 dated Jun. 13, 2023, 4 pages.
Adams et al., "Theoretical design and evaluation of endoluminal ultrasound applicators for thermal therapy of pancreatic cancer under image guidance," AIP Conference Proceedings, Mar. 17, 2017, vol. 1821, No. 1, 6 pages.
Al Sakere et al., "Tumor Ablation with Irreversible Electroporation," PLoS One, Nov. 7, 2007, No. 11, e1135, 8 pages.
Arena et al., "Advances in Therapeutic Electroporation to Mitigate Muscle Contractions," Journal of Membrane Science & Technology, 2012, vol. 2, No. 10.4172, pp. 2155-9589.
Arena et al., "Theoretical Considerations of Tissue Electroporation With High-Frequency Bipolar Pulses," IEEE Transactions on Biomedic, Dec. 23, 2010, vol. 58, No. 5, pp. 1474-1482.
Armstrong, M., Interview—Fractyl aims at the root of diabetes, Evaluate Vantage, Dec. 14, 2015, 2 pages.
AU Radiation Protection and Nuclear Safety Agency, "Exposure of Humans to Ionizing Radiation for Research Purposes—Code of Practice," May 2005, 36 pages.

Bakheet et al., "Endoluminal bariatric and metabolic therapies: state-of-the-art," Current Opinion in Gastroenterology, Sep. 2023, vol. 39, No. 5, pp. 362-369.
Ball et al., "Irreversible Electroporation a New Challenge in "Out of Operating Theater" Anesthesia," Anesthesia & Analgesia, May 2010, vol. 110, No. 5, pp. 1305-1309.
Benov et al., "Oxidative Damage of the Membrane Lipids after Electroporation," Gen. Physiol. Biophys., Apr. 4, 1994, vol. 13, pp. 85-97.
Bhonsle et al., "Mitigation of impedance changes due to electroporation therapy using bursts of high-frequency bipolar pulses," Dec. 2015, Biomed Eng Online, vol. 14, No. S3. pp. 1-4.
Bilska er al., "Theoretical modeling of the effects of shock duration, frequency, and strength on the degree of electroporation," Bioelectrochemistry, Jun. 1, 2000, vol. 51, No. 2, pp. 133-143.
Brethauer et al., "Gastrointestinal devices for the treatment of type 2 diabetes," Surgery for Obesity and Related Diseases, Jul. 2016, vol. 12, No. 6, pp. 1256-1261.
Busch et al., "Re-Cellularization via Electroporation Therapy (Recet) Combined With GLP-1RA to Replace Insulin Therapy in Patients With Type 2 Diabetes 6 Months Results of the Eminent Study," Gastrointestinal Endoscopy, Jun. 1, 2023, vol. 97, No. 6, AB298, 1 page.
Busko, "Duodenal Mucosal Resurfacing Shows Early Promise in Diabetes," Medscape, Jun. 12, 2016, 3 pages.
Cassanelli et al., "Alteration of Membrane Permeability of Bacteria and Yeast by High Frequency Alternating Current (HFAC)," The Open Microbiology Journal, Apr. 4, 2008, vol. 2, pp. 32-37.
Chang et al., "High efficiency gene transfection by electroporation using a radio-frequency electric field," Biochim Biophys Acta (BBA)—Molecular Cell Research, Apr. 17, 1991, vol. 1092, No. 2, pp. 153-160.
Chathadi et al., "The role of endoscopy in ampullary and duodenal adenomas," Gastrointest Endosc., Nov. 2015, vol. 82, No. 5, pp. 773-781.
Cherrington et al., "Hydrothermal Duodenal Mucosal Resurfacing: Role in the Treatment of Metabolic Disease," Gastrointest Endosc Clin N Am., Apr. 2017, vol. 27, No. 2, pp. 299-311.
ClinicalTrials.gov, "Evaluation of Duodenal Mucosal Resurfacing in Subjects With Type 2 Diabetes," [database online], published Apr. 10, 2014, last updated Feb. 14, 2024, 16 pages, retrieved Apr. 18, 2024, retrieved online: https://clinicaltrials.gov/study/NCT02413567.
Daskalov et al., "Exploring new instrumentation parameters for electrochemotherapy. Attacking tumors with bursts of biphasic pulses instead of single pulses," IEEE Engineering in Medicine and Biology Magazine, Jan.-Feb. 1999 vol. 18, No. 1, pp. 62-66.
Davalos et al., "Tissue ablation with irreversible electroporation," Annals of Biomedical Engineering, Feb. 2005, vol. 33, pp. 223-231.
Dotsinksy et al., "New Modality for Electrochemotherapy of Surface Tumors," Biotechnology and Biotechnological Equipment, Apr. 16, 2014, vol. 26, No. 6, pp. 3402-3406.
Fractyl Health, "First Patients Enrolled in Multicenter Clinical Trial of Fractyl Revita DMR System," Press Release from Fractyl Health, Jul. 16, 2015, 2 pages.
Fractyl Health, "Fractyl Labs Announces Approval to Initiate Multicenter Clinical Trial of Revita DMR Procedure," Press Release from Fractyl Health, Jan. 12, 2015, 1 page.
Galveo Neto et al., "Endoscopic Duodenal Mucosal Resurfacing Improves Glycemic and Hepatic Parameters in Patients With Type 2 Diabetes: Data From a First-in-Human Study," Gastroenterology, Apr. 2016, vol. 150, No. 4, Supp. 1, 1 page.
Gehl et al., "In vivo electroporation of skeletal muscle: threshold, efficacy and relation to electric field distribution," Biochimica et Biophysica Acta (BBA)—General Subjects, Aug. 5, 1999, vol. 1428, Nos. 2-3, pp. 233-240.
Gianulis et al., "Electroporation of mammalian cells by nanosecond electric field oscillations and its inhibition by the electric field reversal." Sci Rep, Sep. 2015, vol. 5, No. 13818, 10 pages.
Goldberg et al., "Towards Electroporation Based Treatment Planning Considering Electric Field Induced Muscle Contractions," Technology in Cancer Research and Treatment, Apr. 2, 2012, vol. 11, No. 2, pp. 189-201.

(56) References Cited

OTHER PUBLICATIONS

Grikscheit et al., "Tissue-engineered small intestine improves recovery after massive small bowel resection," Ann Surg., Nov. 1, 2004, vol. 240, No. 5, pp. 748-754.
Hibino et al., "Time courses of cell electroporation as revealed by submicrosecond imaging of transmembrane potential," Biophysical Journal 64.6 (1993): pp. 1789-1800. https://www.cell.com/biophysj/pdf/S0006-3495(93)81550-9.pdf.
Hofmann et al., "Electrochemotherapy: Transition from Laboratory to the Clinic," IEEE Engineering in Medicine and Biology, Nov./Dec. 1996, pp. 124-132 (Abstract only.
Hollerbach et al., "The EndoRotor®: endoscopic mucosal resection system for non-thermal and rapid removal of esophageal, gastric, and colonic lesions: initial experience in live animals," Endoscopy International Open, Apr. 2016, vol. 4, No. 4, E475-9.
International Preliminary Report on Patentability for International Application No. PCT/US2022/025630 dated Nov. 2, 2023, 8 pages.
Kaufman et al., "Society of Interventional Radiology Clinical Practice Guideline for Inferior Vena Cava Filters in the Treatment of Patients with Venous Thromboembolic Disease," JVIR, Oct. 2020, vol. 31, No. 10, pp. 1529-1544.
Kekez et al., "Contribution to the biophysics of the lethal effects of electric field on microorganisms," Biochemica et Biophysica Acta (BBA)—Biomembranes, Jan. 12, 1996, vol. 1278, No. 1, pp. 79-88.
Kotnok et al., "Cell membrane electropermeabilization by symmetrical bipolar pulses. Part I. Increased efficiency of permeabilizartion," Bioelectrochemistry. Aug. 1, 2001, vol. 54, No. 1, pp. 91-95.
Lavee et al., "A Novel Nonthermal Energy Source for Surgical Epicardial Atrial Ablation: Irreversible Electroporation," Heart Surg Forum, Mar. 2007, vol. 10, No. 2, E162-E167.
Li et al, "The Effects of Irreversible Electroporation (IRE) on Nerves," PLoS ONE, Apr. 14, 2011, vol. 6, No. 4, e18831, 7 pages.
Lissidini et al., "Emergency pancreaticoduodenectomy: When is it needed? A dual non-trauma centre experience and literature review," International Journal of Surgery, Sep. 2015, vol. 21, Supp. 1, pp. S83-S88.
Maor et al., "Endovascular Nonthermal Irreversible Electroporation: A Finite Element Analysis," J Biomech Eng., Mar. 2010, vol. 132, No. 3, 7 pages.
Maor et al., "Irreversible Electroporation Attenuates Neointimal Formation After Angioplasty," IEEE Transactions on Biomedical Engineering, Sep. 2008, vol. 55, No. 9, pp. 2268-2274.
Mathus-Vliegan et al., "Endobarrier: a unique but still premature concept," Nederlands Tijdschrift Voor Geneeskunde, Jan. 1, 2012, vol. 156, No. 13, A4590, 1 page.
Miklavcic et al., "The effect of high frequency electric pulses on muscle contractions and antitumor efficiency in vivo for a potential use in clinical electrochemotherapy," J Bioelectrochemistry, Feb. 2005, vol. 65, No. 2, pp. 121-128.
Miklovic et al., "A Comprehensive Characterization of Parameters Affecting High-Frequency Irreversible Electroporation Lesions," Ann. Biomed Eng., Jul. 2017, vol. 45, pp. 2524-2534.
Miyawaki et al., "Inhibition of gastric inhibitory polypeptide signaling prevents obesity," Nat Med., Jul. 2002, vol. 8, No. 7, pp. 738-742.
Patel et al., "Endoscopic ampullectomy: techniques and outcomes," Journal of Clinical Gastroenterology, Jan. 1, 2012, vol. 46, No. 1, pp. 8-15.
Pemberton et al., "High-frequency electroporation and maintenance of pUC- and pBR-based cloning vectors inPseudomonas stutzeri," Current Microbiology, Jul. 1992, vol. 25, pp. 25-29.
Rodriguez et al., "O.145 Duodenal Mucosal Resurfacing (DMR)—a New Endoscopic Treatment for Type 2 Diabetes (T2DM) a Safety and Proof-Of-Principle Cohort Study," Abstract from the 19th World Congress of the International Federation for the Surgery of Obesity & Metabolic Disorders (IFSO) Montreal, CA, Aug. 26-30, 2014, 1 page.
Rodriguez, L. et al., "Type 2 diabetes: Renew duodenal mucosa with thermal ablation," Med Online, May 25, 2015, retrieved online at https://medonline.at/news/uncategorized/162382/typ-2-diabetes-thermal-ablation/, 3 pages.
Rowan et al., "Pulsed electric field inactivation of diarrhoeagenic Bacillus cereus through irreversible electroporation," Letters in Applied Microbiology, Aug. 1, 2000, vol. 31, No. 2, pp. 110-114.
Rubino et al., "Potential of surgery for curing type 2 diabetes mellitus," Ann Surg. Nov. 2002, vol. 236, No. 5, pp. 554-559.
Rubino, F. et al., "Metabolic Surgery in the Treatment Algorithm for Type 2 Diabetes: A Joint Statement by International Diabetes Organizations," Diabetes Care, May 13, 2016, vol. 39, No. 6, pp. 861-877.
Rubinsky et al., "Irreversible Electroporation: A New Ablation Modality—Clinical Implications," Technology in Cancer Research and Treatment, Feb. 2007, vol. 6, No. 1, pp. 37-48.
Rubinsky et al., "Optimal Parameters for the Destruction of Prostate Cancer Using Irreversible Electroporation," J Urol., Dec. 2008, vol. 180, No. 6, pp. 2668-2674.
Sarria et al., "Morphometric study of the layers of the canine small intestine at five sampling sites," Veterinary Journal, Jun. 1, 2012, vol. 192, No. 3, pp. 498-502.
Sartoretto et al., "Duodenal Mucosal Regeneration Induced by Endoscopic Pulsed Electric Field Treatment Improves Glycemic Control in Patients With Type II Diabetes—Interim Results From a First-In-Human Study," Endoscopic Technology, Jun. 2023, vol. 97, Issue 6, Supp. AB704-AB705.
Scuderi et al., "The use of high-frequency short bipolar pulses in cisplatin electrochemotherapy in vitro," Radiology & Oncology, Jun. 2019, vol. 53, No. 2, pp. 194-205.
Semkova et al., "Autologous transplantation of genetically modified iris pigment epithelial cells: A promising concept for the treatment of age-related macular degeneration and other disorders of the eye," Proceedings of the National Academy of Sciences, Oct. 1, 2002, vol. 99, No. 20, pp. 13090-13095.
Sen et al., "Autologous transplantation of endothelial progenitor cells genetically modified by adeno-associated viral vector delivering insulin-like growth factor-1 gene after myocardial infarction," Hum Gene Ther., Oct. 2010, vol. 21, No. 10, pp. 1327-1334.
Tiver, "Duodenum resurfacing procedure improved type 2 diabetes markers," Endocrine Today, Oct. 2014, vol. 12, Iss. 10, p. 20.
Tolman et al., "Spectrum of liver disease in type 2 diabetes and management of patients with diabetes and liver disease," Diabetes Care, Mar. 1, 2007, vol. 30, No. 3, pp. 734-743.
Tomizawa et al., "Clinical Outcome of Endoscopic Mucosal Resection (EMR) of Sporadic, Non-Ampullary Duodenal Adenoma (SNADA) : Predictor Analysis of Safety and Efficacy From a High Volume U.S. Tertiary Referral Center," Gastrointestinal Endoscopy, May 1, 2017, vol. 85, Issue 5, Supplement, p. AB72.
Tovar et al., "Electroporation and recovery of cardiac cell membrane with rectangular voltage pulses," American Journal of Physiology—Heart and Circulatory Physiology, Oct. 1992, vol. 263, No. 4, pp. H1128-H1136.
Tsiamoulos, Z.P. et al., "Endoscopic mucosal ablation: a novel technique for a giant nonampullary duodenal adenoma," Endoscopy, Dec. 2013, vol. 45, No. 2, pp. E12-E13.
Tyurin et al., "Electrotransformation of Clostridium acetobutylicum ATCC 824 using high-voltage radio frequency modulated square pulses," J App. Microbio., Feb. 1, 2000, vol. 88, No. 3, pp. 220-227.
Van Baar et al., "Alternative treatments for type 2 diabetes and associated metabolic diseases: medical therapy or endoscopic duodenal mucosal remodelling?" Gut, Nov. 1, 2021, vol. 70, No. 11, pp. 2196-2204.
Van Baar et al., "Single Catheter for Duodenal Mucosal Resurfacing Demonstrates Similar Safety Profile with Improved Procedure Time when Compared to Original Dual Catheter: Multicenter Study of Subjects with Type 2 Diabetes," Gastroenterology, Apr. 2017, vol. 152, Issue 5, Supplement 1, p. S825.
Wong et al., "Approaches to endoscopic ampullectomy," Current Opinions in Gastroenterology, Sep. 2004, vol. 20, No. 5, pp. 460-467.

(56) References Cited

OTHER PUBLICATIONS

Yuan et al., "835-P: First-in-Human Duodenal Endoscopic Recellularization via Electroporation Therapy for Type 2 Diabetes—An Interim Report," Clinical Therapeutics, Jun. 20, 2023, vol. 72, Supp. 1, p. 835.
Zald et al., "Improved Transfection Efficiency of 293 Cells by Radio Frequency Electroporation," Biotechniques, Mar. 2000, vol. 28, No. 3, pp. 418-420.
Zimmerman, D. et al., "Endoscopy jumps the boundaries," Healthcare in Europe, Jul. 1, 2015, retrieved online at https://healthcare-in-europe.com/en/news/endoscopy-jumps-the-boundaries.html, 6 pages.
International Preliminary Report on Patentability for International Application No. PCT/US2022/049653 mailed May 23, 2024, 8 pages.
Non-Final Office Action for U.S. Appl. No. 17/529,037 dated Mar. 14, 2024, 13 pages.
Non-Final Office Action for U.S. Appl. No. 17/725,449 mailed Aug. 30, 2024, 19 pages.
International Search Report and Written Opinion for International Application No. PCT/US2022/025630 dated Aug. 8, 2022, 14 pages.
Rajagopalan, H. et al. (2016). "Endoscopic Duodenal Mucosal Resurfacing for the Treatment of Type 2 Diabetes: 6-Month Interim Analysis From the First-in-Human Proof-of-Concept Study," Diabetes Care 39:2254-2261.
Arena et al. (2011). "High-frequency irreversible electroporation (H-FIRE) for non-thermal ablation without muscle contraction," Biomedical Engineering OnLine 10:102, 21 total pages.
Cersosimo, E. et al. (2020). "Pathogenesis of Type 2 Diabetes Mellitus," In Feingold KR, Anawalt B, Boyce A et al., ed. *Endotext* [*Internet*]. South Dartmouth (MA): MDText.com, Inc.; 2020:3-7, 45 total pages.
Dong, S. et al. (2018). "First Human Trial of High-Frequency Irreversible Electroporation Therapy for Prostate Cancer," *Technolology in Cancer Res. Treat.* 17:1-9.
DPP Research Group (2002). "The Diabetes Prevention Program (DPP)," Diabetes Care 25:2165-2171.
Extended European Search Report mailed on Aug. 20, 2019, for EP Application No. 16 854 413.8, filed on Oct. 7, 2016, 12 pages.
International Search Report mailed on Dec. 29, 2016, for PCT Application No. PCT/US2016/055966, filed on Oct. 7, 2016, 2 pages.
Gilmer, T.P. et al. (1997). "The cost to health plans of poor glycemic control," *Diabetes Care* 20:1847-1853.
Knavel, E.M. et al. (2013). "Tumor Ablation: Common Modalities and General Practices," *Tech. Vasc. Interv. Radiol.* 16:192-200.
Martin, R.C.G. II (2015). "Use of irreversible electroporation in unresectable pancreatic cancer," 4:211-215.
Narayanan, G. (2015). "Irreversible Electroporation," *Semin Interv Radiol.* 32:349-355.
Non-Final Office Action mailed on Oct. 19, 2020, for U.S. Appl. No. 15/766,604, filed Apr. 6, 2018, 16 pages.
O'Brien, T.J. et al. (2019). "Experimental High-Frequency Irreversible Electroporation Using a Single-Needle Delivery Approach for Nonthermal Pancreatic Ablation In Vivo," *J. Vasc. Interv. Radiol.* 30:854-862.
Partial Supplementary Search Report mailed on May 15, 2019, for EP Application No. 16 854 413.8, filed on Oct. 7, 2016, 13 pages.
Qaseem, A. et al. (2018). Hemoglobin $A_{1c}$ Targets for Glycemic Control With Pharmacologic Therapy for Nonpregnant Adults With Type 2 Diabetes Mellitus: A Guidance Statement Update From the American College of Physicians, Annals of Int. Med. 168:569-576.
Ringel-Scaia, V.M. et al. (2019). "High-frequency irreversible electroporation is an effective tumor ablation strategy that induces immunologic cell death and promotes systemic anti-tumor immunity," *EBioMedicine* 44:112-125.
Sami, S.S. et al. (2012). "The Los Angeles Classification of Gastroesophageal Reflux Disease," *Video J. Encycl. GI Endosc.* 1:103-104.
Siddiqui, I.A. et al. (2017). "High-Frequency Irreversible Electroporation: Safety and Efficacy of Next-Generation Irreversible Electroporation Adjacent to Critical Hepatic Structures," *Surg. Innov.* 24:276-283.
Theodorakis, M.J. et al. (2006). "Human duodenal enteroendocrine cells: source of both incretin peptides, GLP-1 and GIP," *Am. J. Physiol. Endocrinol. Metab.* 290:E550-E559.
Van Baar, A.C.G. et al. (2019). "Endoscopic duodenal mucosal resurfacing for the treatment of type 2 diabetes mellitus: one year results from the first international, open-label, prospective, multicentre study," Gut 69:295-303.
Verdam, F.J. et al. (2011). "Small Intestinal Alterations in Severely Obese Hyperglycemic Subjects," *J. Clin. Endocrinol. Metab.* 96:E379-E383.
Wagner, E.H. et al. (2001). "Effect of Improved Glycemic Control on Health Care Costs and Utilization," *JAMA* 285:182-189.
Written Opinion of the International Searching Authority mailed on Dec. 29, 2016, for PCT Application No. PCT/US2016/055966, filed on Oct. 7, 2016, 12 pages.

\* cited by examiner

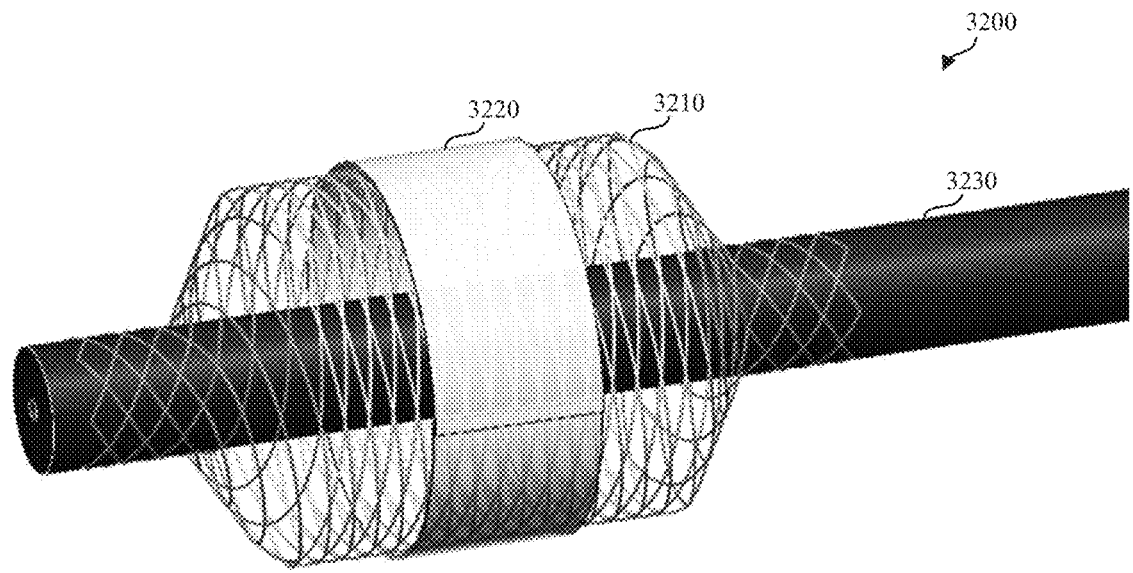
FIG. 32
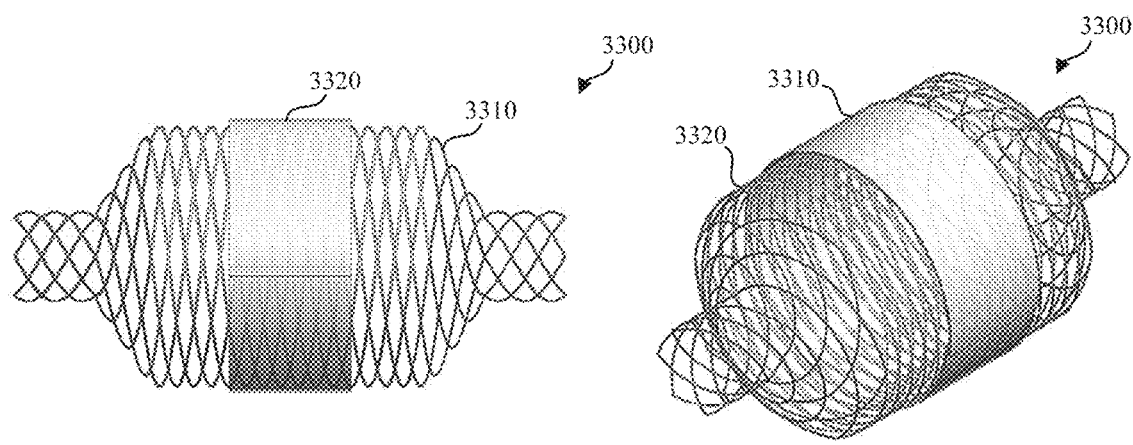
FIG. 33A
FIG. 33B

Four principle planes to inspect the fields above the electrode plane

DEVICES, SYSTEMS, AND METHODS FOR PULSED ELECTRIC FIELD TREATMENT OF THE DUODENUM

CROSS-REFERENCE TO RELATED APPLICATIONS

This application claims the benefit of U.S. Provisional Application No. 62/924,100, filed Oct. 21, 2019, and U.S. Provisional Application No. 63/029,275, filed May 22, 2020, the content of each of which is hereby incorporated by reference in its entirety.

TECHNICAL FIELD

Devices, systems, and methods herein relate to applying pulsed electric fields to tissue to treat a chronic disease, including but not limited to diabetes.

BACKGROUND

Diabetes is a widespread condition, affecting millions worldwide. In the United States alone, over 20 million people are estimated to have the condition. Diabetes accounts for hundreds of billions of dollars annually in direct and indirect medical costs. Depending on the type (Type 1, Type 2, and the like), diabetes may be associated with one or more symptoms such as fatigue, blurred vision, and unexplained weight loss, and may further be associated with one or more complications such as hypoglycemia, hyperglycemia, ketoacidosis, neuropathy, and nephropathy.

The treatment of chronic diseases such as obesity and diabetes through duodenal resurfacing has been proposed. For example, removing the majority of the mucosal cells from the section of the large intestine nearest the stomach may allow a rejuvenated mucosal layer to be regenerated, thereby restoring healthy (non-diabetic) signaling. Conventional treatments that apply thermal energy to the duodenum risk excessively heating and thus damaging more layers of the duodenum (e.g., muscularis) than desired, and/or must compensate for this excessive thermal heating. Conversely, conventional solutions may generate incomplete and/or uneven treatment. As such, additional systems, devices, and methods for treatment of duodenal tissue may be desirable.

SUMMARY

Described here are devices, systems, and methods for applying pulsed or modulated electric fields to tissue. These systems, devices, and methods may, for example, treat duodenal tissue of a patient to treat diabetes. Furthermore, the systems and devices may include temperature feedback and visualization of the procedure. In some variations, a device may comprise a first elongate body comprising a lumen, a second elongate body at least partially positioned within the lumen, and an expandable member rolled about the second elongate body. The expandable member may comprise an inner end coupled to the second elongate body, an outer end coupled to the first elongate body, and an electrode array.

In some variations, the expandable member may comprise a plurality of turns about the second elongate body. In some variations, a connector may couple the first elongate body to the outer end of the expandable member. In some variations, the second elongate body may be configured to rotate relative to the first elongate body to transition the expandable member between a rolled configuration and an unrolled configuration. In some of these variations, the expandable member may comprise a lumen of at least 10 mm in diameter in the unrolled configuration.

In some of these variations, a system comprising the device may further comprise a third elongate body disposed within the lumen of the expandable member. In some of these variations, the third elongate body may comprise an endoscope.

In some variations, the device may further comprise a distal dilator and a proximal dilator coupled to one of the first elongate body and the second elongate body. The expandable member may be disposed between the distal dilator and the proximal dilator.

In some variations, the device may further comprise one or more of a gear and friction roller coupled to the second elongate body. The expandable member may comprise a track configured to couple to the one or more of the gear and friction roller. In some of these variations, the track may comprise a plurality of spaced apart openings in the expandable member. In some variations, the expandable member may comprise one or more fluid openings. In some variations, the expandable member may comprise one or more fluid channels.

In some variations, a signal generator may be coupled to the electrode array. The signal generator may be configured to generate a pulsed or modulated electric field waveform comprising a frequency between about 250 kHz and about 950 kHz, a pulse width between about 0.5 µs and about 4 µs, a voltage applied by the electrode array of between about 100 V and about 2 kV, and a current density between about 0.6 A and about 100 A from the electrode array per square centimeter of tissue.

In some variations, the signal generator may be configured to inhibit delivery of the pulse waveform based on a temperature of the tissue. In some variations, the electrode array may be configured to generate a therapeutic electric field at a first tissue depth of about 1 mm and a non-therapeutic electric field at a second tissue depth of at least about 1.5 mm. In some variations, the expandable member may comprise a temperature sensor comprising a serpentine shape. In some variations, the expandable member may define one or more openings through the expandable member. In some variations, the electrode array may be configured to generate a therapeutic electric field that treats a predetermined set of cell types and not muscularis tissue. In some variations, the electrode array may be configured to generate a therapeutic electric field that treats cells but leaves intact tissue scaffolding.

Also described here are devices comprising an elongate body, and a plurality of elongate electrodes coupled to the elongate body. The plurality of elongate electrodes may comprise a ratio of a center-to-center distance between proximate electrodes to a width of the electrodes between about 2.3:1 and about 3.3:1. In some variations, the plurality of elongate electrodes comprise a center-to-center distance between proximate electrodes of less than about 5 mm.

In some variations, a signal generator may be coupled to the plurality of electrodes. The signal generator may be configured to generate a pulsed or modulated electric field waveform comprising a frequency between about 250 kHz and about 950 kHz, a pulse width between about 0.5 µs and about 4 µs, a voltage applied by the electrode array of between about 100 V and about 2 kV, and a current density between about 0.6 A and about 100 A from the electrode array per square centimeter of tissue.

In some variations, an expandable member may be coupled to the elongate body and comprise the plurality of electrodes. The expandable member may comprise a compressed configuration and an expanded configuration. In the expanded configuration, the expandable member may comprise a lumen. A second elongate body may be disposed within the lumen of the expandable member. The second elongate body may comprise an endoscope.

In some variations, a proximal portion and a distal portion of the expandable member may be transparent. In some variations, a second expandable member may be coupled to the elongate body. In some of these variations, the second expandable member may be inflatable.

In some variations, the plurality of elongate electrodes may comprise a first electrode and a second electrode in parallel to the first electrode. In some variations, the plurality of elongate electrodes may comprise a first electrode and a second electrode in an interdigitated configuration. In some variations, the center-to-center distance between proximate electrodes and the width of the plurality of elongate electrodes may be substantially equal. In some variations, the plurality of elongate electrodes comprise a center-to-center distance between proximate electrodes of less than about 5 mm.

In some variations, a tissue contact layer may be disposed over the elongate electrodes. The tissue contact layer may comprise a conductivity less than a conductivity of the elongate electrodes.

In some variations, the conductivity of the tissue contact layer may be between about 0.03 S/m and about 0.9 S/m. For example, the conductivity of the tissue contact layer may be between about 0.03 S/m and about 0.6 S/m or between about 0.03 S/m and about 0.3 S/m. In some variations, the tissue contact layer may comprise a thickness of between about 10% and about 20% of a width of the electrode. In some variations, at least one of the electrodes may comprise a semi-elliptical cross-sectional shape. In some variations, a ratio of a height of an electrode to a width of an electrode is between about 1:4 and about 1:8. In some variations, the proximate electrodes may be spaced apart by a weighted average distance of between about 0.3 mm and about 6 mm. In some variations, a hydrophilic layer may be disposed over the plurality of electrodes. In some variations, a conductive layer may be disposed over the plurality of electrodes. The conductive layer may comprise one or more of a polymer and conductive media comprising graphite, silver, metals, and the like. In some variations, the conductive layer may be a coating. In some variations, a surface area of the plurality of electrodes may comprise between about 20% and about 45% of a surface area of the expandable member in a predetermined configuration (e.g., expanded configuration).

In some variations, a fluid source may be in fluid communication with the expandable member. In some variations, one or more of the plurality of elongate electrodes may comprise a fluid opening. In some variations, one or more of the plurality of elongate electrodes may comprise one or more fluid channels. In some variations, a fluid source may be in fluid communication with the plurality of elongate electrodes.

In some variations, a system of the device may comprise a fluid source in fluid communication with one or more of the expandable member and the plurality of elongate electrodes. In some variations, one or more of the plurality of elongate electrodes may comprise the fluid opening. In some variations, one or more of the plurality of elongate electrodes may comprise one or more fluid channels. In some variations, the center-to-center distance between proximate electrodes of the plurality of elongate electrodes may be less than about 5 mm.

Also described herein are devices comprising an elongate body and an expandable member coupled to the elongate body. The expandable member may comprise a lumen and a plurality of elongate recesses formed by coupling an outer surface of the expandable member to an inner surface of the expandable member. A plurality of electrodes may be coupled to the expandable member.

In some variations, the expandable member may be concentrically coupled to the elongate body. In some variations, the elongate body may be coupled to a sidewall of the expandable member. In some variations, a second expandable member may be coupled to the elongate body and disposed distal to the expandable member. In some variations, at least a proximal end and a distal end of the second expandable member may be transparent. In some variations, a second elongate body may be disposed within a lumen of the expandable member. In some variations, the plurality of electrodes comprises a plurality of parallel elongate electrodes. In some variations, the plurality of electrodes may comprise a plurality of interdigitated electrodes.

In some variations, a system may comprise an elongate body and an expandable member coupled to the elongate body. The elongate body comprises a lumen, a compressed configuration, and an expanded configuration. The expandable member comprises an electrode array. The lumen of the expandable member may be configured to releasably couple to a visualization device. In some variations, the lumen defines a central longitudinal axis of the expandable member. In some variations, the expandable member may comprise the fluid opening. In some variations, the expandable member may comprise one or more fluid channels.

Also described herein are systems comprising an elongate body, an expandable member coupled to the elongate body comprising a compressed configuration and an expanded configuration. The expandable member may further comprise an electrode array comprising a plurality of electrodes, and a signal generator coupled to the electrode array. The signal generator may be configured to deliver a pulsed or modulated electric field waveform to the electrode array to generate a therapeutic electric field at a first tissue depth of about 1 mm and a non-therapeutic electric field at a second tissue depth of at least about 1.5 mm.

Also described herein are systems comprising an elongate body and an expandable member coupled to the elongate body and comprising a lumen, a compressed configuration, and an expanded configuration. The expandable member may comprise an electrode array. The lumen of the expandable member may be configured to releasably receive a visualization device.

In some variations, the lumen may define a central longitudinal axis of the expandable member. In some variations, the expandable member may comprise one or more openings extending through the expandable member. In some variations, the visualization device may be configured to suction tissue through the one or more openings at a pressure between about 10 mmHg and about 200 mmHg.

Also described herein are systems comprising an elongate body and an expandable member coupled to the elongate body and comprising a lumen, a compressed configuration, and an expanded configuration. The expandable member may comprise an electrode array. A visualization device may be configured to releasably couple to a lumen of the expandable member. In some variations, the visualization device comprises a suction lumen. In some variations, the visualization device comprises an irrigation lumen.

Also described here are methods of treating diabetes comprising advancing a pulsed electric field device into a duodenum of a patient. The pulsed electric field device may comprise an elongate body and an expandable member coupled to the elongate body. The expandable member may comprise an electrode array. A pulsed waveform may be delivered to the electrode array to generate a pulsed or modulated electric field thereby treating the duodenum.

In some variations, the electrode array may comprise a plurality of spaced apart electrodes forming parallel lines and/or an interdigitated configuration. In some of these variations, proximate parallel lines of the electrode array may be configured with alternating polarity. In some variations, the plurality of electrodes may comprise a plurality of interdigitated electrodes. In some variations, the pulsed or modulated electric field may spatially vary up to about 20% at a predetermined treatment distance from the electrode array.

In some variations, the expandable member may comprise a lumen therethrough and the method may further comprise advancing an endoscope through the lumen of the expandable member. In some variations, the endoscope may be retracted to view duodenal tissue proximal of the expandable member. In some variations, each of the plurality of electrodes may be an elongate electrode. In some variations, each of the plurality of electrodes may be a hemi-elliptical electrode. In some variations, a temperature at the expandable member during delivery of the pulsed waveform may be measured. In some variations, delivery of the pulse waveform may be inhibited based on the measured temperature. In some variations, the pulsed or modulated electric field may be a therapeutic electric field at a first tissue depth of about 1 mm and a non-therapeutic electric field at a second tissue depth of at least about 1.5 mm. In some variations, tissue may be suctioned to the expandable member at a pressure between about 10 mmHg and about 200 mmHg. In some variations, fluid may be output between the pulsed electric field device and the duodenum from the expandable member.

Also described here are methods of treating diabetes comprising advancing a pulsed electric field device toward a first portion of a duodenum of a patient. The pulsed electric field device may comprise an expandable member comprising an electrode array. The expandable member may be transitioned into an expanded configuration. A first pulse waveform may be delivered to the electrode array to generate a first pulsed or modulated electric field thereby treating the first portion. The pulsed electric field device may be advanced toward a second portion of the duodenum. A second pulse waveform may be delivered to the electrode array to generate a second pulsed electric field thereby treating the second portion.

In some variations, the expandable member may comprise a temperature sensor. A temperature of the tissue may be measured using the temperature sensor. Pulse waveform delivery may be modulated (e.g., inhibited) based on one or more of the measured temperature and a rate of temperature change. In some variations, the expandable member may be unrolled to transition the expandable member into the expanded configuration. In some variations, the expandable member may comprise a lumen having a first diameter in the compressed configuration and a second diameter in the expanded configuration. The second diameter may be larger than the first diameter. A third elongate body may be advanced through the lumen in the expanded configuration.

In some variations, the expandable member may comprise a second expandable member disposed distal to the expandable member. The second expandable member may be inflated. In some variations, unrolling the expandable member comprises unrolling one or more turns of the expandable member. In some variations, the first and second pulse waveforms comprise a frequency between about 250 kHz and about 950 kHz, a pulse width between about 0.5 µs and about 4 µs, a voltage applied by the electrode array of between about 100 V and about 2 kV, and a current density between about 0.6 A and about 100 A or between about 0.6 A and about 65 A from the electrode array per square centimeter of tissue. For example, the current density may be between about 0.6 A and about 13 A from the electrode array per square centimeter of tissue. In some variations, fluid may be output between the pulsed electric field device and the duodenum from the expandable member.

In some variations, one or more of the first pulsed or modulated electric field and second pulsed or modulated electric field may be a therapeutic electric field at a first tissue depth of about 1 mm and a non-therapeutic electric field at a second tissue depth of at least about 1.5 mm.

In some variations, tissue may be suctioned to the expandable member during one or more of the delivery of the first pulse waveform and the second pulsed waveform.

Also described here are methods of treating diabetes comprising advancing a pulsed electric field device into a duodenum of a patient. The pulsed electric field device may comprise a first elongate body, a second elongate body positioned within the first elongate body, and an expandable member rolled about the second elongate body. The expandable member may comprise an electrode array. The second elongate body may rotate relative to the first elongate body to unroll the expandable member and contact duodenal tissue with the electrode array. A pulse waveform may be delivered to the electrode array to generate a pulsed or modulated electric field thereby treating the duodenal tissue.

In some variations, a visualization device may be advanced through a lumen of the unrolled expandable member. In some variations, rotating the first elongate body unrolls one or more turns of the expandable member. In some variations, the expandable member comprises a temperature sensor, and further comprises measuring a temperature of the tissue using the temperature sensor. Pulse waveform delivery may be modulated based on the measured temperature.

In some variations, rotating the first elongate body may transition the expandable member into the expanded configuration. In some variations, the expandable member may comprise a lumen having a first diameter in the compressed configuration and a second diameter in the expanded configuration. The second diameter may be larger than the first diameter. A third elongate body may be advanced through the lumen in the expanded configuration. In some variations, the expandable member may comprise a second expandable member disposed distal to the expandable member. The second expandable member may be inflated. In some variations, the pulse waveform may comprise a frequency between about 250 kHz and about 950 kHz, a pulse width between about 0.5 µs and about 4 µs, a voltage applied by the electrode array of between about 100 V and about 2 kV, and a current density between about 0.6 A and about 100 A or between about 0.6 A and about 65 A from the electrode array per square centimeter of tissue. For example, the current density may be between about 0.6 A and about 13 A from the electrode array per square centimeter of tissue. In some variations, fluid may be output between the pulsed electric field device and the duodenum from the expandable member.

In some variations, the pulsed or modulated electric field may be a therapeutic electric field at a first tissue depth of about 1 mm and a non-therapeutic electric field at a second tissue depth of at least about 1.5 mm. In some variations, tissue may be suctioned to the expandable member during delivery of the pulse waveform.

Also described are methods of treating diabetes comprising advancing a pulsed electric field device to a distal portion of a duodenum of a patient. The pulsed electric field device may comprise an expandable member. The expandable member may comprise an electrode array and a temperature sensor. The expandable member may transition into an expanded configuration. A first pulse waveform may be delivered to the electrode array to generate a first pulsed or modulated electric field thereby treating the distal portion. A visual marker may be generated on the distal portion using a temperature sensor. The pulsed electric field device may be retracted to a portion of the duodenum proximal to the distal portion based on a position of the visual marker. A second pulse waveform may be delivered to the electrode array to generate a second pulsed or modulated electric field thereby treating the second portion.

In some variations, fluid may be output between the pulsed electric field device and the duodenum from the expandable member. In some variations, the visual marker may comprise one or more vertices. In some variations, a visual marker may be generated on the duodenum by increasing a temperature of mucosa tissue to about 49° C. for less than about 2.5 seconds. In some variations, the visual marker may be configured to visually fade after about one day.

Also described are devices comprising an elongate body and an expandable member coupled to the elongate body. The expandable member may be configured to transition to an expanded configuration. An electrode array may be coupled to the expandable member. The electrode array may comprise a substrate, a first elongate electrode, and a second elongate electrode parallel to and spaced apart from the first elongate electrode. In some variations, the first and second elongate electrodes may comprise an interdigitated configuration. A first tissue temperature sensor may be disposed on the substrate between the first and second elongate electrodes.

In some variations, the first sensor may comprise a temperature resolution of less than about 0.5° C. In some variations, the first sensor may comprise a thermal diffusion time constant of less than about 5 milliseconds.

In some variations, a second temperature sensor may be configured to generate a visual marker on tissue. In some of these variations, the second sensor may be disposed on the substrate along a perimeter of the first and second elongate electrodes. The second sensor may comprise a spiral or serpentine shape.

In some variations, the first sensor may comprise an insulator configured to sustain without dielectric breakdown a pulse waveform configured to generate a pulsed or modulated electric field for treating tissue. In some variations, the insulator may comprise a thickness of at least about 0.02 mm. In some variations, the first sensor may comprise a width of up to about 0.07 mm and a length of at least about 2 cm. In some variations, a distance between the first sensor and either the first or second elongate electrode may be at least about 0.2 mm. In some variations, the first sensor may extend substantially parallel to the first and second elongate electrodes. In some variations, the expandable member may comprise the fluid opening. In some variations, the expandable member may comprise one or more fluid channels.

Also described herein are methods of treating diabetes comprising advancing a pulsed electric field device into a duodenum of a patient. The pulsed electric field device may comprise an expandable member. The expandable member may comprise an electrode array and a temperature sensor. The expandable member may be transitioned into an expanded configuration. A pulse waveform may be delivered to the electrode array to generate a pulsed or modulated electric field thereby treating the duodenum. A temperature of duodenal tissue may be measured using a temperature sensor. In some variations, the fiducial generator is the temperature sensor. In some variations, a visual marker may be generated on the duodenal tissue using a fiducial generator. In some variations, the visual marker may be visualized. A treatment area may be identified based on the visual marker. In some variations, fluid may be output between the pulsed or modulated electric field device and the duodenum from the expandable member. In some variations, the pulsed or modulated electric field may be a therapeutic electric field at a first tissue depth of about 1 mm and a non-therapeutic electric field at a second tissue depth of at least about 1.5 mm. In some variations, tissue may be suctioned to the expandable member during the delivery of the pulse waveform.

Also described are systems comprising an elongate body, an expandable member coupled to the elongate body comprising a compressed configuration and an expanded configuration. The expandable member may further comprise an electrode array comprising a plurality of electrodes. A signal generator may be coupled to the electrode array. The signal generator may be configured to deliver a pulsed or modulated electric field waveform to the electrode array to generate an electric field that spatially varies up to about 20% at a predetermined treatment distance from the electrode array. In some variations, the electrode array may comprise a plurality of electrodes comprising a ratio of a center-to-center distance between proximate electrodes to a width of the electrodes between about 2.3:1 and about 3.3:1. In some variations, the plurality of elongate electrodes comprise a center-to-center distance between proximate electrodes of less than about 5 mm. In some variations, a surface area of the plurality of electrodes comprises between about 4% and about 100% of a circumference of a duodenum. In some variations, a fluid source may be in fluid communication with the electrode array. In some variations, one or more of the plurality of electrodes may comprise the fluid opening. In some variations, one or more of the plurality of electrodes may comprise a fluid channel in fluid communication with the fluid opening. In some variations, the system may be configured to generate a therapeutic electric field at a first tissue depth of about 1 mm and a non-therapeutic electric field at a second tissue depth of at least about 1.5 mm.

Also described are devices comprising an elongate body and an electrode array coupled to the elongate body. The electrode array may comprise a plurality of electrodes and a fluid opening. In some variations, one or more of the plurality of electrodes comprises a fluid channel. In some variations, one or more of the plurality of electrodes comprises the fluid opening. In some of these variations, the fluid opening is disposed at an apex of one or more of the plurality of electrodes.

In some variations, the electrode array may comprise a substrate comprising a fluid opening. In some of these variations, the substrate may comprise one or more fluid channels. In some variations, a fluid source may be in fluid communication with the electrode array. In some variations, the expandable member may comprise a fluid opening. In some variations, the expandable member may comprise one or more fluid channels. In some variations, fluid may be output between the pulsed electric field device and the duodenum from the expandable member. In some variations, the plurality of elongate electrodes may comprise a center-to-center distance between proximate electrodes of less than about 5 mm. In some variations, the visual marker may be visualized. A treatment area may be identified based on the visual marker.

In some variations, a signal generator may be coupled to the electrode array, the signal generator configured to generate a pulse waveform comprising a frequency of about 500 kHz, a pulse width from about 0.5 μs to about 4 μs, a voltage applied by the electrode array of about 2500 V, and a current density from about 0.6 A to about 100 A from the electrode array per square centimeter of tissue. In some variations, a ratio of depth of the pulsed or modulated electric field to a depth of duodenal tissue treated may be between about 0.3 and about 0.5. In some variations, a ratio of dilated to undilated mucosa tissue of the duodenum may be between about 0.40 and about 0.60, and a ratio of dilated to undilated submucosa tissue of the duodenum may be between about 0.15 and about 0.35. In some variations, the expandable member may comprise one or more openings between proximate electrodes. In some variations, the one or more openings may be configured for one or more of fluid egress, fluid suction, and tissue suction. In some variations, the treated duodenum may be histologically indistinguishable from native tissue after about 30 days. In some variations, the pulsed or modulated electric field may be substantially uniform at a predetermined tissue treatment depth of from about 0.5 mm to about 1.5 mm.

In some variations, the signal generator may be configured to inhibit delivery of the pulse waveform based on a temperature. In some variations, the signal generator may be configured to resume delivery of the pulse waveform based on one or more of a predetermined time period and temperature. In some variations, the temperature may be a change in temperature of up to about 6° C. In some variations, the tissue temperature may be about 43° C. In some variations, the predetermined time period may be up to about 60 seconds. In some variations, the electrode array may comprise a height of between about 0.003 in and about 0.015 in, a distance between adjacent electrodes of between about 1.0 mm and about 1.4 mm, and a pad width of between about 0.5 mm and about 0.7 mm. In some variations, the electrode array may comprise a bipolar configuration. In some variations, electrodes of the electrode array may be spaced apart between about 0.5 mm and about 2 mm. In some variations, the pulse waveform may comprise a voltage between about 450 V and about 700 V. In some variations, the device may be configured to generate a therapeutic electric field at a first tissue depth of about 1 mm and a non-therapeutic electric field at a second tissue depth of at least about 1.5 mm. In some variations, the expandable member may comprise a temperature sensor comprising a serpentine shape. In some variations, the expandable member may comprise a temperature sensor disposed generally perpendicular to the electrode array. In some variations, the fiducial generator may be configured to generate visual marker on tissue comprising one or more vertices. In some variations, the fiducial generator may be configured to generate a visual marker on tissue comprising a polygonal shape. In some variations, the fiducial generator may be configured to generate a visual marker on tissue comprising a length of at least about 1 mm. In some variations, the fiducial generator may be configured to increase a temperature of mucosa tissue to about 49° C. for less than about 2.5 seconds. In some variations, the fiducial generator may be configured to generate a visual marker on tissue configured to visually fade after about one day. In some variations, the fiducial generator may be configured to generate a visual marker on tissue comprising a depth of about 0.25 mm. In some variations, one or more of the openings of the expandable member may be configured to receive suction at a pressure between about 10 mmHg and about 200 mmHg. In some variations, one or more of the openings of the expandable member may be configured to suction tissue through the one or more of the openings. In some variations, a set of twisted pair lead wires may be coupled to the electrode array.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 32 is a perspective view of an illustrative variation of a pulsed electric field device.

FIG. 33A is a side view of an illustrative variation of a pulsed electric field device. FIG. 33B is a perspective view of the pulsed electric field device shown in FIG. 33A.

DETAILED DESCRIPTION

Described here are devices, systems, and methods for treating tissue to address a chronic disease. For example, devices, systems, and methods may include those for treating diabetes by treating duodenal tissue of a patient. In some variations, treatment of the duodenum may comprise treating at least about 30% of the mucosal lining of the duodenum with minimal trauma, damage or scarring to the submucosa, vasculature, and muscles. For example, a mucosa layer of the duodenum may be treated using a pulsed electric field (PEF) system.

Figure 1A:
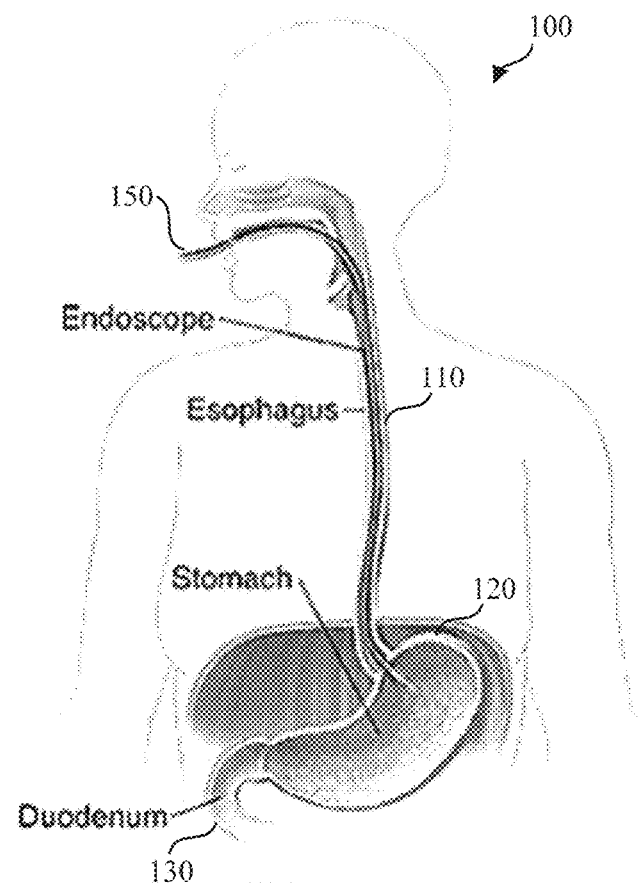
FIG. 1A is a cross-sectional representation of a gastrointestinal tract showing various anatomical structures.
Figure 1B:
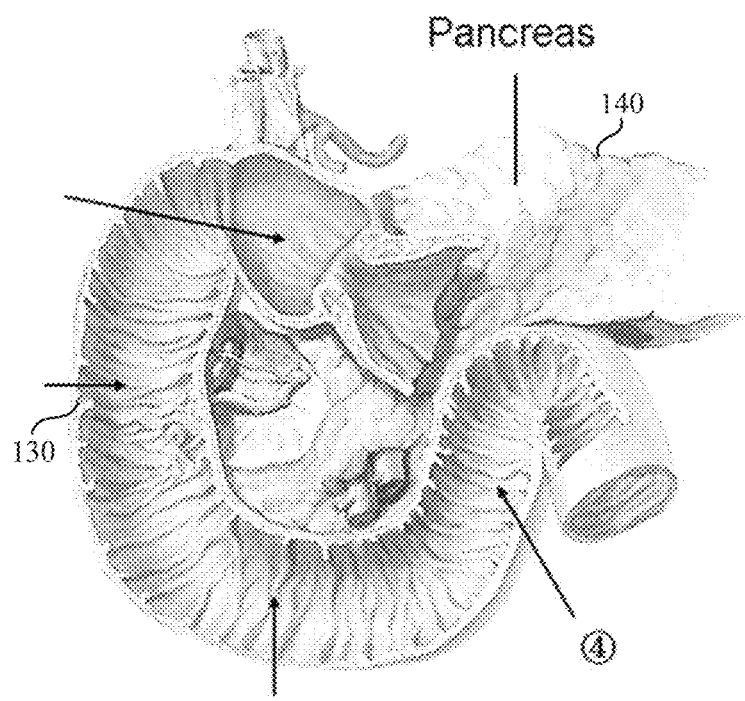
FIG. 1B is a cross-sectional representation of a duodenum.
Figure 2A:
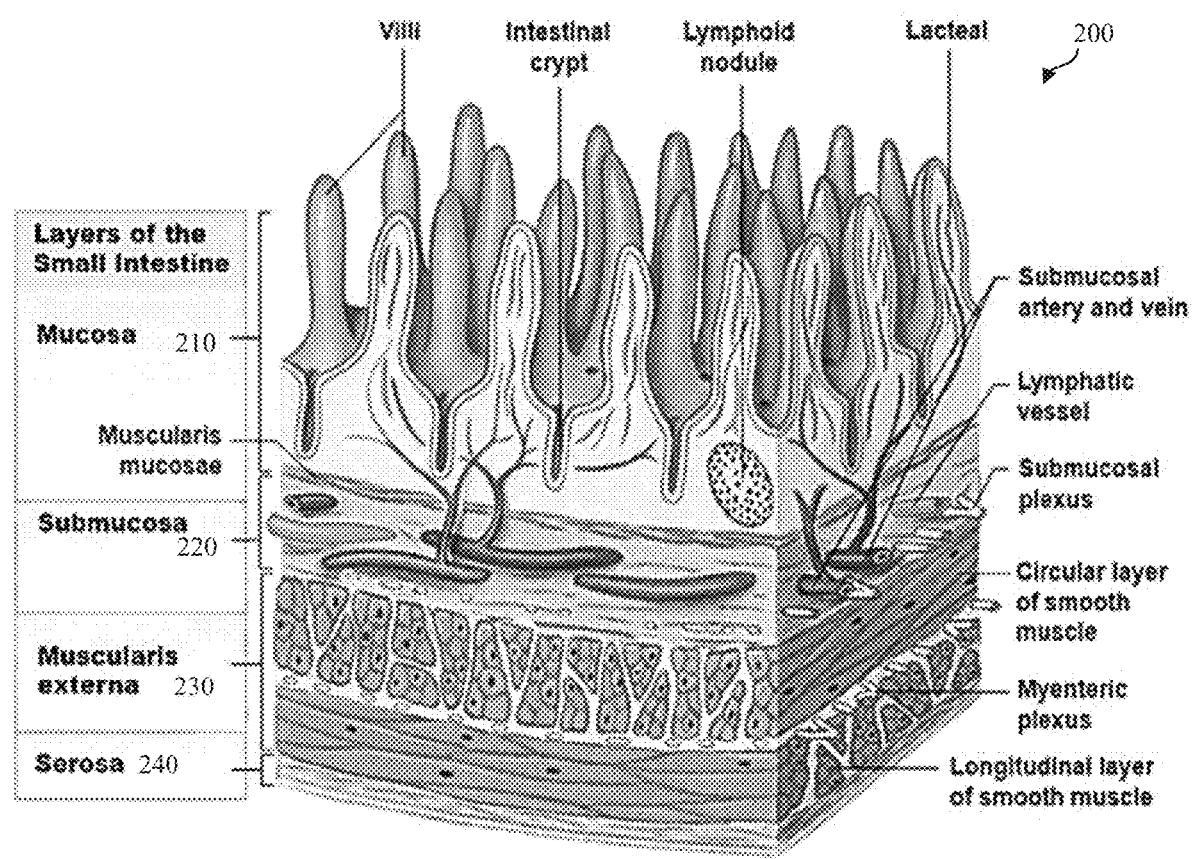
FIGS. 2A-2C are cross-sectional schematic views of a portion of the small intestine.
Figure 2B:
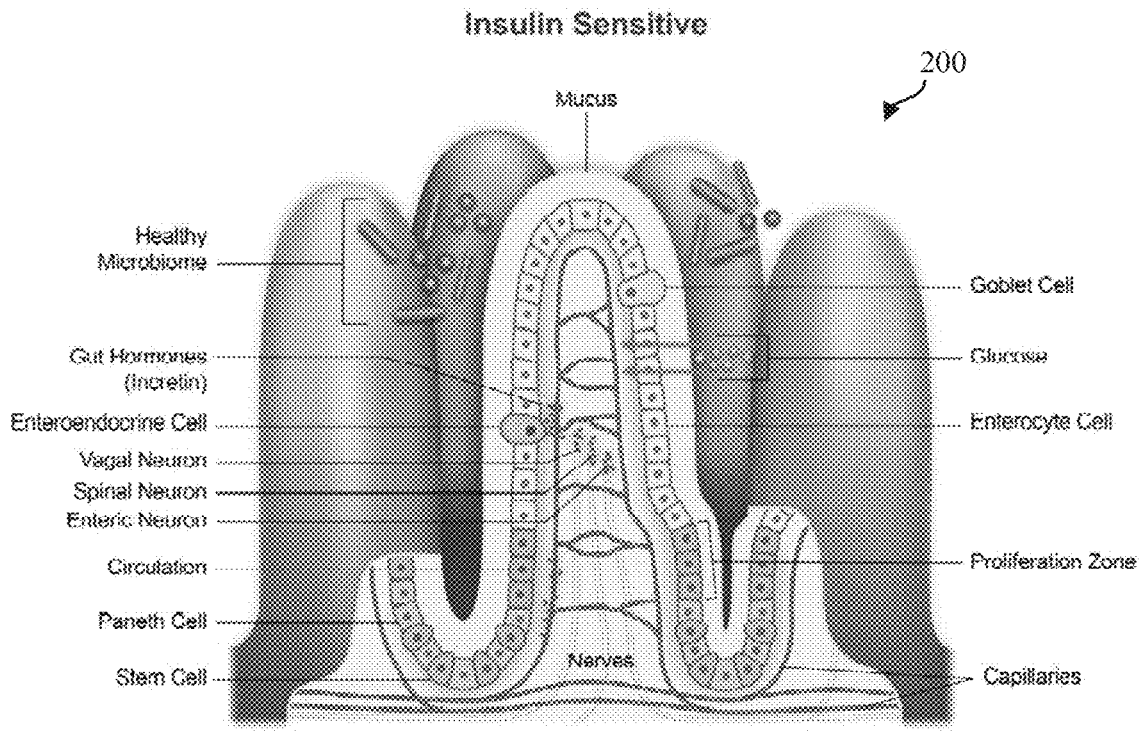
Figure 2C:
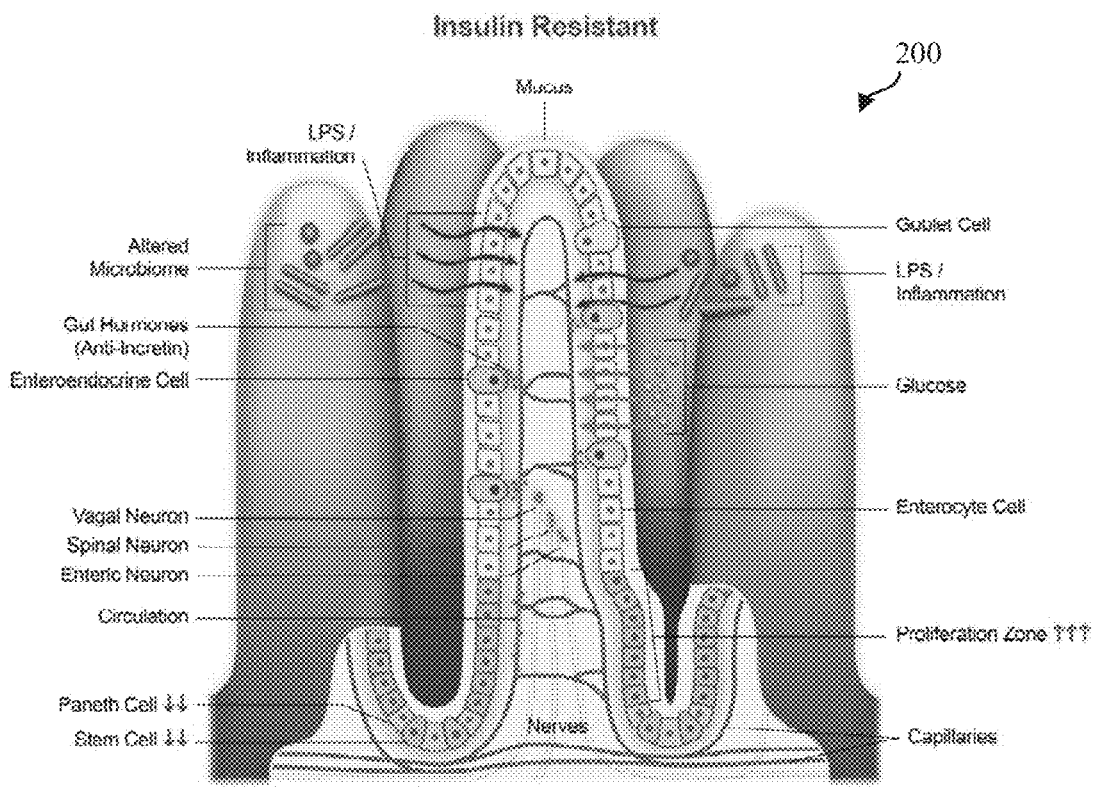

It may be helpful to briefly identify and describe the relevant small intestine anatomy. FIG. 1A is a cross-sectional view of the gastrointestinal tract of a patient (100). Shown there is a visualization device (150) (e.g., endoscope) advanced into the stomach (120) through the esophagus (110). The stomach (120) is connected to the duodenum (130). FIG. 1B is a detailed cross-sectional view of the duodenum (130), which surrounds the head of the pancreas (140). The duodenum is a "C" shaped hollow jointed tube structure that is typically between about 20 cm and about 35 cm in length and about 20 mm and about 45 mm in diameter. FIGS. 2A-2C are cross-sectional schematic views of the layers of the small intestine (200) including the mucosa (210), submucosa (220), muscularis externa (230), and serosa (240). Treatment of the duodenum may comprise resurfacing the mucosa (210) as described herein. Access to the duodenum may be performed by advancing the systems and devices described herein through one or more of the esophagus, stomach, pylorus, lower esophageal junction, crackle pharyngeal junction, and several acute small radius bends throughout the length of the digestive tract.

It may further be helpful to briefly discuss electroporation and the role of ohmic heating. Electroporation is the application of an electric field to living cells to cause ions of opposite charge to accumulate on opposite sides of cell membranes. Generally, electroporation requires a potential difference across the cell membrane on the order of about 0.5 to about 1 volt and for a cumulative duration on the order of about 1 to about 2 milliseconds. Electroporation necessarily generates ohmic heating but there is considerable confusion in the literature about this, including a significant number of references that incorrectly assert the existence of non-thermal electroporation. For example, an external uniform electric field of magnitude E applied to an intracellular fluid with ionic conductivity $\sigma_{ic}$ will generate a current density $\Sigma\sigma_{ic}$ and dissipate a thermal power density $E^2\sigma_{ic}$. If the medium has a heat capacity $C_p$ and density $\rho$, the resulting rate of temperature rise is given by equation (1):

$$\frac{dT}{dt} = \frac{E^2 \sigma_{ic}}{C_p \rho} \qquad \text{eqn. (1)}$$

For example, a 1 KV/cm electric field acting on tissue with a conductivity of about 0.3 S/m, a heat capacity of about 3.7 joule/(gm° C.), and a density of about 1 gm/cc will heat the tissue at a rate of about 800° C./second. Note that, without current passing through the tissue, there is no electric field in the tissue since the tissue is an ionic conductor. The initial time after an external field is abruptly applied to the membrane to accumulate charge may be on the order of about 30 nanoseconds, which suggests that, during an initial membrane-charging phase, the average temperature rise may be in the tens of microdegrees. When an external electric field is applied, and ionic currents have charged the membrane surfaces to collapse the field into the lipid bilayers, leakage current may still flow, though the heating may be confined to the membranes for sub-microsecond timescales. For example, using a lipid layer conductivity of $\sigma_{11}=0.002$ S/m, a 1 volt potential across an 8 nm layer may locally heat at an instantaneous rate of about 8° C./microsecond. This heating rate drops with time from the application of the external electric field, as the heat may diffuse further from the membrane.

If the ionic currents are confined to pores in the cell membranes, current crowding will cause the heating rate in the pores to be correspondingly higher. Since the pore area might be 1% or less of the membrane area, the current density in the pores may be one hundred times higher than in the bulk tissue. This gives a ten thousand times increase in heating rate, leading to local heating rates on the order of 10° C./microsecond.

Local temperature rise is a contributing mechanism to the transition from electroporation to irreversible electroporation. Thermal diffusion lowers the local temperature excursions. For example, assuming a tissue thermal diffusivity $\kappa$ of 0.13 mm$^2$/s, the thermal diffusion length at 10 μsec is $\sqrt{(10\mu s)(0.13 mm^2/s)}$ or 1.1 micron, which is much larger than a typical pore. At 1 millisecond, the thermal diffusion length is on the order of the cell size, so the localized heating effects may be ignored.

The bulk tissue remains a good ionic conductor during the electroporation treatment, heating at a rate on an order of magnitude of about 800° C./s while the external field is being applied. If the external field is removed, the cell membranes may discharge on the order of about 30 nanoseconds, obliging the continued application of external voltage and current to induce pore formation and growth. As the maximum tolerable temperature rise of the bulk tissue may be on the order of about 13° C., the maximum duration that the external field may be applied, even in a bipolar configuration, may be within an order of magnitude of about 10 milliseconds. As this heat is generated to a treatment depth in the tissue of about several millimeters, the required time to cool the tissue by conduction may be about 70 seconds (e.g., (3 mm$^2$)/(0.13 mm$^2$/sec)). Blood convection likely dominates the observed cooling times that are on the order of about 10 seconds. Electroporation may also increase with the temperature of the bulk tissue due to the phase transition of the lipid cell membrane, which for some cells on the duodenum is 41° C. The phase transition temperature may be the temperature required to induce a change in the lipid physical state from the ordered gel phase to the liquid crystalline phase.

Figure 3A:
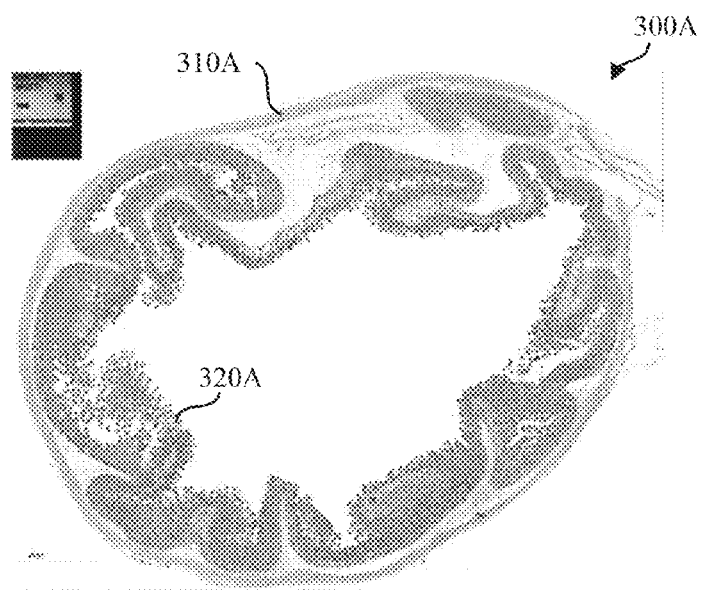
FIG. 3A is a cross-sectional image of a duodenum.

Electroporation parameters may be varied to produce different effects on tissue. FIG. 3A is a cross-sectional image of an untreated duodenum (300A) including a muscular layer (310A) and villi (320A). FIG. 3D is an image of an illustrative variation of duodenal tissue in its native untreated state including a muscularis layer (310D), submucosa (330D), villus crypts (340D) and villi (320D). As described in more detail herein, FIG. 3E depict duodenal tissue that has undergone majority thermal heat treatment and FIG. 3F depict duodenal tissue that has undergone majority pulsed or modulated electric field treatment. The treatments described herein (e.g., FIG. 3F) that primarily treat the mucosa layer with preserved tissue architecture appearing similar to the native tissue reduces trauma to tissue relative to the thermal treatment shown in FIG. 3E.

The application of a pulsed electric field to duodenal tissue results in non-thermal tissue changes. For example, FIG. 3D is an image of normal untreated (e.g., native tissue) porcine duodenal mucosa. FIG. 3F is an image of the initial mucosal histologic appearance with evolving epithelial loss and lamina propria structural/architectural preservation. For example, FIG. 3F depicts the histologic evolution with complete native epithelial loss and early crypt regeneration within the preserved lamina propria. The glandular layer across FIGS. 3A-3D and 3F demonstrates the structural preservation of the lamina propria following treatment. For example, histopathology confirms that the PEF treatment as described herein applied at a depth of about 1 mm in duodenal tissue will treat the mucosal layer without the pulsed electric field energy affecting the muscularous propria at a therapeutic level.

In some variations, a pulsed electric field (PEF) treatment may be combined with localized thermal treatment. For example, thermal treatment may be applied to surface tissue or near-surface tissue while PEF treatment may be applied to relatively deeper tissue. As described in more detail herein, the depth of tissue treatment received by one or more layers may be adjusted based on one or more of electrode design, applied voltage, time or duration of energy delivery, frequency of applied energy, and tissue configuration. An example of such control is thermal treatment applied up to a tissue depth of about 0.1 mm and a PEF treatment applied to a tissue depth of up to about 1 mm. The ratio and depth of thermal treatment to PEF treatment may be based on a desired clinical outcome (e.g., effect). In some variations, thermal treatment may be applied up to a tissue depth of about 3 mm, and PEF treatment may be applied up to a tissue depth of about 5 mm. Therefore, in some variations, more thermal treatment than PEF treatment may be applied to tissue. Based on a depth or type of tissue, different healing cascades may be optimal. In some variations, the villas mucosa at up to about 1 mm may be thermally treated to allow substantially the entire tissue architecture to be replaced, while the submucosa may be PEF treated to preserve the tissue architecture and promote rapid healing of that layer. Furthermore, neither the thermal treatment nor PEF treatment may affect the deeper muscularis propria layer.

Figure 3B:
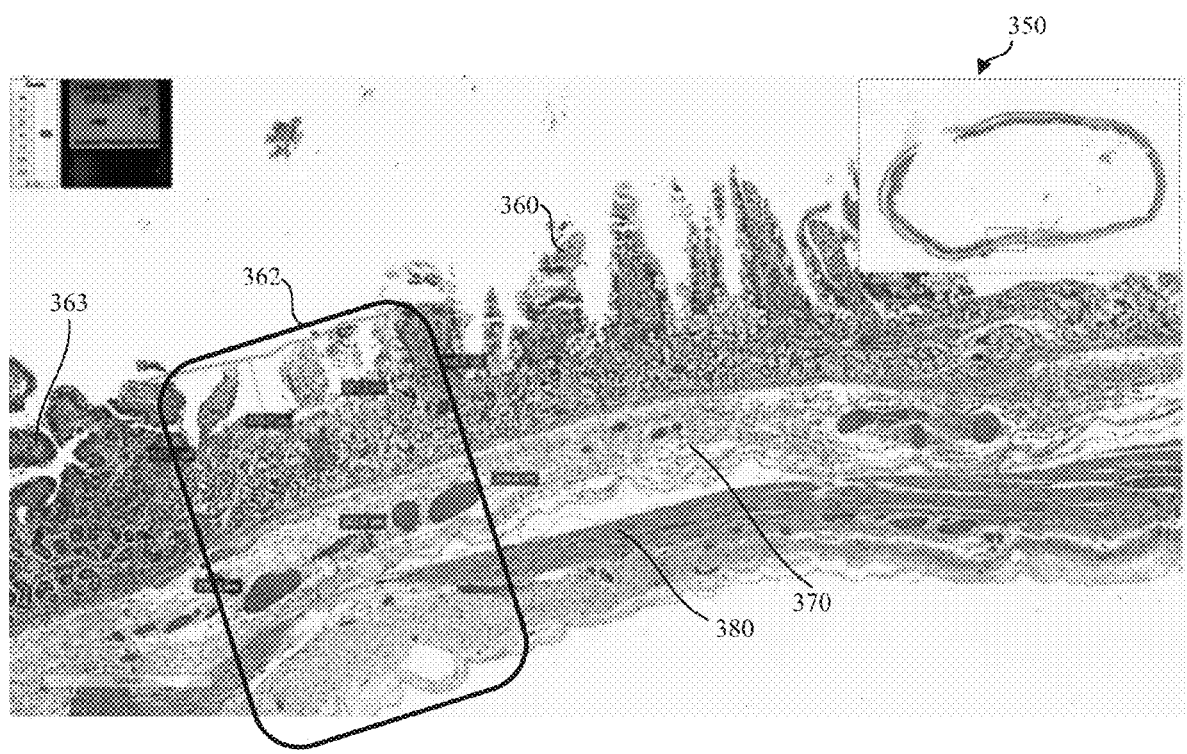
FIGS. 3B-3F are detailed cross-sectional images of various duodenal tissue.

FIG. 3B is an image of an illustrative variation of duodenal tissue that has undergone different treatments. In particular, the tissue (360) was treated with pulsed or modulated electric field energy and first mucosa region (362) was further subjected to radiofrequency energy. The ablated villi of the first mucosa region (362) have broken cellular membranes and destroyed cell structures such that those cells are no longer viable or functioning. By contrast, a second mucosa region (360) has cells that have undergone cell lysis where the cellular membranes remain intact but the cells are no longer viable and functioning. That is, cell lysis corresponds to functional cell death with intact cellular structures while ablation refers to loss of both cell structure and function. The submucosa (370) and muscularis (380) remain healthy (e.g., viable and fully functioning with cell integrity). In FIG. 3B, villi in the first mucosa region (362) are thermally ablated while the cell lysis in the second mucosa region (360) is generated by a pulsed or modulated electric field. A third mucosa region (363) adjacent to the thermal lesion of the first mucosa region (362) is not treated at all and comprises viable tissue.

Figure 3C:
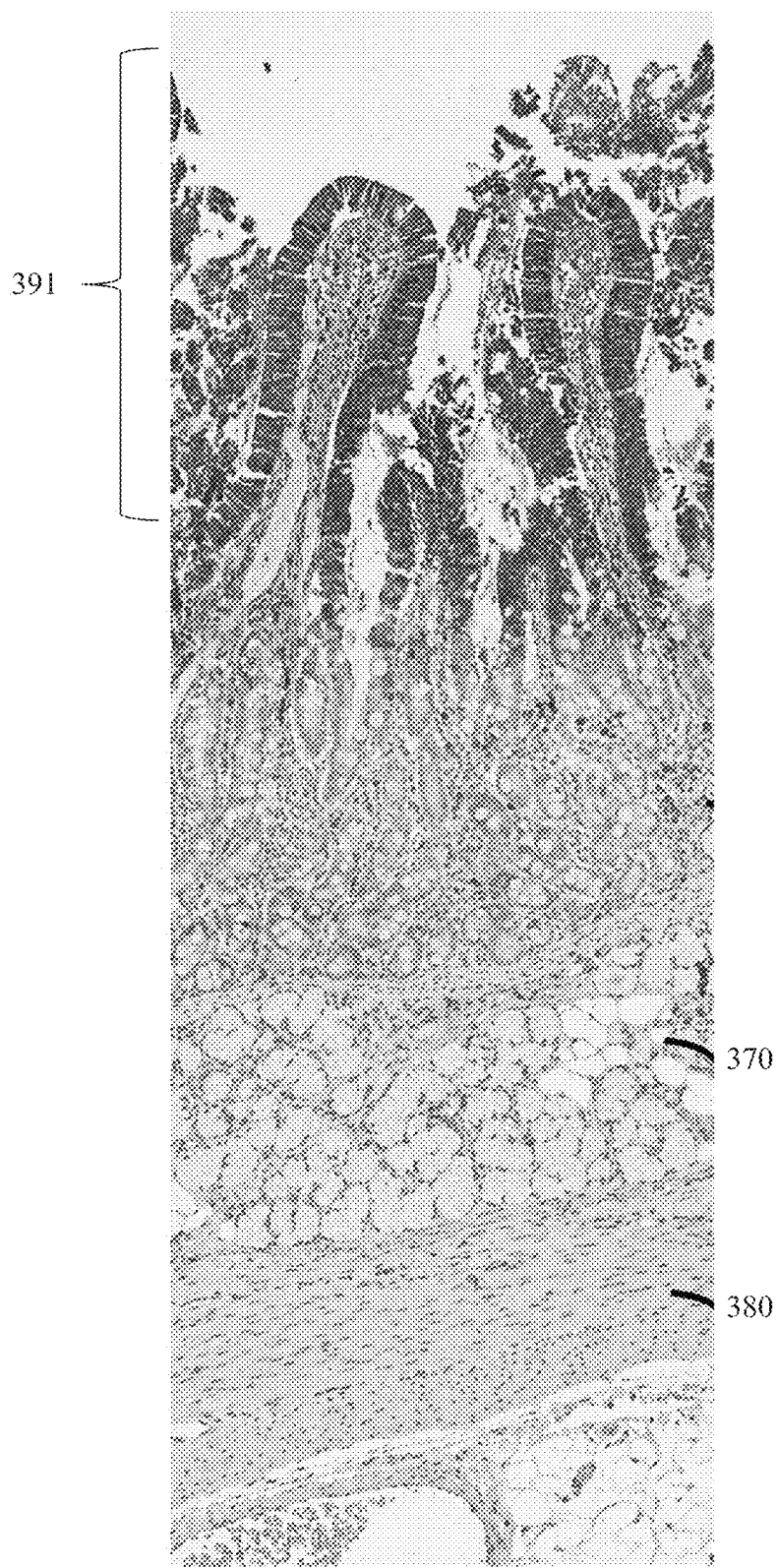
Figure 3D:
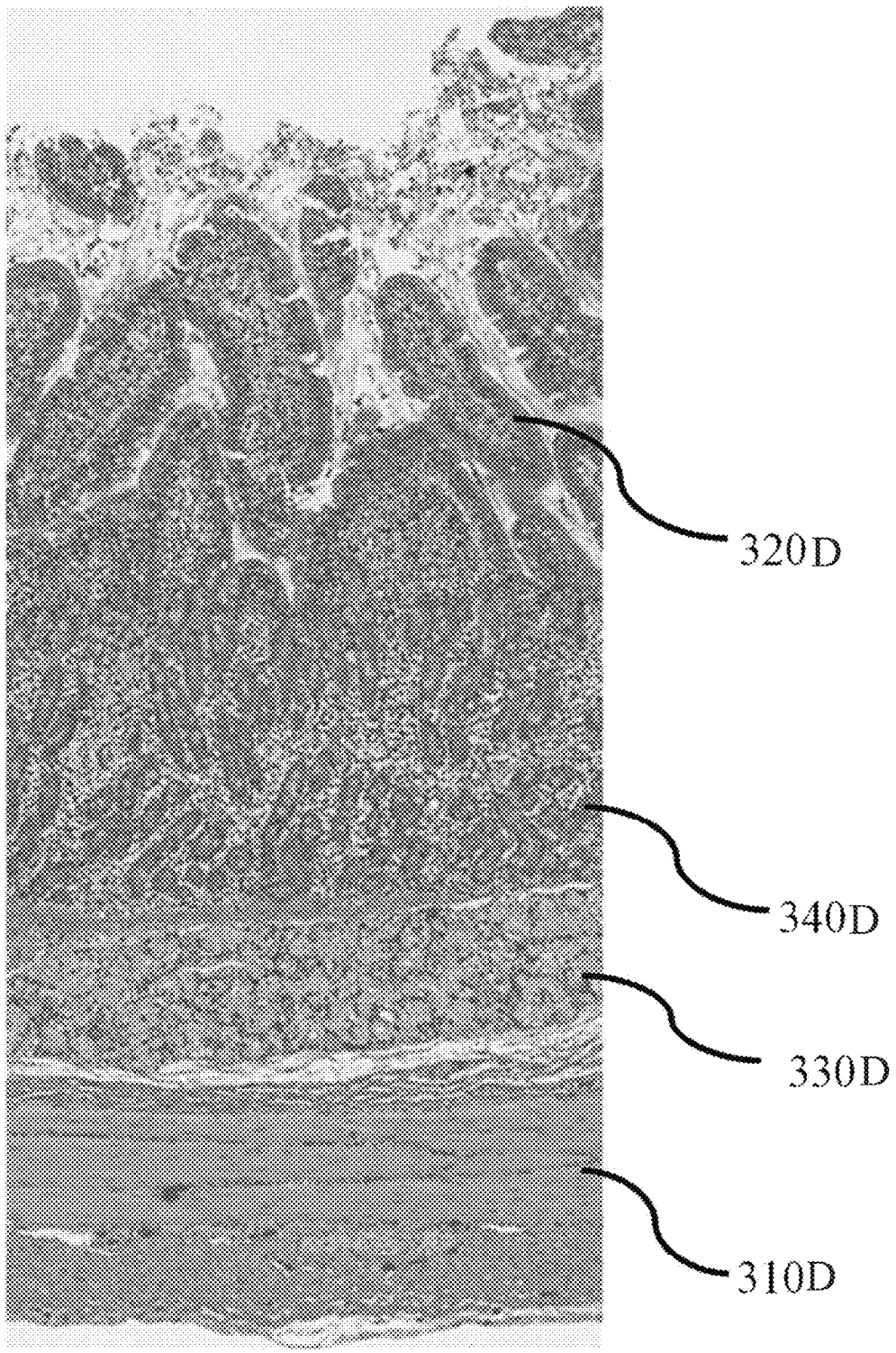
Figure 3E:
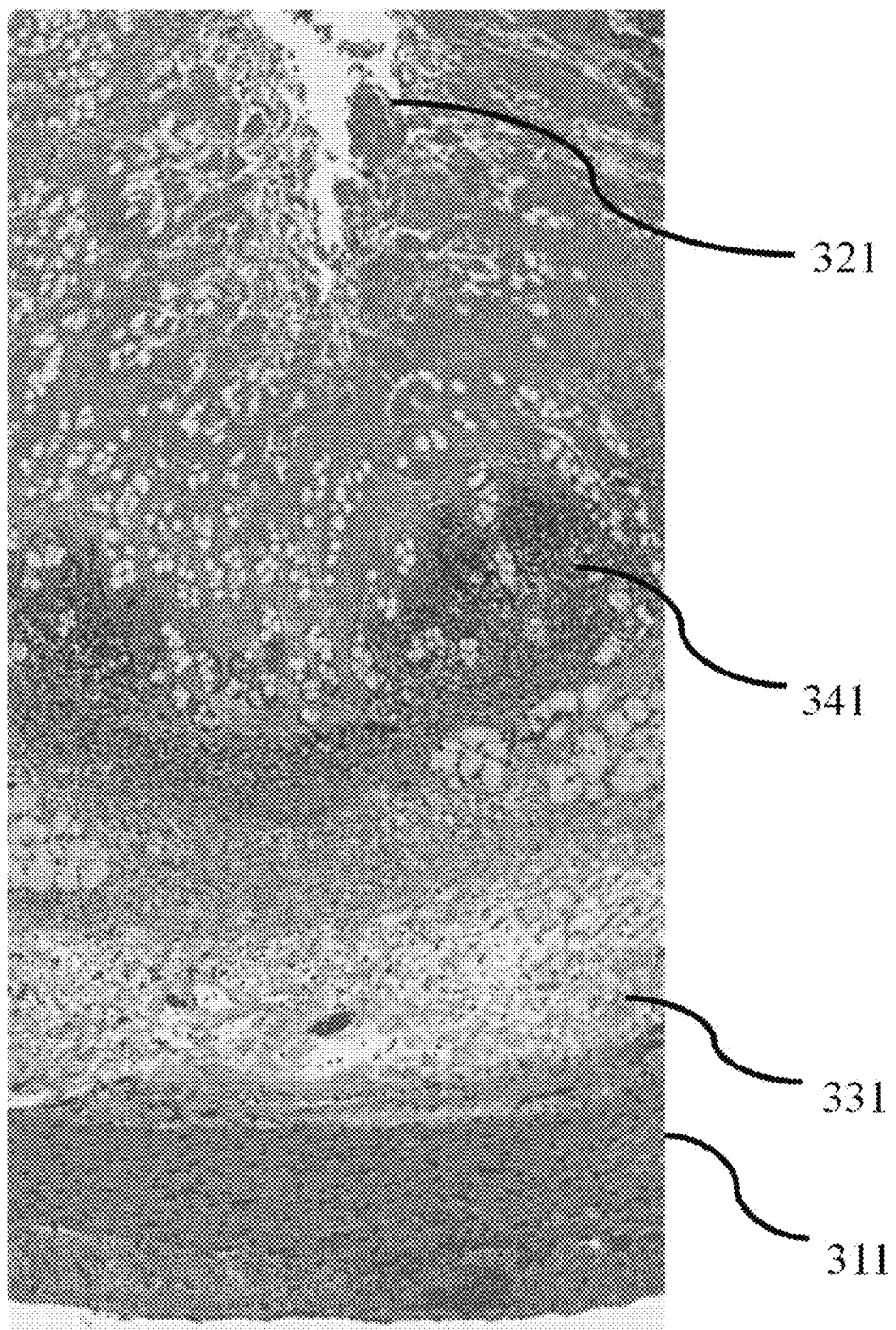
Figure 3F:
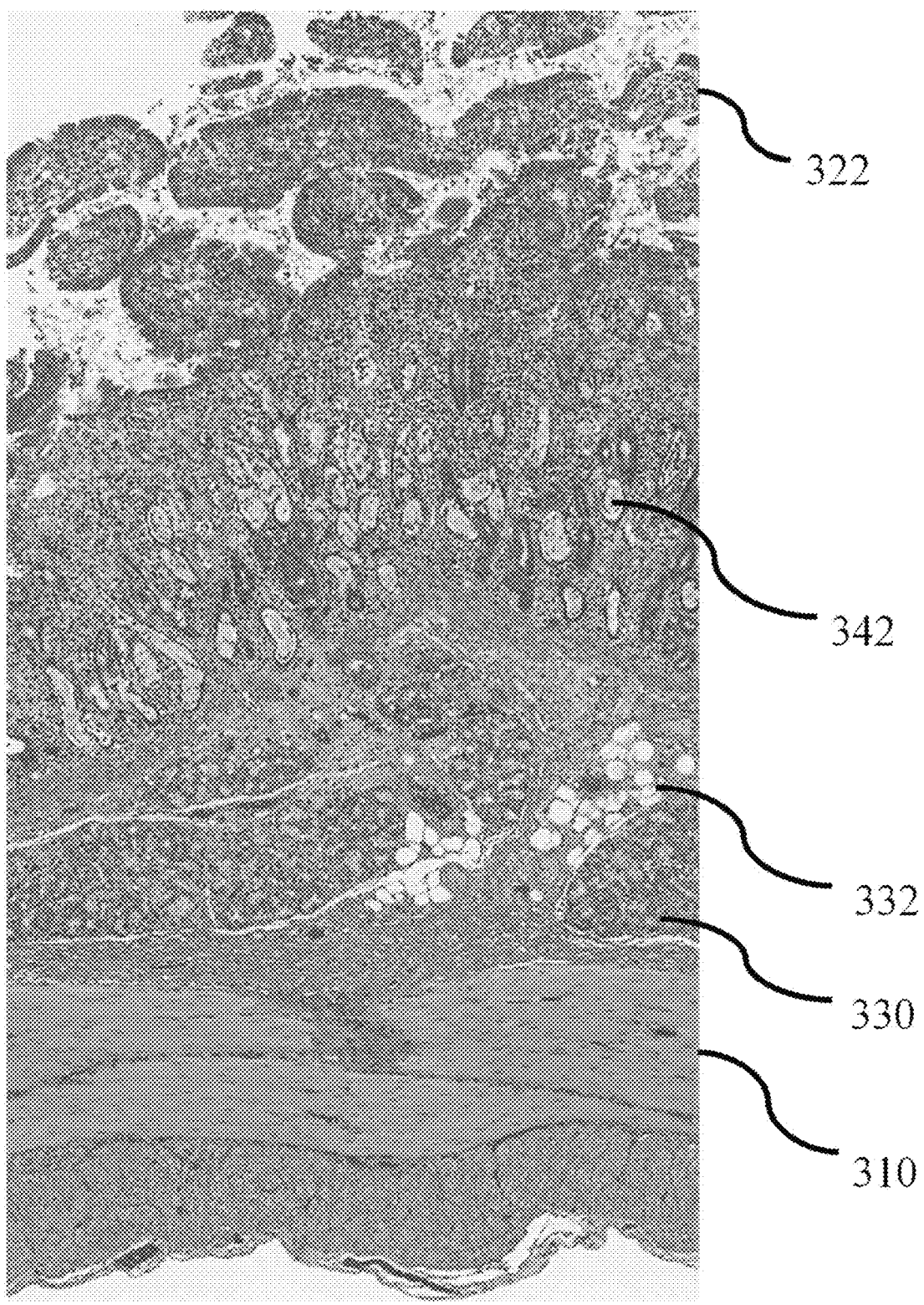

FIG. 3C illustrates a histological slide of the duodenum from tissue about 24 hours after treatment with heat and pulsed electric field, showing a partial treatment of the mucosa down to the crypt layer, with injured cells. A fourth mucosa region (391) corresponds to thermal/heat fixed tissue of the villi, including the villi-associated enteroendocrine cells. The fourth mucosa region (391) demonstrates architectural and cytological preservation with cellular detail with hyperchromatic nuclear and hypereosinophilic cytoplasmic staining. Overall, interstitial hemorrhage and infiltrating post-treatment-associated inflammatory cells are not identified. The heat fixed tissue may be expected to slough off, followed by surface re-epithelialization and villous structural healing with crypt cell repopulation. The crypt tissues are partially affected by a combination of heat and pulsed electric field effects. The tissue healing timeline is expected to be longer than that of a pulsed electric field treatment without thermal effect. The submucosa (370) and muscularis (380) are histologically unaffected. FIG. 3E is an image of an illustrative variation of 24 hour porcine duodenal histology following an isolated hyperthermic tissue treatment (i.e., no concomitant pulsed electrical field exposure) which destroys the lamina propria in that tissue scaffolding is burned and destroyed, and will be sloughed off and removed during healing. This demonstrates the histologic features of a thermal tissue dose, consistent with thermal/heat-induced coagulative necrosis without thermal/heat fixation. In this region, the glandular epithelium and neuroendocrine cells (321) show a loss of cytologic detail, consistent with cellular "ghost images." Interstitial hemorrhage and reactive inflammatory cells of the mucosal layer (341) are present at the region's edge. The submucosa (331) and muscularis (311) also show injury related changes. This region may be anticipated to heal similar to an ischemic type coagulative necrosis with resorption and remodeling with mucosal regeneration. The thermal lesion destroyed the lamina propria. Scaffolding is burned and destroyed and will be sloughed off and removed during healing. The tissue healing time frame for this region should be longer than that expected for a pulsed electric field treatment.

FIG. 3F is an image of an illustrative variation of duodenal tissue that has undergone treatment with pulsed or modulated electric field energy to a controlled depth not including the muscularis, untreated muscularis propria layer (310), submucosa (330), treated submucosa (332), treated villus crypts, with partial cell lysis and maintained tissue scaffolding (342), and treated villi with villas sloughing (322). The treated submucosa (332) also maintains tissue scaffolding. These treated tissues illustrate cells that have undergone a cell death where the cellular membranes remain intact but the cells are no longer viable and functioning. The healing cascade will replace these cells without infiltration of large number of inflammatory cells, and the surface will re-epithelialize and with villous structural healing and crypt cell repopulation. The muscularis (310) remains healthy (e.g., viable and fully functioning with cell integrity) without therapeutic effect from the pulsed electric field energy. That is, with pulsed or modulated electric field energy cell death corresponds to functional cell death with intact cellular structures while ablation refers to loss of both cell structure and function and an aggressive necrotic inflammatory response healing cascade.

Figure 75:
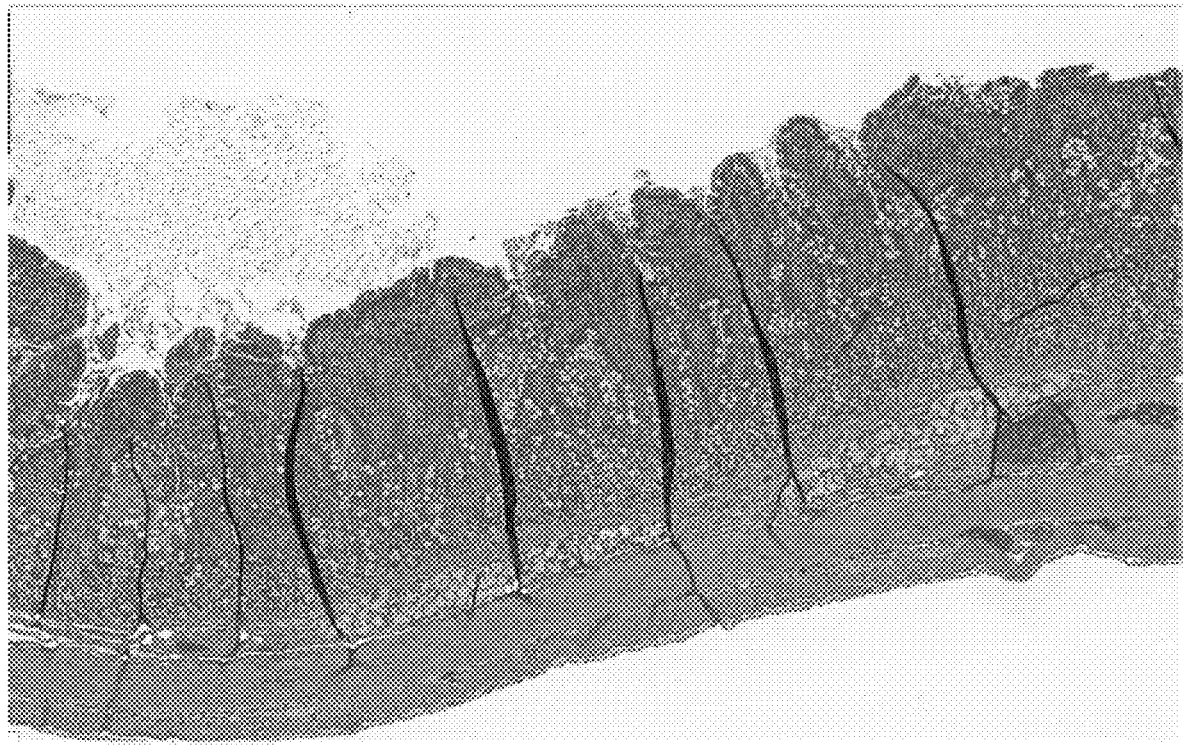
FIG. 75 is a detailed cross-sectional image of duodenal tissue about fourteen days after treatment.

In some variations, a target depth of treatment includes the mucosal layer but excludes treatment of the muscularous propria. Human tissue data assessed through histopathology supports about a 1 mm target depth for PEF tissue treatment where the pulsed electric field does not penetrate through to the muscularous propria at a therapeutic level. As a result, the mucosa exhibits a healing progression with a first day initiation of crypt and glandular epithelial regeneration (e.g., FIGS. 72A, 72B), a third day continuation of epithelial development with surface re-epithelization (e.g., FIG. 73), a seventh day of early cobblestone-like blunted villous development (e.g., FIGS. 74A, 74B), and continues through a fourteenth day of villous elongation and narrowing (FIG. 75). Based on the methods described herein, the healing response may be essentially completed in about thirty days. Moreover, the systems, devices, and methods described herein may provide uniform treatment coverage throughout a circumference and length of the duodenum.

Some methods for treating diabetes may include treating the submucosa layer of the duodenum without treating the muscularis. Conventional solutions do not consistently treat the submucosa layer without negatively impacting the muscularis. Instead, conventional solutions may add complicated mitigating steps such as lifts with saline injection in an attempt to protect the muscularis. For reference, the mucosal layer typically has a thickness between about 0.5 mm to about 1 mm, the submucosa layer typically has a thickness of about 0.5 mm and about 1 mm, and the muscularis typically has a thickness of about 0.5 mm. Inducing injury to the muscularis may result in adverse clinical outcomes. Furthermore, the anatomical structure along a circumference of the duodenum is not uniform, thus complicating efforts to treat just the submucosa and not the muscularis.

The methods described herein may selectively change tissue viability without losing the integrity of the majority of the treated tissue in the duodenum by applying a predetermined pulsed or modulated electric field and, optionally, without other treatment of the tissue to mitigate the pulsed or modulated electric field to a portion of tissue. By contrast, RF based energy treatment may predominantly generate heat-induced cell lysis (e.g., cell death) or ablation that may indiscriminately damage tissue and destroy cellular structure, and which may be difficult to modulate, thus negatively impacting treatment outcomes. In some variations, the methods described here may comprise applying a pulsed or modulated electric field to thermally-induce local necrotic cell death (e.g., local ablation) for duodenal tissue immediately adjacent to an electrode array and to induce cell lysis (e.g., functional cell death) within a predetermined range of depths of duodenal tissue (e.g., up to about 1 mm, between about 0.5 mm and 0.9 mm) while minimizing the physiological impact to tissue greater than the selected depth.

FIG. 3F is an image of an illustrative variation of duodenal tissue that has undergone treatment with pulsed or modulated electric field energy to a controlled depth. In FIG. 3F, the muscularis layer (310) and a portion of the submucosa (330) are untreated (i.e., energy delivered to tissue does not affect the tissue) and the villus crypts (342), villi (322) and a different portion of the submucosa (332) have been treated. Thus, the treatment applied to the duodenal tissue shown in FIG. 3F results in a more superficial (e.g., closer to the tissue surface) treated submucosa (332) and a deeper, untreated muscularis layer (310). The treated tissues contain cells that have undergone cell lysis where the tissue scaffolding remain intact but the cells are no longer viable and functioning. A mild healing cascade will replace these cells. The muscularis (310) adjacent to the treated submucosa (332) remains healthy (e.g., viable and fully functioning with cell integrity).

The pulsed or modulated electric fields near an electrode array may generate some thermal heating of tissue leading to tissue ablation that destroys both cell structure and function. However, cell lysis in tissue resulting from the pulsed or modulated electric fields applied herein are at least 50% pore-induced and less than 50% heat-induced such that a majority of cell death comprises functional cell death with intact cellular structures. For example, the thermal heating generated by a pulsed or modulated electric field is generally localized to a relatively small radius from each electrode of an electrode array and does not affect deeper layers of tissue such as the muscularis.

The systems, devices, and methods described herein deliver energy to provide treatment characteristics optimized for each tissue layer to improve treatment outcomes. Near the surface of the tissue (e.g., less than about 0.5 mm, between about 0.1 mm and about 0.5 mm), thermal heating may generate local necrotic cell death of tissue that may slough off after treatment. At a tissue depth of between about 0.5 mm and about 1.3 mm (e.g., mucosa of duodenum), cell lysis may be generated by the pulsed or modulated electric field while thermal heating is limited (e.g., to less than about a 13° C. increase or 6° C. increase). For example, an electric field strength at about 1.0 mm may be about 2.5 kV/cm. At tissue depths beyond 1.0 mm, the energy delivered to tissue generates reversible electroporation with even less thermal heating such that deeper tissue may be substantially untreated. Thus, thermal heating may be limited to a surface tissue layer (e.g., less than about 0.5 mm, between about 0.1 mm and about 0.5 mm) while still delivering pulsed or modulated electric field energy for cell lysis of the mucosa.

For example, FIG. 3C is an image of an illustrative variation of duodenal tissue that has undergone a method of treating duodenal tissue described herein where villi (391) has been treated by a combination of thermal heating (e.g., more than 50%) and pore-induced cell death (e.g., less than 50%). The pulsed or modulated electric field applied to the villus crypts and submucosa (370) has treated the tissue to a majority (e.g., more than 50%) of pore-induced cell death with a lesser contribution (e.g., less than 50%) of cell death due to thermal heating. The muscularis (380) is substantially untreated by the pulsed or modulated electric field or other methods. For example, the submucosa in FIG. 3C is not subject to saline injection. The depth of treatment may be controlled such that a predetermined portion of the mucosal layer such as the villus crypts may remain untreated if desired. The configuration and geometry of the electrode arrays as described herein may enable the tissue treatment characteristics described herein.

By contrast, conventional solutions that apply other forms of thermal energy (e.g., steam, radiofrequency, laser, heated liquid) to the duodenum thermally ablate through multiple layers of the tissue (e.g., inducing more than 50% heat-induced necrotic cell death and less than 50% pore-induced cell death), thereby destroying the cellular structure of the mucosa at similar depths and which may detrimentally thermally damage the muscularis. In an attempt to mitigate the risk of unintentional thermal damage during application of thermal energy to deeper layers (e.g., muscularis) of the duodenum, saline may be injected into portions of duodenal tissue (e.g., the submucosa (330)). This additional step further complicates the procedure and is not always sufficient to prevent unwanted thermal tissue damage. The pulsed or modulated electric field based methods described here eliminate this additional step and provide greater protection against unwanted tissue damage by improving the energy delivery characteristics generated by a pulsed electric field device.

In some variations, pulsed electric field treatment may be applied while monitoring and/or minimizing tissue temperature increases. For example, a predetermined rise in tissue temperature (e.g., about 1° C., about 2° C., about 3° C.) may be followed by a pause (e.g., of a predetermined time interval) in energy delivery to allow the tissue to cool. In this manner, the total energy delivered may increase the tissue temperature below a predetermined threshold (e.g., below a safety limit). In some variations, the predetermined threshold may be up to about 3° C., about 6° C., about 10° C., about 13° C., including all ranges and sub-values in-between.

Moreover, the difficulty faced by conventional solutions in controlling unwanted thermal tissue damage would lead one of ordinary skill away from using the pulsed or modulated electric field energy levels and methods described herein. In some variations, the tissue power densities generated by a pulsed or modulated electric field may be several orders of magnitude higher than the tissue power densities generated by radiofrequency ablation. For example, a power density ratio of an analogous design for radio frequency ablation may be about 576 where a radiofrequency device is driven at about 25 $V_{rms}$ and a pulsed electric field device is driven at about 600 $V_{rms}$. Thus, it would be unexpected for the pulsed or modulated electric field methods described here to not only treat tissue, but to do so without excess thermal tissue damage requiring mitigation procedures. Furthermore, the increased power densities may require additional insulation and protection of the pulsed electric field device, as well as a signal generator capable of generating such peak power levels. Generally, the duty cycle for PEF treatment may be several orders of magnitude lower than radio frequency ablation in order to keep a bulk tissue temperature rise below about 10° C.). For example, radio frequency ablation energy may generally be delivered continuously for several seconds. In some variations, PEF treatment may collectively accumulate about 15 milliseconds of ON time over about 10 seconds, for a net duty cycle of about 0.0015.

Figure 70:
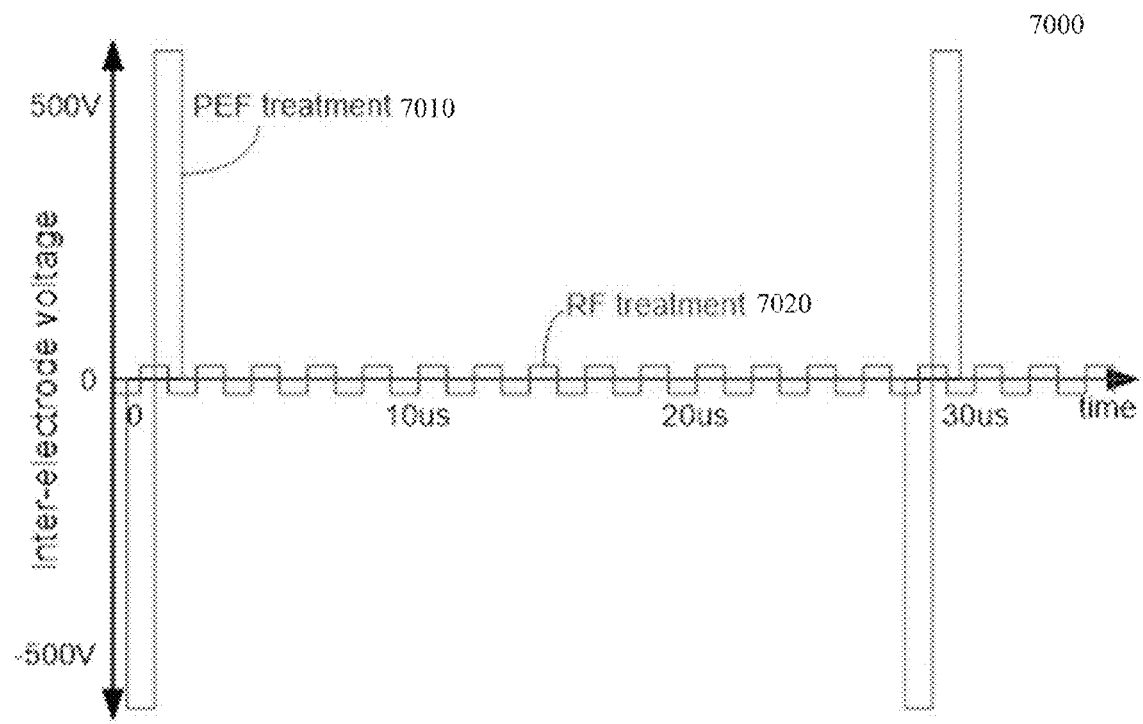
FIG. 70 is an illustrative variation of a voltage plot comparing the voltage output of pulsed electric field treatment to the voltage output of radiofrequency treatment over time.

FIG. 70 is plot (7000) comparing the voltage output of pulsed electric field treatment (7010) to the voltage output of radiofrequency treatment (7020) over time. During the RF treatment (7020) energy may be delivered continuously within the time scale of FIG. 70, while during PEF treatment (7010) energy is pulsed intermittently with a voltage output being orders of magnitude higher than the voltage output for the RF treatment (7020).

Generally, the devices described here may comprise an elongate body coupled to an electrode array, which may be disposed in a lumen of a duodenum. In some variations, the devices may further comprise an expandable member configured to releasably engage to a portion of the duodenum. The expandable member may comprise or be coupled to an electrode array configured to generate a pulsed or modulated electric field. The electrodes of the electrode array may have predetermined dimensions and spacing configured to generate a pulsed or modulated electric field having predetermined uniformity for treating desired tissue while limiting damage to other tissue. In some variations, the expandable member may expand and compress as necessary to engage an inner diameter of the duodenum. In some variations, a system comprising the devices described herein may further comprise a signal generator configured to generate a pulse waveform for delivery to the electrode array to thereby treat the engaged tissue.

Also described here are methods. In some variations, a method of treating duodenal tissue, to, for example, treat diabetes, may include advancing a pulsed electric field device toward a first portion of a duodenum of a patient. The pulsed electric field device may comprise an expandable member comprising an electrode array. The expandable member may be transitioned from a compressed configuration into an expanded configuration bringing the expandable member (and the electrode array) closer to or in contact with the inner surface of the duodenum. The expandable member may comprise a flexibility to apply force against and conform to an inner circumference of the duodenum that may itself comprise a range of diameters. A first pulse waveform may be delivered to the electrode array to generate a first pulsed or modulated electric field, which may treat the tissue in the first portion. The pulsed electric field device may be moved (e.g., advanced or retracted) toward a second portion of the duodenum (which may be distal or proximal to the first portion), and a second pulse waveform may be delivered to the electrode array to generate a second pulsed or modulated electric field thereby treating the tissue in the second portion. For example, in some variations, a signal generator may generate a drive voltage of between about 400 V and about 1500 V that may correspond to an electric field strength of about 400 V/cm and about 7000 V/cm at the treatment portions of the duodenum. The expandable member may be in a compressed configuration, semi-expanded configuration, and expanded configuration during movement of the pulsed electric field device. In some variations, a visualization device may be configured to visualize one or more of the pulsed electric field device and tissue. In some variations, temperature sensor measurements may be used to monitor and/or control pulse waveform delivery. In some variations, current and voltage measurements may be used to monitor and/or control pulse waveform delivery.

I. System

Overview

Figure 4:
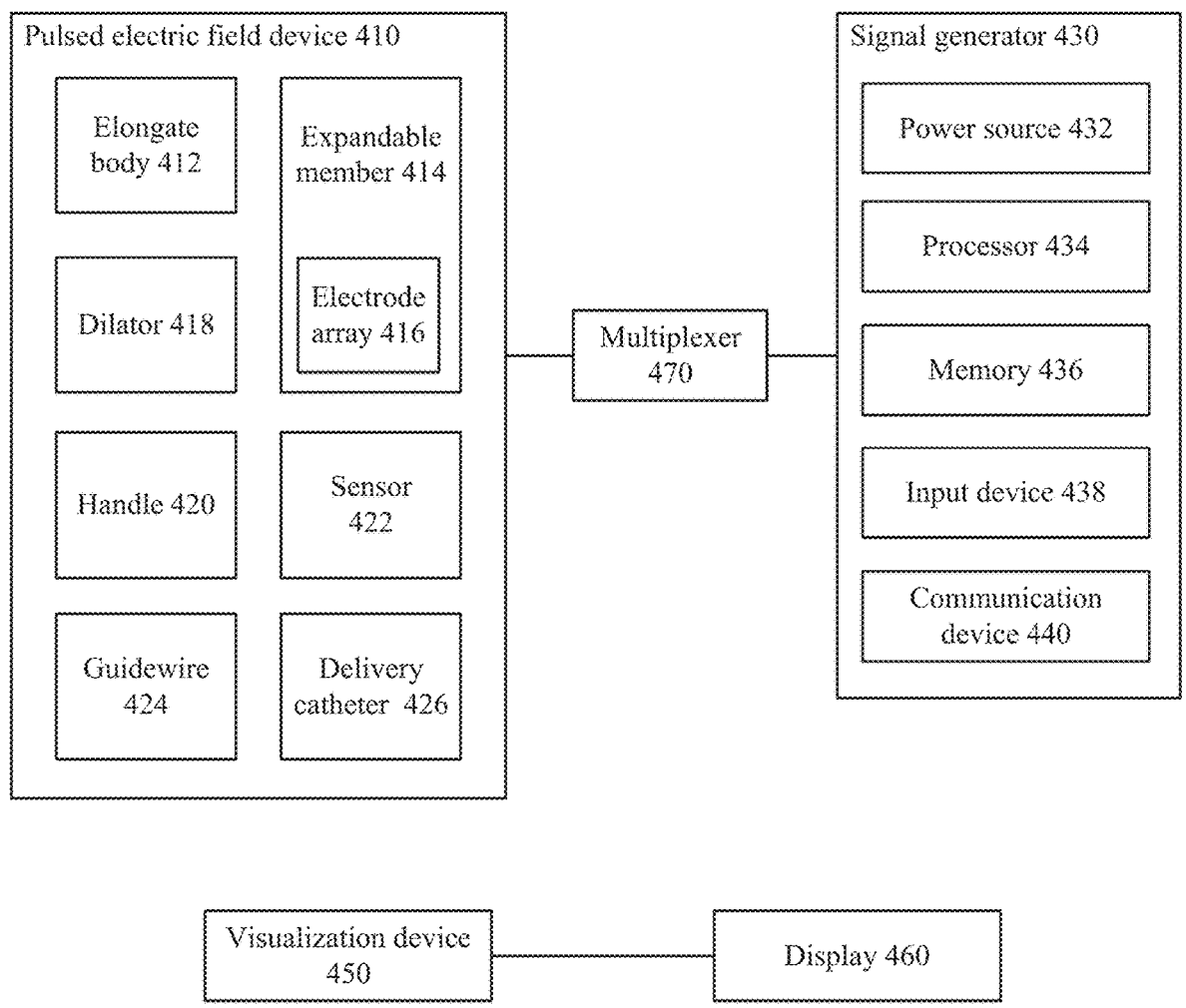
FIG. 4 is a block diagram of an illustrative variation of a pulsed electric field system.

Systems described here may include one or more of the components used to treat tissue, such as, for example, a pulsed electric field device and a visualization device. FIG. 4 is a block diagram of a variation of a pulsed electric field system (400) comprising one or more of a pulsed electric field device (410), a signal generator (430), multiplexer (470), a visualization device (450), and a display (460).

In some variations, the pulsed electric field device (410) may comprise one or more (e.g., a first and a second) elongate bodies (412) sized and shaped to be placed in one or more body cavities of the patient such as, for example, an esophagus, a stomach, and small intestine. In some variations, the pulsed electric field device (410) may further comprise one or more expandable members (414), one or more electrode arrays (416), one or more dilators (418), a handle (420), one or more sensors (422), a guidewire (424), and a delivery catheter (426). A distal end of the pulsed electric field device (410) may comprise the dilator (418), and the guidewire (424) may extend from a lumen of the dilator (418). The expandable member (414) may comprise the electrode array (416). For example, as will be described in more detail herein, in some variations the electrode array (416) may be coupled to a surface (e.g., outer surface) of the expandable member (416), while in other variations, the electrode array itself may form the expandable member and/or the electrode array may be integral with the expandable member. In some variations, the expandable member (414) and/or the electrode array (416) may be disposed adjacent to one or more dilators, for example, between at least a pair of dilators (418). In some variations, the pulsed electric field system (400) may optionally comprise a delivery catheter (426) configured to advance over the pulsed electric field device (410). Additionally or alternatively, the pulsed electric field device (410) may comprise one or more sensors (422) configured to measure one or more predetermined characteristics such as temperature, pressure, impedance and the like.

As mentioned above, the pulsed electric field system (400) may comprise a visualization device (450). In some variations, the visualization device (450) may be configured to visualize one or more steps of a treatment procedure. The visualization device (450) may aid one or more of advancement of the pulsed electric field device (410), positioning of the pulsed electric field device and/or components thereof (e.g., the electrode array (416)), and confirmation of the treatment procedure. For example, the visualization device (450) may be configured to generate an image signal that is transmitted to a display (460) or output device. In some variations, the visualization device (450) may be advanced separately from and alongside the pulsed electric field device (410) during the treatment procedure. For example, an expandable member (414) of the pulsed electric field device (410) may be configured to hold the visualization device (450) such that the pulsed electric field device (410) translates together with the visualization device (450) as they are moved through the body. The expandable member (414) may expand to release the visualization device (450), thus allowing freedom of movement for the visualization device (450). In other variations, the visualization device (450) may be integrated with the pulsed electric field device (450). For example, the dilator (418) may comprise the visualization device (450).

The visualization device (450) may be any device (internal or external to the body) that assists a user in visualizing a treatment procedure. In some variations, the visualization device (450) may comprise one or more of an endoscope (e.g., chip-on-the-tip camera endoscope, three camera endoscope), image sensor (e.g., CMOS or CCD array with or without a color filter array and associated processing circuitry), camera, fiberscope, external light source, and ultrasonic catheter. In some variations, an external light source (e.g., laser, LED, lamp, or the like) may generate light that may be carried by fiber optic cables. Additionally or alternatively, the visualization device (450) may comprise one or more LEDs to provide illumination. For example, the visualization device (450) may comprise a bundle of flexible optical fibers (e.g., a fiberscope). The bundle of fiber optic cables or fiberscope may be configured to receive and propagate light from an external light source. The fiberscope may comprise an image sensor configured to receive reflected light from the tissue and the pulsed electric field device. It should be appreciated that the visualization device (450) may comprise any device or devices that allows for or facilitates visualization of any portion of the pulsed electric field device and/or of the internal structures of the body. For example, the visualization device may comprise a capacitive sensor array and/or a fluoroscopic technique for real-time X-ray imaging.

In some variations, the signal generator (430) may be configured to provide energy (e.g., energy waveforms, pulse waveform) to the pulsed electric field device (410) to treat predetermined portions of tissue, such as, for example, duodenal tissue. In some variations, a PEF system as described herein may include a signal generator that comprises an energy source and a processor. The signal generator may be configured to deliver a bipolar waveform to an electrode array, which may deliver energy to the tissue (e.g., duodenal tissue). The delivered energy may aid in resurfacing the mucosa of the duodenum while minimizing damage to surrounding tissue. In some variations, the signal generator may generate one or more bipolar waveforms. In some variations, the signal generator may be configured to control waveform generation and delivery in response to received sensor data. For example, energy delivery may be modulated (e.g., inhibited) unless a measured temperature falls within a predetermined range.

In some variations, in order to limit nerve stimulation, a pulse waveform may, on average, comprise a net current of about zero (e.g., generally balanced positive and negative current), and have a non-zero time of less than about 2 μsec or less than about 5 μsec. In some variations, the pulse waveform may comprise a square waveform. For example, the pulse waveform may comprise a square shape in voltage drive and in current drive, or the pulse waveform may comprise a square shape in voltage drive and a sawtooth shape in current drive. In some variations, one or more pulses may comprise a half sine-wave for both current and voltage. In some variations, one or more pulses may comprise two exponentials with different rise and fall times. In some variations, one or more pulses may comprise bipolar pulse at a first potential followed by pulse pairs at a second potential less than the first potential.

In some variations, a multiplexer (470) may be coupled to the pulsed electric field device (410). For example, the multiplexer (470) may be coupled between the signal generator (430) and the pulsed electric field device (410), or the signal generator (430) may comprise the multiplexer (470). The multiplexer (470) may be configured to select a subset of electrodes of an electrode array (416) receiving a pulse waveform generated by the signal generator (430) according to a predetermined sequence. Additionally or alternatively, the multiplexer (470) may be coupled to a plurality of signal generators and may be configured to select between a waveform generated by one of the plurality of signal generators (430) for a selected subset of electrodes.

Pulsed Electric Field Device

Generally, the pulsed electric field devices described herein may comprise an elongate body and an expandable member comprising an electrode array. The pulsed electric field devices may be configured to facilitate deployment in, and treatment of, the duodenum. In some variations, the pulsed electric field device may be configured to apply pulsed or modulated electric field energy to an inner circumference of the duodenum. The devices described herein may be used to treat only a particular, pre-specified portion of the duodenum, and/or an entire length of the duodenum. In some variations, an electrode array of the pulsed electric field device may generate an electric field strength of from about 400 V/cm to about 1500 V/cm, from about 1500 V/cm to about 4500 V/cm, including all values and sub-ranges in-between, at a treatment depth of from about 0.5 mm to about 1.5 mm from an inner surface of the duodenum, for example, at about 1 mm. In some variations, the electric field may decay such that the electric field strength is less than about 400 V/cm at about 3 mm from the inner surface of the duodenum. In some variations, a predetermined bipolar current and voltage sequence may be applied to an electrode array of the pulsed electric field device to generate the pulsed or modulated electric field. The generated pulsed or modulated electric field may be substantially uniform to robustly induce cell lysis in a predetermined portion of duodenal tissue. For example, a generated pulsed or modulated electric field may spatially vary up to about 20% at a predetermined depth of tissue, between about 5% and about 20%, between about 10% and 20%, and between about 5% and about 15%, including all ranges and sub-values in-between. Furthermore, the pulsed electric field device may be biocompatible and resistant to stomach acids and intestinal fluids.

Expandable Member

Generally, the expandable members described here may be configured to change configurations to aid in positioning of the electrode array relative to the duodenum during a treatment procedure. For example, the expandable member may expand to contact tissue to hold the pulsed electric field device in place (e.g., elongate body, electrode array, sensor) relative to the tissue. The expandable member may also partially expand to hold a visualization device in place relative to the pulsed electric field device. The expandable members may comprise a compressed configuration and an expanded configuration. As will be discussed in more detail herein, in some instances, the compressed configuration may be a rolled configuration and the expanded configuration may be an unrolled configuration. Moreover, in some variations, the expandable member may comprise a semi-expanded (or partially unrolled) configuration between the compressed configuration and the expanded configuration. Placing the expandable member in the compressed configuration may allow the pulsed electric field device to be compact in size, which may allow for easier advancement through one or more body cavities. Once appropriately positioned, the expandable member may be transitioned to the expanded configuration, which may allow an electrode array of the expandable member to contact all or a portion of an inner circumference of the duodenum. In some variations, the semi-expanded configuration may allow the expandable member to hold another device (e.g., visualization device) within a lumen of the expandable member. Additionally or alternatively, a lumen may refer to a tubular or non-tubular structure having one or more openings, apertures, holes, slots, combinations thereof, and the like.

Figure 5A:
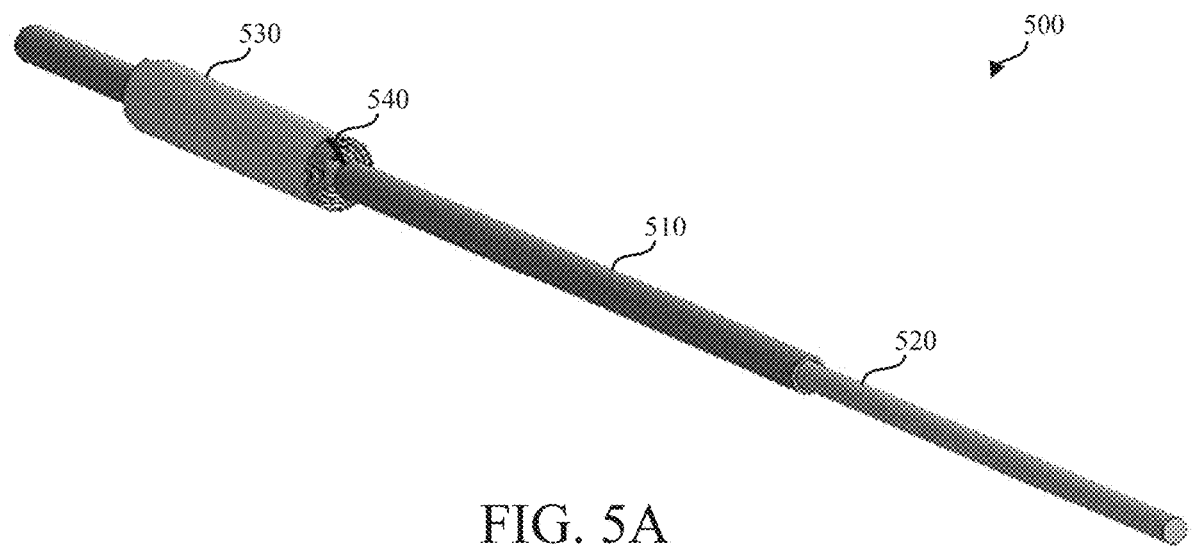
FIG. 5A is a perspective view of an illustrative variation of a pulsed electric field device in a compressed configuration.

FIG. 5A is a perspective view of a variation of a pulsed electric field device (500). As depicted there, the pulsed electric field device (500) may comprise a first elongate body (510) comprising a lumen therethrough and a second elongate body (520) at least partially positioned within the lumen of the first elongate body (510). The pulsed electric field device (500) may further comprise an expandable member (530), which may be rolled around (e.g., in mechanical contact with) the second elongate body (520) about a longitudinal axis thereof. For example, as shown in FIGS. 5A-5D, the expandable member (530) may comprise a plurality of turns about the second elongate body (520) such that the expandable member (530) forms a plurality (e.g., two, three, four, five, or more) layers wrapped around or rolled about the second elongate body (520). That is, the expandable member (530) may be in mechanical contact with the second elongate body (520). In some variations, the expandable member (530) (e.g., circuit substrate, flex circuit) may comprise an electrode array (not shown for the sake of clarity), which may comprise any of the electrode arrays described herein. For example, in some variations, the expandable member may be a flex circuit, while in other variations, the expandable member may comprise a base layer and a flex circuit may be coupled to the base layer. The electrode array may be disposed on an outer surface of the expandable member (530). In some variations, a connector (540) may couple the first elongate body (510) to the expandable member (530). For example, the connector (540) may be configured to provide structural support to the expandable member (530) such that at least a portion of the expandable member (530) may be substantially fixed relative to the first elongate body (510).

Figure 5B:
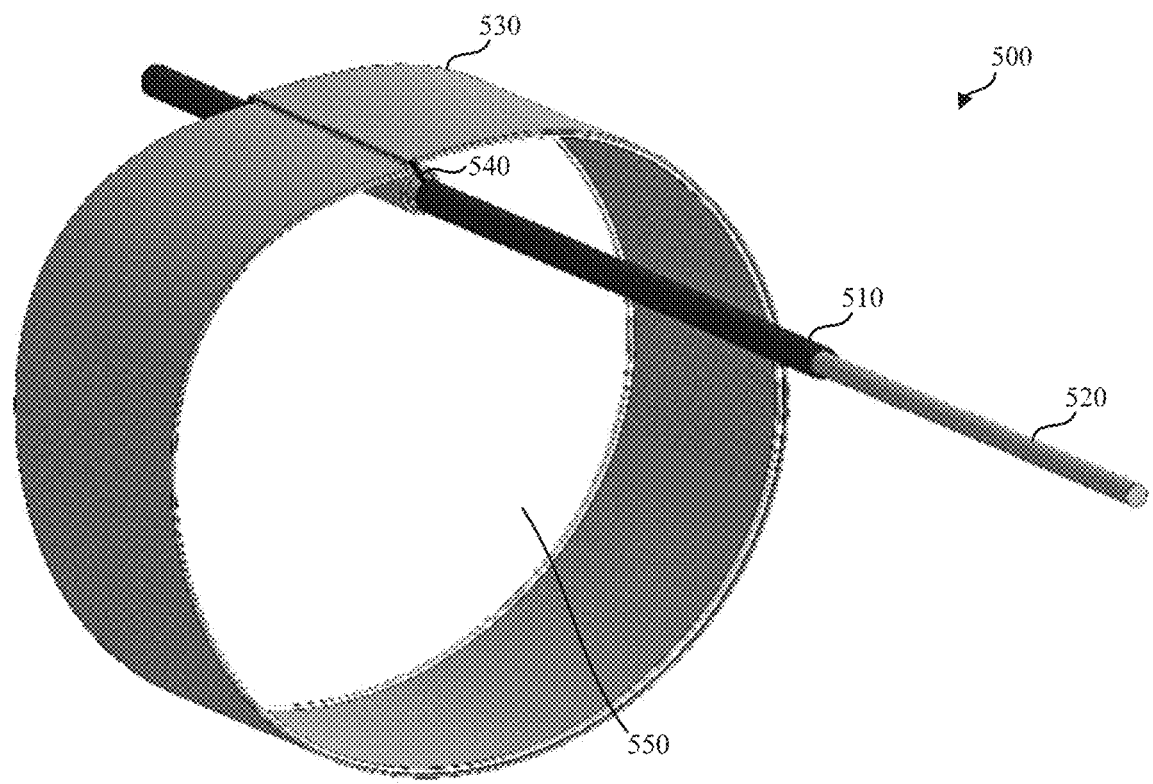
FIG. 5B is a perspective view of an illustrative variation of a pulsed electric field device in an expanded configuration.

FIG. 5A depicts the pulsed electric field device (500) with the expandable member (530) in a compressed or rolled configuration configured for advancement through one or more body cavities. When in the compressed or rolled configuration, the expandable member (530) may have a generally cylindrical shape with a first inner diameter (e.g., lumen diameter) and a first outer diameter. FIG. 5B depicts the pulsed electric field device (500) with the expandable member (530) in an expanded or unrolled configuration configured for engagement with tissue such as an inner surface of a duodenum (not shown for the sake of clarity). When in the expanded or unrolled configuration, the expandable member (530) may have a generally elliptic or cylindrical shape with a second inner diameter and a second outer diameter having a predetermined larger than a respective first inner diameter and first outer diameter. The expandable member in the expanded configuration may have a predetermined flexibility configured to conform to a shape of the tissue to which it is engaged.

In some variations, the first and second elongate bodies (510, 520) may be configured to axially rotate relative to one another to transition the expandable member (530) between the compressed configuration, the expanded configuration, and the semi-expanded configuration therebetween. For example, the second elongate body (520) (e.g., inner torsion member, rotatable member) may be rotatably positioned within a lumen of the first elongate body (510), such that rotation of the second elongate body (520) relative to the first elongate body (510) may transition the expandable member (530) between a rolled configuration and an unrolled configuration. In some of these variations, the inner diameter of the lumen (550) of the expandable member (530) may be at least about 8 mm in the unrolled configuration, at least about 10 mm, or from about 8 mm to about 10 mm, including all values and sub-ranges in-between. As described in more detail herein, a visualization device (not shown) may be disposed within the lumen (550) of the expandable member (530) to aid in visualization. It should be appreciated that the pulsed electric field device (500) may be advanced next to a visualization device and/or over a guidewire. In some variations, a visualization device may be used to guide advancement and to visualize a treatment procedure such that a guidewire and/or other visualization modalities (e.g., fluoroscopy) are not needed.

In some variations, the expandable member (530) may be configured to transition to a configuration between the compressed and expanded configurations. For example, the expandable member (530) may transition to a partially or semi-expanded configuration (between the compressed configuration and expanded configuration) that may allow a visualization device (e.g., endoscope) to be disposed within a lumen of the expandable member (530). In some variations, an inner surface of the expandable member may engage and hold a visualization device in a semi-expanded configuration.

Figure 5C:
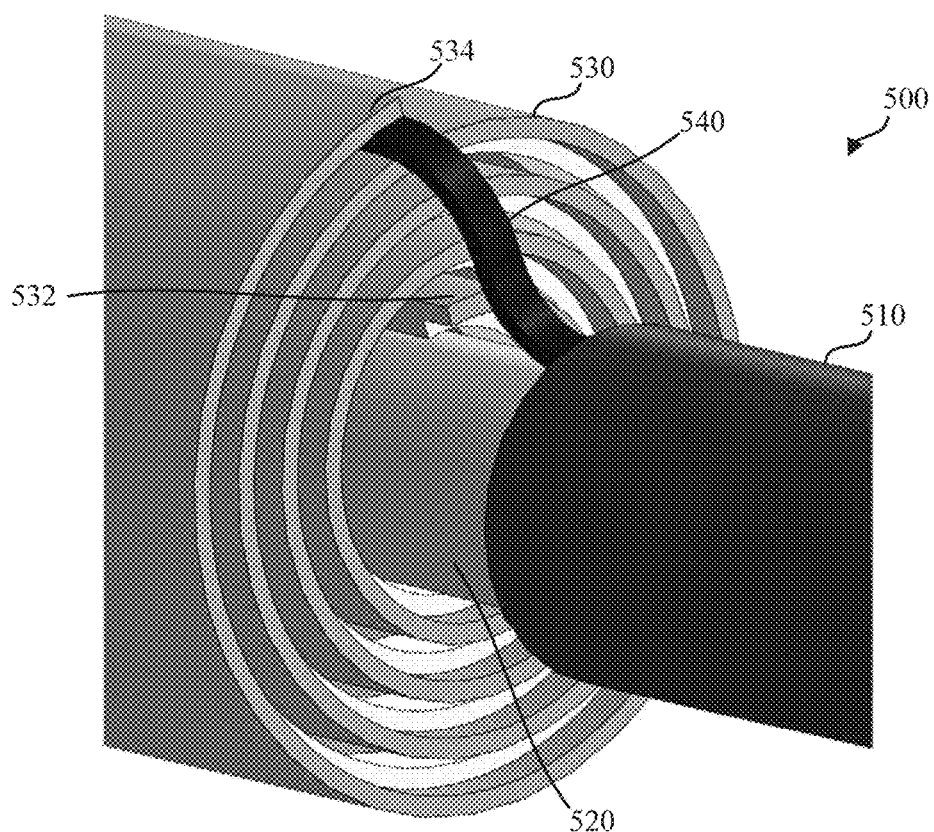
FIG. 5C is a detailed perspective view of the pulsed electric field device shown in FIG. 5A.
Figure 5D:
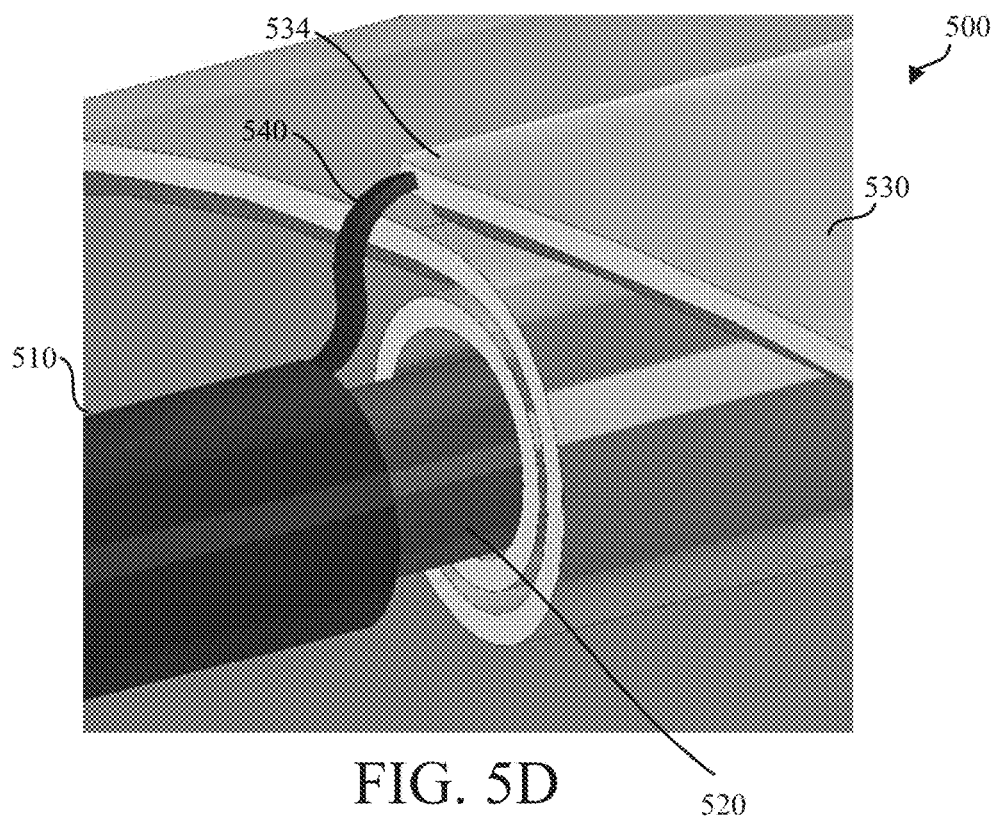
FIG. 5D is a detailed perspective view of the pulsed electric field device shown in FIG. 5B.

As shown in the detailed perspective views of FIGS. 5C and 5D, the expandable member (530) may comprise an inner end (532) (e.g., innermost portion of roll) and an outer end (534) (e.g., outermost portion of roll). FIG. 5C depicts the expandable member (530) in the compressed configuration and FIG. 5D depicts the expandable member (530) in the expanded configuration. In some variations, the inner end (532) may be coupled to the second elongate body (e.g., attached to an external surface thereof) (520) and the outer end (534) may be coupled to the first elongate body (510) (e.g., an external surface thereof). Coupling the ends of the expandable member (530) to the first and second elongate bodies (510, 520) in this way allows for better control over the size and shape of the expandable member (530). For example, an edge of the inner end (532) substantially parallel to a longitudinal axis of the second elongate body (520) may be attached to an outer surface of the second elongate body (520) such that the inner end (532) rotates with the rotation of the second elongate body (520). A direction of the rotation (e.g., clockwise, counter-clockwise) of the second elongate body (520) may determine the configuration (e.g., expansion or compression) of the expandable member (530). For example, rotating the second elongate body (520) in a clockwise direction relative to the first elongate body (510) may expand or unroll the expandable member (530), while rotating the second elongate body (520) in a counter-clockwise direction relative to the first elongate body (510) may compress or roll the expandable member, or vice versa.

In some variations, a connector (540) may couple the first elongate body (510) to the outer end (534) of the expandable member (530), which may allow the expandable member (530) to expand and compress while maintaining its relative position to the first elongate body (510). In some variations, the connector may function as a torsional control arm between the expandable member (530) and the first elongate body (510). In some variations, the connector (540) may comprise a curved shape such as an "S" shape, or may be straight (linear). The configurations shown in FIGS. 5C and 5D minimize the size of the connector (540) to facilitate advancement of the device (500) in the compressed configuration by reducing a diameter of the compressed device (500).

In some variations, an electrode array may be electrically coupled to the first elongate body (510) through the connector (540). For example, one or more leads may be coupled to the electrode array through a lumen of the first elongate body (510) and a lumen of the connector (540). Additionally or alternatively, one or more leads may be coupled to the electrode array through a lumen of the second elongate body (520). In some variations, the connector (540) may be composed of a rigid or semi-rigid material or combination thereof such that the position of the outer end (534) relative to the first elongate body (510) remains substantially the same between a compressed configuration and an expanded configuration. Additionally or alternatively, the expandable members described herein may comprise a bimetallic strip configured to expand and compress through ohmic heating.

Figure 6A:
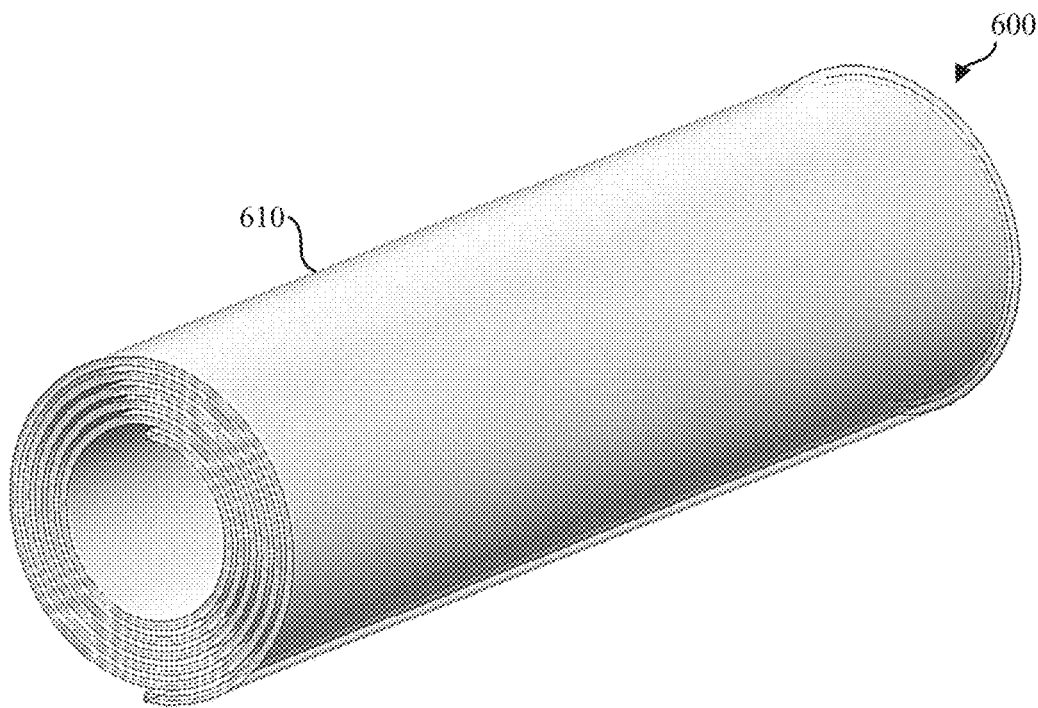
FIG. 6A is a perspective view of an illustrative variation of an expandable member in a rolled configuration.
Figure 6B:
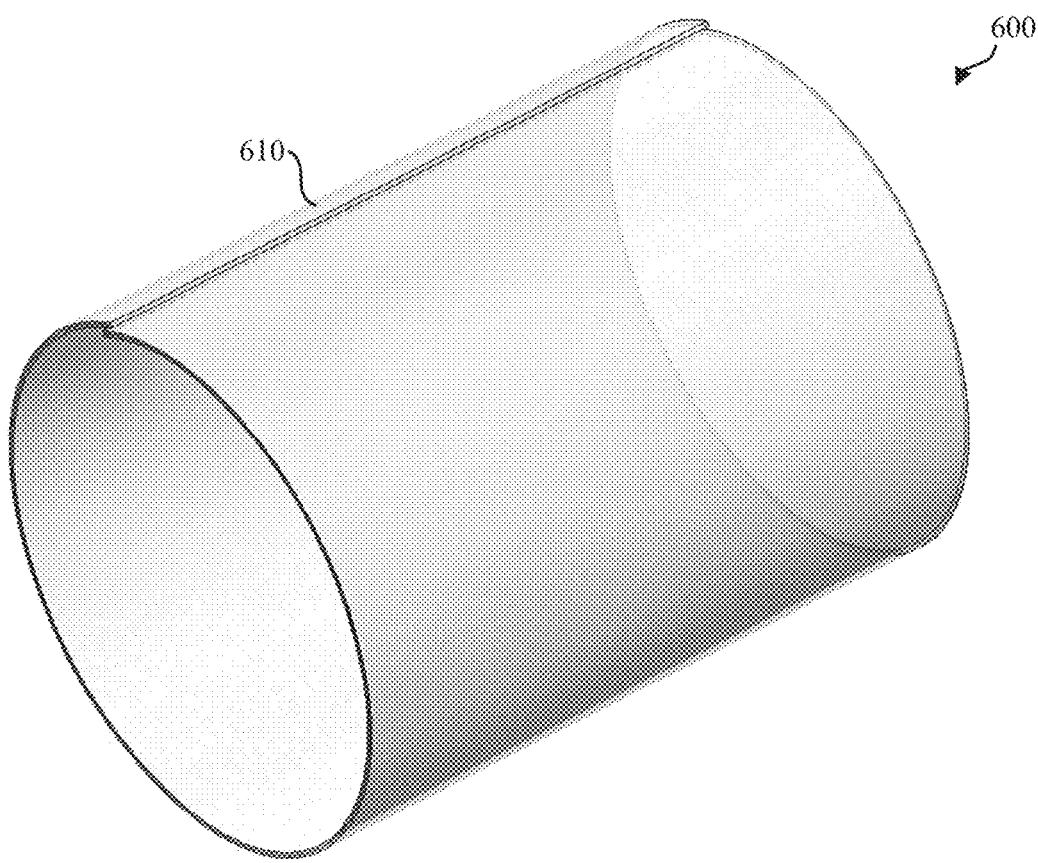
FIG. 6B is a perspective view of an illustrative variation of an expandable member in an unrolled configuration.

FIG. 6A is a perspective view of a variation of an expandable member (600) in a rolled configuration and FIG. 6B is a perspective view of the expandable member (600) in an unrolled configuration. In some variations, the expandable member (600) may comprise a substrate (610) such as a flex circuit. Furthermore the expandable member (600) may comprise or be coupled to an electrode array (not shown). In some variations, the expandable member (600) may be composed of a self-expanding material biased to expand to a predetermined shape and/or diameter. For example, the expandable member (600) may comprise one or more of a flexible polymeric material (e.g., polyamide, PET), nitinol, stainless steel, copper, gold, other metals, adhesives, combinations thereof, and the like. In some variations, the expansion and compression of an expandable member (600) may be caused by respective retraction and advancement of a sheath (e.g., delivery catheter) over the expandable member (600). The expandable member in the rolled configuration may comprise one or more turns. In some variations, the expandable member (600) in the rolled configuration may have a diameter between about 6 mm and about 15 mm, including all ranges and sub-values in-between. In some variations, the expandable member (600) in the expanded configuration may have a diameter between about 10 mm and about 50 mm, including all ranges and sub-values in-between.

Figure 7A:
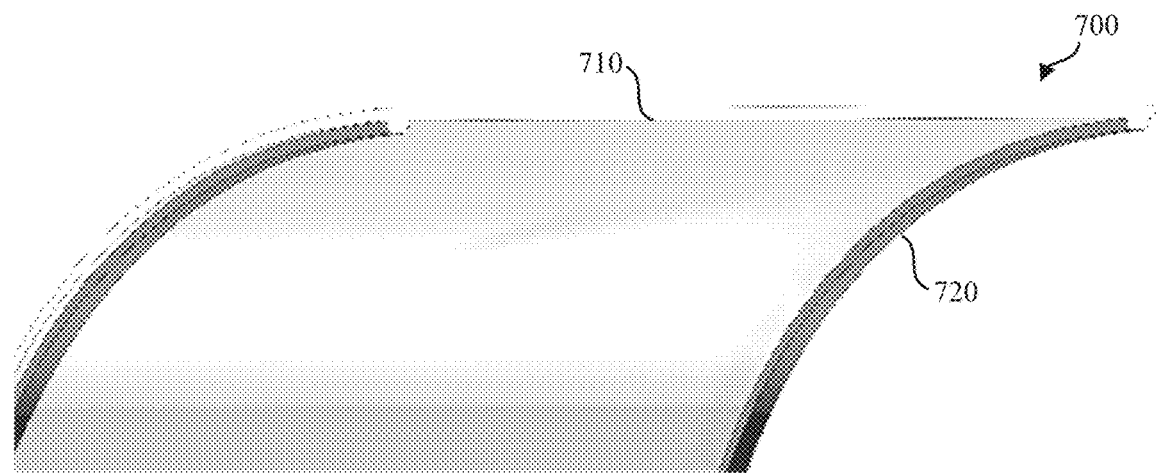
FIG. 7A is a cross-sectional perspective view of an illustrative variation of an expandable member in an unrolled configuration.

FIG. 7A is a cross-sectional perspective view of a portion of an expandable member (700) in an unrolled configuration. In some variations, the expandable member (700) may comprise a substrate (710) such as a flex circuit and a support (720). In these variations, the support (720) may provide structural reinforcement to allow the expandable member (700) to expand and appose an inner surface of a duodenum. That is, the support (720) may help apply appositional force against tissue to allow engagement with the expandable member (700) during a procedure. In some variations, the support (720) may comprise a stiffness greater than that of the substrate (710) and/or may comprise one or more components (e.g., sensors, fiducial generators). In some instances, the support (720) may extend circumferentially along a radial edge of the expandable member (700). In some variations, the support (720) may be configured to add stiffness to the substrate (710) coupled to the electrode array. In some variations, the support (720) may be disposed along a surface of the substrate (710) opposite the electrode array (730). In some variations, the support (720) may be composed of a rigid or semi-rigid material or a combination thereof configured to facilitate expansion and compression of the expandable member (700), and may include one or more of nitinol, stainless steels, carbon, polymers, and the like.

Figure 7B:
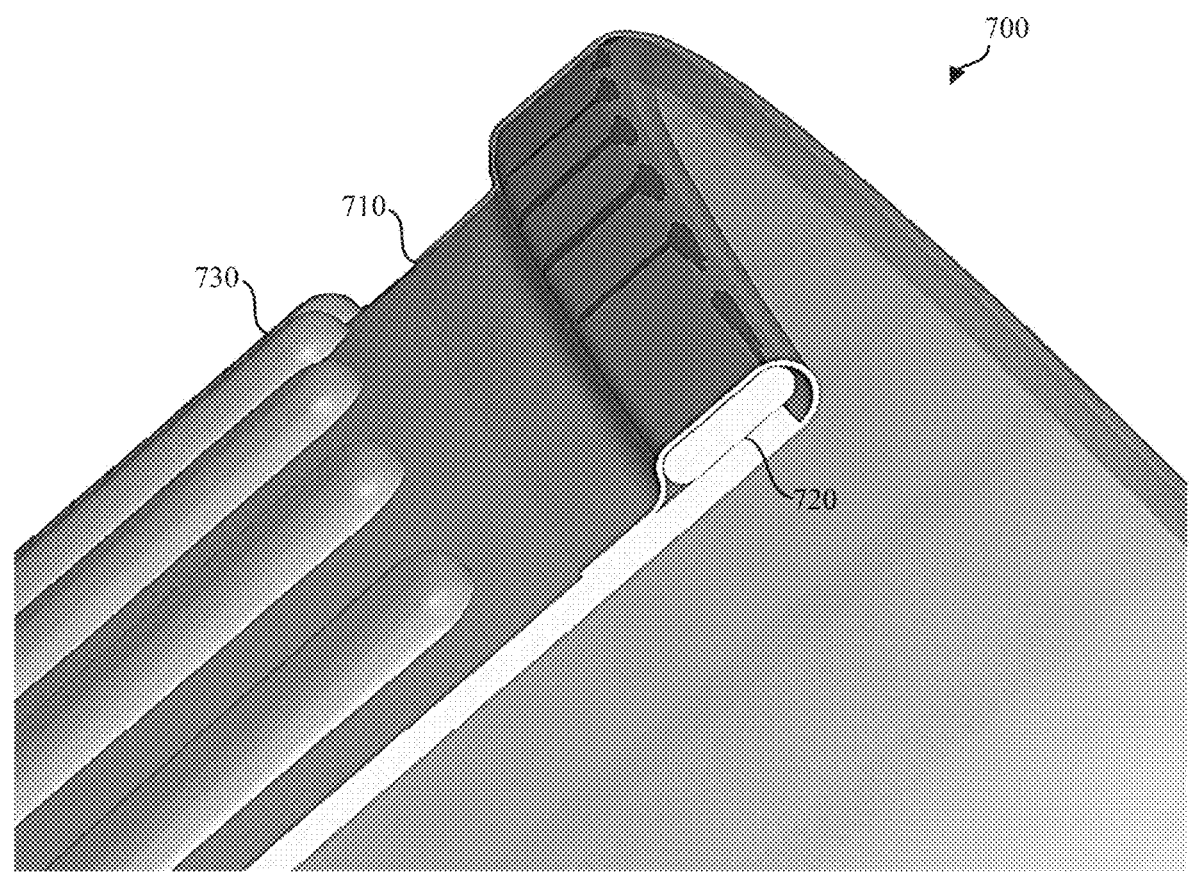
FIG. 7B is a detailed cross-sectional perspective view of the expandable member shown in FIG. 7A.

FIG. 7B is a detailed cross-sectional perspective view of the expandable member (700) comprising the substrate (710), the support (720), and the electrode array (730). As depicted in FIG. 7B, the electrode array (730) may comprise a plurality of substantially parallel elongate electrodes disposed on an outer surface of the substrate (710). Additionally or alternatively, the plurality of elongate electrodes may comprise an interdigitated configuration. For example, the plurality of elongate electrodes may comprise a curved shape (e.g., S-shape, W-shape).

The electrode array (730) may be configured to modify a flexural stiffness of the expandable member (700) to facilitate consistent expansion and compression of the expandable member (700). In some variations, the electrode array (730) may comprise a plurality of electrodes comprising a ratio of a center-to-center distance between proximate electrodes to a width of the electrodes between about 2.3:1 and about 3.3:1, and about 2.8:1 and about 3.0:1. In some variations, the plurality of elongate electrodes comprise a center-to-center distance between proximate electrodes of less than about 5 mm. In some instances, the electrode array may comprise a plurality of hemi-elliptical electrodes. In some variations, the electrode array (730) may comprise a plurality of electrodes configured to protrude and/or recess relative to a surface of the substrate (710). In some variations, one or more electrodes of the electrode array (730) may differ in height relative to the substrate (710) between about −0.25 mm and about 0.765 mm.

Figure 8A:
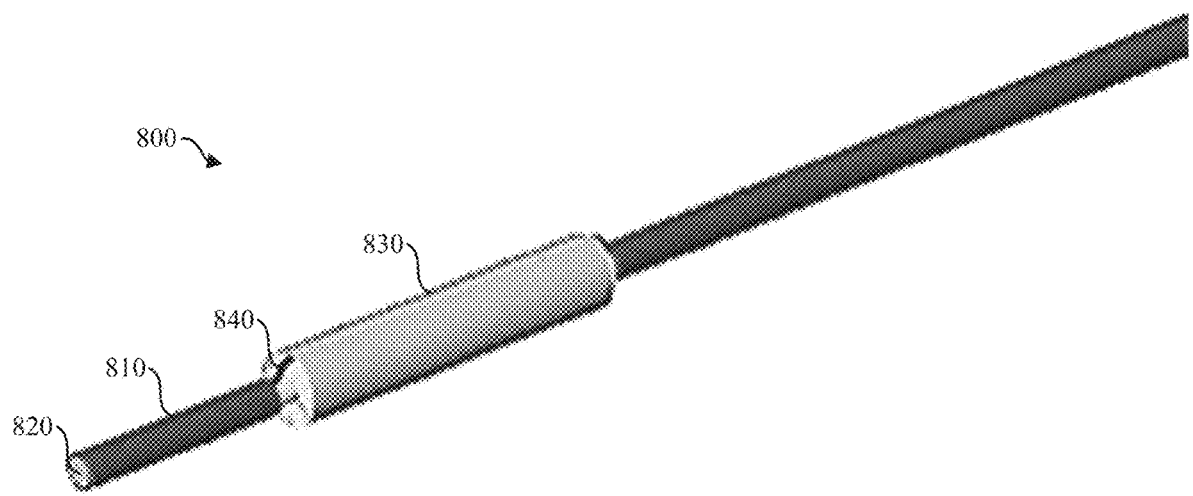
FIG. 8A is a perspective view of an illustrative variation of a pulsed electric field device in a rolled configuration.

FIGS. 8A-33B illustrate additional pulsed electric field device variations. FIG. 8A is a perspective view of a variation of a pulsed electric field device (800) in a rolled configuration. The device (800) in the rolled configuration may be configured to be advanced through one or more body cavities. In some variations, the pulsed electric field device (800) may comprise a first elongate body (810) comprising a lumen therethrough and a second elongate body (820) at least partially positioned within the lumen of the first elongate body (810). An expandable member (830) may be rolled about or around the second elongate body (820). For example, the expandable member (830) may comprise a plurality of turns about the second elongate body (820). The expandable member (830) may be coupled to a distal portion of the first elongate body (810) and second elongate body (820). In some variations, the expandable member (830) (e.g., circuit substrate, flex circuit) may comprise an electrode array (not shown for the sake of clarity) which may comprise any of the electrode arrays described herein. For example, the electrode array may be disposed on an outer surface of the expandable member (830). In some variations, a connector (840) may couple the first elongate body (810) to the expandable member (830).

Figure 8B:
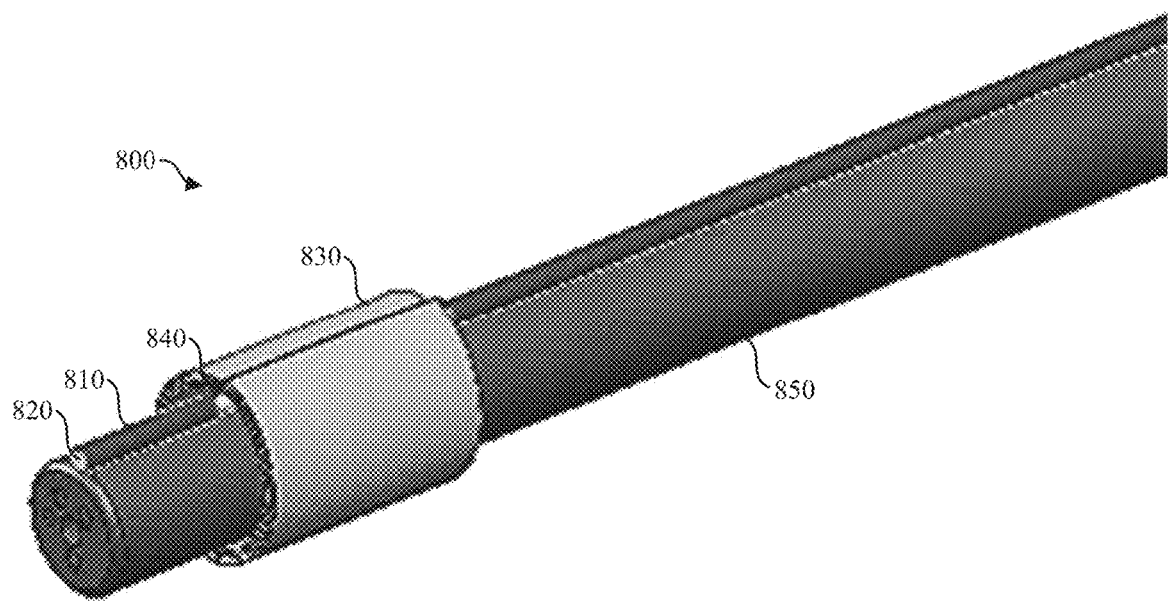
FIG. 8B is a perspective view of an illustrative variation of a visualization device and the pulsed electric field device shown in FIG. 8A in a partially unrolled configuration.

In some variations, a system comprising the device (800) further comprises a third elongate body (850) disposed within the lumen of the expandable member (830). In some of these variations, the third elongate body (850) comprises a visualization device (e.g., an endoscope). FIG. 8B is a perspective view of a variation of a visualization device (850) (e.g., endoscope) and the pulsed electric field device (800). In FIG. 8B, the expandable member (830) may transition to a partially unrolled configuration (e.g., semi-expanded) sufficient for the visualization device (850) to be disposed within a lumen of the expandable member (830). For example, the device (800) may be configured to hold the visualization device (850) in place relative to the device (800). In this manner, the pulsed electric field device (800) and visualization device (850) may be advanced together through one or more body cavities to facilitate navigation and delivery to the duodenum. Once delivered to a target tissue area, the visualization device (850) may be decoupled from the pulsed electric field device (800) such that the visualization device (850) may move independently of the pulsed electric field device (800). Additionally or alternatively, the device (800) may comprise a coupling mechanism configured to releasably couple the device (800) to the visualization device (850). For example, the coupling mechanism may comprise one or more of a snare, snap fitting, wire loop, grabber, forceps, combinations thereof, and the like.

Figure 8C:
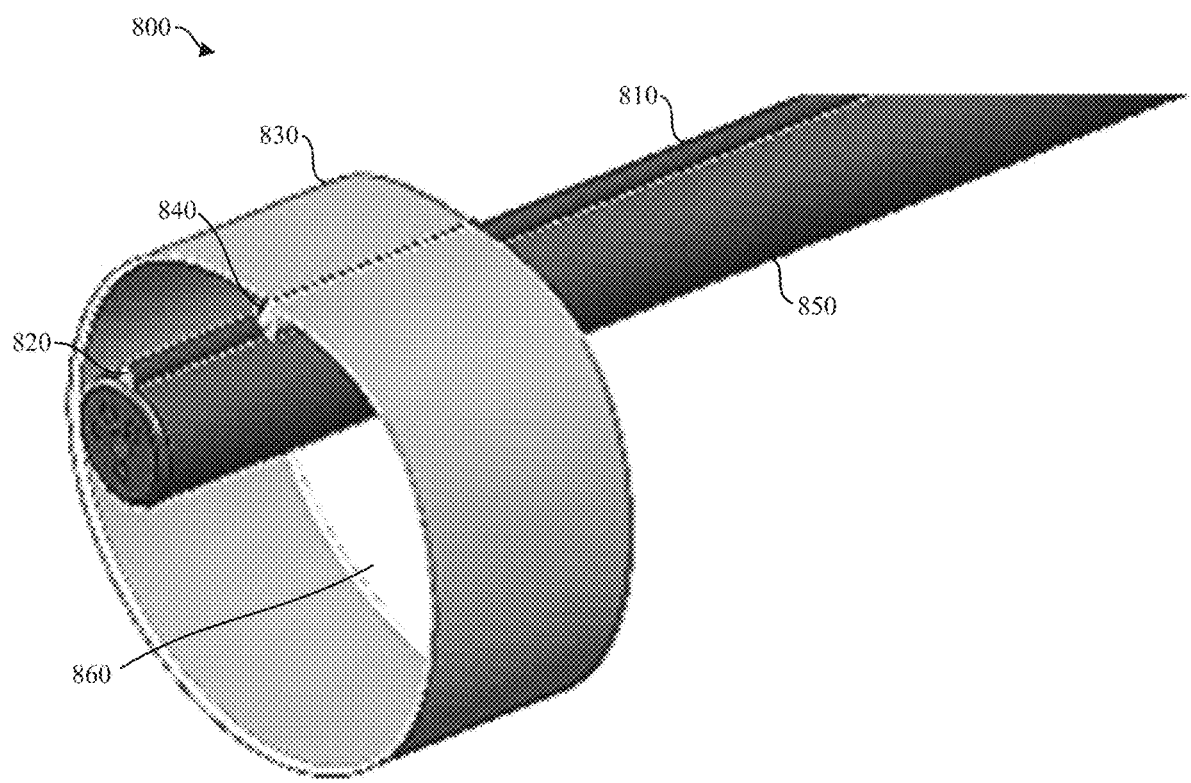
FIG. 8C is a perspective view of the visualization device and the pulsed electric field device shown in FIG. 8B in an unrolled configuration.

FIG. 8C is a perspective view of the visualization device (850) and the pulsed electric field device (800) in an unrolled (i.e., fully unrolled) configuration. For example, the third elongate body (850) may be configured to be translated relative to the first elongate body (810) in the unrolled configuration. The pulsed electric field device (800) and the expandable member (830) in FIG. 8C depicts an unrolled configuration configured for engagement with tissue such as an inner surface of a duodenum (not shown for the sake of clarity). In some variations, the second elongate body (820) (e.g., inner torsion member, rotatable member) may be configured to rotate relative to the first elongate body (810) to transition the expandable member (830) between the rolled configuration and the unrolled configuration. In some of these variations, the expandable member (830) may comprise a lumen (860) of at least 10 mm in diameter in the unrolled configuration.

Similar to the pulsed electric field device (500) of FIGS. 5A-5D, the expandable member (830) may comprise an inner end (e.g., innermost portion of roll) and an opposite outer end (e.g., outermost portion of roll) and the inner end may be coupled to the second elongate body (820) and the outer end may be coupled to the first elongate body (810). A direction of the rotation (e.g., clockwise, counter-clockwise) of the second elongate body (820) may determine the expansion or compression of the expandable member (830), as described in more detail above with respect to FIGS. 5A-5D.

In some variations, the connector (840) may couple the first elongate body (810) to the outer end of the expandable member (830). In some variations, the electrode array may be electrically coupled to the first elongate body (810) through the connector (840). For example, one or more leads may couple to the electrode array through the first elongate body (810) and connector (840). Additionally or alternatively, one or more leads may couple to the electrode array through the second elongate body (820). In some variations, the connector (840) may be composed of a rigid or semi-rigid material or a combination thereof such that the position of the outer end relative to the first elongate body (810) remains substantially the same between the rolled configuration and unrolled configuration.

Figure 9A:
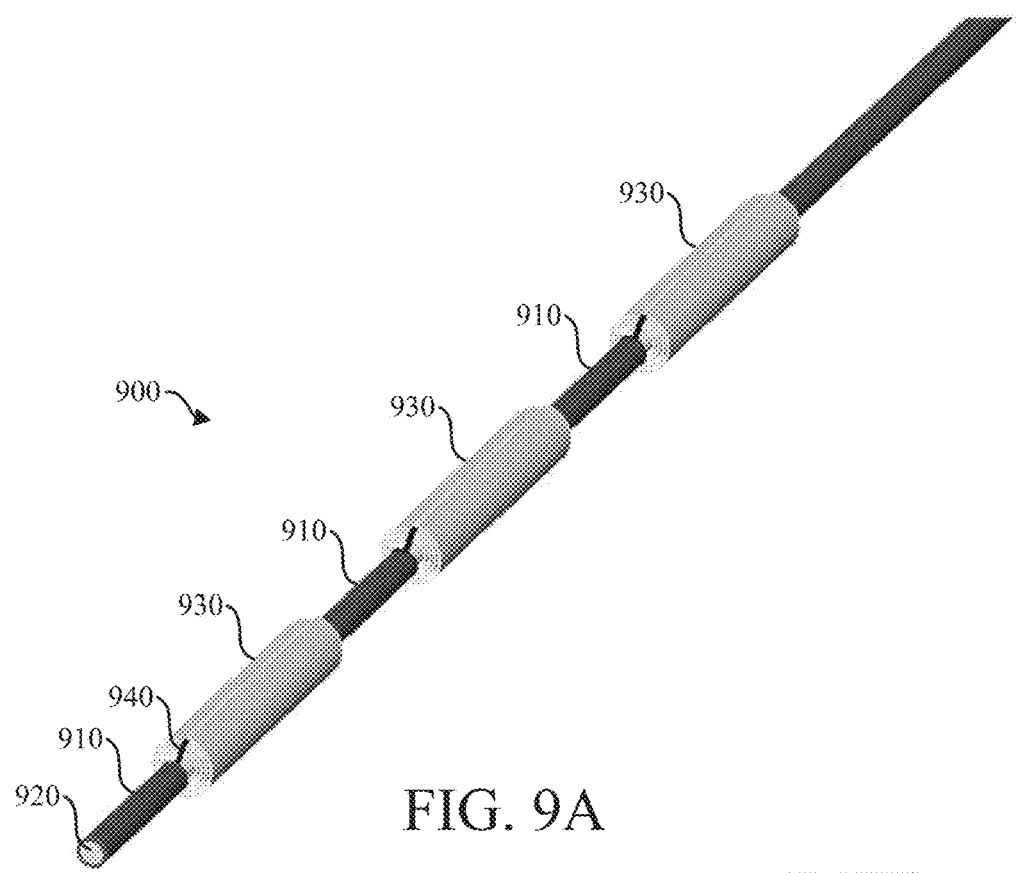
FIG. 9A is a perspective view of an illustrative variation of a pulsed electric field device in a rolled configuration.

FIG. 9A is a perspective view of a variation of a pulsed electric field device (900) comprising a plurality of expandable members in a rolled configuration. The device (900) in the rolled configuration may be configured to be advanced through one or more body cavities. In some variations, the pulsed electric field device (900) may comprise a plurality of outer elongate bodies (910) each comprising a lumen and a second elongate body (920) at least partially positioned within each lumen of the outer elongate bodies (910). A plurality of expandable members (930) may be disposed along a length of the device (900) and rolled about the second elongate body (920). For example, each expandable member (930) may comprise a plurality of turns about the second elongate body (920). The plurality of expandable members (930) may be coupled to a distal portion of the second elongate body (920). In some variations, each of the expandable members (930) (e.g., circuit substrate, flex circuit) may comprise an electrode array (not shown for the sake of clarity) which may comprise any of the electrode arrays described herein. The expandable members (930) may comprise the same electrode arrays or different electrode arrays. The electrode arrays may be disposed on an outer surface of each of the expandable members (930). In some variations, each expandable member (930) may be coupled to a respective outer elongate body (910) by a respective connector (940). Thus, in some variations, the pulsed electric field device (900) may comprise two, three, or more connectors (940), and one or more for each expandable member (930). A pulsed electric field device (900) comprising a plurality of expandable members (930) may allow a longer length of tissue to be treated at once, thereby reducing the need to reposition the device (900) multiple times for different portions of tissue. The length of each expandable member (930) and spacing between each expandable member (930) may be the same or different. Energy may be delivered to a plurality of the electrode arrays of the device (900) in any predetermined sequence. For example, the electrode arrays may simultaneously generate a pulsed or modulated electric field or in series with the same or different pulsed waveforms. That is, the electrode arrays may be operated independently.

Figure 9B:
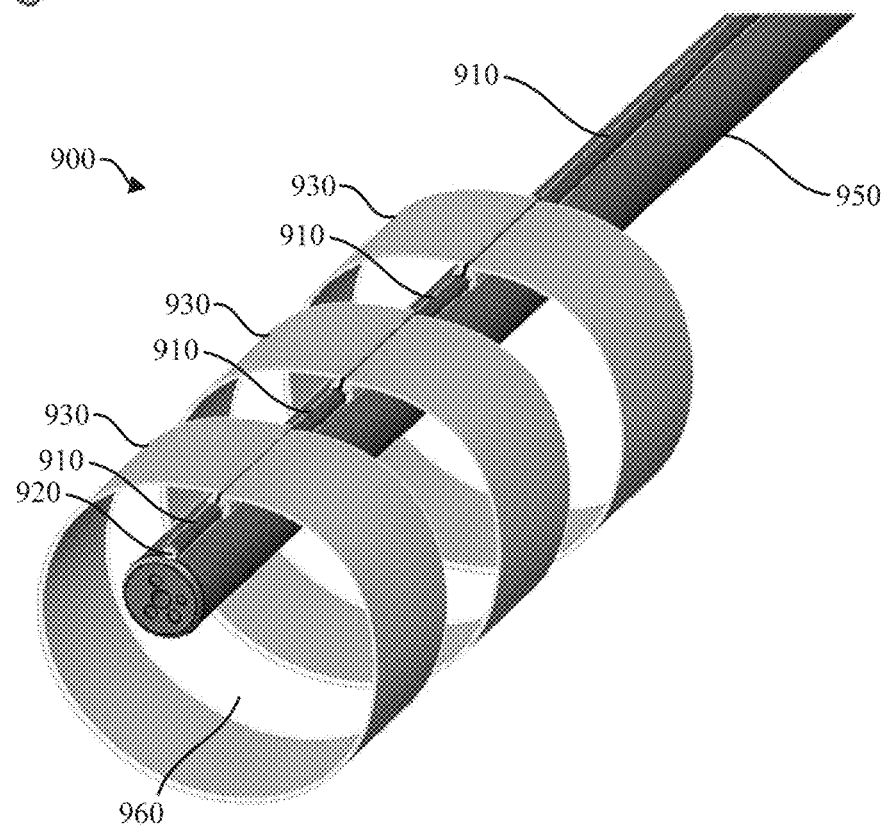
FIG. 9B is a perspective view of an illustrative variation of a visualization device and the pulsed electric field device shown in FIG. 9A in an unrolled configuration.

In some variations, a system comprising the pulsed electric field device (900) may further comprise a third elongate body (950) disposed within a lumen of the expandable member (930). In some of these variations, the third elongate body (950) may comprise a visualization device (e.g., an endoscope). FIG. 9B is a perspective view of a variation of a visualization device (950) (e.g., endoscope) and the pulsed electric field device (900). For example, the third elongate body (950) may be configured to be translated relative to the first elongate body (910) in the unrolled configuration. The pulsed electric field device (900) and expandable member (30) in FIG. 9B depicts an unrolled configuration configured for engagement with tissue such as an inner surface of a duodenum (not shown for the sake of clarity). In some variations, the inner elongate body (920) (e.g., inner torsion member, rotatable member) may be configured to rotate relative to the outer elongate bodies (910) to transition the plurality of expandable members (930) between the rolled configuration and the unrolled configuration. In some of these variations, the plurality of expandable members (930) may each comprise a lumen (960) of at least 10 mm in diameter in the unrolled configuration. In some variations, the visualization device (950) may be disposed within a respective lumen (960) of the plurality of expandable members (930).

Similar to the pulsed electric field device (500) of FIGS. 5A-5D, each of the expandable members (930) may comprise an inner end (e.g., innermost portion of roll) and an outer end (e.g., outermost portion of roll) where the inner end is coupled to the inner elongate body (920) and the outer end is coupled to at least one of the outer elongate bodies (910) and the electrode array. A direction of the rotation (e.g., clockwise, counter-clockwise) of the inner elongate body (920) may determine the expansion or compression of each of the plurality of expandable members (930), as described in more detail above with respective to FIGS. 5A-5D.

In some variations, the connectors (940) may couple the outer elongate body (910) to the outer end of a respective expandable member (930). In some variations, the electrode array of each expandable member may be electrically coupled to the outer elongate body (910) through the connectors (940). For example, one or more leads may couple to each electrode array through the outer elongate body (910) and the connector (940). Additionally or alternatively, one or more leads may couple to the electrode array through the inner elongate body (920). In some variations, each connector (940) may be composed of a rigid or semi-rigid material or a combination thereof such that the position of the outer end relative to the outer elongate body (910) remains substantially the same between the rolled configuration and unrolled configuration. In some variations, each electrode may comprise independent leads.

Figure 10A:
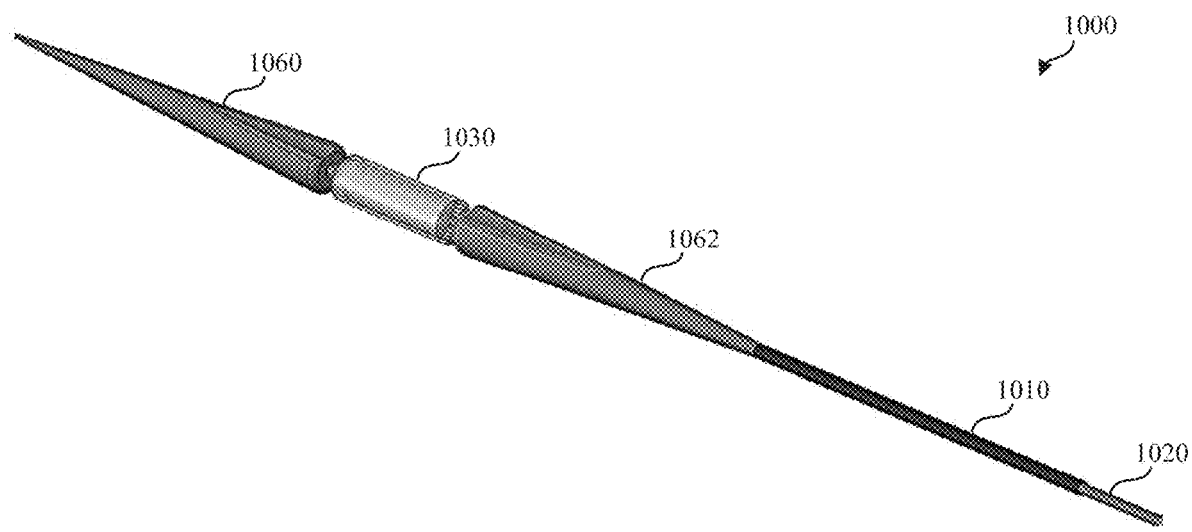
FIG. 10A is a perspective view of an illustrative variation of a pulsed electric field device in a rolled configuration.

In some variations, a pulsed electric field device may comprise one or more dilators configured to aid advancement of the device through one or more body cavities. FIG. 10A is a perspective view of a variation of a pulsed electric field device (1000) in a rolled configuration. As shown there, the pulsed electric field device (1000) may comprise a first elongate body (1010) comprising a lumen therethrough and a second elongate body (1020) at least partially positioned within the lumen of the first elongate body (1010). An expandable member (1030) may be rolled about the second elongate body (1020) as described in more detail herein. For example, the expandable member (1030) may comprise a plurality of turns about the second elongate body (1020). The expandable member (1030) may be coupled to a distal portion of the first elongate body (1010) and second elongate body (1020).

In some variations, the expandable member (1030) (e.g., circuit substrate, flex circuit) may comprise an electrode array (not shown for the sake of clarity) which may comprise any of the electrode arrays described herein. For example, the electrode array may be disposed on an outer surface of the expandable member (1030). In some variations, the pulsed electric field device (1000) may further comprise one or more dilators. For example, the pulsed electric field device (1000) may comprise a distal dilator (1060) and a proximal dilator (1062), each coupled to one of the first elongate body (1010) and the second elongate body (1020). The dilators (1060, 1062) may assist in smoothly advancing and/or retracting the pulsed electric field device (1000) through one or more body cavities and may assist in preventing the expandable member from catching on tissue. For example, dilators (1060, 1062) may be configured to protect an edge of the expandable member (1030) from contacting tissue as it is being advanced through a body cavity. One or more of the dilators may comprise a recess (1064). In some variations, the recces (1064) may have a shape configured to facilitate the mating or coupling with another elongate member such as a visualization device (e.g., endoscope). The expandable member (1030) may be disposed between the distal dilator (1060) and the proximal dilator (1062). The length and taper of the dilators of the device may be the same or different. For example, a distal dilator (1060) may have a steeper taper than the proximal dilator (1062). In some variations, the pulsed electric field device (1000) may comprise just a single distal dilator (1060).

Figure 10B:
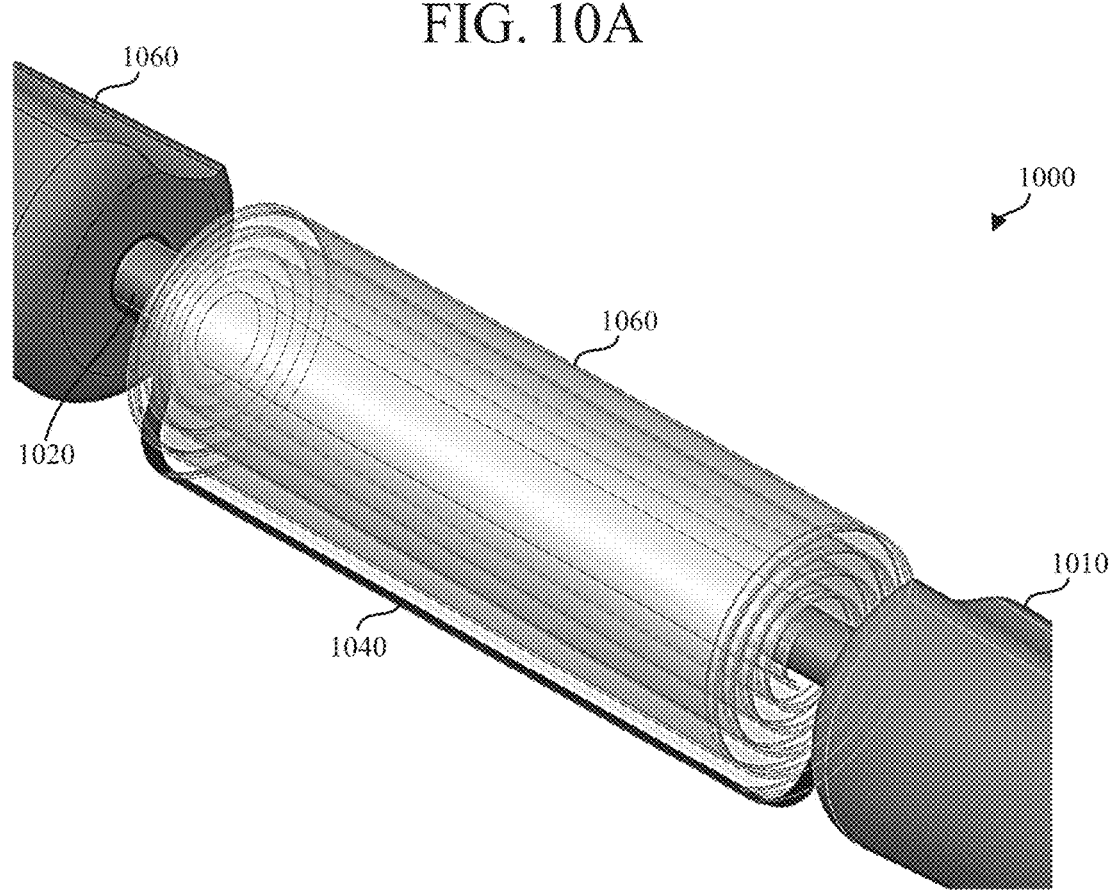
FIG. 10B is a detailed perspective view of the pulsed electric field device shown in FIG. 10A.

FIG. 10B is a detailed perspective view of the pulsed electric field device (1000) with the expandable member (1030) in the rolled configuration. In some variations, the pulsed electric field device (1000) may further comprise a connector (1040), which may couple one or more of the first elongate body (1010), the distal dilator (1060), and the proximal dilator (1062) to the expandable member (1030). For example, the connector (1040) may couple the first elongate body (1010) to the outer end of the expandable member (1030). In some variations, the electrode array may be electrically coupled to the first elongate body (1010) through the connector (1040). For example, one or more leads may couple to the electrode array through the first elongate body (1010) and the connector (1040). Additionally or alternatively, one or more leads may couple to the electrode array through the second elongate body (1020). In some variations, the connector (1040) may be composed of a rigid or semi-rigid material, or a combination thereof, such that the position of the outer end relative to the first elongate body (1010) remains substantially the same between the rolled configuration and unrolled configuration. In some variations, the distal dilator (1060) and proximal dilator (1062) are attached to the first elongate body (1010). In some variations, the maximum diameter of the dilator (1060, 1062) may be about the same as a diameter of the expandable member in the rolled configuration. For example, the dilator (1060, 1062) may have a maximum diameter of between about 10 mm and about 15 mm, including all ranges and sub-values in-between where the expandable member (1030) in the rolled configuration may have a diameter between about 8 mm and about 15 mm, including all ranges and sub-values in-between.

Figure 10C:
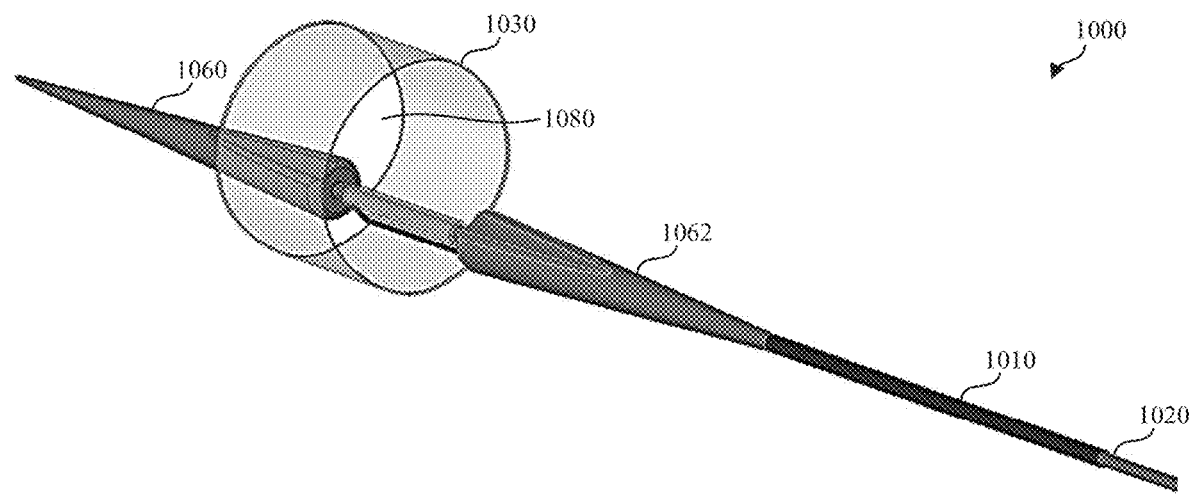
FIGS. 10C and 10D are perspective views of an illustrative variation of a pulsed electric field device in an unrolled configuration.
Figure 10D:
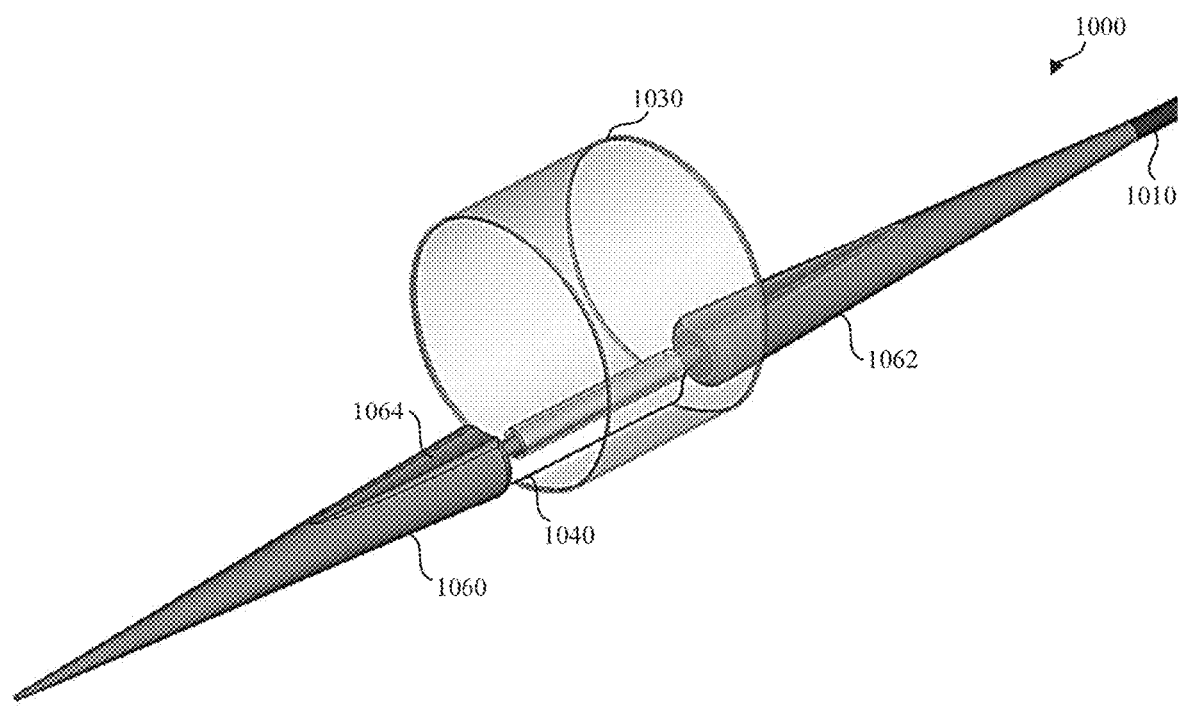
Figure 10E:
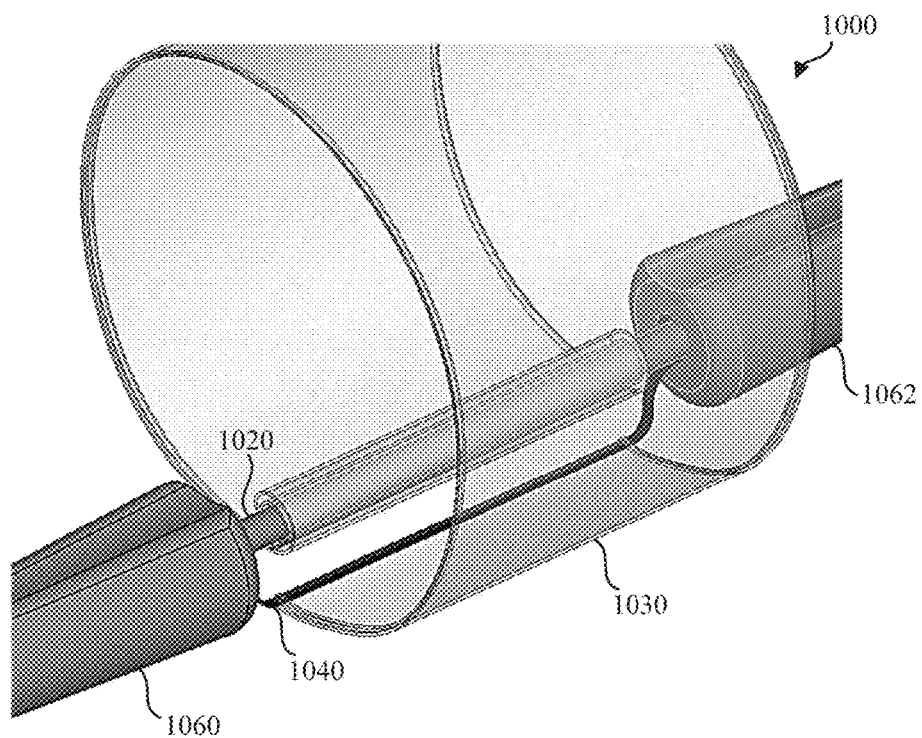
FIG. 10E is a detailed perspective view of the pulsed electric field device shown in FIG. 10D.

FIGS. 10C, 10D, and 10E are perspective views of the pulsed electric field device (1000) with the expandable member (1030) in an unrolled configuration. In the unrolled configuration, the expandable member (1030) may be configured for engagement with tissue, such as an inner surface of a duodenum (not shown for the sake of clarity). In some variations, the second elongate body (1020) (e.g., inner torsion member, rotatable member) may be configured to rotate relative to the first elongate body (1010) to transition the expandable member (1030) between the rolled configuration and the unrolled configuration. For example, the second elongate body (1020) may be rotatably positioned within a lumen of the first elongate body (1010). In some of these variations, the expandable member (1030) may comprise a lumen (1080), the diameter of which may enlarge between the rolled and unrolled configurations. In some variations, the diameter of the lumen of the expandable member may be at least 8 mm in the unrolled configuration. In some variations, the expandable member (1030) in the unrolled configuration may have a diameter between about 10 mm and about 50 mm, and between about 15 mm and about 50 mm, including all ranges and sub-values in-between.

Figure 11:
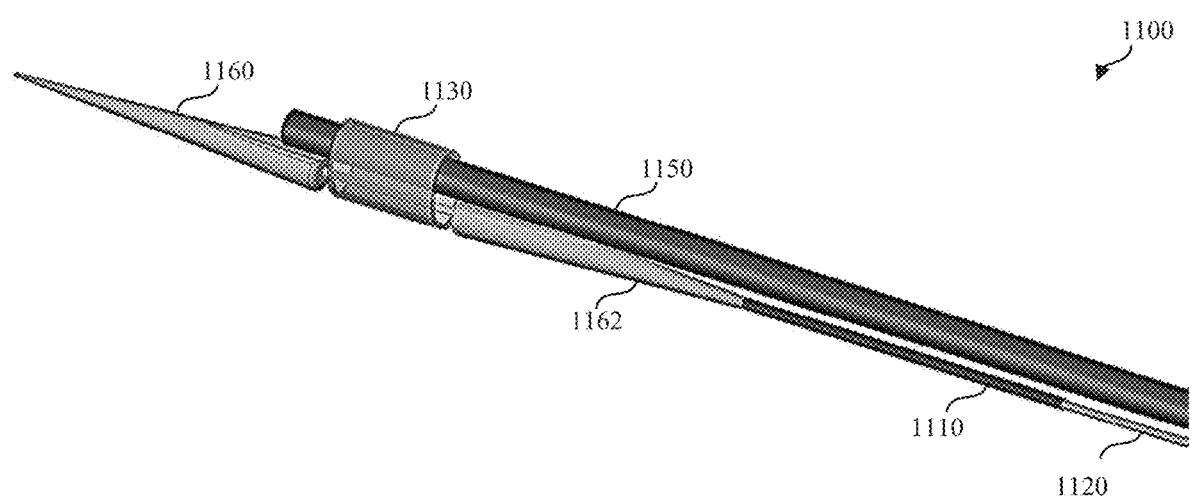
FIG. 11 is a perspective view of an illustrative variation of a visualization device and a pulsed electric field device in a partially unrolled configuration.

In some variations, a system comprising the device may further comprise a third elongate body disposed within the lumen of the expandable member. In some of these variations, the third elongate body comprises a visualization device (e.g., an endoscope). FIG. 11 is a perspective view of a variation of a visualization device (1150) (e.g., endoscope) and a pulsed electric field device (1100). The pulsed electric field device (1100) may comprise a first elongate body (1110) comprising a lumen therethrough and a second elongate body (1120) at least partially positioned within the lumen of the first elongate body (1110). An expandable member (1130) may be rolled about the second elongate body (1120). In some variations, the pulsed electric field device (1100) may further comprise one or more dilators. For example, the pulsed electric field device (1100) may comprise a distal dilator (1160) and a proximal dilator (1162), each coupled to one of the first elongate body (1110) and the second elongate body (1120). In FIG. 11, the expandable member (1130) may transition to a partially unrolled configuration sufficient for the visualization device (1150) to be disposed within a lumen of the expandable member (1130). For example, the device (1100) may be configured to hold the visualization device (1150) in place relative to the device (1100). In this manner, the pulsed electric field device (1100) and visualization device (1150) may be advanced together through one or more body cavities.

Figure 12A:
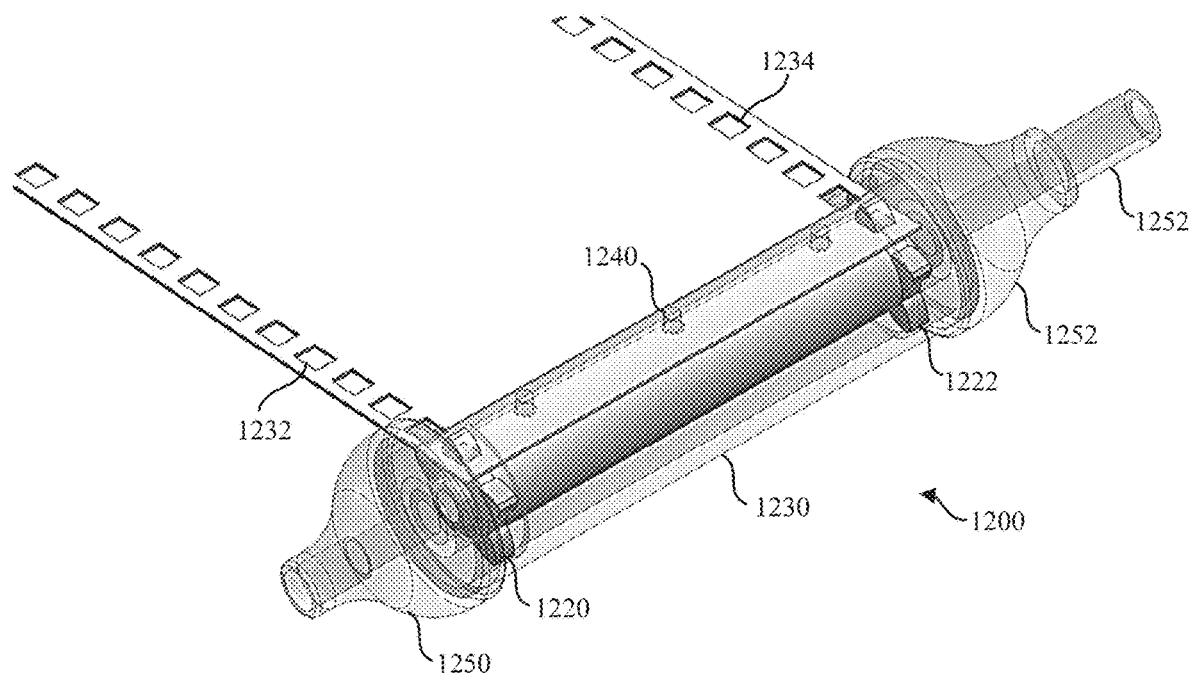
FIG. 12A is a perspective view of an illustrative variation of a pulsed electric field device.
Figure 12B:
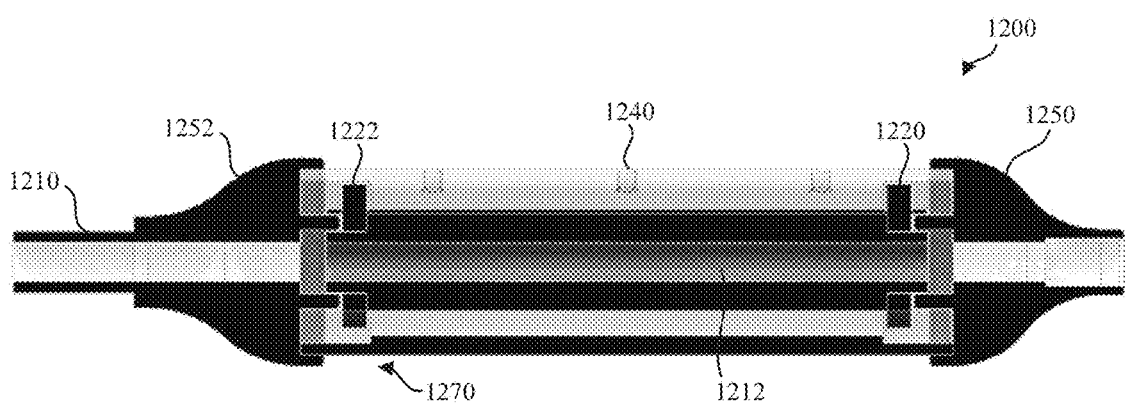
FIG. 12B is a cross-sectional side view of the pulsed electric field device shown in FIG. 12A.

In some variations, a rolled expandable member of a pulsed electric field device may transition configurations by using an actuator that allows improved control over the expansion and/or compression of the expandable member. For example, the actuator may comprise a set of gears and/or friction rollers (e.g., knurled friction rollers), and tracks configured for consistent transmission of rotational torque from the rotating elongate body to the expandable member. FIG. 12A is a perspective view and FIG. 12B is a cross-sectional side view of a variation of a pulsed electric field device (1200) comprising an actuator (1270). As shown there, the pulsed electric field device (1200) may comprise a first elongate body (1210) comprising a lumen therethrough and a second elongate body (1212) at least partially positioned within the lumen of the first elongate body (1210), and an actuator (1270). The pulsed electric field device (1200) may further comprise an expandable member (1230) rolled about the second elongate body (1212), as described in more detail herein, and operably coupled to the actuator (1270). In some variations, the pulsed electric field device (1200) may further comprise one or more dilators, for example, a distal dilator (1250) and a proximal dilator (1252), coupled to one of the first elongate body (1210) and the second elongate body (1212). In some variations, one or more of the dilators (1250, 1252) may have a sigmoidal shape. The actuator (1270) may be disposed between the distal dilator (1250) and the proximal dilator (1252). The expandable member (1230) may be disposed between the distal dilator (1250) and the proximal dilator (1252). The dilators (1250, 1252) may allow the pulsed electric field device (1200) to be smoothly translated through one or more body cavities, as described in more detail herein.

Figure 12C:
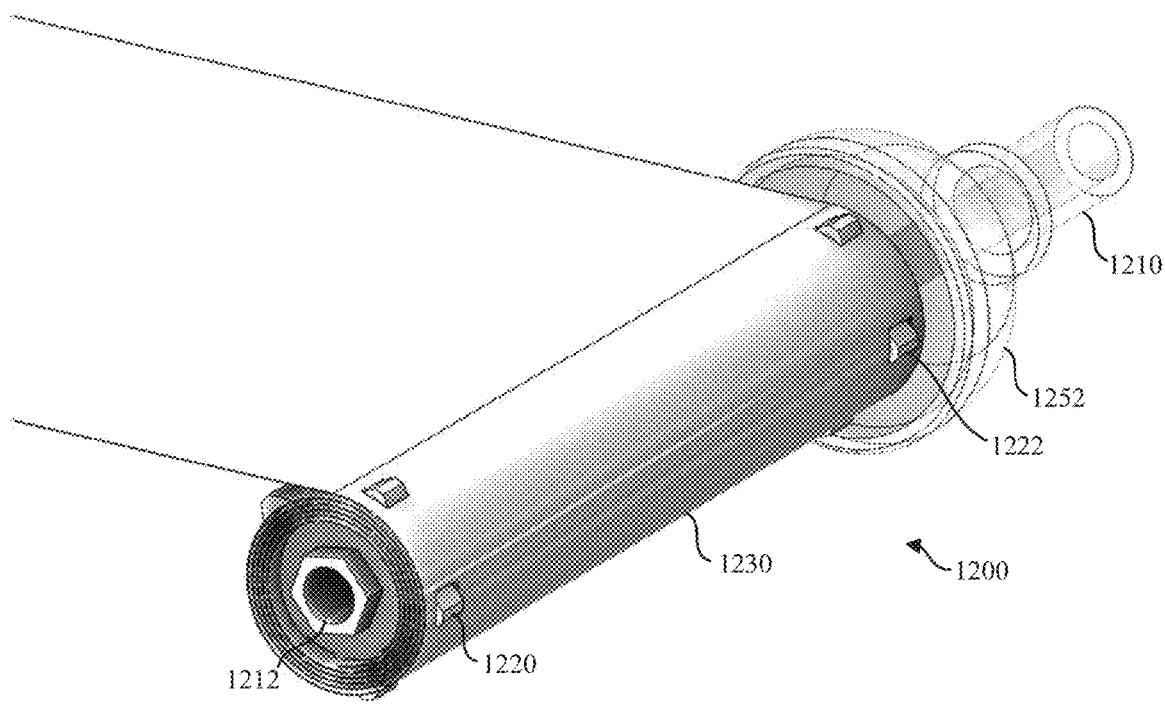
FIG. 12C is a detailed cutaway perspective view of the pulsed electric field device shown in FIG. 12A.

As mentioned above, the pulsed electric field device (1200) may comprise an actuator operably coupled to the expandable member (1230) and configured to assist in expanding (e.g., unrolling) and compressing (e.g., rolling) the expandable member (1230). In some variations, the actuator may comprise one or more gears, which may interface with one or more tracks formed in the expandable member (1230). For example, in the variation depicted in FIGS. 12A-12C, the actuator (1270) may comprise a first gear (1220) and a second gear (1222), each of which may be coupled to the second elongate body (1212). The expandable member (1230) may further comprise a first track (1232) on a first side thereof and a second track (1234) on a second side thereof. The first track (1232) may be operably coupled to the first gear (1220) and the second track (1234) may be operably coupled to the second gear (1222). In some of these variations, the first and/or second tracks (1232, 1234) may comprise a plurality of spaced apart openings in the expandable member (1230) configured to receive the teeth of the respective gears (1220, 1222). The expandable member (1230) may be coupled to the second elongate body (1212) via the gears (1220, 1222). FIG. 12C is a detailed cutaway perspective view of the pulsed electric field device (1200) depicting engagement of the teeth of the gears (1220, 1222) with the respective tracks (1232, 1234) of the expandable member (1230). Additionally or alternatively, the actuator may comprise a metal roller comprising a plurality of teeth textures configured to directly press against the expandable member (1230). The metal roller may be configured to operate with a drum plotter or a film canister type of mechanism. Similar to the pulsed electric field device (500) of FIGS. 5A-5D, the expandable member (1230) may comprise an inner end (e.g., innermost portion of roll) and an outer end (e.g., outermost portion of roll) where the inner end is coupled to the second elongate body (1212) and the outer end is coupled to the first elongate body (1210). A direction of the rotation (e.g., clockwise, counter-clockwise) of the second elongate body (1212) may determine the expansion or compression of the expandable member (1230). In some variations, a connector (1240) may couple the second elongate body (1212) to the inner end of the expandable member (1230). An outer end of the expandable member (1230) may be coupled to one or more of the dilators (1220, 1222) and the first elongate body (1210). However, FIG. 12A shows an unattached outer end of the expandable member (1230) for the sake of illustration. In some variations, the expandable member (1230) in the rolled configuration may have a diameter between about 6 mm and about 15 mm, including all ranges and sub-values in-between. The expandable member (1230) in the rolled configuration may comprise one or more turns. In some variations, the expandable member (1230) in the expanded configuration may have a diameter between about 10 mm and about 50 mm, including all ranges and sub-values in-between.

In some variations, the electrode array may be electrically coupled to the second elongate body (1212) through the connector (1240). For example, one or more leads may couple to the electrode array through the second elongate body (1212) and connector (1240). Additionally or alternatively, one or more leads may couple to the electrode array through the first elongate body (1210).

Figure 13A:
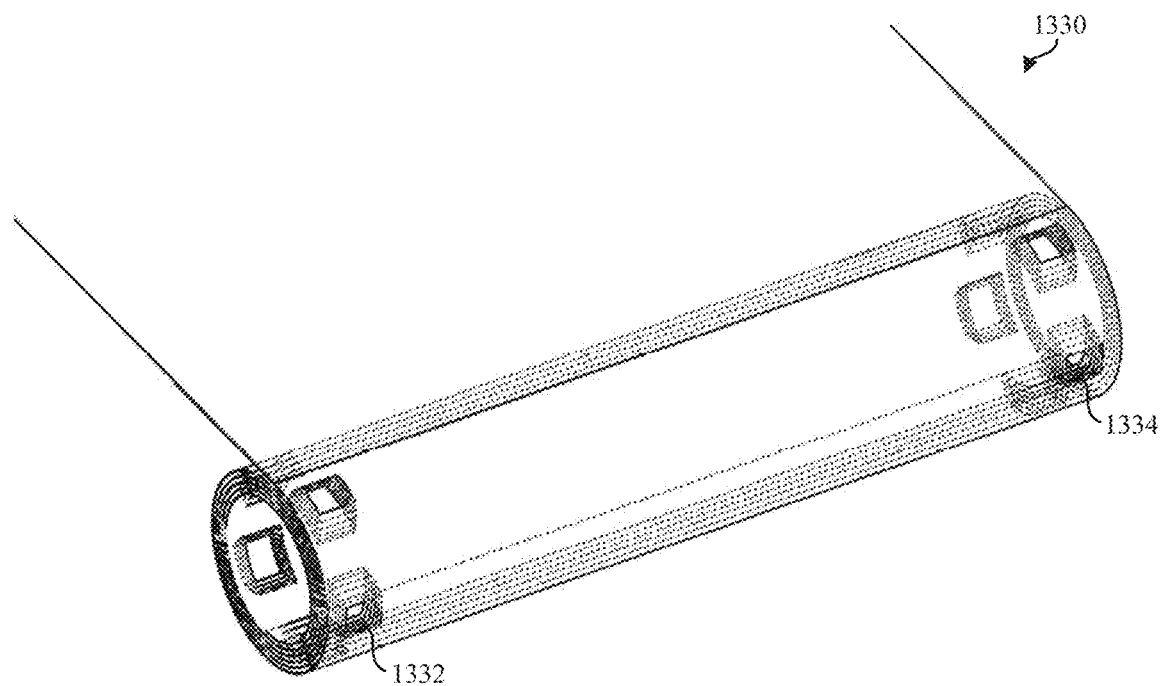
FIG. 13A is a perspective view of an illustrative variation of an expandable member.

FIG. 13A is a perspective view of a variation of an expandable member (1330) of the pulsed electric field device (1300) depicting the expandable member (1330) in the compressed configuration and corresponding alignment of the openings of the tracks (1332, 1334). The openings of the tracks (1332, 1334) may be sized and positioned to substantially overlap with each other when the expandable member (1330) is in the compressed configuration such that the teeth of the gears (e.g., gears (1220, 1222)) may pass through and be positioned within a plurality of the openings in a track (1332, 1334), as will be described in more detail herein. In some variations, the size and spacing of the tracks (1332, 1334) may change along a length of the expandable member (1330) to aid smooth rolling and unrolling.

Figure 13B:
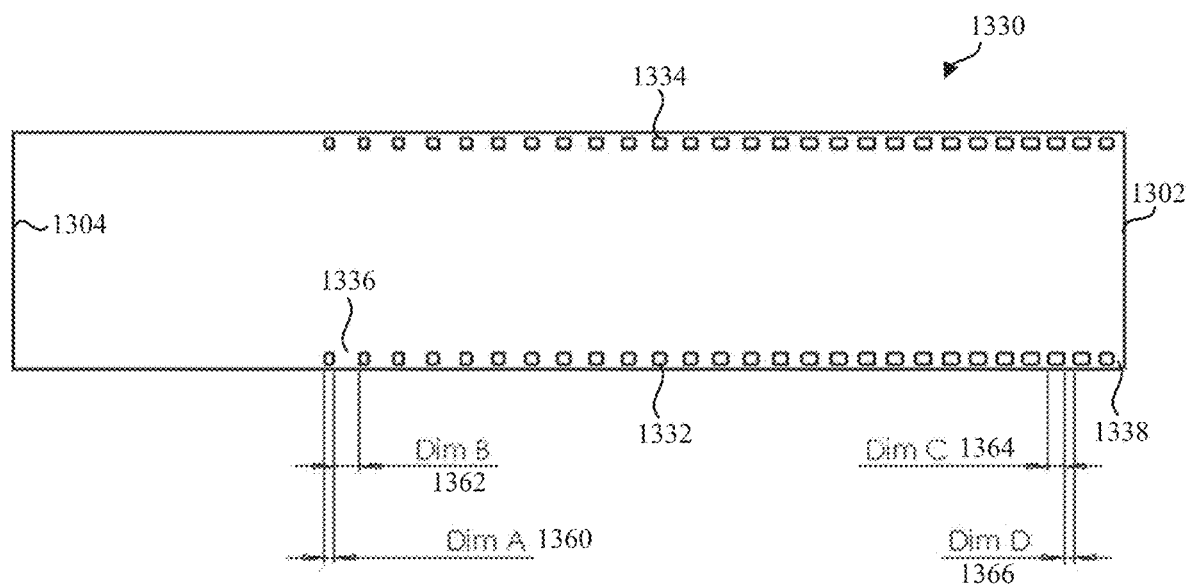
FIG. 13B is a plan view of the expandable member shown in FIG. 13A in an unrolled configuration.

FIG. 13B is a plan view of the expandable member (1330) and the tracks (1332, 1334) in an unrolled configuration. In some variations, a distance between adjacent openings (e.g., tracks) (1362, 1366) may change along a length of the expandable member (1330). In particular, a distance (1362, 1366) between adjacent openings may increase along a longitudinal axis of the expandable member (1330) from a first end (1302) of the expandable member to a second end (1304) of the expandable member. For example, Dim D (1366) adjacent to or near the first end (1302), or in a first portion of the expandable member (1330) at the first end (first end portion), may be smaller than Dim B (1362) adjacent to or near the second end (1304), or in a second portion of the expandable member (1330) at the second end (second end portion). Conversely, a length of each opening (1360, 1364) may decrease along a longitudinal axis of the expandable member (1330) from the first end (1302) to the second end (1304). For example, a length of Dim C (1364) adjacent to or near the first end (1302) or in the first end portion may be greater than a length of Dim A (1360) adjacent to or near the second end (1304) or in the second end portion. This spacing and opening geometry may allow the expandable member to form a more precise and compact shape about a gear in the rolled configuration, as shown in FIG. 13C described in more detail below.

Figure 13C:
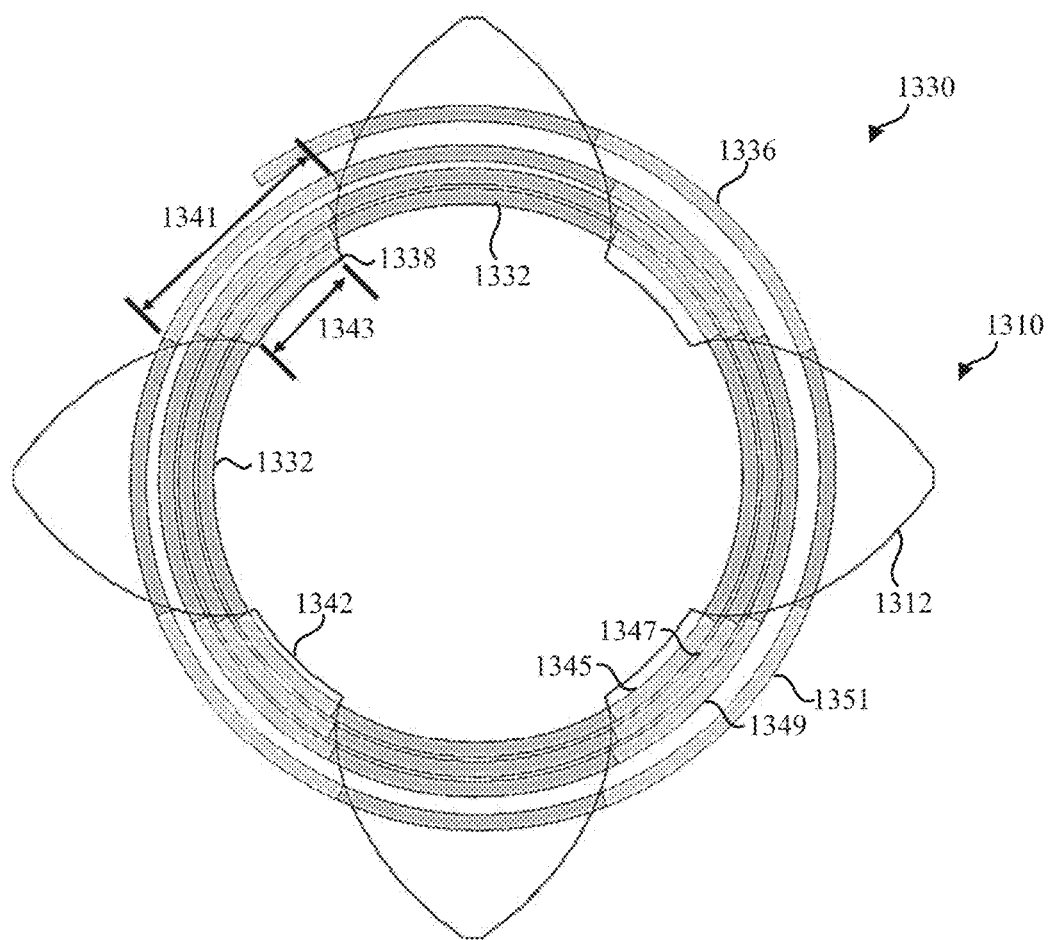
FIG. 13C is a cross-sectional view of an illustrative variation of an expandable member in a rolled configuration and gear.

An expandable member (1330) comprising variable length openings and distances between openings may allow for a more compact rolled configuration around a gear comprising a gear body (1342) and curved or angled teeth extending therefrom, as shown FIG. 13C. FIG. 13C is an illustrative variation of an expandable member (1330) (such as the expandable member shown in FIG. 13B) in a rolled configuration. The expandable member (1330) is depicted rolled around a gear (1310) comprising one or more teeth (1312). While depicted in FIG. 13C as a cylindrical gear (e.g., having a cylindrical body), the gear (1310) need not be and the gear body (1342) may have any suitable cross-sectional shape, such as, for example, elliptical, square, rectangular, and the like. Each tooth (1312) may comprise a predetermined tapered (e.g., sloped, curved) shape configured to facilitate equal load transfer between openings of the tracks (1332, 1334). The variable spacing and opening geometry of the expandable member (1330) may facilitate precise rolling of the expandable member about the gear (1310). In the rolled configuration shown in FIG. 13C, the expandable member (1330) may comprise one or more overlapping layers (e.g., turns). For example, in a radial outward direction from a radial center of the rolled expandable member (1330), the expandable member (1330) may comprise a first layer (1345) (inner most layer), a second layer (1347), third layer (1349), and a fourth layer (1351) (outer most layer). A number of layers of the expandable member (1330) in a rolled configuration may be based at least on a length and thickness of the expandable member, a diameter of a gear, a number of teeth, and the like. A distance (1341, 1343) (e.g., spiral pitch) between adjacent openings (e.g., tracks) may increase from the first layer (1345) to the fourth layer (1351) (e.g., in a radial outward direction). A length (1341) of an opening (1332) may decrease from the first layer (1345) to the fourth layer (1351) (e.g., in a radial outward direction). This may allow the expandable member (1330) to be rolled around the gear (1310) with minimal spacing between layers. Therefore, the openings the tracks (1332, 1334) may fit smoothly onto and/or around the gear teeth (1312), while the portions of the expandable member (1330) between the tracks (1332, 1334) may fit smoothly around the gear body between the gear teeth (1312), which may reduce interference, binding, and bunching of the expandable member (1330) in the rolled configuration.

In some variations, the expandable member (1330) (e.g., circuit substrate, flex circuit) may comprise an electrode array (not shown for the sake of clarity) which may comprise any of the electrode arrays described herein. For example, the electrode array may be disposed on an outer surface of the expandable member (1330).

In some variations, a distance (1341, 1343) (e.g., spiral pitch) between the openings of the tracks (1332, 1334) may be a function of a thickness of the expandable member (1330) and the number of turns (e.g., layers) of the expandable member (1330). For example, the expandable member (1330) may comprise one or more electrodes (e.g., electrode pad) of an electrode array (not shown in FIG. 13A-13C) that may increase a thickness of those portions of the expandable member (1330). The length of an opening (1332, 1334) and/or distance between adjacent openings may increase with increasing thickness of the expandable member (1330).

In some variations, the second elongate body (1312) (e.g., inner torsion member, rotatable member) may be configured to rotate relative to the first elongate body (1310) to transition the expandable member (1330) between the rolled configuration and the unrolled configuration. In some of these variations, the expandable member (1330) may comprise a lumen of at least 10 mm in diameter in the unrolled configuration.

Figure 14A:
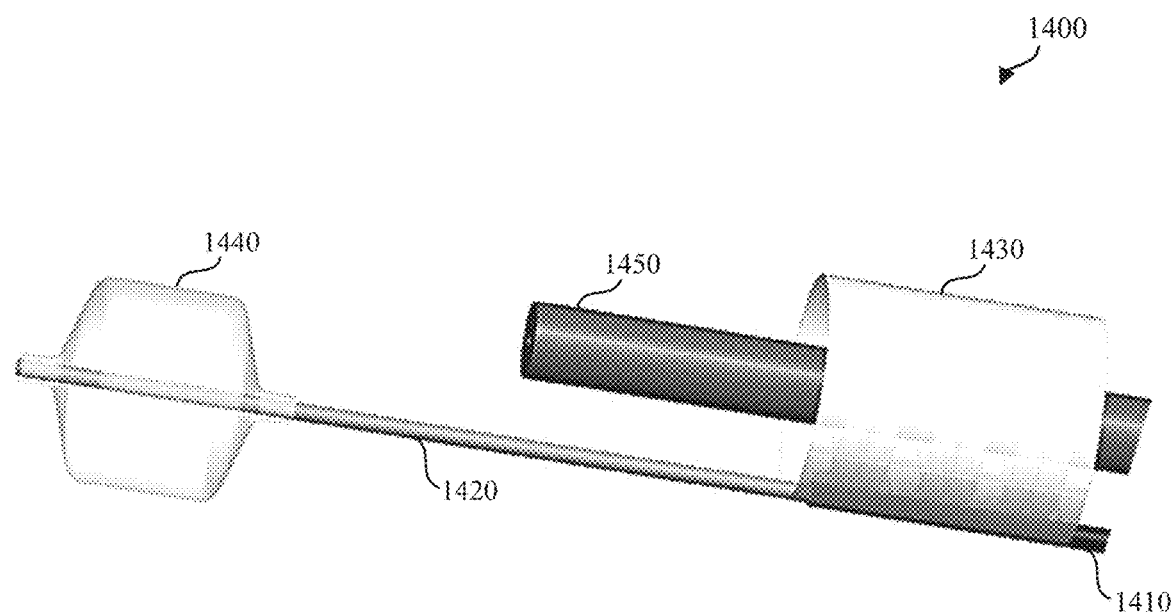
FIG. 14A is a perspective view of an illustrative variation of a pulsed electric field device and visualization device.
Figure 14B:
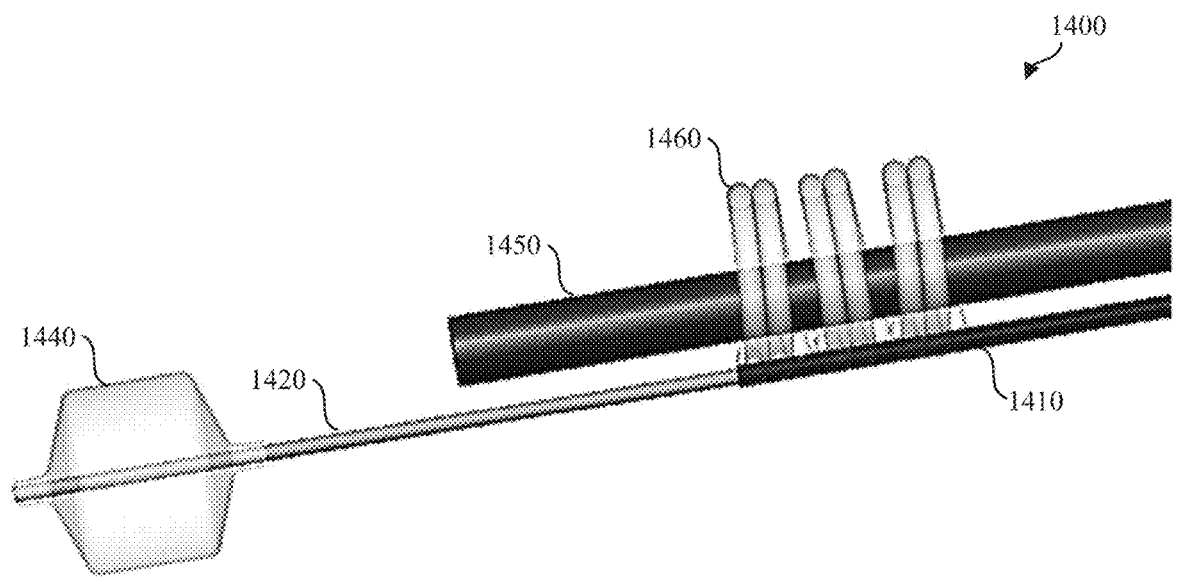
FIG. 14B is a cutaway perspective view of the pulsed electric field device and visualization device shown in FIG. 14A.

FIGS. 14-29B illustrate additional pulsed electric field device variations including expandable members comprising inflatable members (e.g., balloons). FIG. 14A is a perspective view of a variation of a pulsed electric field device (1400) and a visualization device (1450). FIG. 14B is a cutaway perspective view of the pulsed electric field device (1400) and the visualization device (1450) without the base layer (1430) and electrode array. In some variations, the pulsed electric field device (1400) may comprise a first elongate body (1410) comprising a lumen and a second elongate body (1420) at least partially positioned within the lumen of the first elongate body (1410). A plurality of expandable members (1460) may be coupled to the first elongate body (1410). For example, a plurality of torus-shaped or spiral tube-shaped expandable members (1460) may be coupled to the first elongate body (1410) in parallel. In some variations, the expandable members (1460) may be helical, spiral, and/or serpentine shaped. For example, one or more expandable members (1460) may comprise one or more spirals or coils. In these variations, the expandable member need not comprise an inner end or outer end coupled to respective elongate bodies. In some variations, the expandable member (1460) may comprise an inflatable member.

In some variations, the expandable members (1460) may comprise a base layer (1430) (e.g., circuit substrate, flex circuit) which may couple to any of the electrode arrays described herein. For example, the electrode array (1430) may be disposed on an outer surface of the expandable members (1460). A second expandable member (1440) may optionally be coupled to the second elongate body (1420) and configured to dilate tissue and/or improve visualization of tissue in a body cavity. For example, the second expandable member (1440) may be coupled concentrically to a distal end of the second elongate body (1420). That is, a central longitudinal axis of the second expandable member (1440) may be coupled to a longitudinal axis of the second elongate body (1420). In some variations, the second expandable member (1440) may be an inflatable member such as a balloon.

FIGS. 14A and 14B depict the pulsed electric field device (1400) and the plurality of expandable members (1460) in an expanded or inflated configuration in which the expandable members (1460) are configured for engagement with tissue such as an inner surface of a duodenum (not shown for the sake of clarity). In some variations, the expandable members (1460) may comprise a lumen of at least 10 mm in diameter in the inflated configuration. In some variations, the plurality of expandable members (1460) may be configured to transition to a configuration between the compressed and expanded configurations, such as a partially or semi-expanded configuration. In some variations, the expandable member (1600) in the expanded configuration may have a diameter between about 10 mm and about 50 mm, and between about 15 mm and about 50 mm, including all ranges and sub-values in-between. The visualization device (1440) may be disposed within the lumen of the expandable members (1460) in the expanded configuration. In some variations, at least a proximal end and a distal end of the second expandable member (1440) may be transparent, thereby allowing the visualization device (1450) to image through the second expandable member (1440).

Figure 15A:
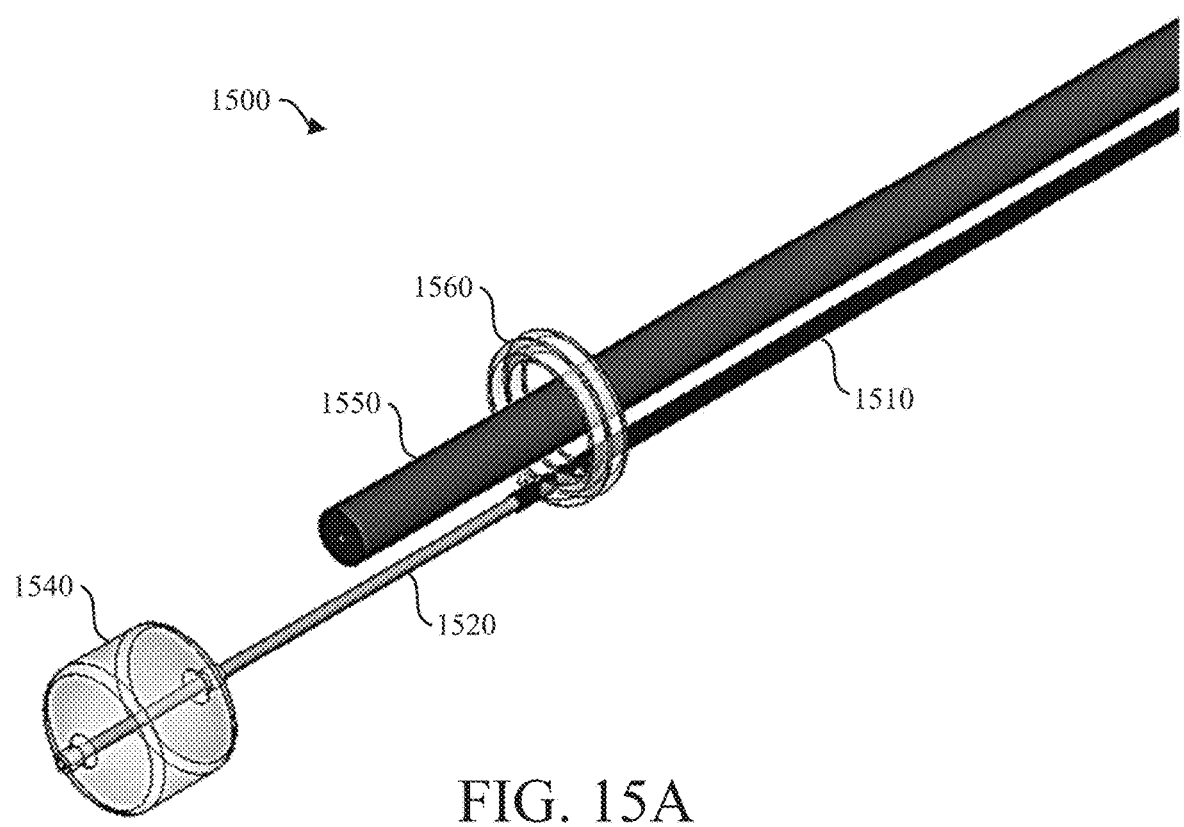
FIGS. 15A and 15B are cutaway perspective views of illustrative variations of a pulsed electric field device and visualization device.
Figure 15B:
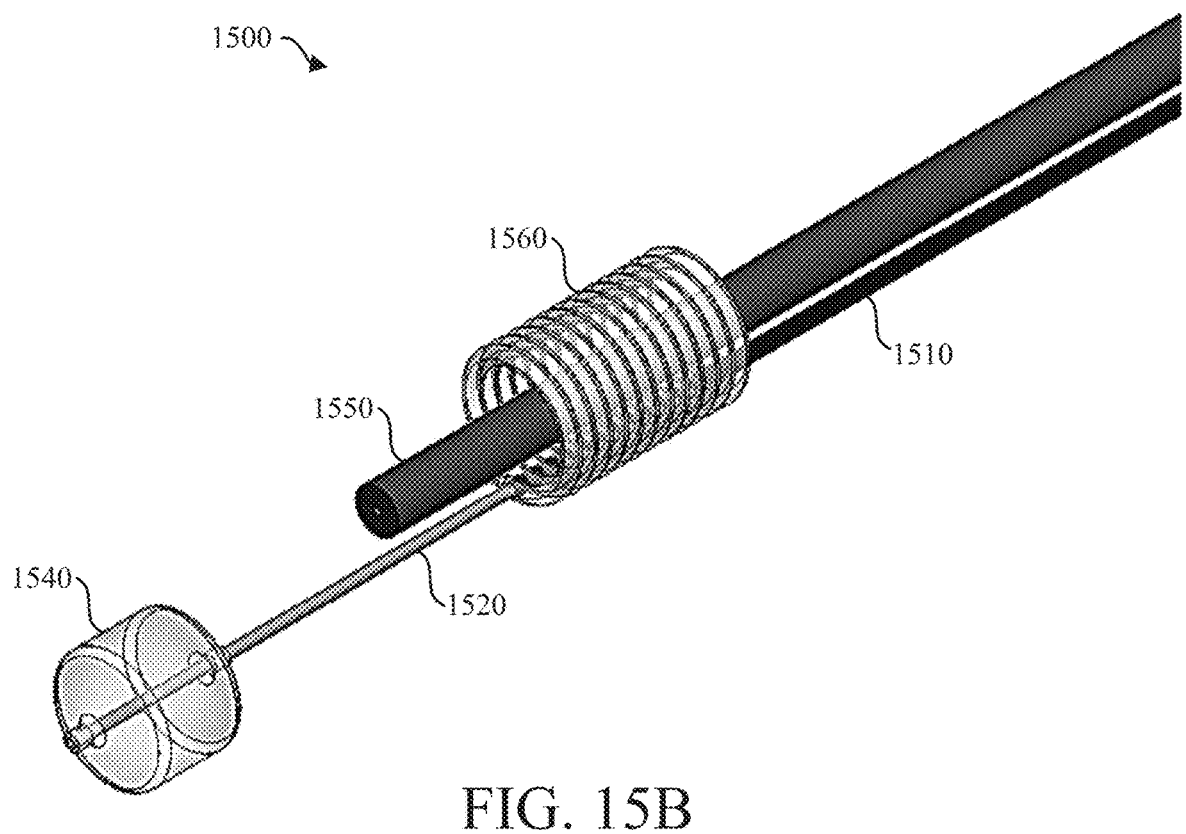

FIGS. 15A and 15B are cutaway perspective views of variations of a pulsed electric field device (1500) and a visualization device (1550) similar to that described for FIGS. 14A and 14B. As shown there, the pulsed electric field device (1500) may comprise a first elongate body (1510)

comprising a lumen therethrough and a second elongate body (1520) at least partially positioned within the lumen of the first elongate body (1510). A plurality of expandable members (1560) may be coupled to the first elongate body (1510). For example, a plurality of torus-shaped expandable members (1560) may be coupled in parallel to the first elongate body (1510).

In some variations, the expandable member (1560) may comprise an electrode array (not shown for the sake of clarity) that may comprise any of the electrode arrays described herein. For example, the electrode array may be disposed on or coupled to an outer surface of the expandable members (1560). A second expandable member (1540) may be coupled to the second elongate body (1520). For example, the second expandable member (1540) may be coupled concentrically to a distal end of the second elongate body (1520). That is, a central longitudinal axis of the second expandable member (1540) may be coupled to a longitudinal axis of the second elongate body (1520). In some variations, the second expandable member (1540) may be an inflatable member such as a balloon. The visualization device (1540) may be disposed within the lumen of the expandable members (1560) in the expanded configuration. In some variations, at least a proximal end and a distal end of the second expandable member (1540) may be transparent, thereby allowing the visualization device (1550) to image through the second expandable member (1540).

Figure 16:
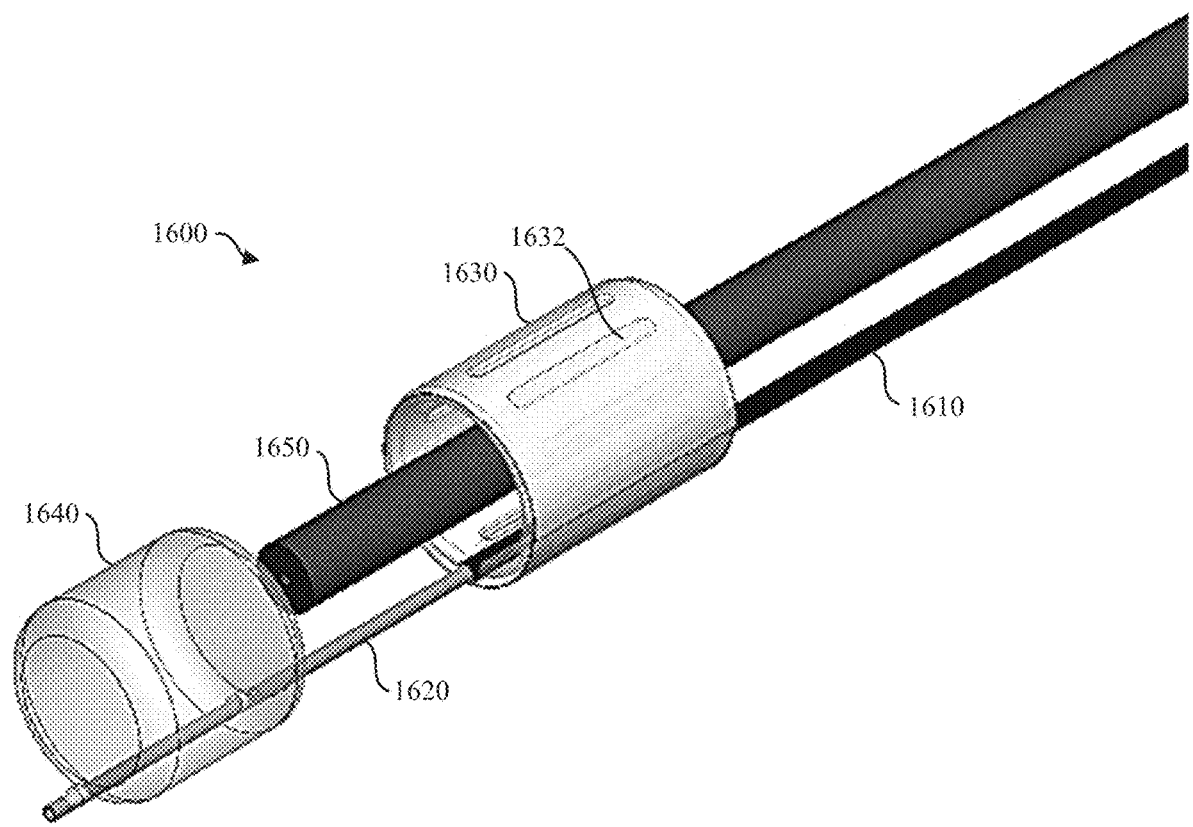
FIG. 16 is a perspective view of an illustrative variation of a pulsed electric field device and visualization device.

FIG. 16 is a perspective view of a variation of a pulsed electric field device (1600) and a visualization device (1650). In some variations, the pulsed electric field device (1600) may comprise a first elongate body (1610) comprising a lumen therethrough and a second elongate body (1620) at least partially positioned within the lumen of the first elongate body (1610). An expandable member (1630) may be coupled to the first elongate body (1610). In some variations, the expandable member (1630) may comprise an electrode array (not shown for the sake of clarity) that may comprise any of the electrode arrays described herein. For example, the electrode array may be disposed on or coupled to an outer surface of the expandable members (1630). The expandable member (1630) may comprise a lumen and a plurality of elongate recesses (1632) formed by longitudinally coupling an outer sidewall of the expandable member (1630) to an inner sidewall of the expandable member (1630). For example, the elongate recess (1632) may be pleated to control an inner diameter and outer diameter of the expandable member (1630). This configuration may aid the expansion of the expandable member (1630) comprising the electrode array (not shown for the sake of clarity). For example, one or more electrodes may be disposed on the expandable member (1630) between elongate recesses (1632).

A second expandable member (1640) may be coupled to the second elongate body (1620). For example, the second expandable member (1640) is offset relative to a longitudinal axis of the second elongate body (1620). For example, a sidewall of the second expandable member (1640) may be coupled to a distal end of the second elongate body (1620). In some variations, the second expandable member (1640) may be an inflatable member such as a balloon. The visualization device (1640) may be disposed within the lumen of the expandable members (1640) in the expanded configuration.

In some variations, the expandable member (1630) may be concentrically coupled to the first elongate body (1610). In some variations, the first elongate body (1610) may be coupled to a sidewall of the expandable member (1630). In some variations, a second expandable member (1640) may be coupled to the second elongate body (1620) and disposed distal to the expandable member (1630). In some variations, the visualization device (1650) may be disposed within a lumen of the expandable member (1630). In some variations, at least a proximal end and a distal end of the second expandable member (1640) may be transparent, thereby allowing the visualization device (1650) to image through the second expandable member (1640). In some variations, a plurality of electrodes may comprise a plurality of parallel elongate electrodes as described in more detail herein. Additionally or alternatively, the plurality of elongate electrodes may comprise an interdigitated configuration. For example, the plurality of elongate electrodes may comprise a curved shape (e.g., S-shape, W-shape).

Figure 17:
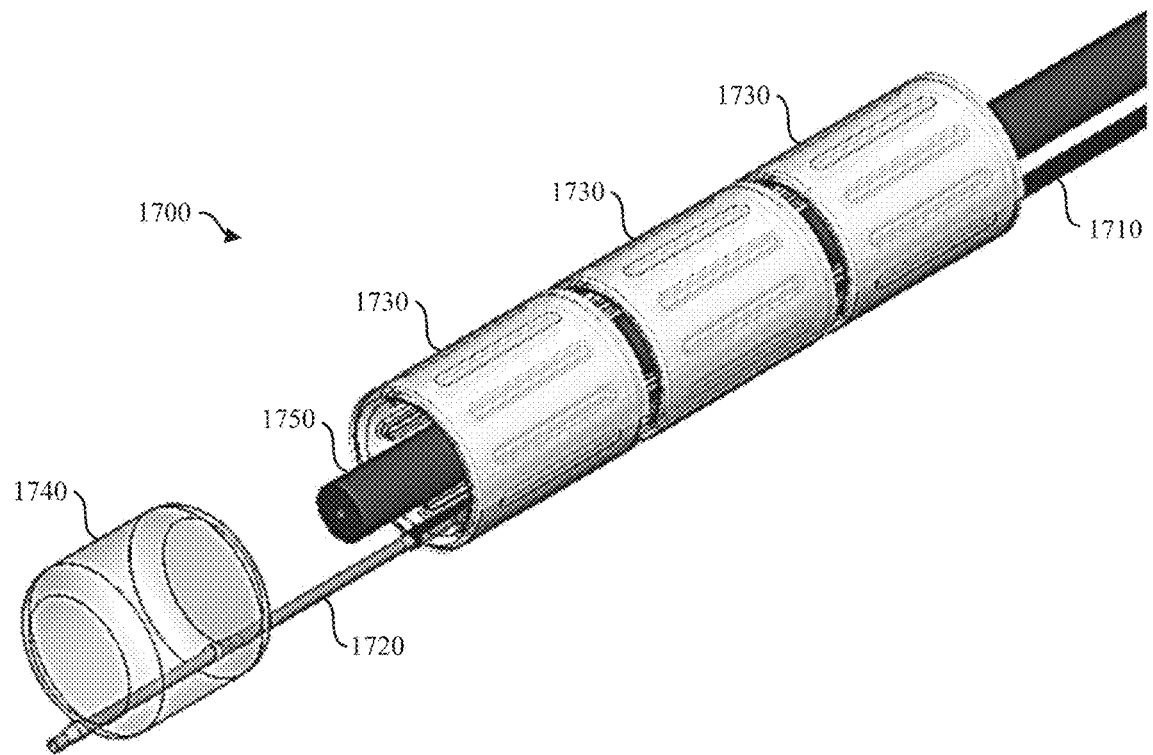
FIG. 17 is a perspective view of an illustrative variation of a pulsed electric field device and visualization device.
Figure 18:
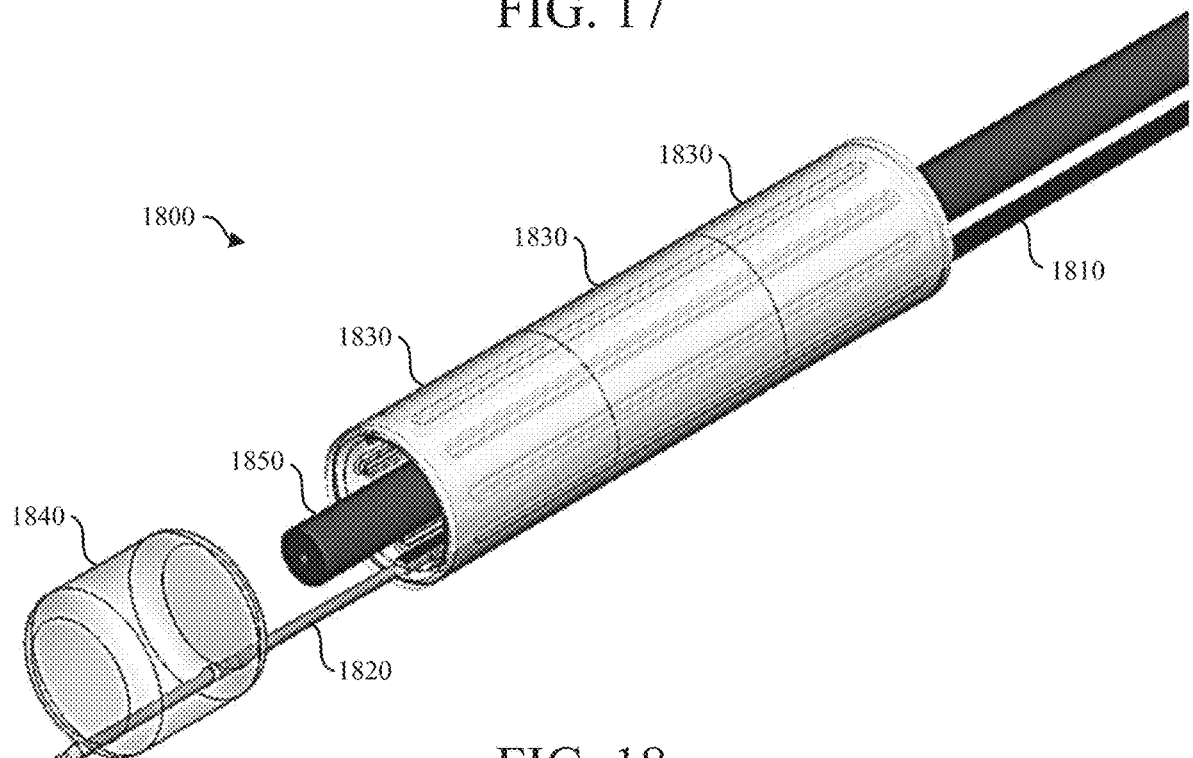
FIG. 18 is a perspective view of an illustrative variation of a pulsed electric field device and visualization device.

In some variations, a pulsed electric field device may comprise an expandable member and/or electrode array of predetermined length to ablate a predetermined length of tissue. FIGS. 17 and 18 are perspective views of variations of a pulsed electric field device (1700, 1800) and a visualization device (1750, 1850) similar to FIGS. 16A and 16B but having a plurality of expandable members (1730, 1830). A spacing between the plurality of expandable members (1730, 1830) may determine the degree to which the distal end of the device (1700, 1800) bends. For example, the device (1700) may have a greater flexibility than the device (1800) due to the larger distance between expandable members (1730).

In some variations, the pulsed electric field devices (1700, 1800) may comprise a first elongate body (1710, 1810) comprising a lumen therethrough and a second elongate body (1720, 1820) at least partially positioned within the lumen of the first elongate body (1710, 1810). A plurality of expandable members (1730, 1830) may be coupled to the first elongate body (1710, 1810). In some variations, the expandable member (1730, 1830) may comprise an electrode array (not shown for the sake of clarity) that may comprise any of the electrode arrays described herein. A second expandable member (1740, 1840) may be coupled to the second elongate body (1720, 1820). For example, the second expandable member (1740, 1840) is offset relative to a longitudinal axis of the second elongate body (1620). In some variations, the second expandable member (1740) may be an inflatable member such as a balloon. The visualization device (1640) may be disposed within the lumen of the expandable members (1640) in the expanded configuration. At least a proximal and distal portion of the expandable member (1740, 1840) may be transparent.

Figure 19:
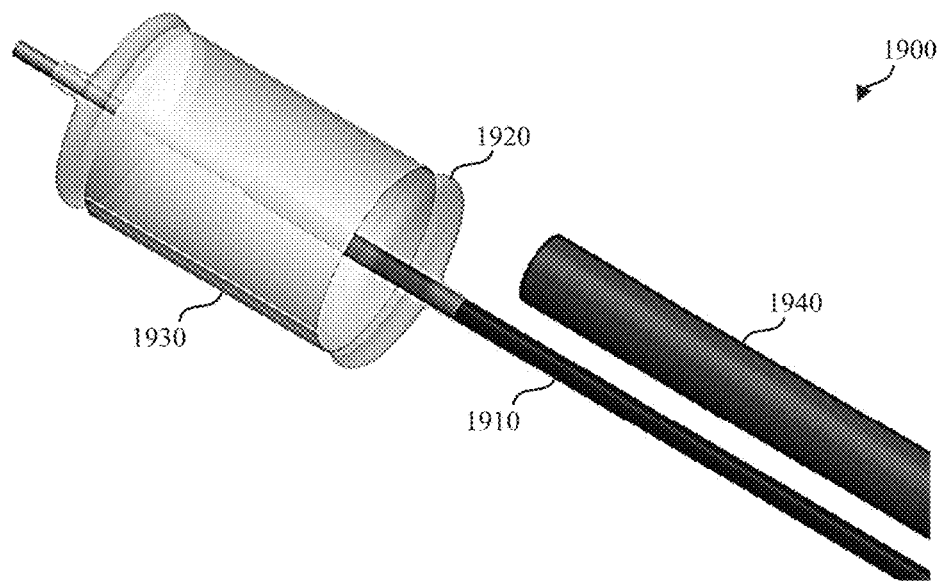
FIG. 19 is a perspective view of an illustrative variation of a pulsed electric field device and visualization device.

In some variations, a pulsed electric field device may comprise an expandable member comprising a transparent inflatable member. FIG. 19 is a perspective view of a variation of a pulsed electric field device (1900) and a visualization device (1940). In some variations, the pulsed electric field device (1900) may comprise an elongate body (1910) and an expandable member (1920) may be coupled to the elongate body (1910). In some variations, the expandable member (1920) may comprise an electrode array (1930) which may comprise any of the electrode arrays described herein. For example, the electrode array may be disposed on or coupled to an outer surface of the expandable member (1920). At least a proximal and distal portion of the expandable member (1920) may be transparent to allow the visualization device (1940) to visualize through the expandable member (1920). In some variations, the expandable member (1920) may be concentrically coupled to a distal end of the elongate body (1920). That is, a central longitudinal axis of the expandable member (1920) may align and be the same as a longitudinal axis of the elongate body (1910).

Figure 20:
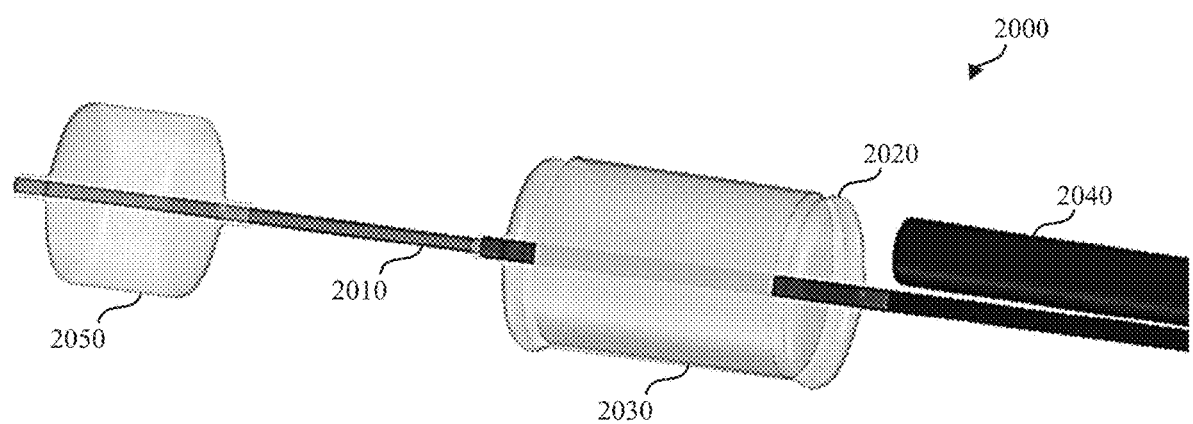
FIG. 20 is a perspective view of an illustrative variation of a pulsed electric field device and visualization device.

FIG. 20 is a perspective view of a variation of a pulsed electric field device (2000) and visualization device (2040) similar to FIG. 19 and further comprising a second expandable member (2050) disposed distal to the expandable member (2020). The second expandable member (2050) may be configured to dilate tissue. The second expandable member (2050) may be an inflatable member such as a balloon. In some variations, the pulsed electric field device (2000) may comprise an elongate body (2010) and an expandable member (2020) may be coupled to the elongate body (2010). In some variations, the expandable member (2020) may comprise an electrode array (2030) which may comprise any of the electrode arrays described herein. At least a proximal and distal portion of the expandable member (2020) may be transparent.

Figure 21:
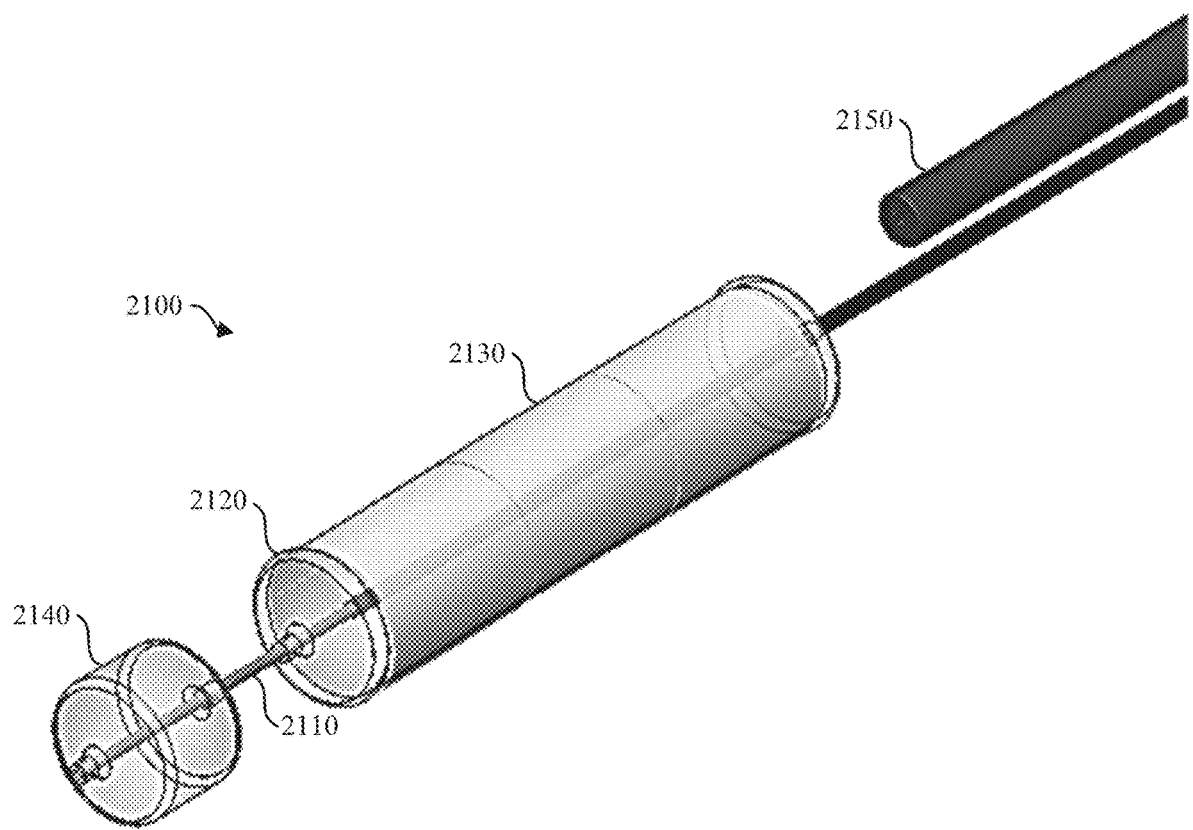
FIG. 21 is a perspective view of an illustrative variation of a pulsed electric field device and visualization device.

FIG. 21 is a perspective view of a variation of a pulsed electric field device (2100) and a visualization device (2150) similar to FIG. 20 but having a plurality of expandable members (2130) proximal to a distal second expandable member (2140) (e.g., inflatable member). A spacing between the plurality of expandable members (2130) may determine the degree to which the distal end of the device (2130) bends. In some variations, the pulsed electric field device (2100) may comprise an elongate body (2110) and the plurality of expandable members (2130) may be coupled to the elongate body (2110). In some variations, the plurality of expandable members (2120) may comprise an electrode array (2130) which may comprise any of the electrode arrays described herein. At least a proximal and distal portion of the expandable member (2120) may be transparent.

Figure 22:
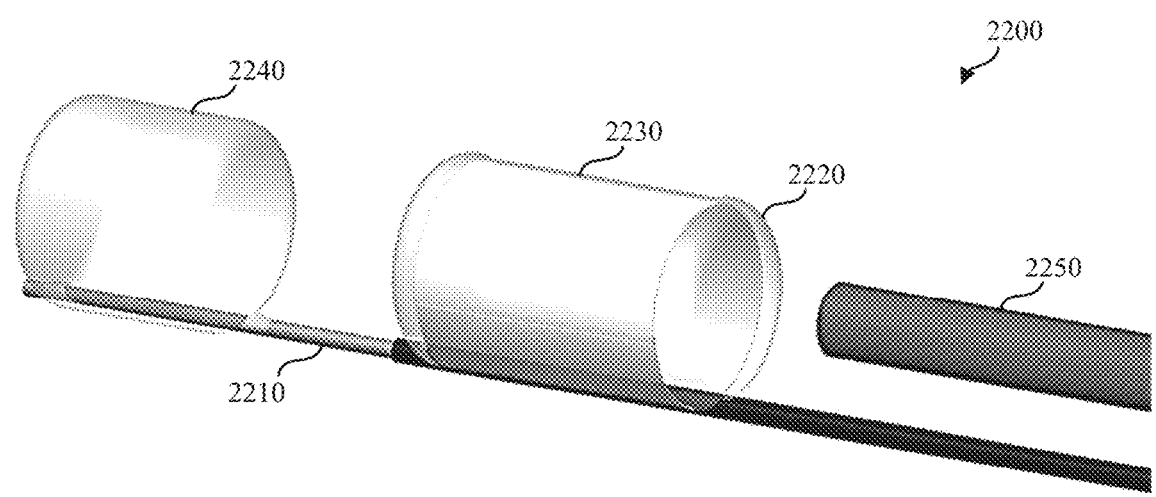
FIG. 22 is a perspective view of an illustrative variation of a pulsed electric field device and visualization device.

FIG. 22 is a perspective view of a variation of a pulsed electric field device (2200) and a visualization device (2250) similar to FIG. 19 but having a sidewall of the expandable member (2220) and second expandable member (2240) attached to the elongate body (2210). This may aid visualization through the device (2200) by a visualization device (2250) since the visualization device (2250) may be aligned to a center of the expandable member (2220). In some variations, the expandable member (2220) may comprise an electrode array (2230) which may comprise any of the electrode arrays described herein. At least a proximal and distal portion of the expandable member (2220) may be transparent.

Figure 23:
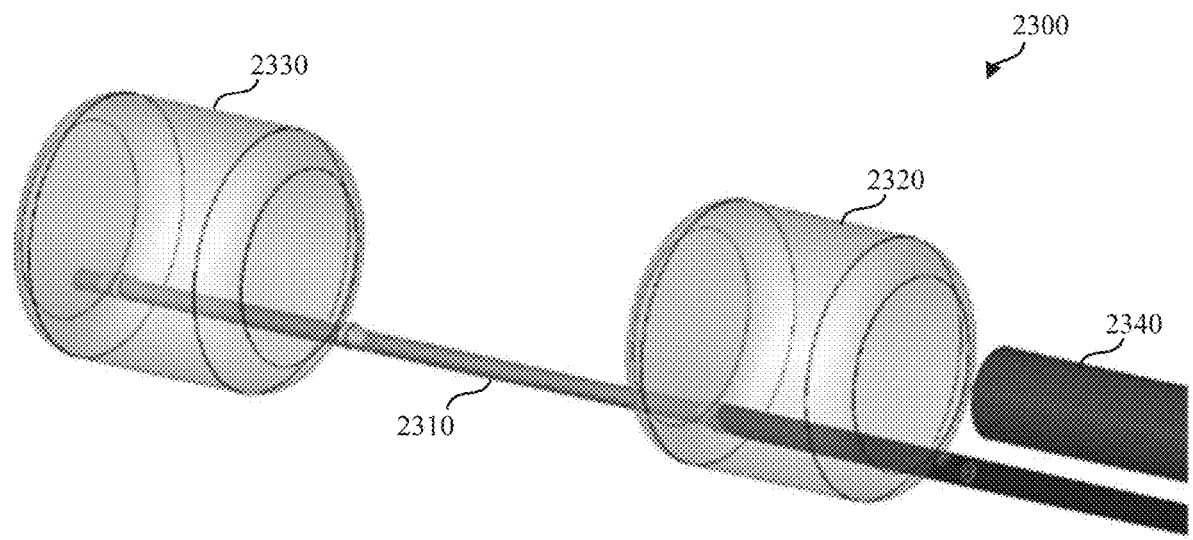
FIG. 23 is a perspective view of an illustrative variation of a pulsed electric field device and visualization device.

FIG. 23 is a perspective view of a variation of a pulsed electric field device (2300) and a visualization device (2340) similar to FIG. 19 but having a sidewall of the expandable member (2320) and second expandable member (2330) attached to the elongate body (2310). This may aid visualization through the device (2300) by a visualization device (2340) since the visualization device (2340) may be aligned to a center of the expandable member (2320). In some variations, the expandable member (2320) may comprise an electrode array (not shown) which may comprise any of the electrode arrays described herein. At least a proximal and distal portion of the expandable member (2320) may be transparent.

Figure 24:
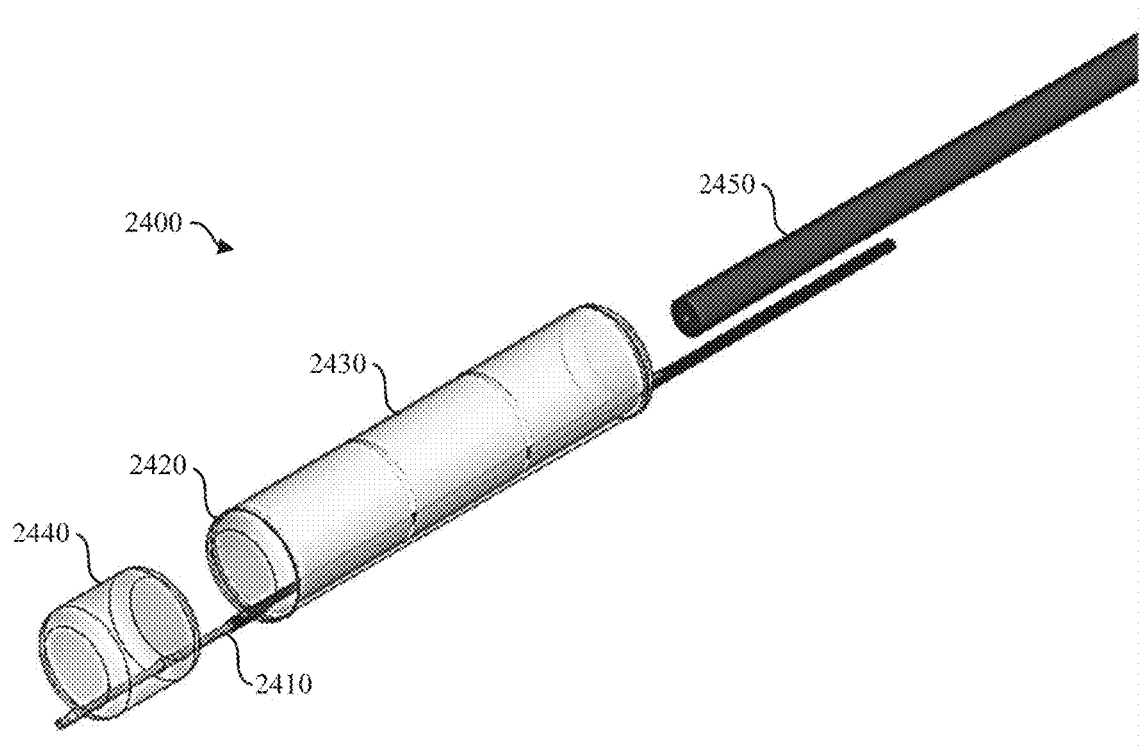
FIG. 24 is a perspective view of an illustrative variation of a pulsed electric field device and visualization device.

FIG. 24 is a perspective view of a variation of a pulsed electric field device (2400) and a visualization device (2450) similar to FIG. 21 but having a sidewall of the expandable member (2420) and second expandable member (2440) (e.g., inflatable member) attached to the elongate body (2410). In some variations, the pulsed electric field device (2400) may comprise an elongate body (2410) and the plurality of expandable members (2420) may be coupled to the elongate body (2410). In some variations, the plurality of expandable members (2420) may comprise an electrode array (2430) which may comprise any of the electrode arrays described herein. At least a proximal and distal portion of the plurality of expandable members (2420) may be transparent. A spacing between the plurality of expandable members (2420) may determine the degree to which the distal end of the device (2400) bends.

Figure 25:
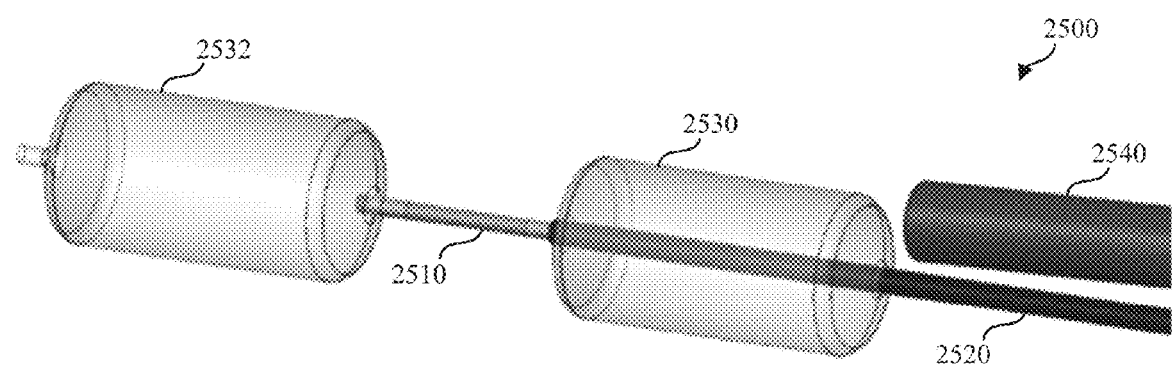
FIG. 25 is a perspective view of an illustrative variation of a pulsed electric field device and visualization device.

FIG. 25 is a perspective view of a variation of a pulsed electric field device (2500) and visualization device (2540) similar to FIG. 23 but having an expandable member (2530) concentrically coupled to a distal end of a first elongate body (2520). That is, a central longitudinal axis of the expandable member (2530) may align and be the same as a longitudinal axis of the elongate body (2520). Similarly, a second expandable member (2330) (e.g., inflatable member) is concentrically coupled to a distal end of a second elongate body (2510) disposed at least partially within a lumen of the first elongate body (2520). In some variations, the expandable member (2530) may comprise an electrode array (not shown) which may comprise any of the electrode arrays described herein. At least a proximal and distal portion of the expandable member (2530) may be transparent.

Figure 26:
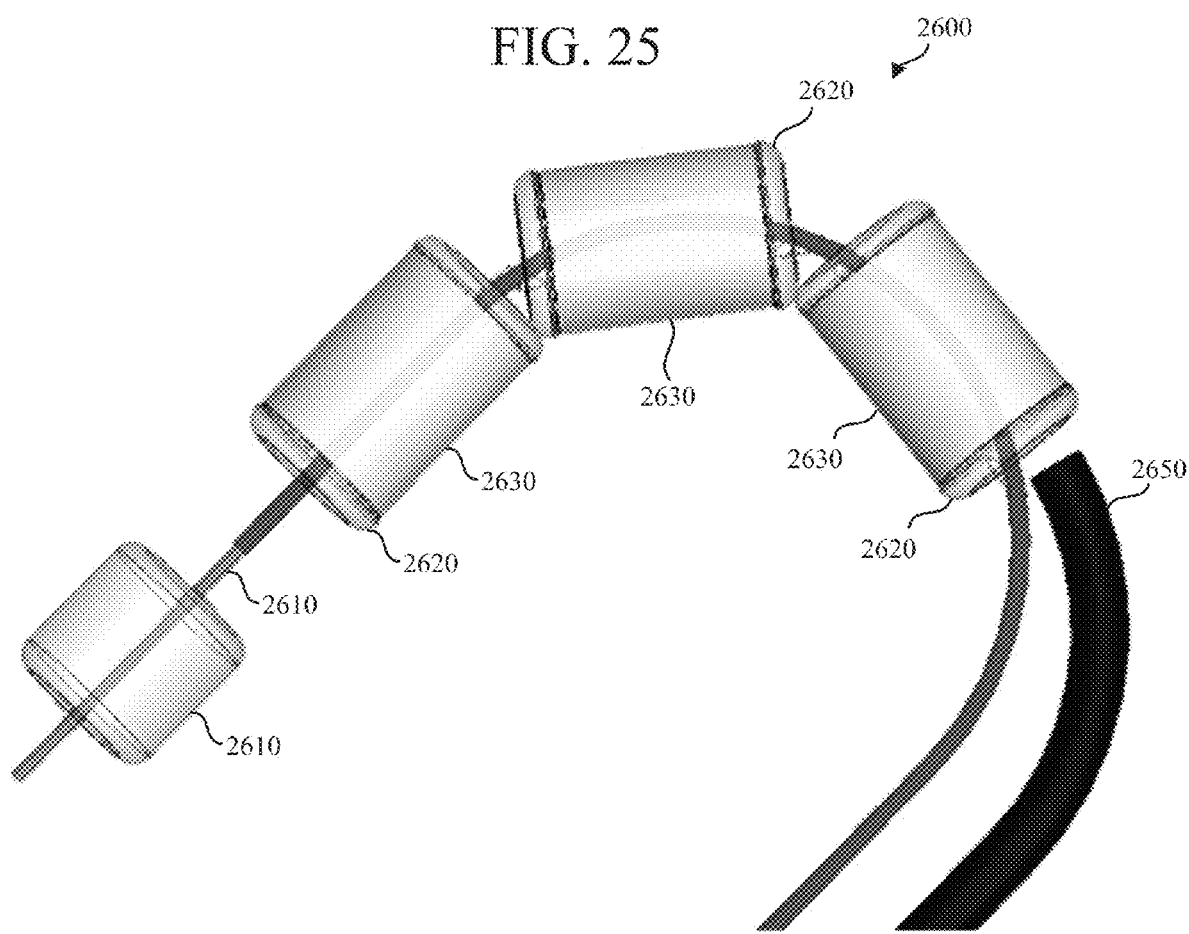
FIG. 26 is a perspective view of an illustrative variation of a pulsed electric field device and visualization device.

FIG. 26 is a perspective view of a variation of a pulsed electric field device (2600) and visualization device (2650) similar to FIG. 21 but bent to show the flexibility of the device (2600). A spacing between the plurality of expandable members (2620) may determine the degree to which the distal end of the device (2600) bends. In some variations, the pulsed electric field device (2600) may comprise an elongate body (2610) and the plurality of expandable members (2620) may be coupled to the elongate body (2610). In some variations, the plurality of expandable members (2620) may comprise an electrode array (2630) which may comprise any of the electrode arrays described herein. At least a proximal and distal portion of the plurality of expandable members (2620) may be transparent. A second expandable member (2610) may be attached to the elongate body (2610) proximal to the plurality of expandable members (2620).

Figure 27:
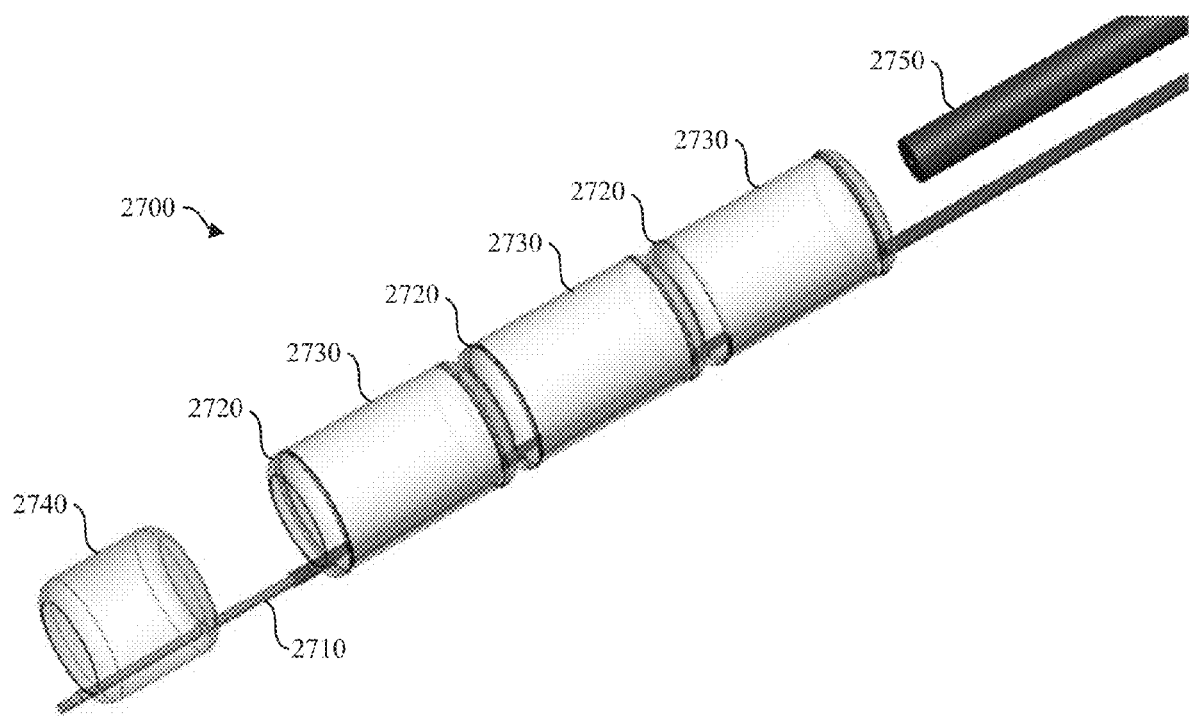
FIG. 27 is a perspective view of an illustrative variation of a pulsed electric field device and visualization device.

FIG. 27 is a perspective view of a variation of a pulsed electric field device (2700) and a visualization device (2750) similar to FIG. 24. For example, a sidewall of each expandable member (2720) and a second expandable member (2740) is attached to the elongate body (2710). In some variations, the plurality of expandable members (2720) may comprise an electrode array (2730) which may comprise any of the electrode arrays described herein. At least a proximal and distal portion of the plurality of expandable members (2720) may be transparent. A spacing between the plurality of expandable members (2720) may determine the degree to which the distal end of the device (2700) bends.

Figure 28A:
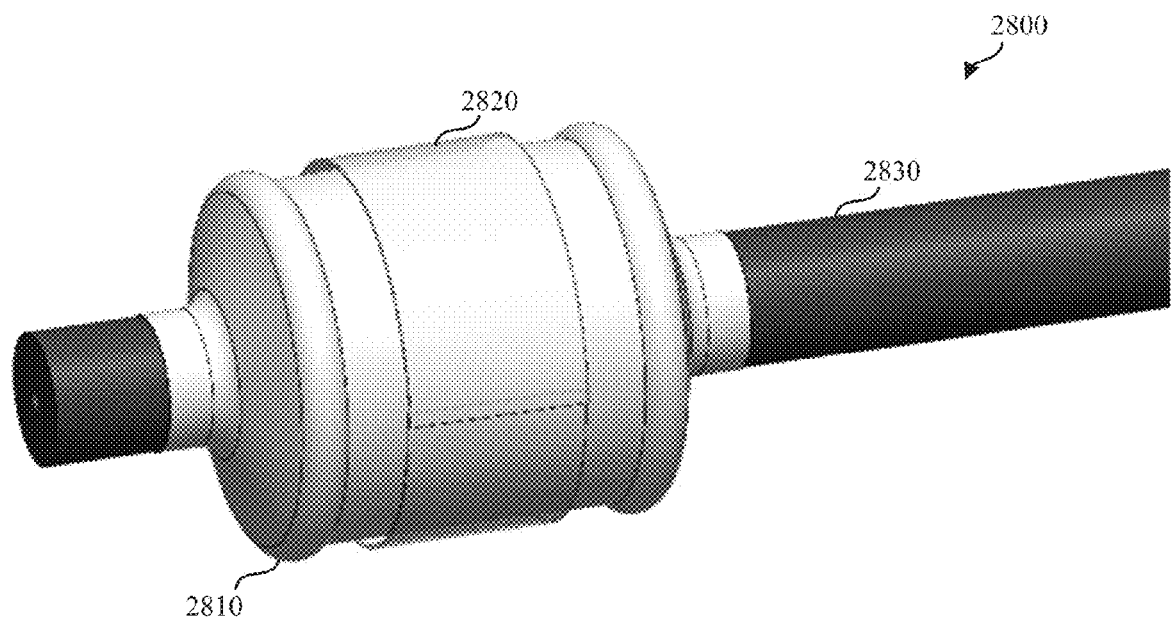
FIG. 28A is a perspective view of an illustrative variation of an expandable member of a pulsed electric field device and visualization device.

FIG. 28A is a perspective view of a variation of an expandable member (2810) of a pulsed electric field device (2800) and a visualization device (2830). FIGS. 28B-28E are perspective views of the pulsed electric field device (2800) and the visualization device (2830). As shown there, in some variations, the pulsed electric field device (2800) may comprise a releasable elongate body (2840) and an expandable member (2810) coupled to the elongate body (2840). The expandable member (2810) may comprise a lumen, a compressed configuration, a semi-expanded configuration, and an expanded configuration. The expandable member (2810) may further comprise an electrode array (2820). The lumen of the expandable member may be configured to releasably couple to a visualization device (2830). In some variations, the lumen defines a central longitudinal axis of the expandable member (2830). The elongate body (2840) may be configured to provide one or more of power to the electrode array (2820) and fluid to the expandable member (2810) for expansion and compression. As used herein, a fluid refers to a liquid, gas, or combinations thereof. For example, in some variations, a gas commonly used in interventional procedures may be used such as $CO_2$ and/or air.

Figure 28B:
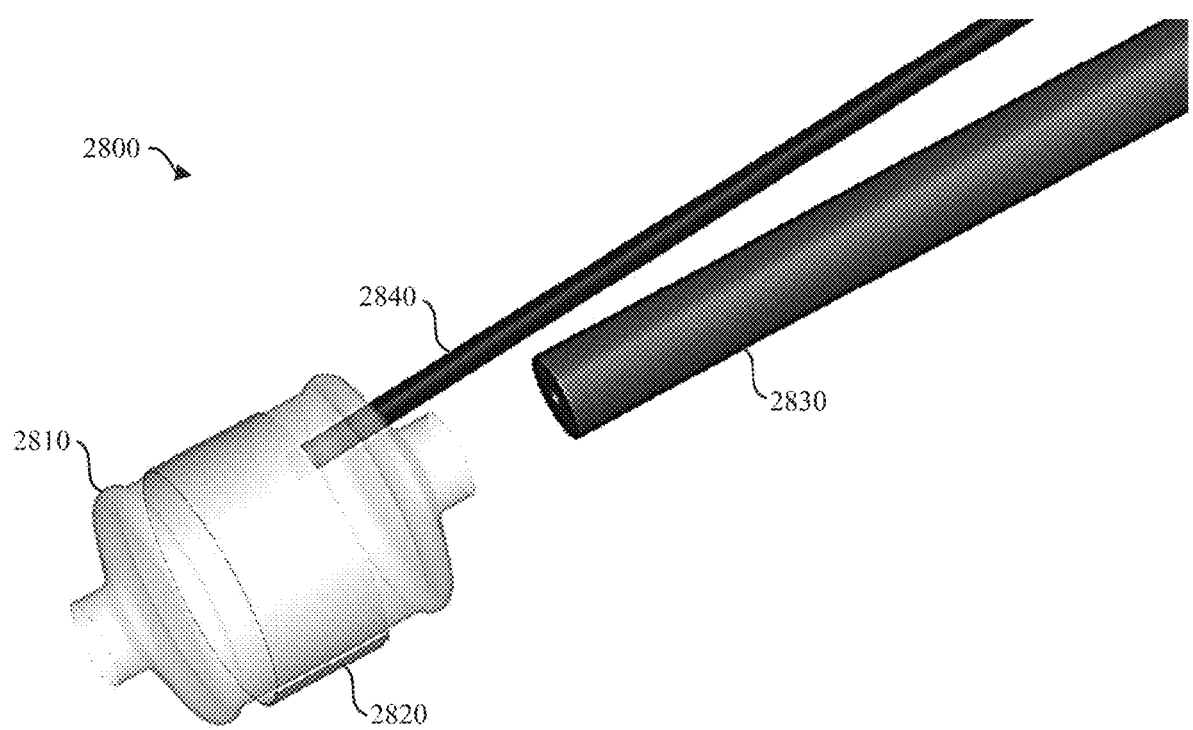
FIGS. 28B-28E are perspective views of the pulsed electric field device and visualization device shown in FIG. 28A.
Figure 28C:
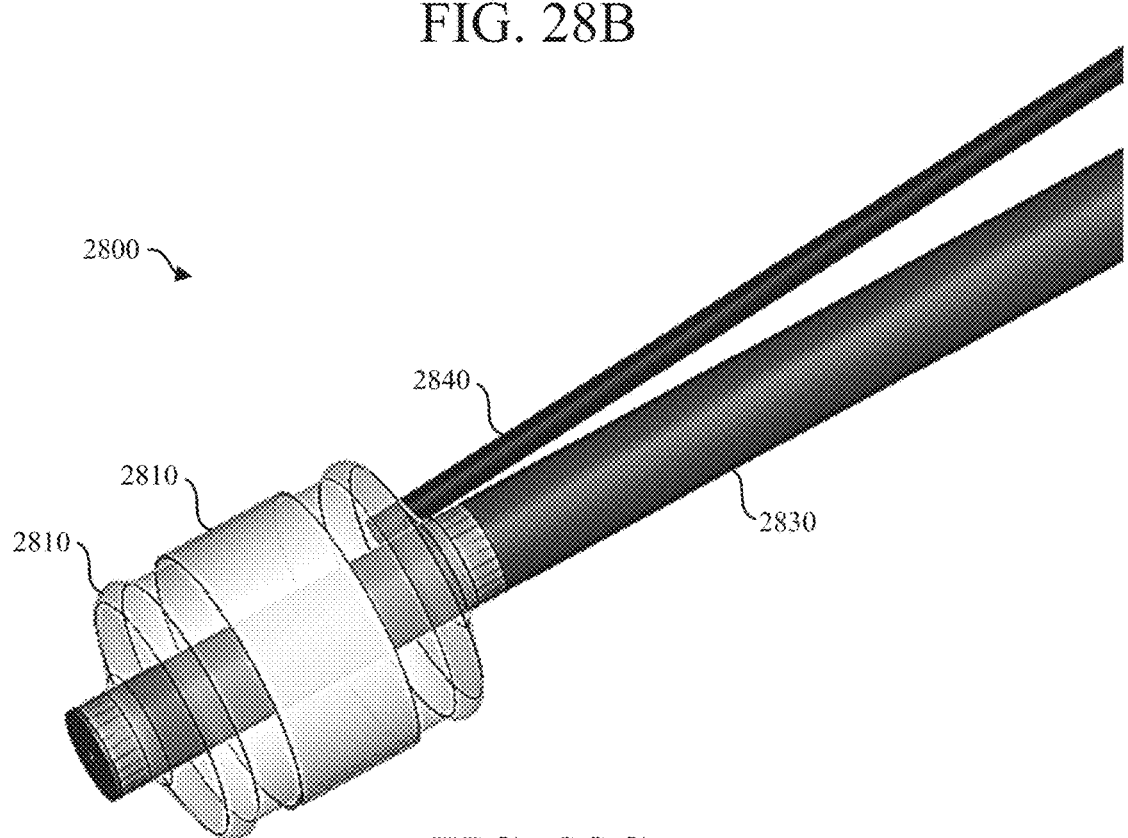
Figure 28D:
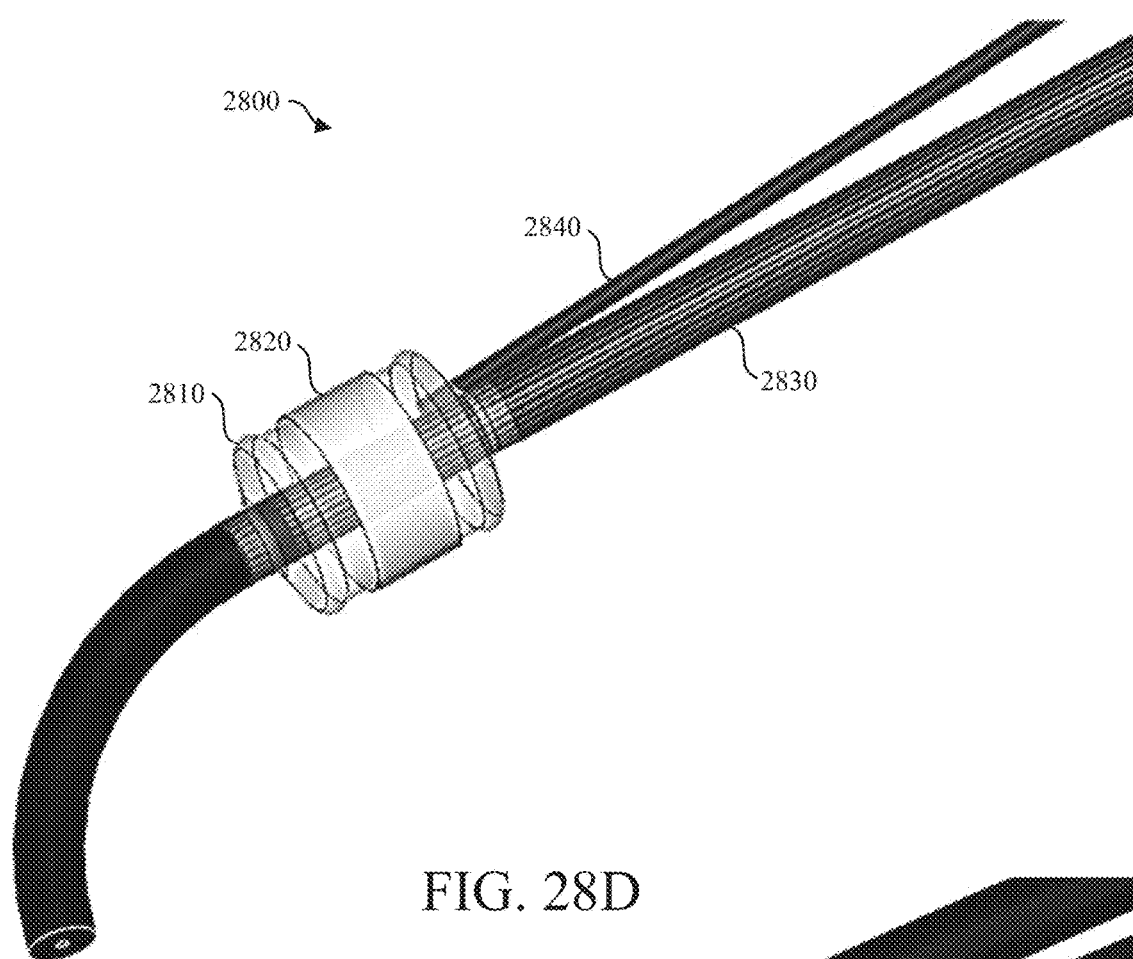
Figure 28E:
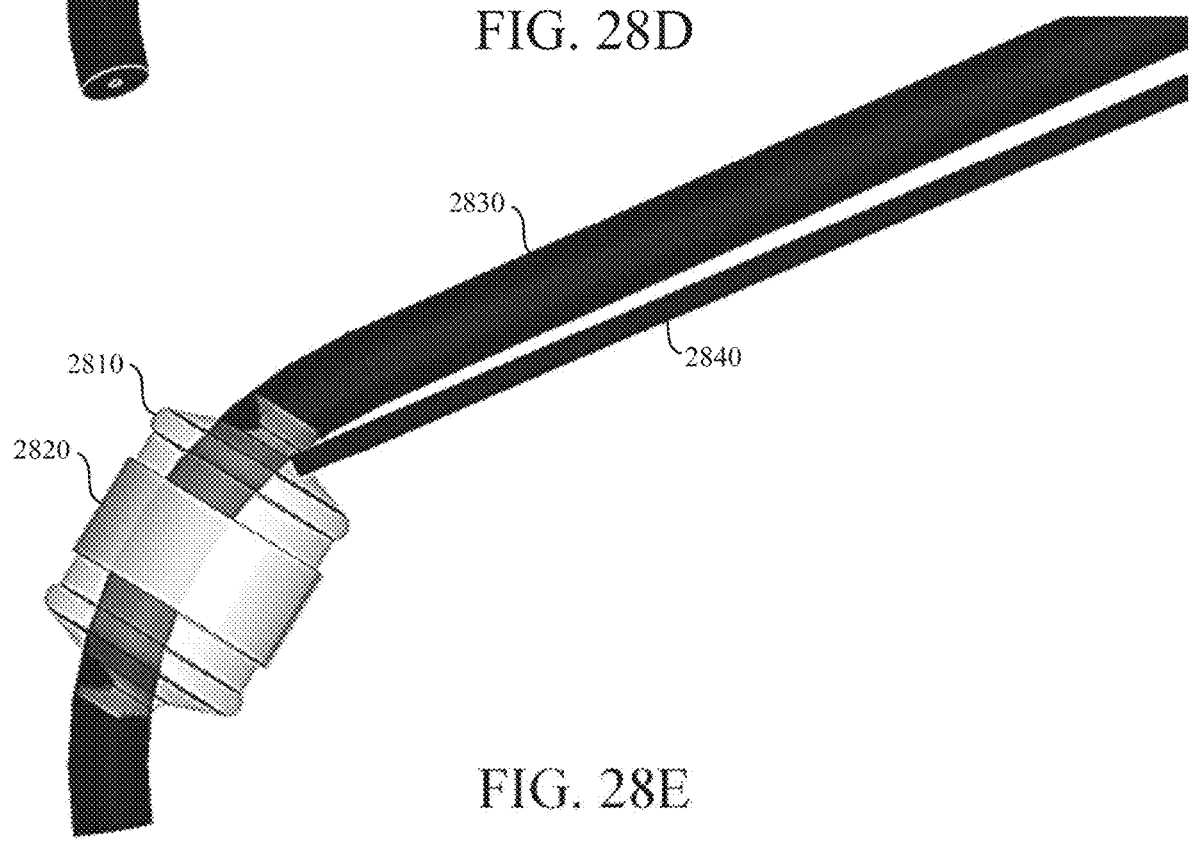

In FIGS. 28A and 28C, the visualization device (2830) is disposed within a lumen of the expandable member (2810) and allows the visualization device (2830) to translate the expandable member (2810) through one or more body cavities. FIG. 28B depicts the visualization device (2830) detached (e.g., decoupled, separated) from the expandable member (2830). This may allow the visualization device (2830) to, for example, image a proximal portion of the expandable member (2810) and maneuver independently of the expandable member (2830). After completion of energy delivery, the visualization device (2830) may be recoupled to the expandable member (2830) and withdrawn from the patient. In FIG. 28D, the visualization device (2830) is further advanced relative to the expandable member (2810) such that a distal end of the visualization device (2830) may bend. In some variations, as shown in FIG. 28E, the visualization device (2830) may bend within a lumen of the expandable member (2810).

Figure 29A:
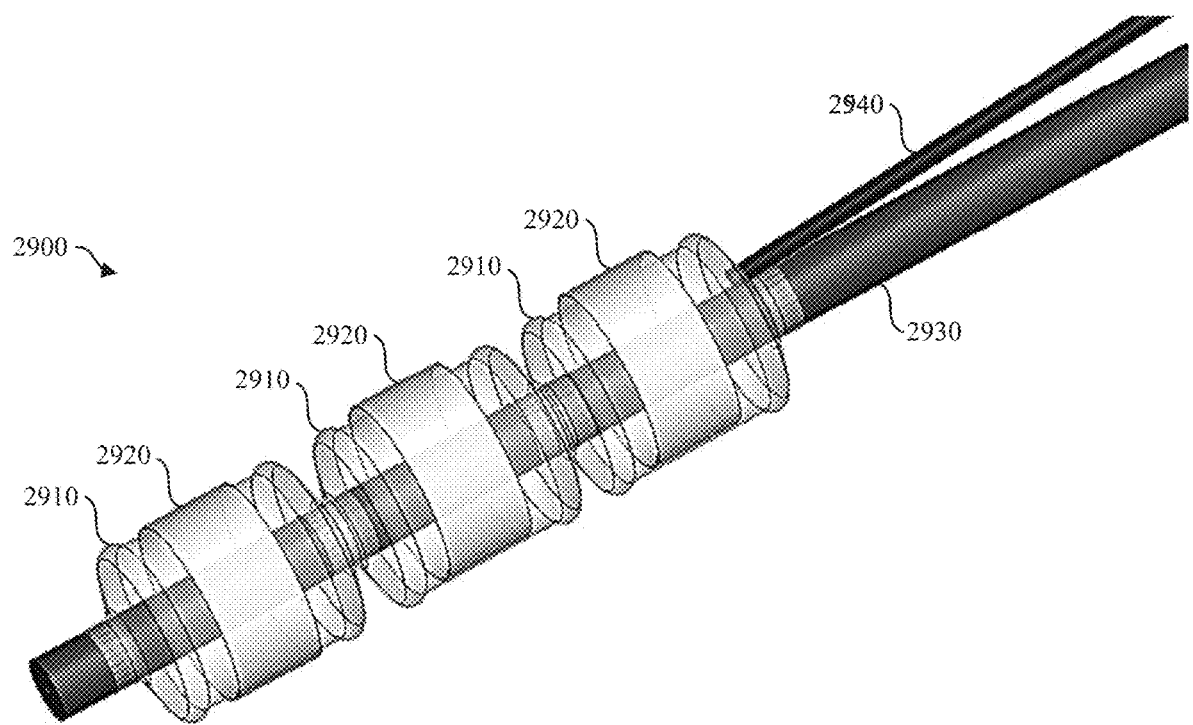
FIG. 29A is a perspective view of an illustrative variation of a pulsed electric field device and visualization device.
Figure 29B:
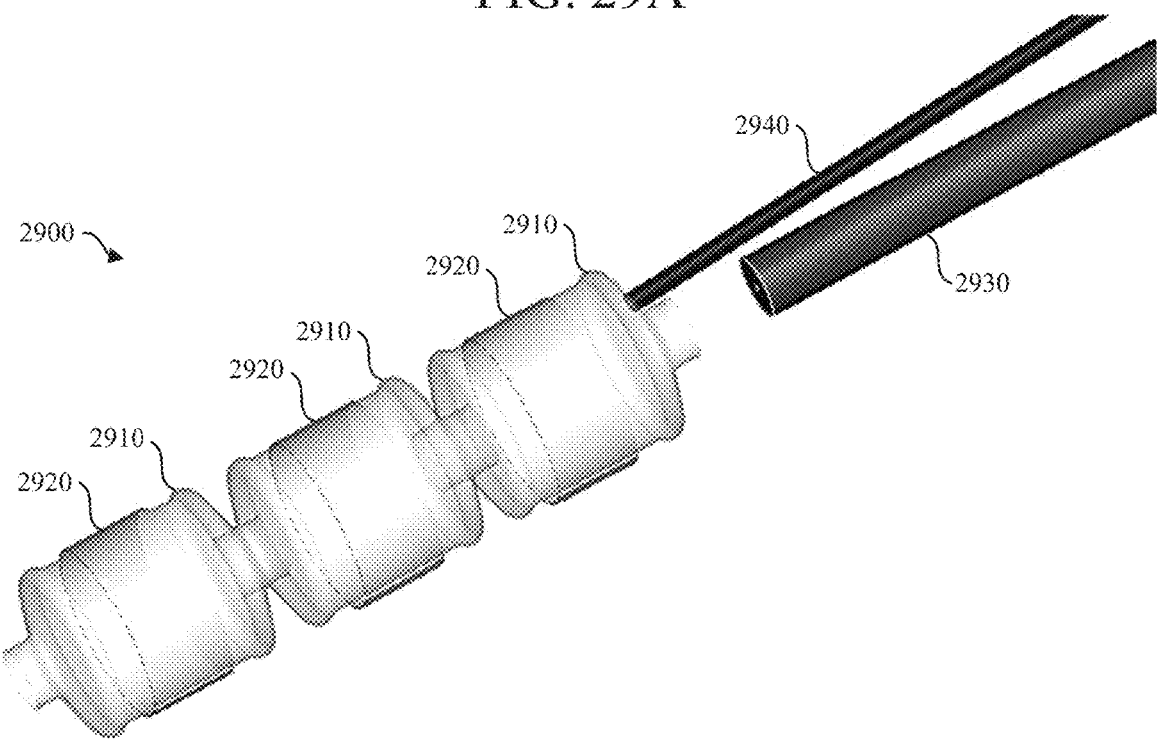
FIG. 29B is a perspective view of the pulsed electric field device detached from the visualization device shown in FIG. 29A.

FIG. 29A is a perspective view of a variation of a pulsed electric field device (2900) and a visualization device (2930) similar to FIGS. 28A-28E but having a plurality of expandable members (2910). A spacing between the plurality of expandable members (2910) may determine the degree to which the distal end of the device (2900) bends. In some variations, the plurality of expandable members (2910) may comprise an electrode array (2920) which may comprise any of the electrode arrays described herein. FIG. 29B is a perspective view of the pulsed electric field device (2900) and the visualization device (2930) detached (e.g., decoupled, separated) from the plurality of expandable members (2910) shown in FIG. 29A.

Figure 30A:
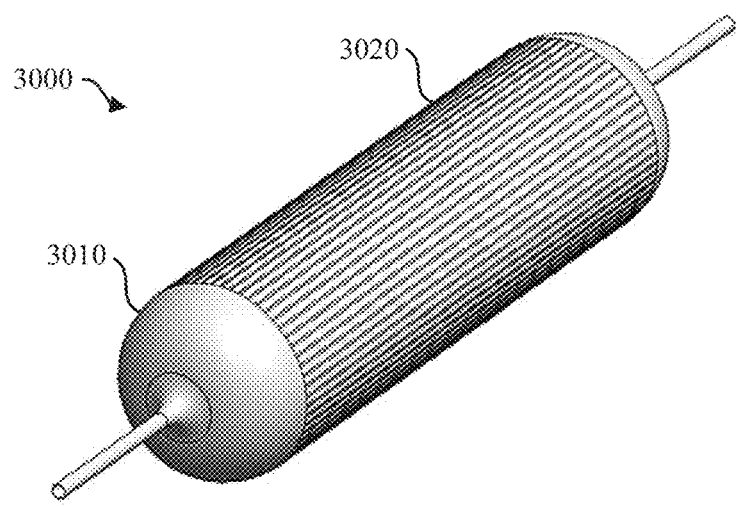
FIG. 30A is a perspective view of an illustrative variation of a pulsed electric field device.
Figure 30B:
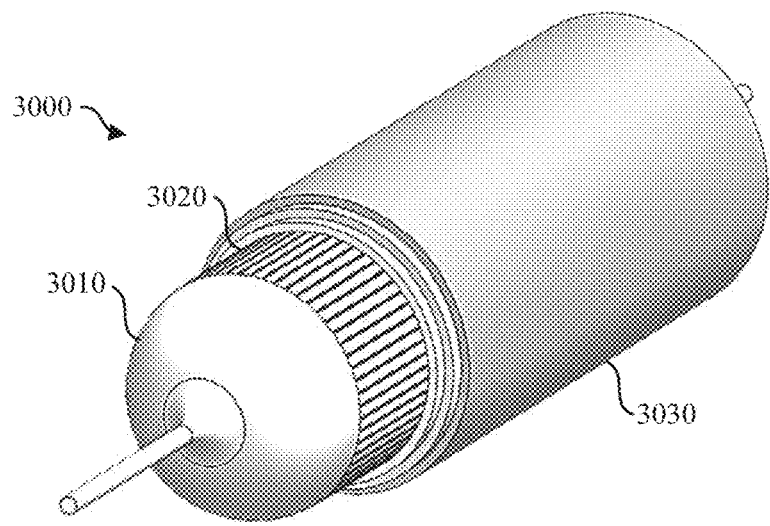
FIG. 30B is a perspective view the pulsed electric field device shown in FIG. 30A in a tissue lumen.

FIG. 30A is a perspective view of a variation of a pulsed electric field device (3000) comprising an expandable member (3010) (e.g., inflatable member) comprising an electrode array (3020). In some variations, the expandable member (3010) may comprise a base layer (e.g., circuit substrate, flex circuit) which may couple to any of the electrode arrays described herein. For example, the electrode array (3020) may be disposed on an outer surface of the expandable member (3010). The electrode array (3020) may comprise a plurality of substantially parallel elongate electrodes disposed circumferentially about a longitudinal axis of the expandable member. The expandable member (3010) in FIG. 30A is shown in the expanded configuration. FIG. 30B is a perspective view the pulsed electric field device (3000) of FIG. 30A positioned within a tissue lumen (3030). The expandable member (3010) in FIG. 30A is shown in the expanded configuration such that the electrode array (3020) contacts the tissue lumen (3030).

Figure 31:
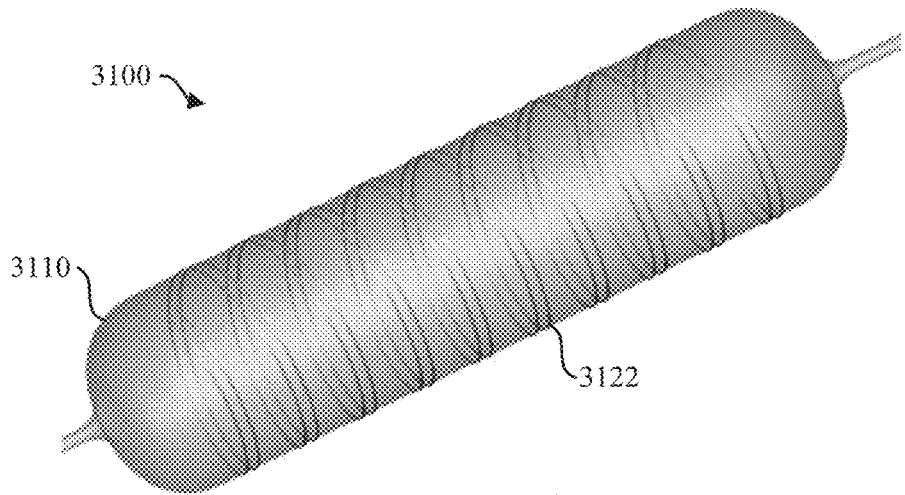
FIG. 31 is a perspective view of an illustrative variation of a pulsed electric field device.

FIG. 31 is a perspective view of a variation of a pulsed electric field device (3100) comprising an expandable member (3110) (e.g., inflatable member) comprising an electrode array (3122). The electrode array (3122) may comprise a helical shape comprising a predetermined number of turns. In some variations, the expandable member (3110) may comprise a base layer (e.g., circuit substrate, flex circuit) which may couple to any of the electrode arrays described herein. For example, the electrode array (3122) may be disposed on an outer surface of the expandable member (3110).

FIG. 32 is a perspective view of a variation of a pulsed electric field device (3200) comprising a visualization device (3230) coupled to an expandable member (3210) comprising an electrode array (3220). The expandable member (3210) may comprise a stent-like structure that may be configured to transition between a compressed configuration and an expanded configuration. For example, the expandable member (3210) may change configurations by one or more of changing length and spiral rotation. In some variations, the expandable member (3210) may comprise a base layer (e.g., circuit substrate, flex circuit) which may couple to any of the electrode arrays described herein. For example, the electrode array (3220) may be disposed on an outer surface of the expandable member (3210). The electrode array (3220) may comprise a plurality of substantially parallel elongate electrodes disposed circumferentially about a longitudinal axis of the expandable member. Additionally or alternatively, the plurality of elongate electrodes may comprise an interdigitated configuration. The expandable member (3210) in FIG. 32 is shown in the expanded configuration. The expandable member (3210) may comprise a lumen configured to receive the visualization device (3230). FIGS. 33A and 33B are a side view and a perspective view, respectively, of an expandable member (3310) similar to the pulsed electric field device (3200) of FIG. 32.

Electrode Array

Generally, the electrodes and electrode arrays described herein may be configured to treat tissue, such as the duodenal tissue, of a patient. In some variations, the electrode array may engage the duodenum and be energized to treat a predetermined portion of tissue to resurface the duodenum. For example, tissue may undergo cell lysis using PEF energy during a treatment procedure. PEF energy tissue treatment may be uniformly delivered at a predetermined depth (e.g., about 1 mm) to quickly and precisely treat tissue without significant damage to surrounding (e.g., deeper) tissue.

In some variations, tissue treatment characteristics may be controlled by the size, shape, spacing, composition, and/or geometry of the electrode array. For example, the electrode array may be flexible to conform to non-planar tissue surfaces. In some variations, the electrode array may be embossed or reflowed to form a non-planar electrode surface. In some variations, the electrode array may comprise a tissue contact layer. In some variations, the tissue contact layer may function as a salt bridge between the electrodes and tissue. In some variations, the electrode array may comprise a hydrophilic coating. In some variations, the electrode array may be divided into sub-arrays to reduce drive current requirements.

In some variations, raised and/or rounded (e.g., semi-ellipsoid) electrodes may generally promote more reliable contact with tissue than flat electrodes and therefore a more uniform electrical field and improved treatment outcomes. For example, tissue contact (e.g., apposition) with the electrodes completes an electrical circuit during energy delivery and therefore provides the resistance in the circuit for a uniform electric field distribution. The raised and/or rounded (e.g., semi-ellipsoid) electrodes may reduce sharp edges to reduce arcing. The spaced-apart electrodes of the electrode array may further reduce ion concentration and associated electrolysis. The electrode array configurations (e.g., geometry, spacing, shape, size) shown and described herein provide uniform and spaced-apart electrodes that also allow a corresponding expandable member to repeatedly expand and compress.

In some variations, one or more of the electrodes (e.g., a plurality of the electrodes, a portion of the electrodes in an array, all of the electrodes in an array) may comprise one or more biocompatible metals such as gold, titanium, stainless steel, nitinol, palladium, silver, platinum, combinations thereof, and the like. In some variations, one or more electrodes (e.g., a plurality of the electrodes, a portion of the electrodes in an array, all of the electrodes in an array) may comprise an atraumatic (e.g., blunt, rounded) shape such that the electrode does not puncture tissue when pressed against tissue. For example, the electrode array may engage an inner circumference of the duodenum.

In some variations, the electrode array may be connected by one or more leads (e.g., conductive wire) to a signal generator. For example, a lead may extend through an elongate body (e.g., outer catheter, outer elongate body) to the electrode array. One or more portions of the lead may be insulated (e.g., PTFE, ePTFE, PET, polyolefin, parylene, FEP, silicone, nylon, PEEK, polyimide). The lead may be configured to sustain a predetermined voltage potential without dielectric breakdown of its corresponding insulation.

In some variations, an electrode array may comprise a plurality of elongate electrodes in a substantially parallel or interdigitated configuration. The shape and configuration of the electrode arrays described herein may generate an electric field of predetermined strength (e.g., between about 400 V/cm and about 7,500 V/cm) at a predetermined tissue depth (e.g., about 0.7 mm, about 1 mm) without excess heat, breakdown, steam generation, and the like. By contrast, some electrode configurations comprise a geometry (e.g., radius of curvature) where the electric fields generated decreases too quickly without application of very high voltages (e.g., thousands of volts) that may lead to the aforementioned excess heat, breakdown, and steam generation.

Figure 34A:
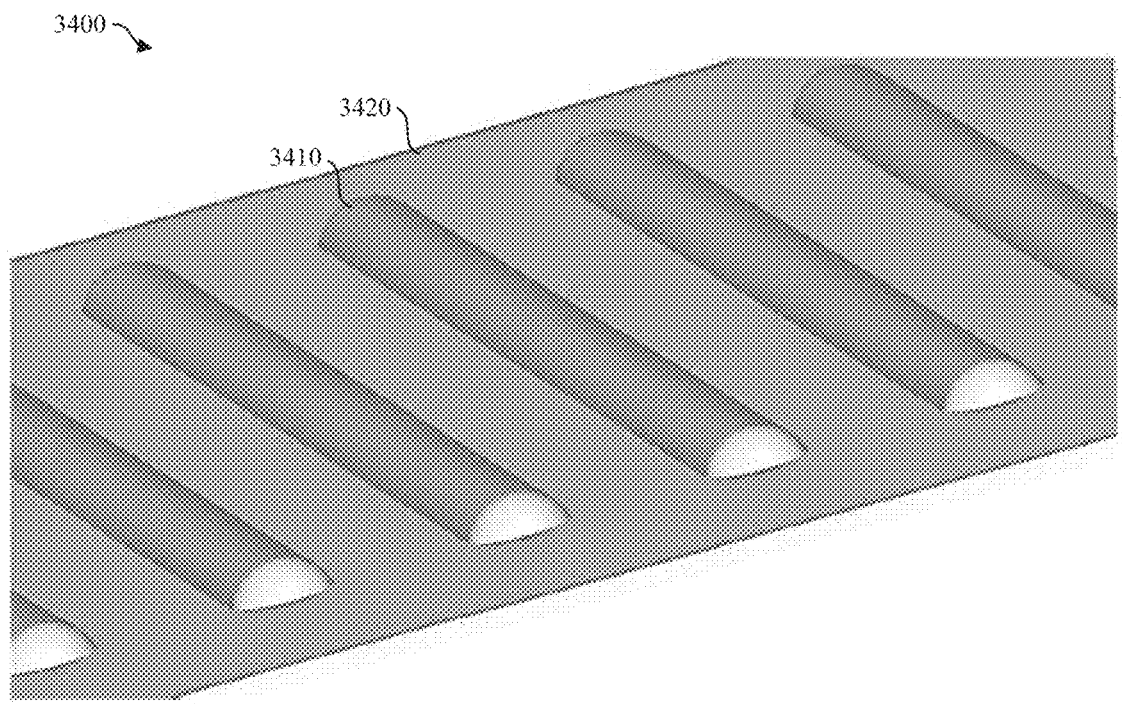
FIG. 34A is a perspective view of an illustrative variation of an electrode array.

FIG. 34A is a perspective view of a variation of an electrode array (3400) comprising a plurality of elongate electrodes (3410) on a substrate (3420). In some variations, at least one of the electrodes (3410) may comprise a semi-elliptical cross-sectional shape. In some instances, all of the electrodes (3410) in the electrode array (3400) may comprise a semi-elliptical cross-sectional shape. Generally, electric fields are intense near points and edges of electrodes due to the high concentration of surface charges there. Sharp-edged electrodes and high electric fields may generate one or more of electric discharge (e.g., arcing), high heat rates (e.g., boiling), high current density (e.g., electrolysis), and bubbles. The semi-elliptical cross-sectional shapes described herein may reduce one or more of these effects relative to sharp-edged electrodes. In some variations, a major axis of the electrode (3410) is twice the electrode width and the minor axis of the electrode is equal to the electrode height in the middle of the electrode.

Figure 37:
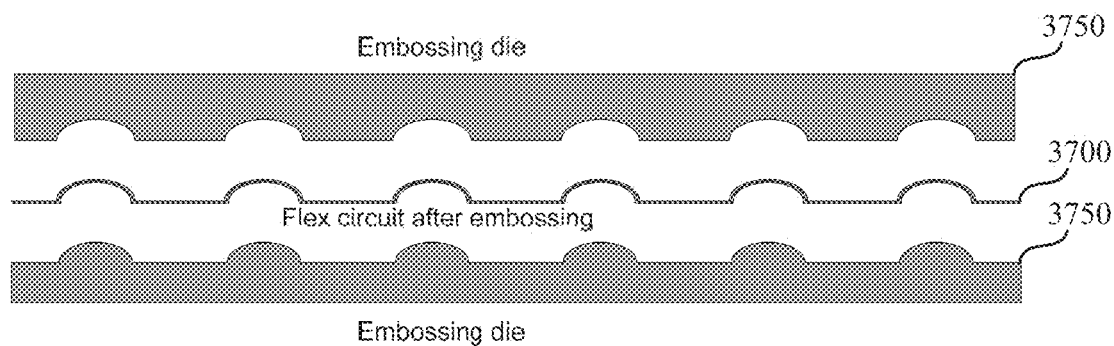
FIG. 37 is a schematic cross-sectional view of an illustrative variation of an electrode array and embossing dies.

The electrode arrays described herein may be formed using any suitable manufacturing technique. For example, as shown in FIG. 37, in some variations an electrode array (3700) may be formed by pressing the electrode array (3700) between a pair of embossing dies (3750) to form a plurality of spaced-apart rounded electrodes. The electrode arrays described herein may be manufactured using any suitable technique including, but not limited to, deposition of solder or other metal, dimpling of the substrate, plating of a metal (e.g., gold), and lamination.

In some variations, additional layers and/or coatings may be applied to the electrode. For example, the electrode array (3800) depicted in FIG. 38 may depict a tissue contact layer (3810) as further described herein.

If the edges of a flat electrode are 2 d apart (the width of the electrode), the equivalent electrical field is provided by an elliptical conductor with a height h (minor axis) and a width 2 w (w being the major axis), where the foci of the ellipse are d from the center. The eccentricity may be given by equation (2):

$$\epsilon = (1+(h/d)^2)^{-1/2} \qquad \text{eqn. (2)}$$

The footprint of the mounded electrode is 2 w=2 d/ϵ, and is increased from the flat electrode by the factor ½ϵ. If mounded or solder-reflowed electrodes are used, they generally will have some mechanical resistance to flexing about a central line other than one parallel to the electrodes.

In some variations, a drive voltage applied to the electrode array may depend at least on the spacing between electrodes of the electrode array as well as electrode dimensions. For example, relatively wide elongate electrodes may reduce the effect of strong electric field intensities at sharply curved edges. In some variations, the electrode array may be configured in a plurality of sets (e.g., groups, zones) to aid energy delivery for a treatment procedure. For example, an electrode array may comprise a plurality of zones disposed along a length of the expandable member. The plurality of zones may, for example, be activated in a predetermined sequence.

Figure 34B:
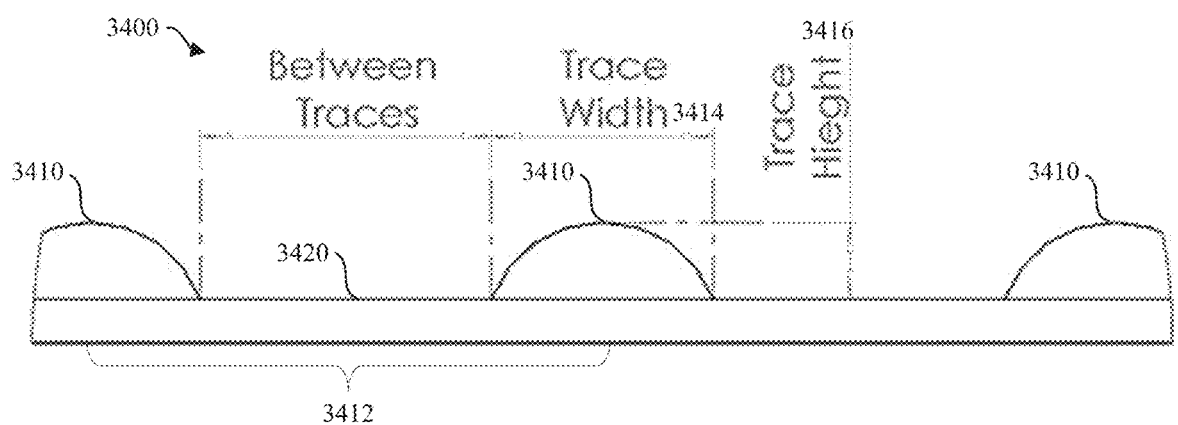
FIG. 34B is a cross-sectional side view of the electrode array shown in FIG. 34A.

FIG. 34B is a cross-sectional side view of the electrode array (3400). In some variations, an electrode array may comprise a plurality (e.g., 4, 8, 12, 16, 20, 24, 30, and any range therein) of elongate electrodes. For example, the electrode array may comprise more than about 6 electrodes. In some variations, the plurality of elongate electrodes may comprise a ratio of a center-to-center distance between proximate (i.e., directly adjacent) electrodes to electrode width (3414) between about 2.3:1 and about 3.3:1, and about 2.8:1 and about 3.0:1. For example, a distance (3412) between proximate electrodes (3410) may be from about 1 mm to about 1.8 mm, a width (3414) of the electrode (3410) may be from about 0.6 mm to about 1.8 mm, and a height (3416) of the electrode (3410) may be from about 0.15 mm to about 0.5 mm, including all values and sub-ranges in between, such as about 0.3 mm. In some variations, the plurality of elongate electrodes comprise a center-to-center distance between proximate electrodes of less than about 10 mm, less than about 7 mm, and less than about 5 mm, including all values and sub-ranges in-between. In some variations, the plurality of elongate electrodes may comprise a first electrode and a second electrode in parallel to the first electrode. Additionally or alternatively, the plurality of electrodes may comprise an interdigitated configuration. In some variations, the center-to-center distance between proximate electrodes and the width of the plurality of elongate electrodes may be substantially equal.

In some variations, the proximate electrodes may be spaced apart by a weighted average distance of between about 0.3 mm and about 6 mm. Weighted average distance may be defined as follows. Each electrode of the plurality of elongate electrodes may comprise coordinates $s(x_i, y_i)$ (equation 3) where x and y are parallel to a surface of the electrode array, a first distance ($s_+$) to the closest electrode of a first polarity (e.g., positive polarity), and a second distance ($s_-$) to the closest electrode of a second polarity (e.g., negative polarity) opposite the first polarity. The weighted average distance (S) may be given by equation (4):

$$s(x_i, y_i) = \frac{s_+ + s_-}{2} \qquad \text{eqn. (3)}$$

$$S = \sum_{i=1}^{n} \frac{s(x_i, y_i)}{n-1} \qquad \text{eqn. (4)}$$

In some variations, a ratio of a height of an electrode to a width of an electrode may be between about 1:4 and about 1:8. In some variations, a surface area of the plurality of electrodes may comprise between about 20% and about 75% of a surface area of the electrode array, including all ranges and sub-values in-between. In some variations, a surface area of the plurality of electrodes comprises between about 20% and about 45% of a surface area of the expandable member in a predetermined configuration, including all ranges and sub-values in-between. In some variations, the electrode array may comprise about 36% conductor by area. In some variations, a surface area of the plurality of electrodes comprises between about 4% and about 30% of a surface area of a duodenum, including all ranges and sub-values in-between. A typical duodenum may comprise a circumference between about 20 mm and about 45 mm, a length between about 25 mm and about 35 mm, and a surface area between about 700 mm$^2$ and about 1850 mm$^2$.

In some variations, an electrode array may comprise a plurality of groups of electrodes (e.g., see zones A, B, C in FIG. 51) where each group may be activated in a predetermined sequence. In some variations, a more uniform treatment of tissue (e.g., in areas where the electrode groups intersect) may be obtained by reducing the widths of the end-most electrodes of each group and reducing the distance between those electrodes. In some variations, a more uniform treatment of tissue (e.g., in areas where the electrode groups intersect) may be enabled by interdigitating the end-most electrodes of each group to overlap the treatment areas.

Figure 34C:
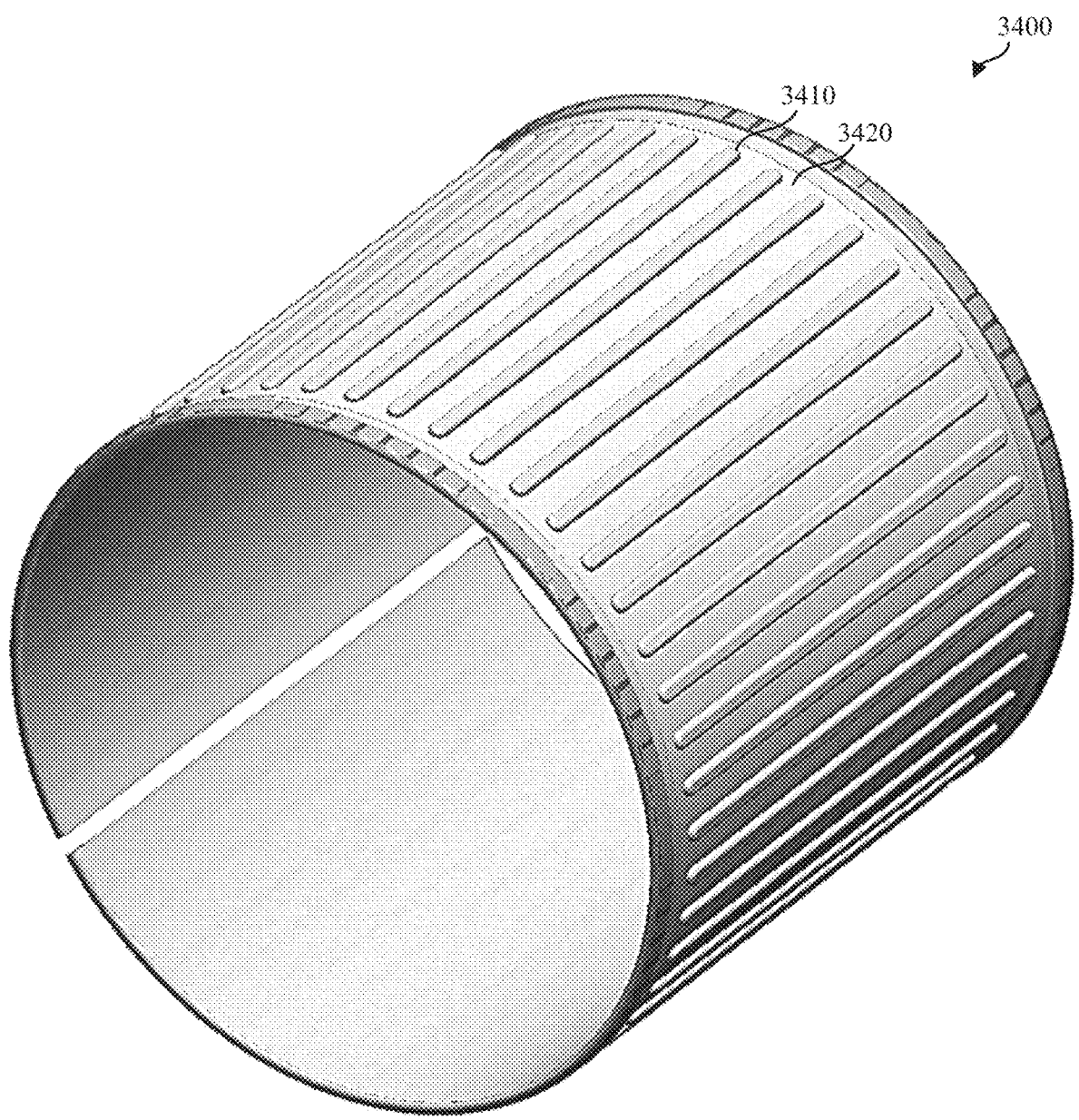
FIG. 34C is a perspective view of an illustrative variation of an electrode array in an unrolled configuration.

As described in detail herein, a pulsed electric field device may comprise an expandable member having a compressed (e.g., rolled) configuration and an expanded (e.g., unrolled) configuration. In some variations, the expandable member may comprise or may otherwise be formed from an electrode array (e.g., a plurality of electrodes). In some variations, the expandable member may comprise a flex circuit comprising a plurality of electrodes. FIG. 34C is a perspective view of an illustrative variation of an expandable member comprising an electrode array (3400). The electrode array (3400) may comprise a plurality of elongate electrodes (3410) on a substrate (3420). In some variations, the electrode array (3400) may be in the form of a flex circuit. As shown there, the flex circuit may comprise an electrode array (3400) or a plurality of electrodes, for example, a plurality of elongate, parallel electrodes. The expandable member is depicted in an unrolled, cylindrical configuration in FIG. 34C.

Figure 35:
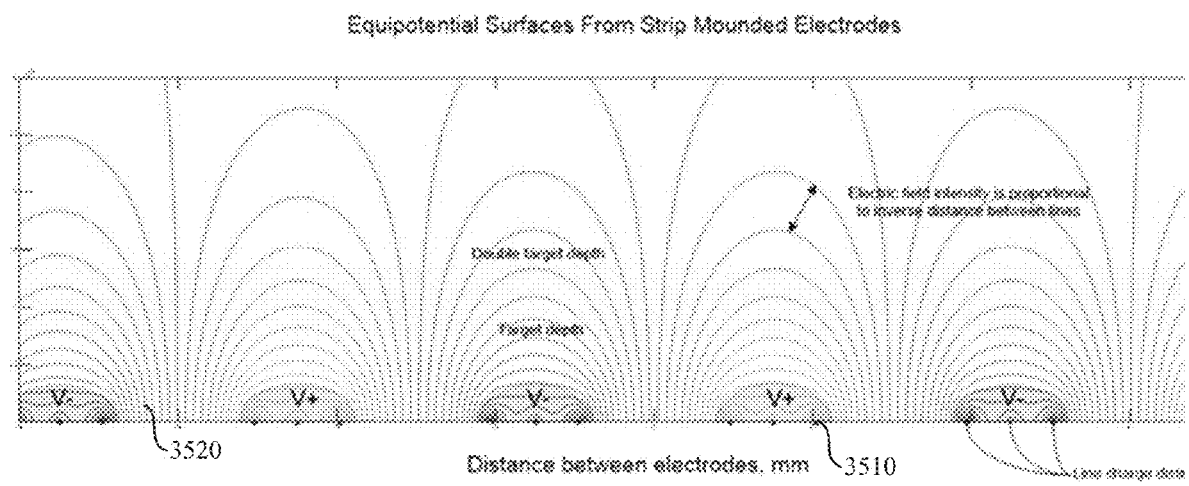
FIG. 35 is an electric field strength plot of an illustrative variation of an electrode array.

FIG. 35 is an electric field strength plot of an electrode array having the ratio of electrode spacing to electrode width described herein. As can be seen there, these electrode arrays generate a substantially uniform electric field. The pulsed or modulated electric field may spatially vary up to about 20% at a predetermined treatment distance from the electrode array. For example, the electric field (3520) generated by the electrodes (3510) may spatially vary up to about 20% at a distance of about 0.7 mm (within a submucosa layer of tissue in contact with the electrode array) from the electrode array. This may improve the consistency of energy delivery and treatment outcomes.

Figure 80A:
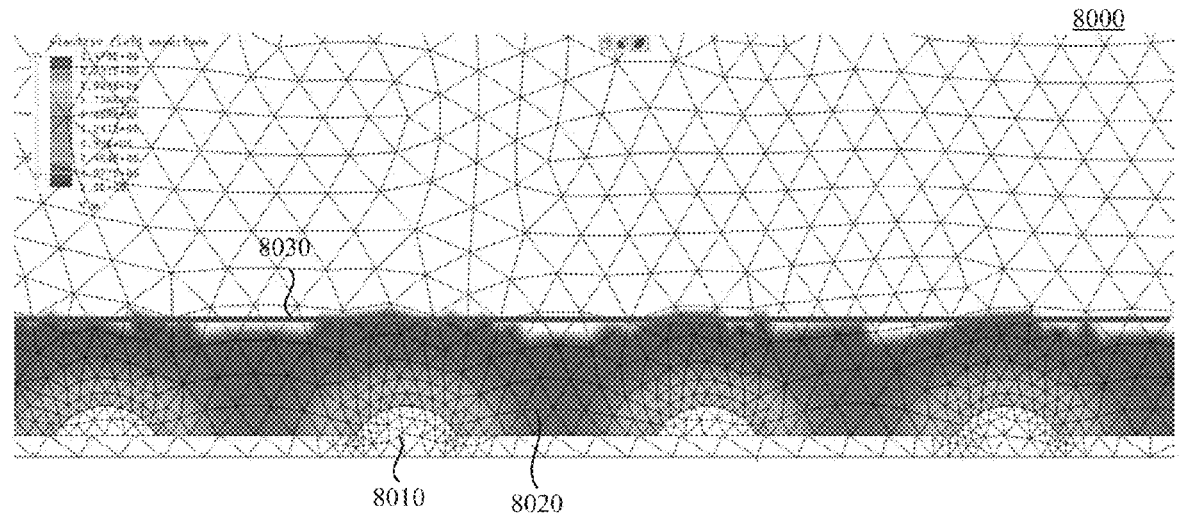
FIGS. 80A and 80B are electric field strength plots of illustrative variations of an electrode array.

FIG. 80A is an electric field strength plot (8000) of a variation of an electrode array (8010). In some variations, the electrode array (8010) may be configured to generate a substantially uniform electric field (8020) at a predetermined tissue treatment depth (8030) across its entire surface. For example, a predetermined tissue depth may be configured to receive a voltage field of about 2,500 V/cm. A voltage of about 600 V with a current of about 50 A and a frequency of about 350 kHz may be applied at the electrodes. This may improve the consistency of energy delivery and treatment outcomes.

Figure 80B:
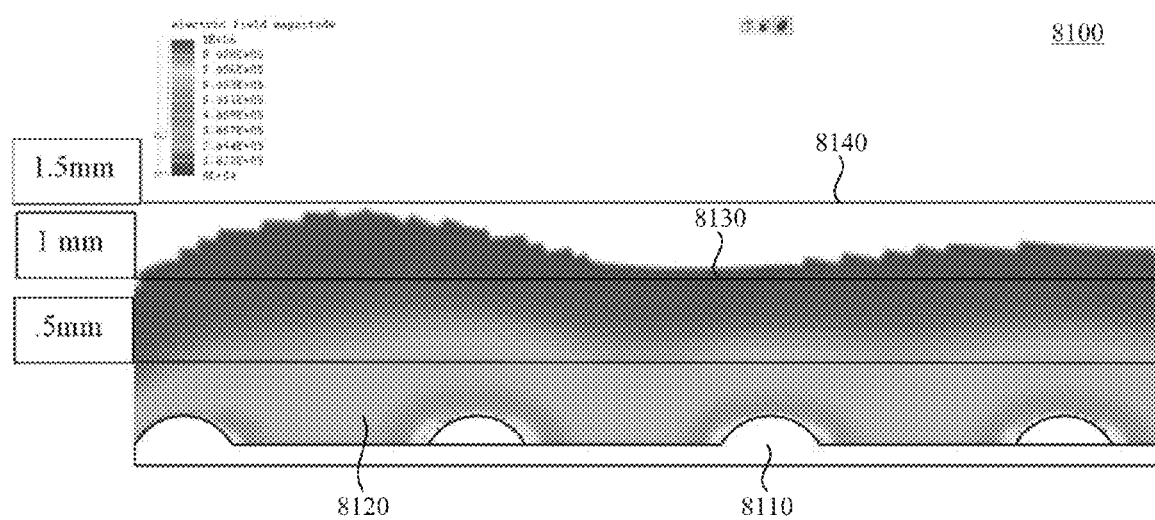

FIG. 80B is an electric field strength plot (8100) of a variation of an electrode array (8110). In some variations, the electrode array (8110) may be configured to generate a substantially uniform electric field (8120) at a first predetermined tissue treatment depth (8130) with an electric field magnitude that falls below a therapeutic treatment threshold at a second predetermined tissue depth (8140). For example, the electrode array (8110) may receive a voltage of about 600 V and generate an electric field (8120) that falls below a therapeutic treatment threshold at a tissue depth of about 1.48 mm.

In some variations, a tissue treatment depth (e.g., mm) receiving about a 2,500 V/cm voltage field may depend on an electrode configuration and the voltage applied to the electrode array. For example, the tissue treatment may require about 2,000 V/cm in which the values in the table would adjust to a deeper tissue treatment for the same applied voltage. The current may depend on tissue conductivity and electrode configuration. Assuming a constant voltage, an electric field penetration is also constant. The tissue treatment ratio may depend on the state of the tissue during treatment (e.g., stretched, compressed, in-contact with the electrodes). The tissue treatment depth may depend on one or more of a tissue treatment ratio, current, effective voltage, and tissue type. Table 1 below provides an illustrative variation of a set of parameters (e.g., voltage, current, power) configured to provide a predetermined ratio of depth of voltage field to depth of tissue treatment.

TABLE 1

| Depth of 2,500 V/cm voltage field (mm) | Effective voltage at electrode (V) | Current (A) | Power (W) | Tissue treatment ratio | Tissue treatment depth (mm) |
|---|---|---|---|---|---|
| 0.2 | 450 | 36 | 16,200 | 0.47 | 0.43 |
| 0.3 | 500 | 40 | 20,000 | 0.47 | 0.64 |
| 0.4 | 550 | 44 | 24,200 | 0.47 | 0.85 |
| 0.5 | 600 | 48 | 28,800 | 0.47 | 1.06 |
| 0.6 | 675 | 54 | 36,450 | 0.47 | 1.28 |
| 0.7 | 750 | 60 | 45,000 | 0.33 | 1.31 |
| 0.8 | 950 | 76 | 72,200 | 0.33 | 1.34 |
| 0.9 | 1100 | 88 | 96,800 | 0.33 | 1.38 |

Figure 36:
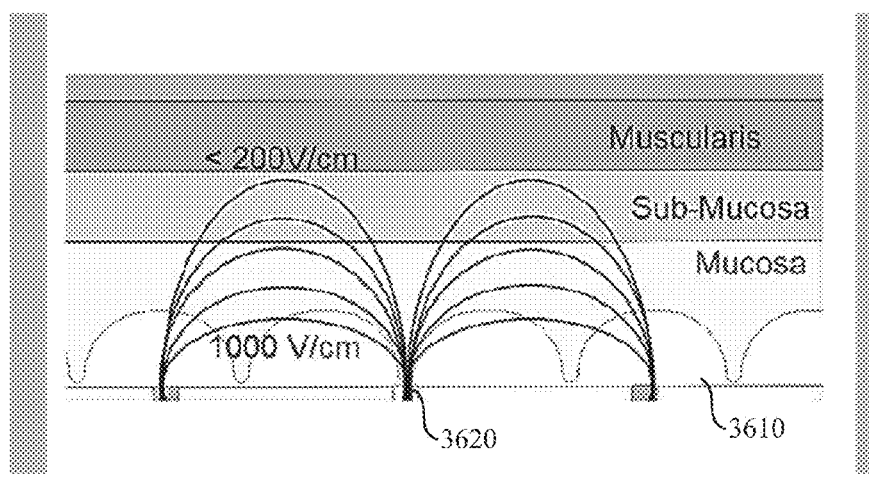
FIG. 36 is an electric field strength plot of a conventional electrode array.

FIG. 36 is an electric field strength plot of a conventional electrode array that lacks electric field uniformity. The electrodes (3610) have a shape and spacing such that the electric field (3620) generated provides an electric field strength of up to about 200 V/cm to some portions of the submucosa while other portions receive little if any of the electric field (3620). Similarly, an electric field strength of up to about 1000 V/cm is provided to some portions of the mucosa while other portions receive little if any of the electric field (3620). Therefore, for conventional electrodes, even if some portions of tissue are delivered a predetermined amount of energy, the poor consistency of energy delivery has limited positive effects on treatment outcomes.

Figure 38:
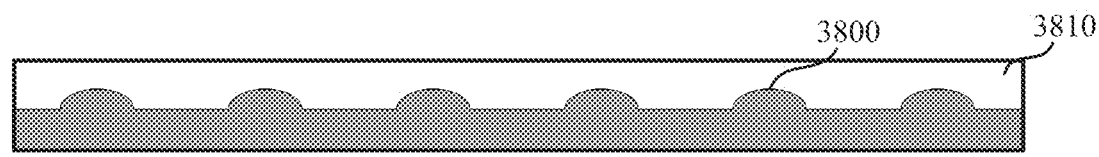
FIG. 38 is a schematic cross-sectional view of an illustrative variation of an electrode array comprising a tissue contact layer.

In some variations, the electrode arrays described herein may further comprise a tissue contact layer. The tissue contact layer may be provided between electrodes and tissue to improve issue conduction and reduce burns from current crowding at the edges of the electrodes. FIG. 38 is a schematic cross-sectional view of an illustrative variation of an electrode array (3800) comprising a tissue contact layer (3810). The electrode array (3800) may be formed by a pair of embossing dies (e.g., dies (3750)) that form a plurality of spaced-apart rounded electrodes (e.g., embossed dimples).

Figure 39:
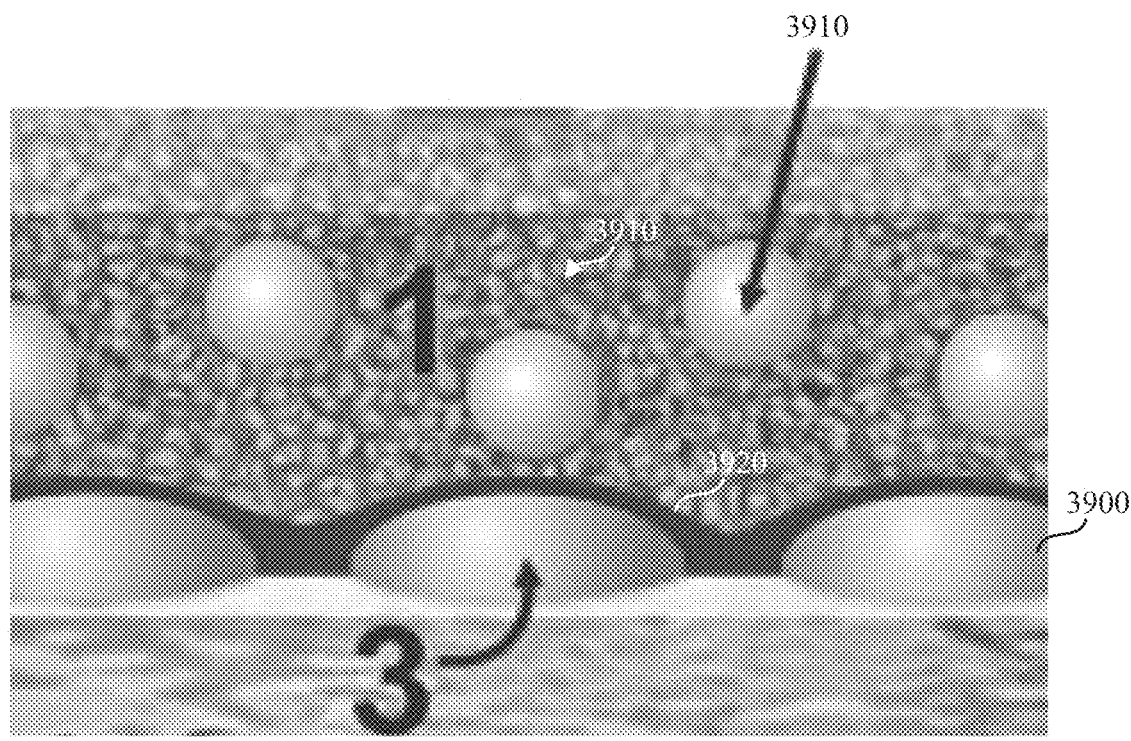
FIG. 39 is a schematic cross-sectional depiction of an illustrative variation of an electrode array comprising a tissue contact layer.

FIG. 39 is a schematic cross-sectional depiction of the electrode array (3900) comprising the tissue contact layer (3920) and in contact with tissue (3910) (e.g., duodenum). In some variations, a tissue contact layer (3920) may be disposed over the electrodes and/or the substrate of the electrode array. The tissue contact layer (3920) may comprise a conductivity less than a conductivity of the electrodes. In some variations, the conductivity of the tissue contact layer may be between about 0.03 S/m and about 0.9 S/m, between about 0.03 S/m and about 0.3 S/m, and between about 0.01 S/m and about 0.7 S/m, including all ranges and sub-values in-between. In some variations, the tissue contact layer may comprise a thickness of between about 10% and about 20% of a width of an electrode. In some variations, the tissue contact layer may be composed of an ohmic electrical conductor such as carbon particulate loaded rubber or a porous material such as an open cell sponge with an ionic conductor such as sodium chloride or carbon.

In some variations, a portion of a tissue contact layer disposed between the electrodes and/or on the edges of the electrodes may comprise a thickness of between about 0.02 mm and about 0.08 mm, and a conductivity of between about 0.02 S/m and about 0.4 S/m, including all ranges and sub-values in-between. The tissue contact layer disposed over the electrode edges may reduce heating by reducing the current draw of the high electric field strength portions of the electrodes. For example, this portion of the tissue contact layer may comprise carbon black disposed in a polymer matrix (e.g., acrylic). For example, one or more electrode edges may comprise a tissue contact layer (e.g., carbon black) comprising a thickness of between about 0.02 mm and about 0.05 mm and a conductivity of between about 0.02 S/m and about 0.4 S/m. Carbon black may improve the performance of an electrode array by absorbing ultraviolet light energy and reducing spark over.

In some variations, the electrode array may further comprise a hydrophilic layer disposed over the electrodes and/or the substrate to improve slidability of a pulsed electric field device relative to tissue. Similarly, a dilator or any component of a pulsed electric field device may comprise a hydrophilic layer to improve slidability of the pulsed electric field device relative to tissue.

Figure 40:
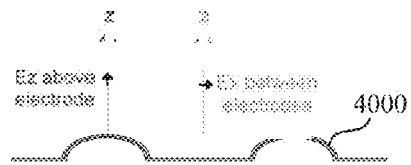
FIG. 40 is a schematic cross-sectional side view of an illustrative variation of an electrode array.

FIG. 40 is a schematic cross-sectional side view of an illustrative variation of an electrode array (4000). To uniformly treat tissue at a predetermined treatment distance away from an electrode (4000), it may be beneficial to have the electric field strength above the electrode (e.g., along $E_z$) and above the space between electrodes (e.g., along $E_x$) be as uniform as possible such that tissue may be treated with the same energy.

Figure 41A:
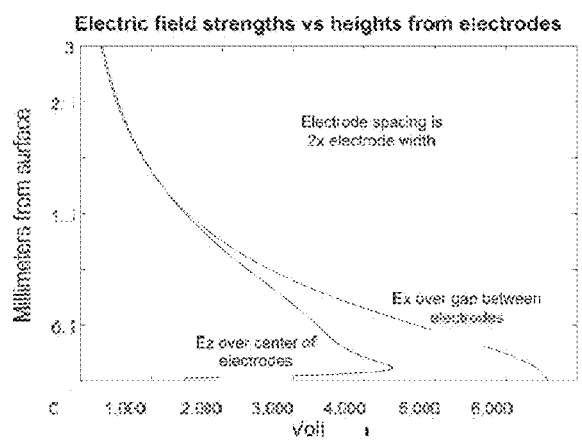
FIGS. 41A-41D are electric field strength plots of illustrative electrode array configurations.
Figure 41B:
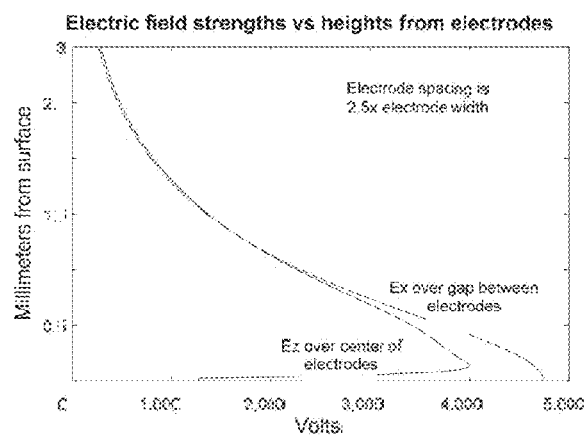
Figure 41C:
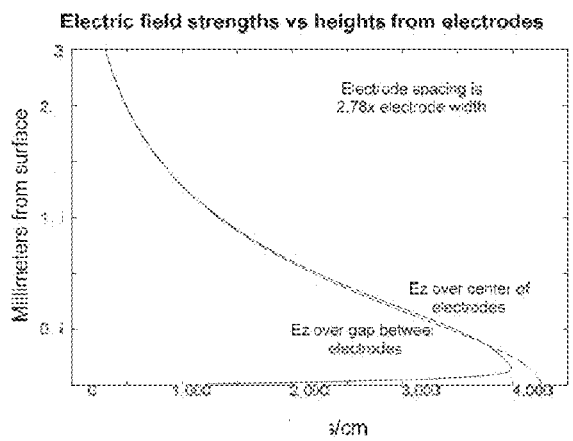
Figure 41D:
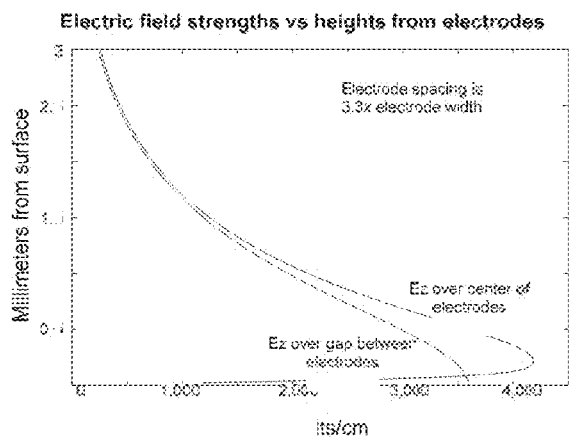

FIGS. 41A-41D are electric field strength plots of illustrative electrode array variations showing how a ratio of center-to-center electrode spacing to electrode width affects electric field strength uniformity. For a treatment depth of 1 mm or less, a ratio of 2:1 (FIG. 41A) may generate a non-uniform electric field, while a ratio between about 2.3:1 and about 3.3:1, and about 2.8:1 and about 3.0:1 (FIGS. 41B-41D) may generate a substantially uniform electric field. For example, at a treatment depth of about 0.7 mm, the difference between $E_x$ and $E_z$ in FIG. 41A is significantly larger than in any of FIGS. 41B-41C.

Figure 42:
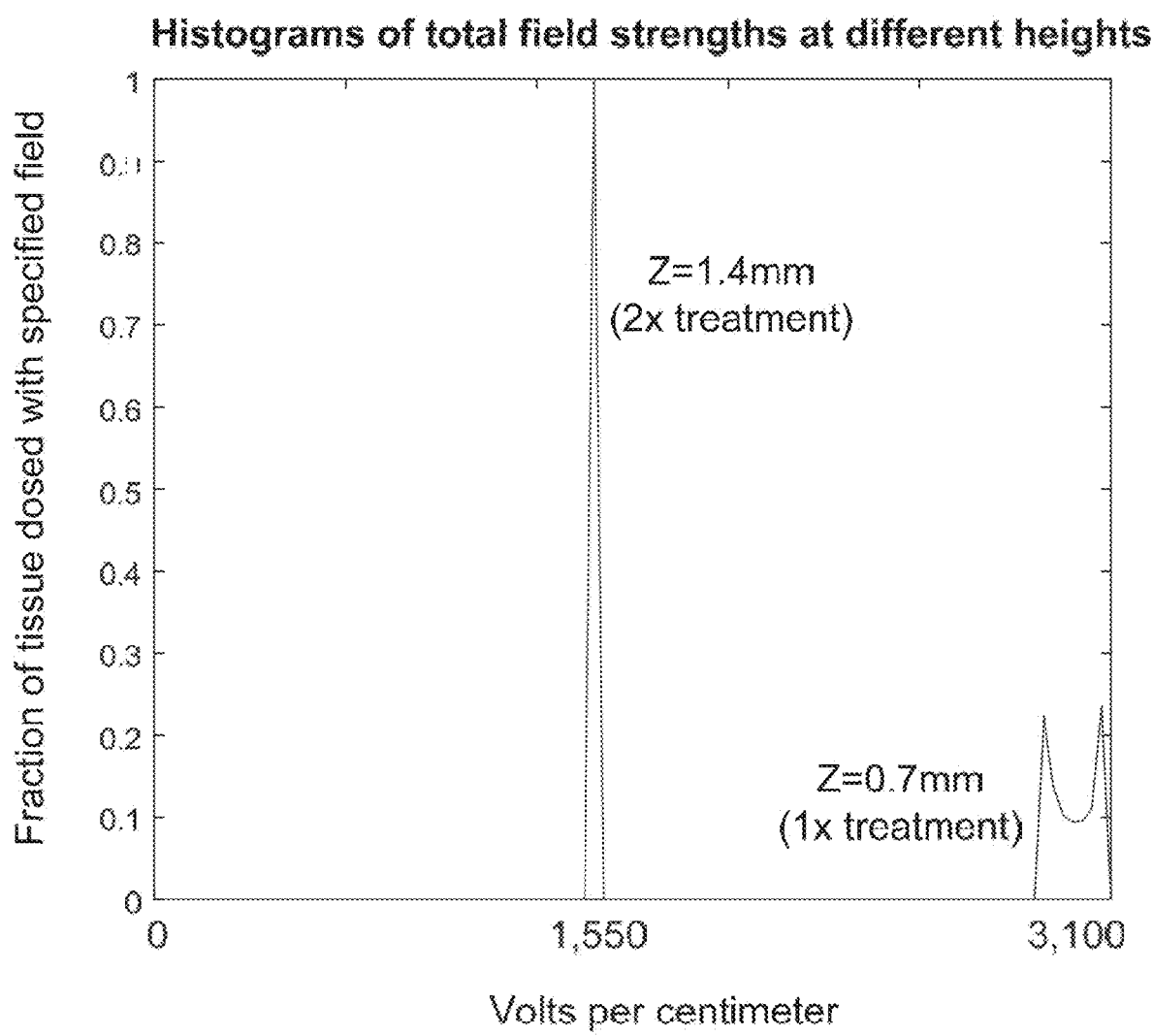
FIG. 42 is an electric field strength plot of an illustrative variation of an electrode array.

FIG. 42 is a histogram of electric field strength of total field strength of an electrode array at a treatment depth of about 0.7 mm and twice the treatment depth at about 1.4 mm. At the treatment depth, there is about a 5% spread in the dose of about 3,100 V/cm. At twice the treatment depth, there is less than 2% spread in the dose of about 1,550 V/cm. Thus, pulsed or modulated electric field energy is substantially delivered uniformly to a predetermined tissue depth.

In some variations, the pulsed electric field systems disclosed herein may comprise a return electrode to draw PEF current out of the patient. In some variation, a catheter (e.g., third elongate body) may comprise a return electrode. In some variations, the return electrode may be external to and in contact with the patient (e.g., a skin patch electrode, grounding pad). For example, a set of return electrodes may be disposed on a back of a patient to allow current to pass from the electrode array through the patient and then to the return electrode. For example, one or more return electrodes may be disposed on a skin of a patient. A conductive gel may be applied between the return electrodes and the skin to improve contact.

Figure 76:
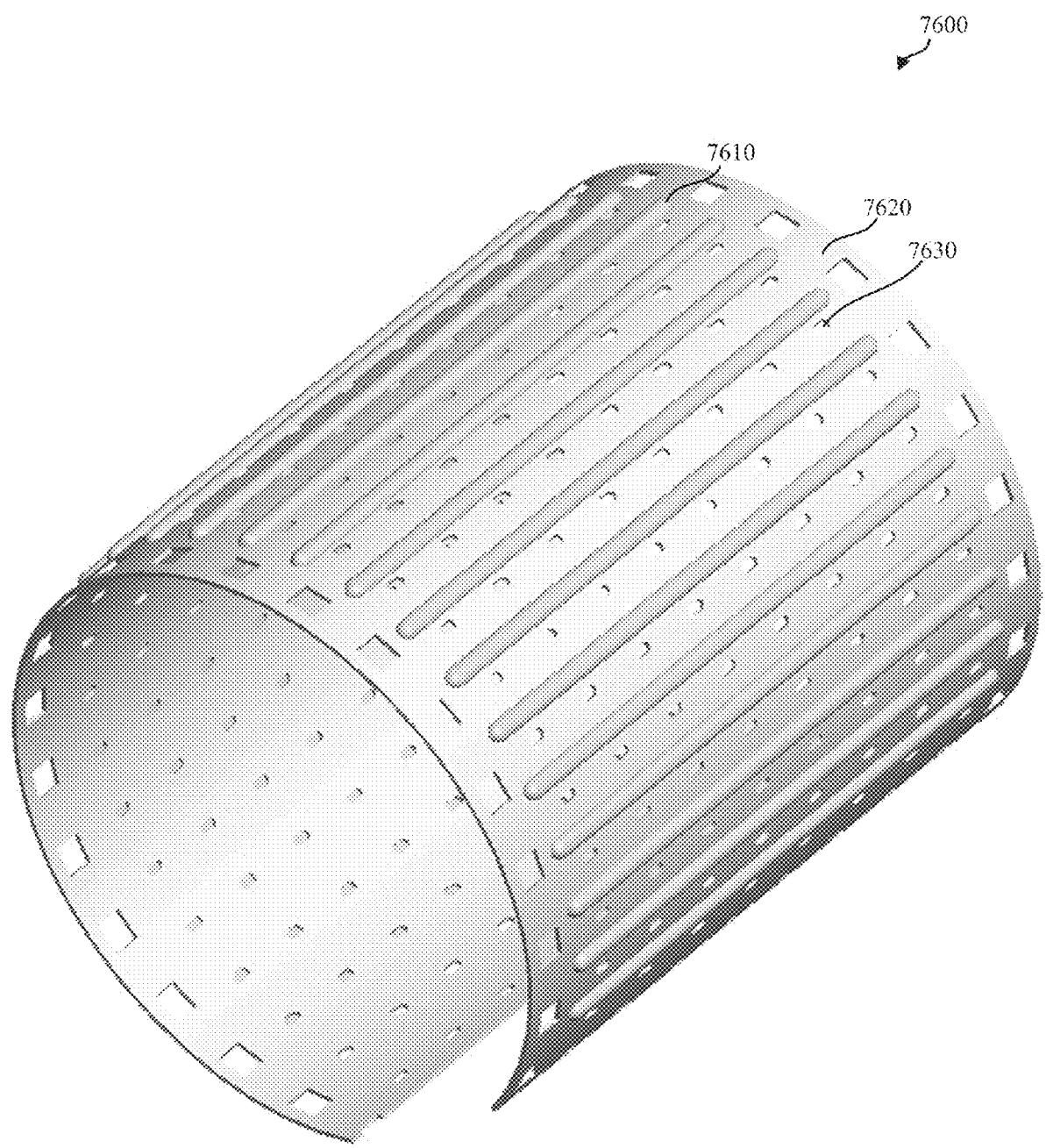
FIG. 76 is a perspective view of an illustrative variation of an electrode array in an unrolled configuration.

FIG. 76 is a perspective view of a variation of an expandable member (e.g., electrode array) (7600) in a partially unrolled or expanded configuration. The electrode array (7600) may comprise a plurality of elongate electrodes (7610) on a substrate (7620). In some variations, the substrate (7620) may comprise a flex circuit comprising a plurality of electrodes. The electrode array (7600) may comprise a plurality of elongate electrodes (7610) on the substrate (7620). As shown there, the flex circuit may comprise an electrode array (7600) or a plurality of electrodes, for example, a plurality of elongate, parallel electrodes.

In some variations, the substrate (7620) of the electrode array (7600) may define one or more openings (7630) (e.g., fluid openings) configured to generate suction (e.g., negative pressure) and/or output fluid (e.g., saline) between adjacent electrodes (7610). The use of suction or negative pressure applied through the openings may draw tissue toward the electrode array (7600) and may facilitate contact between the tissue and the electrode array (e.g., may increase a contact area between the surface of the tissue and the electrode surface). For example, the electrode array (7600) may be engaged to the duodenum via suction through the one or more openings (7630) that may promote more reliable (e.g., consistent) electrical contact between the pulsed electric field device and tissue, and therefore a more uniform electric field and an improvement to treatment outcomes. In some variations, a plurality of openings (7630) (e.g., row of openings (7630)) may be disposed between each pair of adjacent electrodes (7610) with a predetermined spacing. For example, the openings (7630) may be spaced apart along a length of an electrode (6920). In some variations, the fluid opening (7630) may be disposed closer to one of the electrodes to promote contact between the tissue and at least one of the electrodes (7610). Additionally or alternatively, the openings (7630) may be disposed equally between adjacent electrodes (7610).

Additionally or alternatively, the openings (7630) may be configured for fluid irrigation. The electrode array (7600)

may be in fluid communication with (e.g., fluidically coupled to) a fluid source (not shown) for fluid irrigation. For example, fluid may be removed from (e.g., suctioned out of) a body cavity after applying the pulsed or modulated electric field using the electrodes (7610). In some variations, removal of the fluid may facilitate apposition and/or contact between the tissue and the electrode array (7600).

In some variations, at least one of the electrodes (7610) may comprise a semi-elliptical cross-sectional shape. In some instances, all of the electrodes (7610) in the electrode array (7600) may comprise a semi-elliptical cross-sectional shape. In some variations, a major axis of the electrode (7610) may be about twice the electrode width and the minor axis of the electrode may be about equal to the electrode height in the middle of the electrode.

Figure 77:
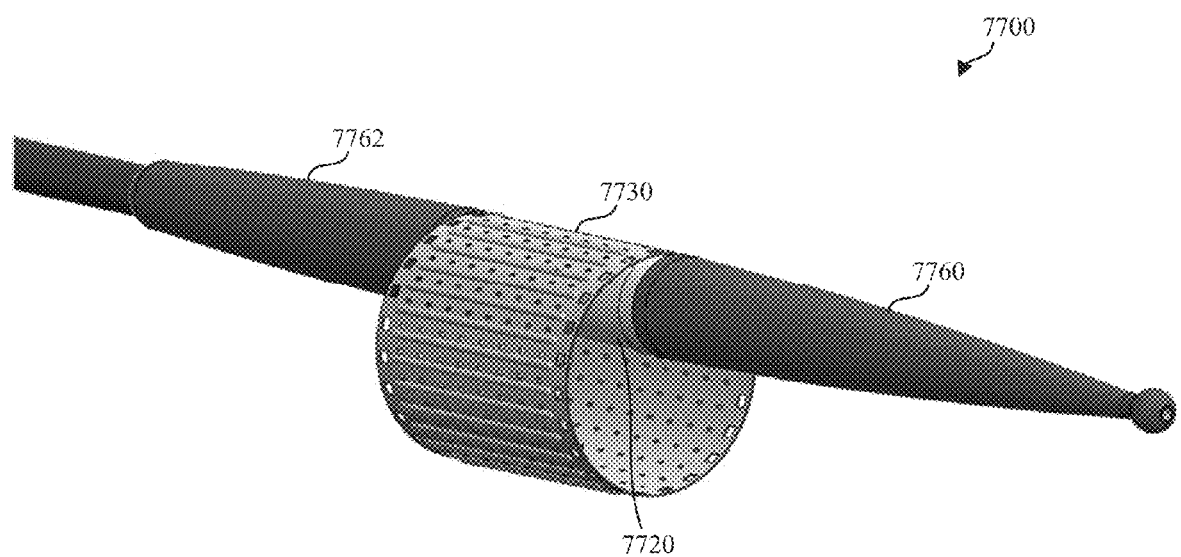
FIG. 77 is a perspective view of an illustrative variation of a pulsed electric field device in an expanded configuration.

FIG. 77 is a perspective view of an illustrative variation of a pulsed electric field device (7700) in an expanded configuration configured for engagement with tissue such as an inner surface of a duodenum (not shown). The pulsed electric field device (7700) may comprise a first elongate body (7710), second elongate body (7720), expandable member (7730), and dilators (7760, 7762). When in the expanded or unrolled configuration, the expandable member (7730) may have a generally elliptic or cylindrical shape with a second inner diameter and a second outer diameter having a predetermined diameter larger than a respective first inner diameter and first outer diameter. The expandable member (7730) in the expanded configuration may have a predetermined flexibility configured to conform to a shape of the tissue to which it is engaged. The expandable member (7730) may comprise, for example, the electrode array (7600) depicted in FIG. 76.

In some variations, the first and second elongate bodies (7710, 7720) may be configured to axially rotate relative to one another to transition the expandable member (7730) between the compressed configuration, the expanded configuration, and the semi-expanded configuration therebetween. For example, the second elongate body (7720) (e.g., inner torsion member, rotatable member) may be rotatably positioned within a lumen of the first elongate body (7710) such that rotation of the second elongate body (7720) relative to the first elongate body (7710) may transition the expandable member (7730) between a rolled configuration and an unrolled configuration. In some of these variations, the inner diameter of the lumen (7750) of the expandable member (7730) may be at least about 8 mm in the unrolled configuration, at least about 10 mm, or from about 8 mm to about 10 mm, including all values and sub-ranges in-between. As described in more detail herein, a visualization device (not shown) may be disposed within the lumen (7750) of the expandable member (7730) to aid in visualization. It should be appreciated that the pulsed electric field device (7700) may be advanced next to a visualization device and/or over a guidewire. In some variations, a visualization device may be used to guide advancement and to visualize a treatment procedure such that a guidewire and/or other visualization modalities (e.g., fluoroscopy) are not needed.

In some variations, the expandable member (7730) may be configured to transition to a configuration between the compressed and expanded configurations. For example, the expandable member (7730) may transition to a partially or semi-expanded configuration (between the compressed configuration and expanded configuration) that may allow a visualization device (e.g., endoscope) to be disposed within a lumen of the expandable member (7730). In some variations, an inner surface of the expandable member may engage and hold a visualization device in a semi-expanded configuration.

Figures 78A, 78B:
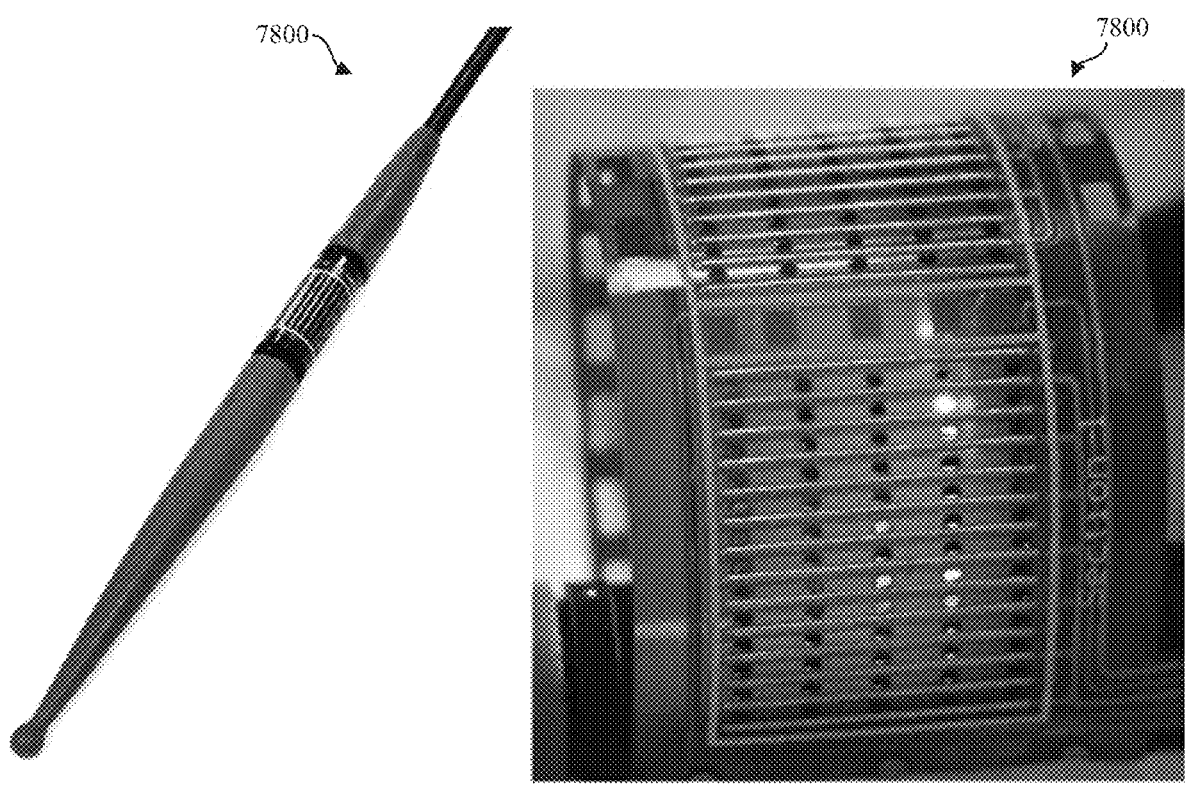
FIG. 78A is an image of an illustrative variation of a pulsed electric field device in a retracted or compressed configuration.
FIG. 78B is a detailed image of an unrolled or expanded electrode array of the pulsed electric field device depicted in FIG. 78B.

FIG. 78A is an image of a pulsed electric field device (7800) in a compressed configuration and FIG. 78B is a detailed image of an unrolled electrode array (7800) of the pulsed electric field device depicted in FIGS. 77 and 78A. The electrodes shown in FIGS. 76-78B may have a generally hemi-spherical shape, as described herein. In some variations, one or more of the electrodes of the electrode array (7610) may have a height of between about 0.07 mm and about 0.38 mm, about 0.178 mm, including all ranges and sub-values in-between. In some variations, a distance between adjacent (e.g., proximate) electrodes (7610) may be between about 1.0 mm and about 1.4 mm, about 1.2 mm including all ranges and sub-values in-between. In some variations, one or more of the electrodes of the electrode array (7610) may have a pad width of between about 0.5 mm and about 0.7 mm, and about 0.6 mm, including all ranges and sub-values in-between. In some variations, a distance between an electrode (7610) and a temperature trace (not shown) may be between about 1.0 mm and about 1.4 mm, about 1.2 mm, including all ranges and sub-values in-between.

Figure 43:
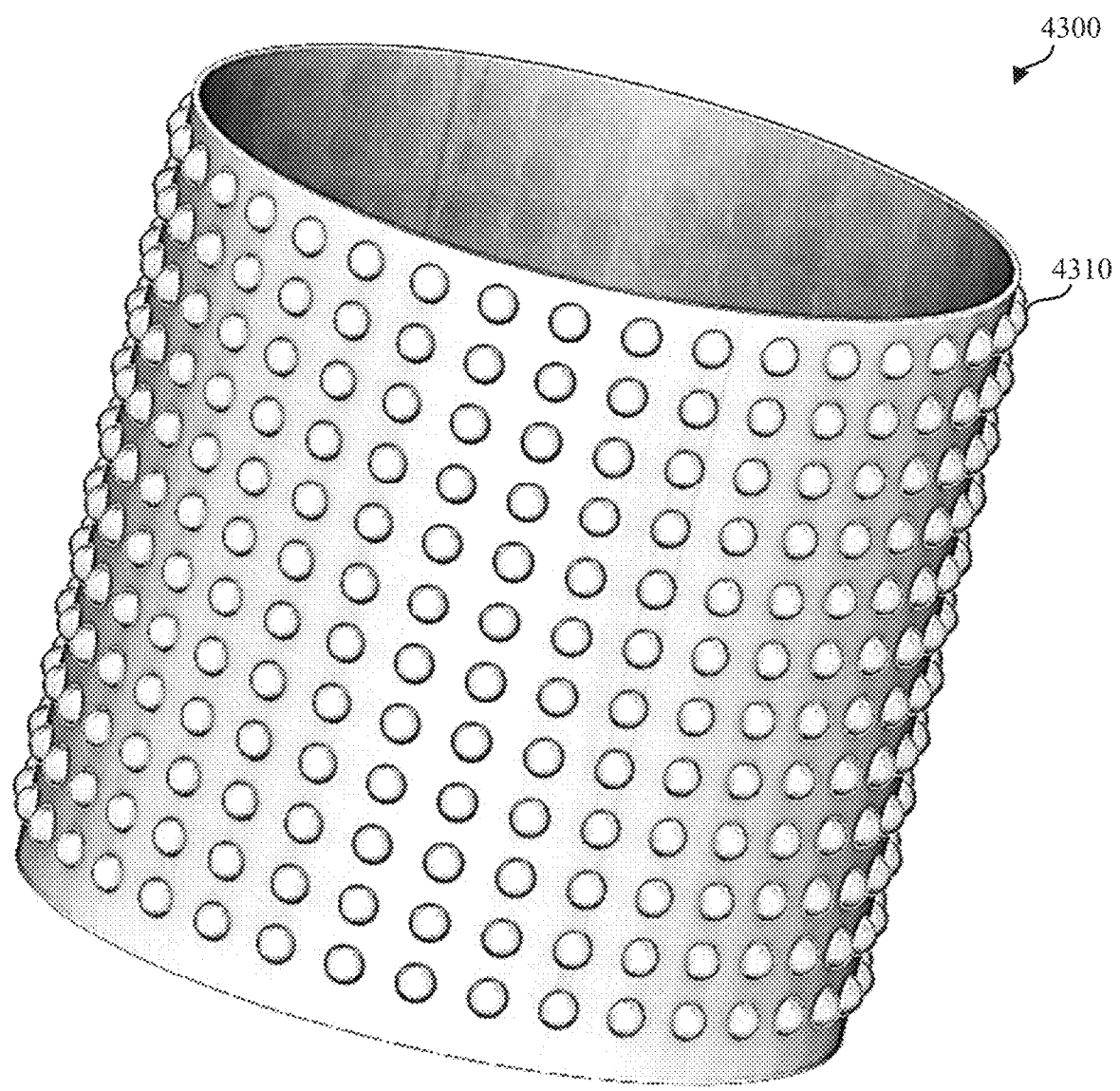
FIG. 43 is a perspective view of an illustrative variation of an expandable member comprising an electrode array.

FIG. 43 is a perspective view of an illustrative variation of an expandable member (4300) comprising an electrode array (4310) comprising a plurality of spaced apart and hemi-elliptical electrodes. The hemi-elliptical electrodes may form a plurality (e.g., 4, 8, 12, 16, 20, or any value therebetween) of parallel or interdigitated lines. Additionally or alternatively, the hemi-elliptical electrodes may be raised relative to a substrate of the electrode array and may comprise a rounded or hemispherical shape. In some variations, the electrode array may comprise a tissue contact layer disposed over one or more of the electrodes and the space between the electrodes, as described in detail herein.

Figure 44:
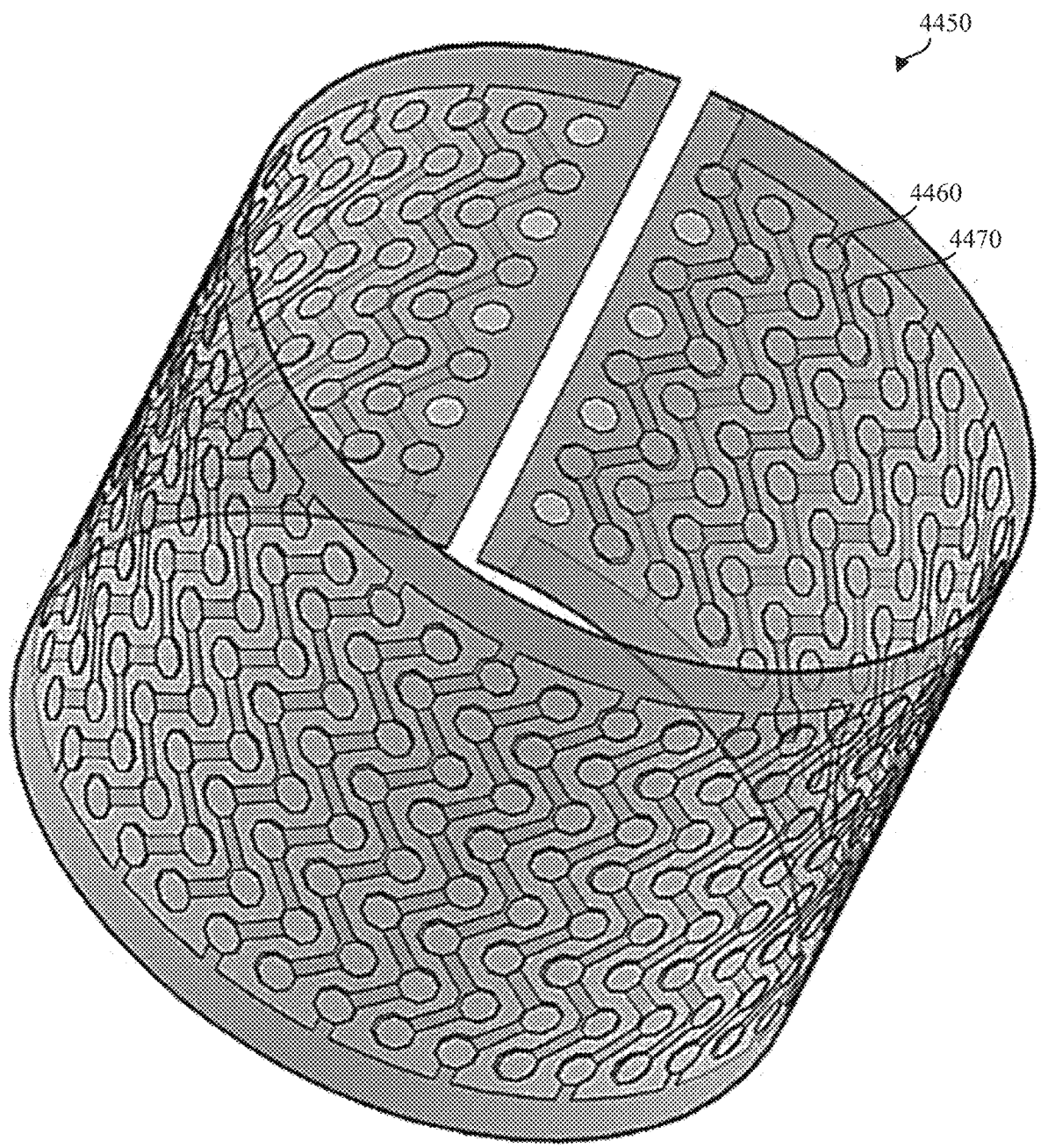
FIG. 44 is a perspective view of an illustrative variation of an expandable member comprising an electrode array.

FIG. 44 is a perspective view of an illustrative variation of another expandable member (4450) comprising an electrode array. As depicted there, the electrode array may comprise a plurality of hemi-elliptical electrodes (4460) and a plurality of leads (4470) coupling two or more of the electrodes to one another in a zig-zag pattern. The electrode array may comprise a flex circuit.

Figure 45A:
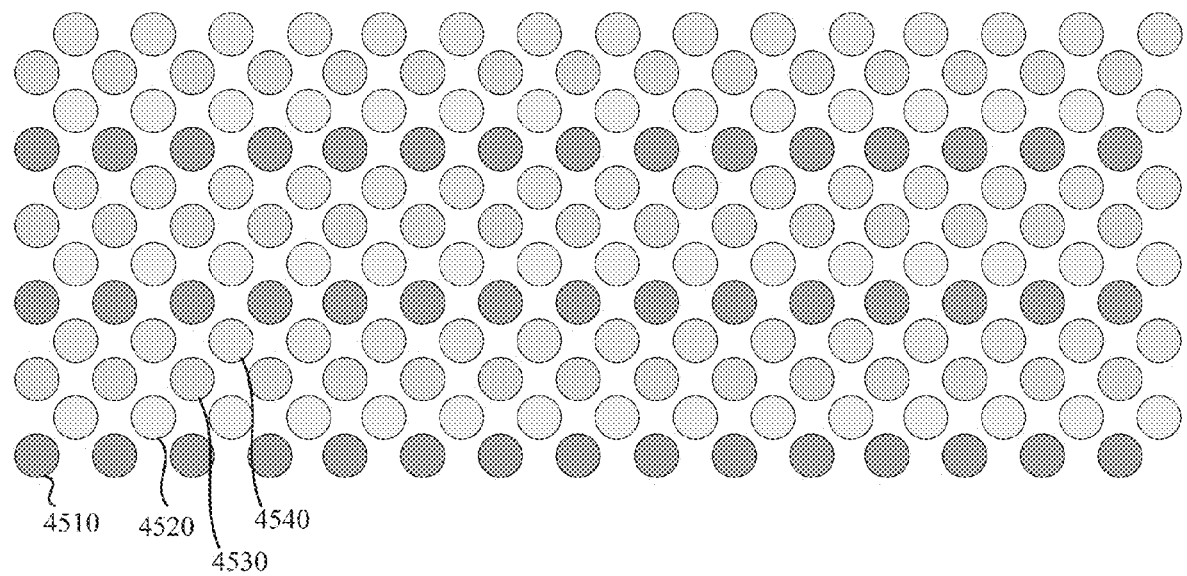
FIGS. 45A-45C are schematic diagrams of an illustrative variation of an electrode array.
Figure 45B:
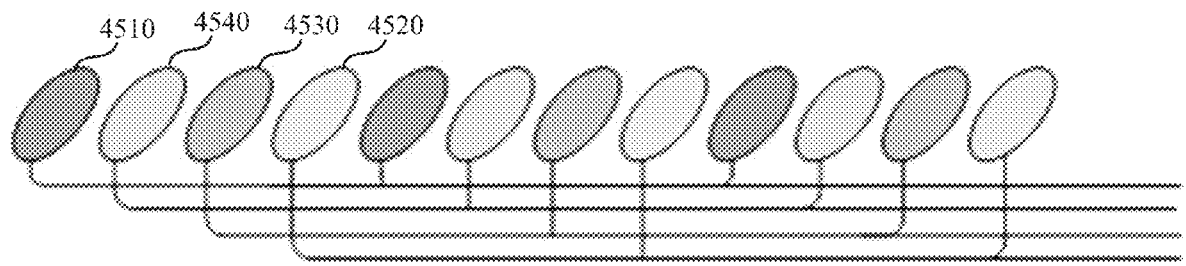
Figure 45C:
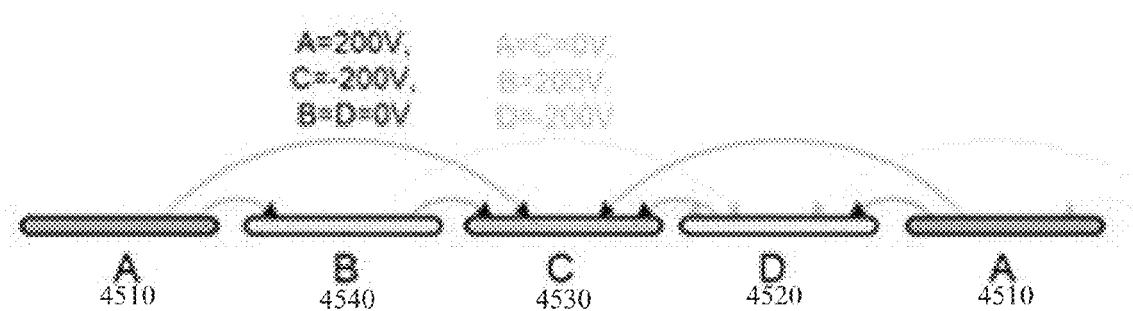

FIGS. 45A-45C are schematic diagrams of an illustrative variation of an electrode array configuration such as a pair of twisted pair wires driven 90 degrees out of phase with alternating polarity. This configuration may allow generation of a substantially uniform pulsed or modulated electric field. For example, electrode pairs A (4510) and C (4530) may comprise opposite polarities while electrode pairs B (4540) and D (4520) may comprise opposite polarities. Other electrode array configurations types may be activated with alternate combinations to yield a uniform treatment in the tissue, (e.g., electrode pair A and B, electrode pair A and C, electrode pair A and D, electrode pair B and C, electrode pair B and D, electrode pair C and D). The distance between the electrode pairs will directly affect the magnitude of the electric field or tissue treatment distance into the tissue. Electrode pairs may be selected by a controller to treat tissue at one or more predetermined tissue treatment depths.

Figure 45D:
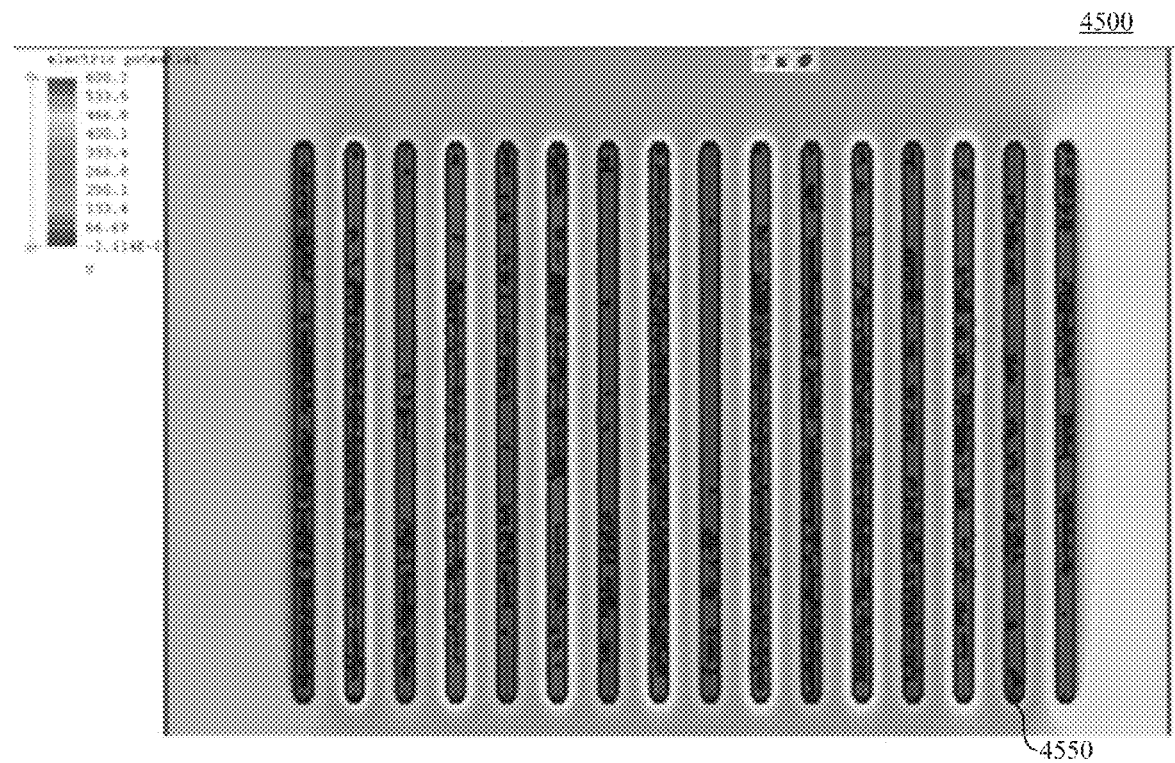
FIG. 45D is a plan view of an electric field strength plot of an illustrative variation of an electrode array.
Figure 45E:
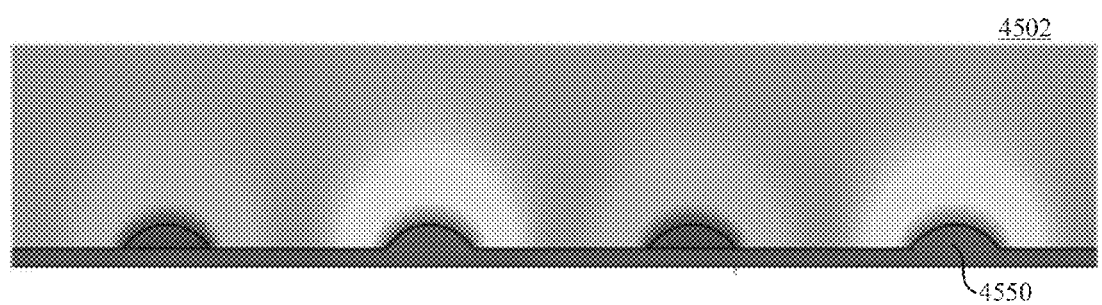
FIG. 45E is a cross-sectional view of an electric field strength plot of the electrode array depicted in FIG. 45D.
Figure 45E:
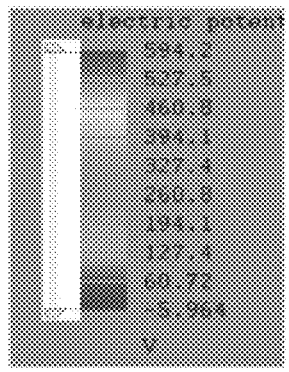

FIG. 45D is a plan view of an electric field strength plot (4500) of an illustrative variation of an electrode array (4550). FIG. 45E is a cross-sectional view of an electric field strength plot (4502) of the electrode array (4550) depicted in FIG. 45D. The electrode array (4550) may be configured in a bipolar configuration and primarily apply non-thermal therapy to duodenal tissue. For example, current passes from anode electrodes to cathode electrodes through tissue.

In some variations, a depth of electric field penetration into tissue may be based at least in part on an electrode spacing (e.g., 1.2 mm) of the electrode array and voltage at the electrode array (e.g., 600 V). For example, the electrode array (4550) may be configured to generate a pulsed electric field that penetrates tissue at a depth of about 1 mm while dissipating rapidly beyond a tissue depth of about 1.5 mm and at the edges of the electrode array (4550).

Figure 46A:
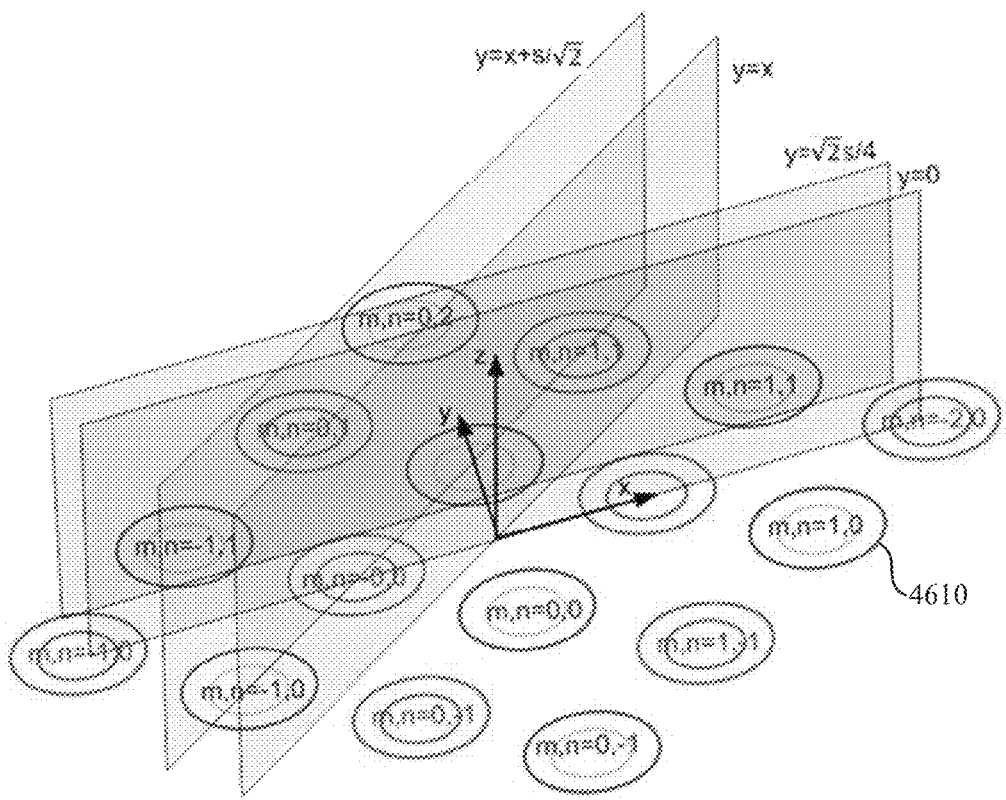
FIG. 46A is a schematic perspective view of an illustrative variation of a coordinate system for an electrode array.
Figure 46B:
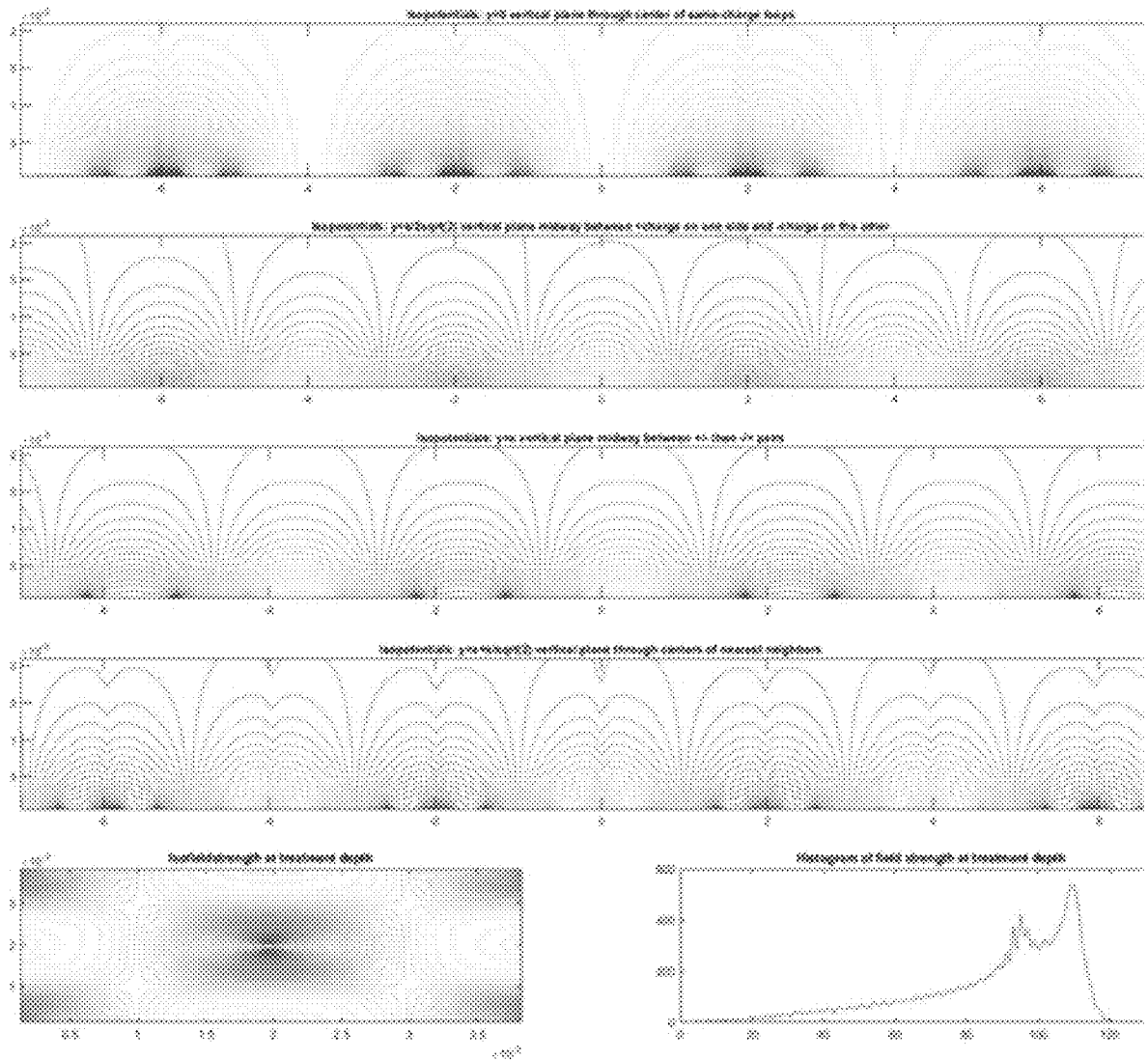
FIG. 46B are electric field strength plots corresponding to the electrode array shown in FIG. 46A.

FIG. 46A is a schematic perspective view of an illustrative variation of a coordinate system of an electrode array (4610) and a corresponding set of planes. FIG. 46B depicts electric field strength plots corresponding to the electrode array (4610) at positions defined with respect to the principle planes depicted in FIG. 46A. The two bottom charts in FIG. 46B illustrate an isopotential plot at a target treatment depth (e.g., z=0.7 mm) and the histogram of the total electric field at the target treatment depth (e.g., z=0.7 mm).

Figure 47A:
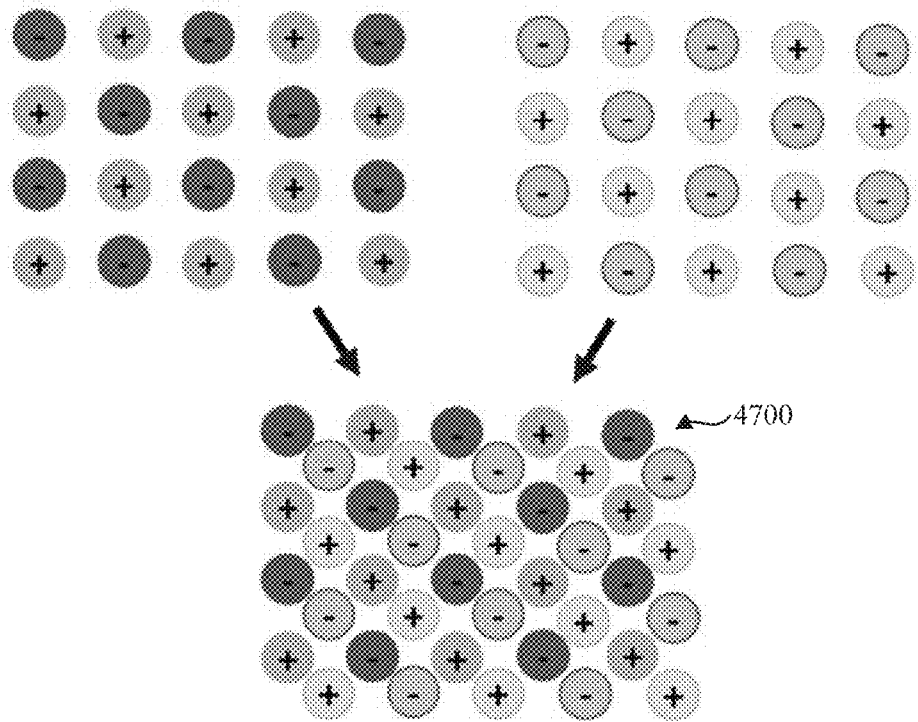
FIG. 47A is a schematic plan view of an illustrative variation of a polarity configuration of an electrode array.
Figure 47B:
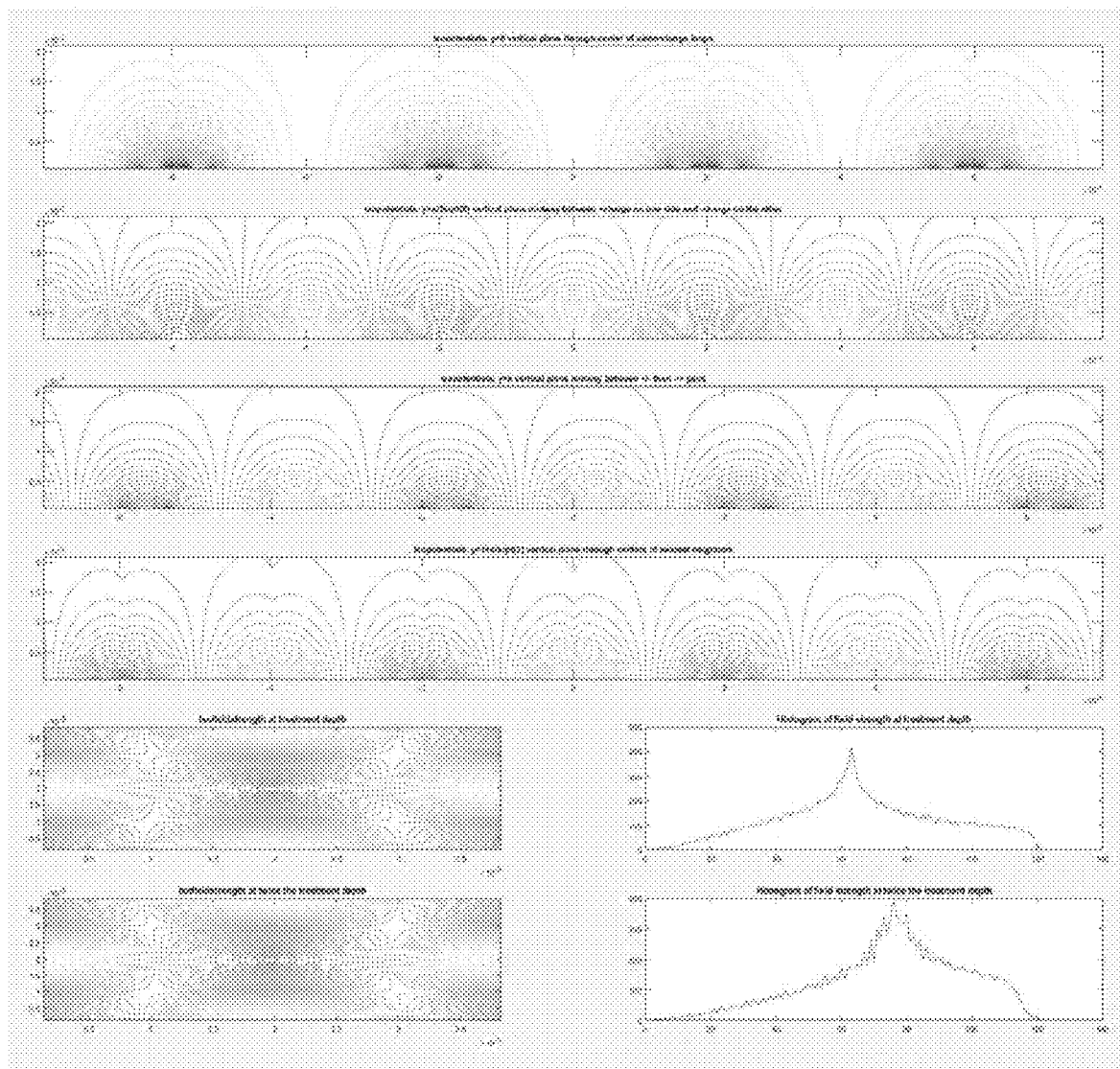
FIG. 47B are electric field strength plots corresponding to the electrode array shown in FIG. 47A.

FIG. 47A is a schematic plan view of an illustrative variation of a polarity configuration of an electrode array (4700). FIG. 47B depicts electric field strength plots corresponding to the electrode array (4700) shown in FIG. 47A at positions defined with respect to the principle planes depicted in FIG. 46A. The two bottom charts in FIG. 47B illustrate an isopotential plot at a target treatment depth (e.g., z=0.7 mm, 1.4 mm) and the histogram of the total electric field at the target treatment depth (e.g., z=0.7 mm, 1.4 mm). The electric field densities depicted in FIG. 47B and corresponding to the electrode array (4700) are denser than those depicted in FIG. 46B and corresponding to electrode array (4600). The corresponding non-active set of electrodes may be floating potentials while the other electrode set is activated.

Figure 48:
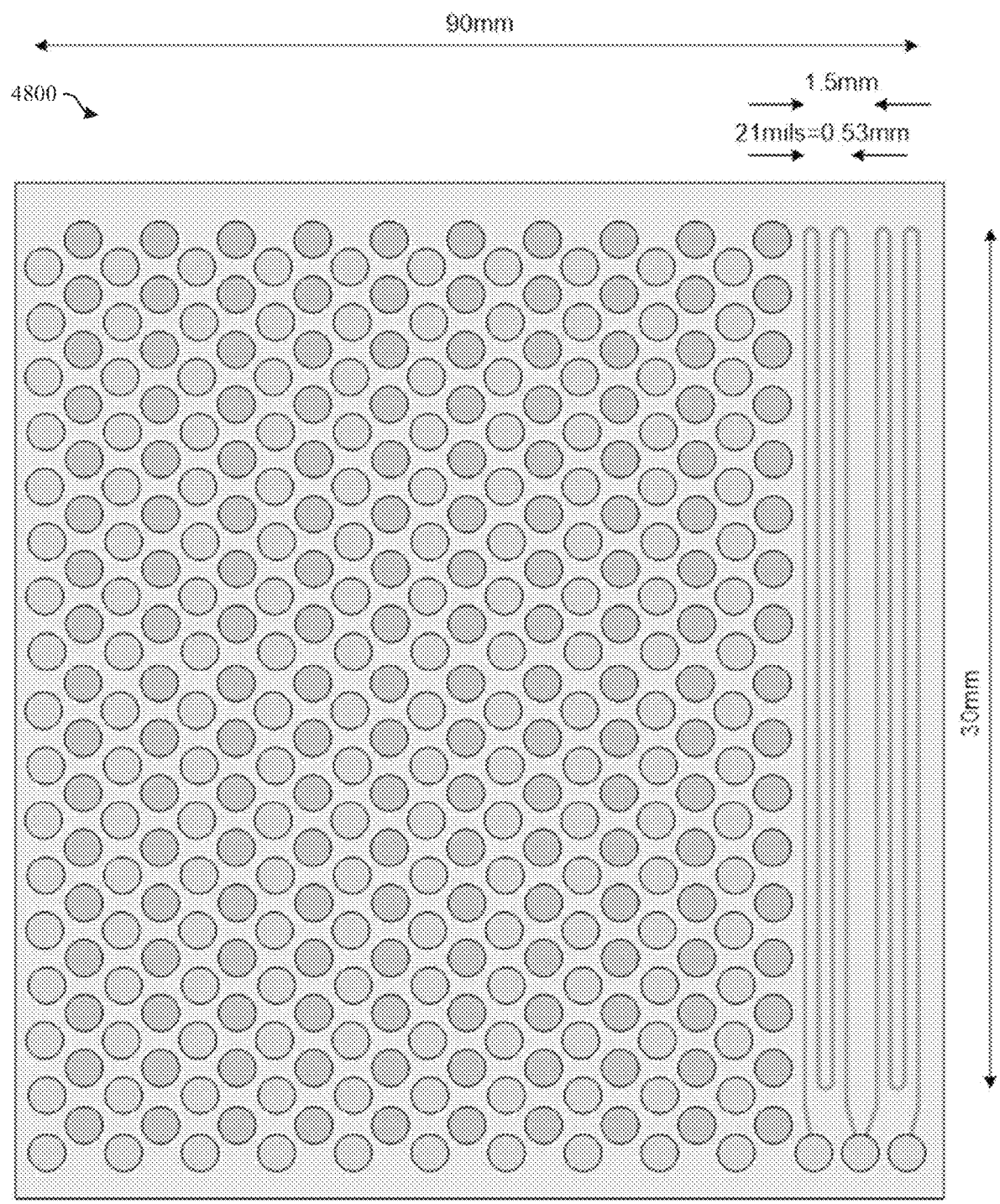
FIG. 48 is a schematic plan view of an illustrative variation of an electrode array.
Figure 49:
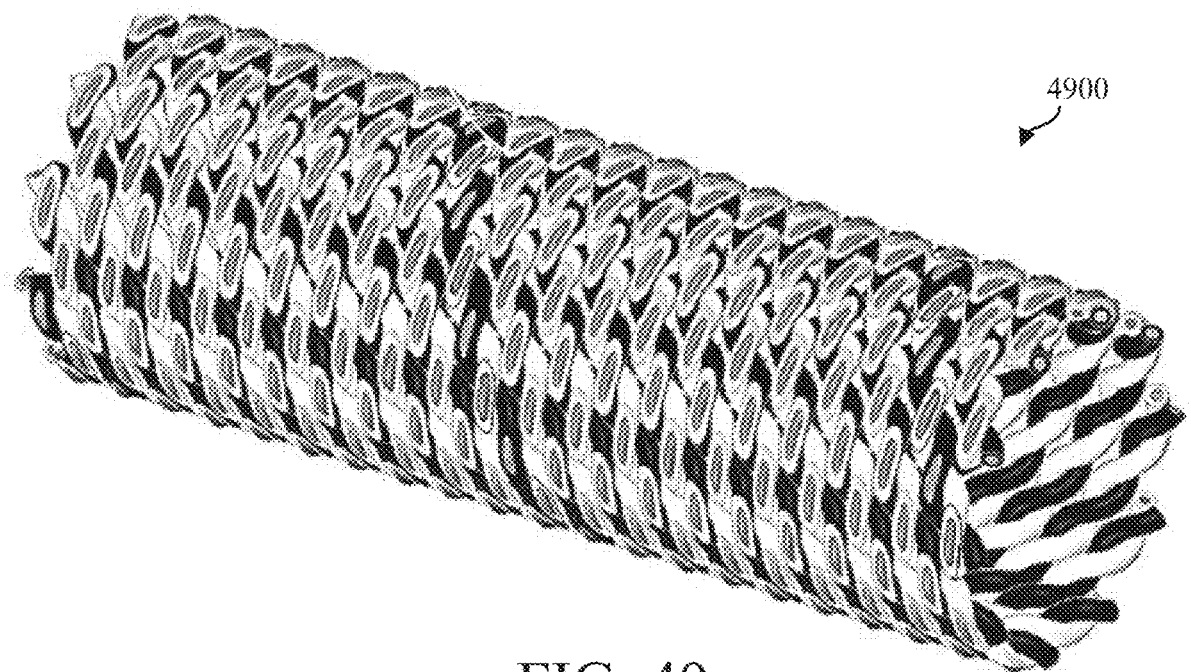
FIG. 49 is a perspective view of an illustrative variation of an electrode array of a pulsed electric field device.
Figure 50:
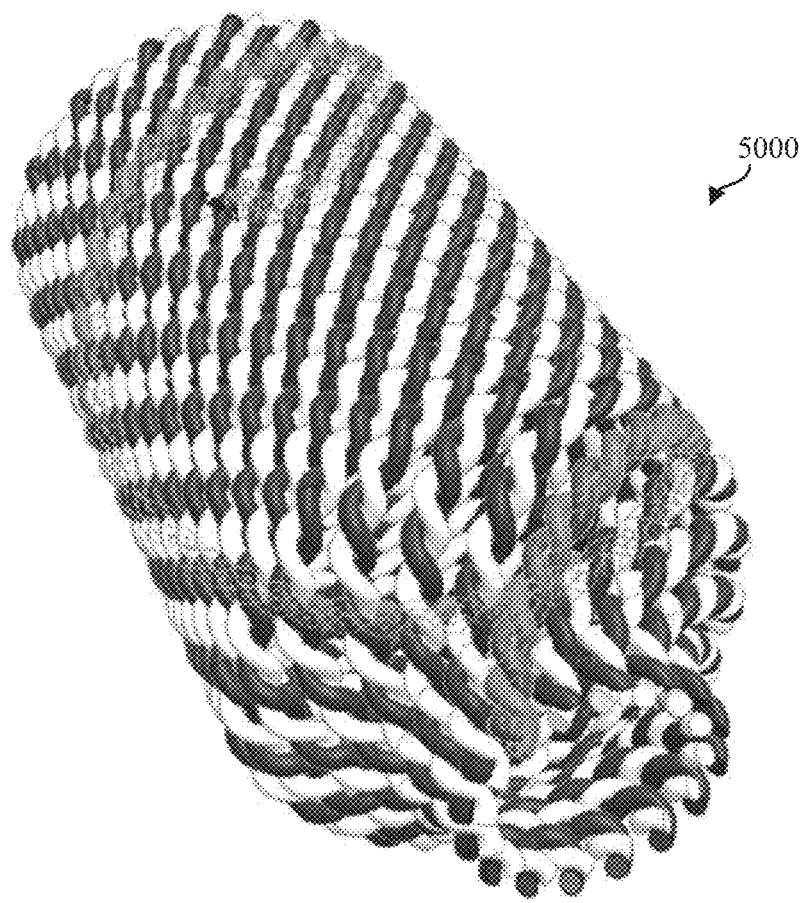
FIG. 50 is a perspective view of an illustrative variation of an electrode array of a pulsed electric field device.

FIG. 48 is a schematic plan view of an illustrative variation of an electrode array (4800) having illustrative dimensions and thermal couple traces on the right side of the electrode array (4800). FIG. 49 is a perspective view of a variation of an electrode array (4900) of a pulsed electric field device comprising a plurality of pairs of twisted pair wires. FIG. 50 is a perspective view of another variation of an electrode array (5000) of a pulsed electric field device comprising a plurality of pairs of twisted pair wires. The twisted pair wires with exposed core locations may function in a similar manner to a dot electrode configuration.

Figure 85:
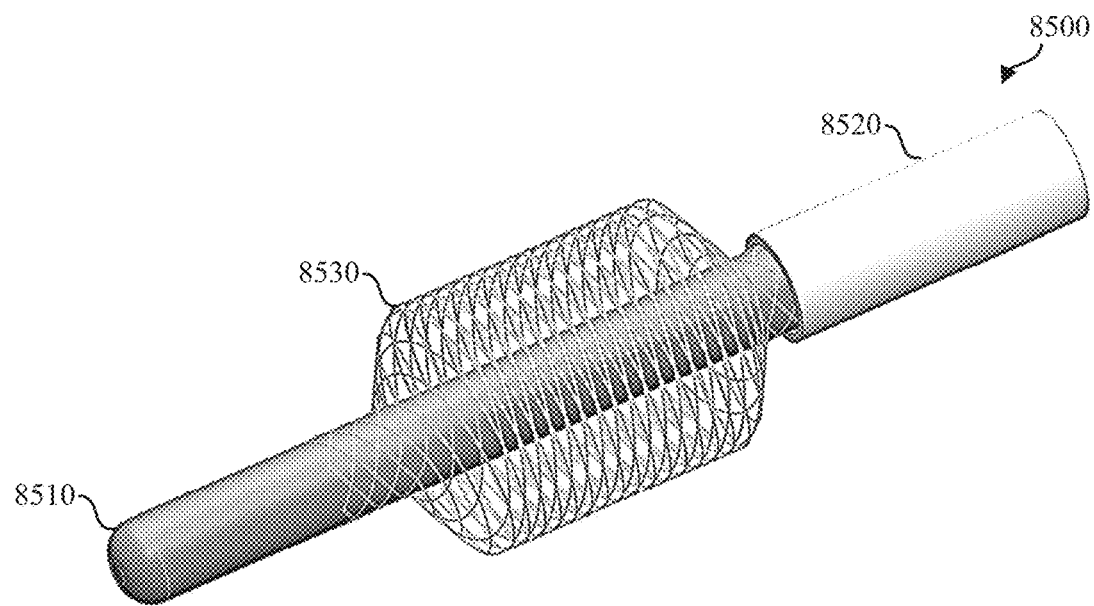
FIG. 85 is a perspective view of an illustrative variation of an electrode array of a pulsed electric field device.

FIG. 85 is a perspective view of a variation of an electrode (8530) of a pulsed electric field device (8500). The pulsed electric field device (8500) may comprise a first catheter (8510) (e.g., inner shaft) and a second catheter (8520) (e.g., outer shaft). In some variations, the second catheter (8520) may be slidably advanced over the first catheter (8510) and the electrode (8530) to hold the electrode (8530) in a compression configuration. As shown in FIG. 85, the first catheter (8510) advanced distally relative to the second catheter (8520) may transition the electrode (8530) o an expanded configuration.). In some variations, The electrode (8530) may be coupled (e.g., attached) to the first catheter (8510) on one end and the second catheter (8520) on the other end. The second catheter (8520) may be slidably advanced and/or retracted over the first catheter (8510). The electrode (8530) may transition between the expanded configuration and the compressed configuration.

The electrode (8510) may comprise an expandable metal mesh and be configured to have a first polarity. Another electrode having a second polarity opposite the first polarity may be disposed, for example, on a skin of the patient (e.g., a grounding pad). In some variations, a size of the grounding pad may have a sufficient surface area to minimize current concentration and heat generation. In some variations, the pulsed electric field device (8500) may be configured in a monopolar configuration or a bipolar configuration. In some variations, the expandable electrode (8510) may be configured to contact tissue in an expanded configuration. In some variations, negative suction may be applied through a lumen of the electrode (8510) to enhance a tissue-electrode interface. In some variations, the pulsed electric field device (8500) may be irrigated using a liquid (e.g., conductive liquid, saline) while treating tissue as described herein. In some variations, the pulsed electric field device (8500) in a compressed configuration may be configured to be slidably advanced through a lumen (e.g., working lumen) of a visualization device (e.g., endoscope). For example, the pulsed electric field device (8500) in a compressed configuration may comprise a diameter of between about 1.5 mm and about 4 mm.

Irrigation

Generally, the tissue treatment procedures using a pulsed electric field device as described herein may optionally comprise fluid delivery (e.g., fluid irrigation) during tissue treatment. In some variations, the tissue treatment procedures may benefit from fluid irrigation that may promote more reliable (e.g., consistent) electrical contact between the pulsed electric field device and tissue and therefore a more uniform electric field and an improvement to treatment outcomes. Fluid irrigation to tissue may further reduce tissue temperature through forced convention and may reduce arcing. Furthermore, fluid delivery may reduce the accumulation of electrically insulating corrosion and electrolysis products. In some variations, the fluid may function as a salt bridge between the electrodes and tissue that allows control of resistivity. In variations in which fluid is delivered, the fluid may be removed from (e.g., suctioned out of) a body cavity after applying the pulsed or modulated electric field. In some variations, the conductivity of the fluid introduced or removed may have an effect on the delivered therapy. For example, adding a solution that is less conductive than the tissue may facilitate more current being introduced into the tissue. Conductivity that is about the same as the tissue may facilitate a transfer of electric field energy into the tissue even if tissue contact between the electrodes and tissue is lacking. Finally, a fluid having a higher conductivity than the tissue may be removed.

Figure 69A:
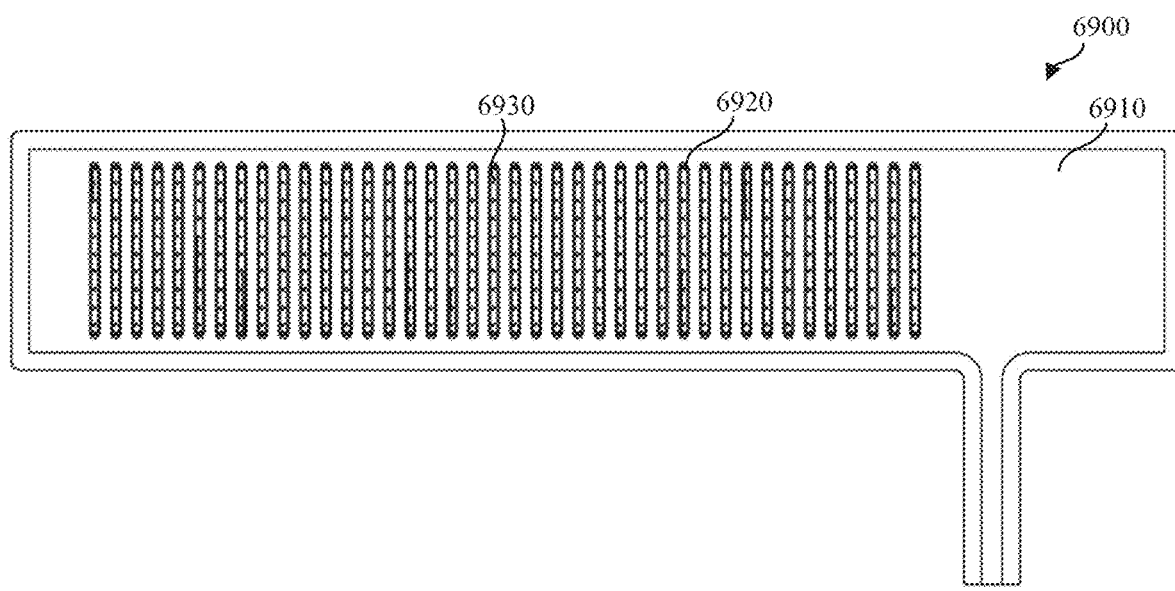
FIG. 69A is a plan view of an illustrative variation of an electrode array.
Figure 69B:
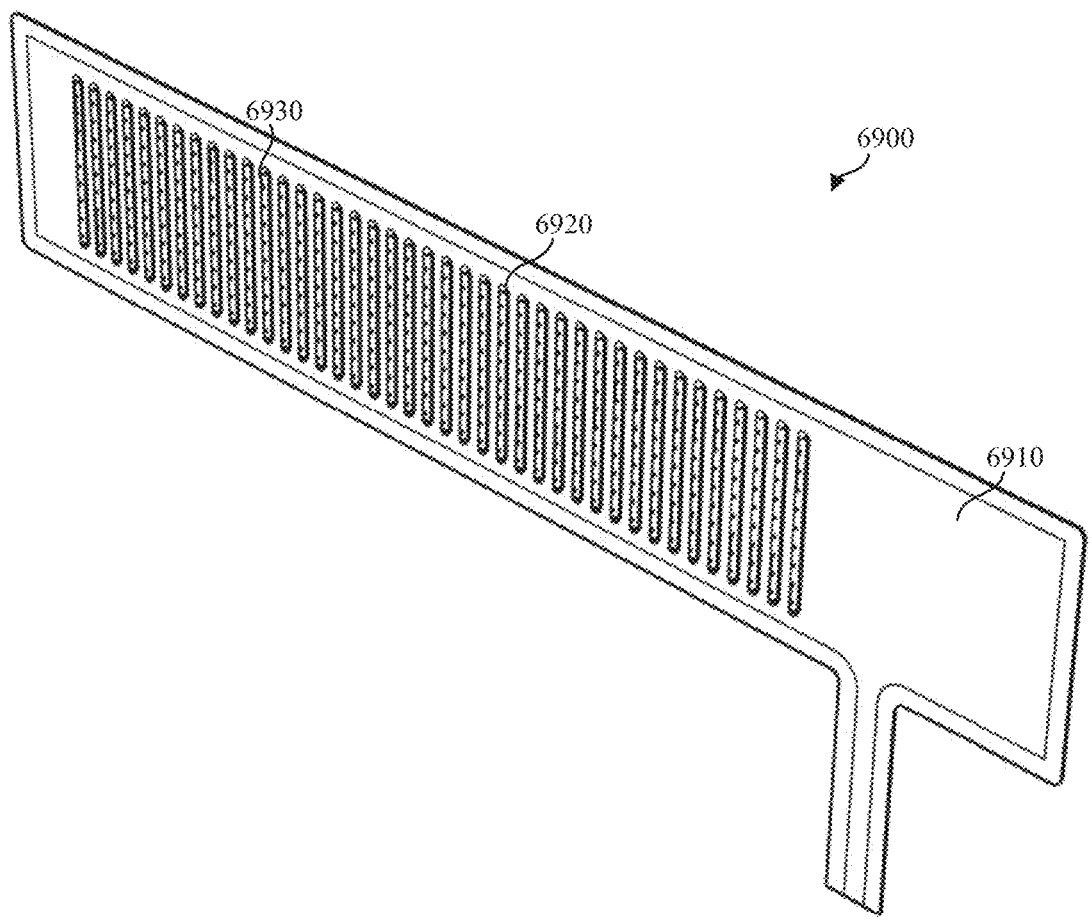
FIGS. 69B and 69C are perspective views of the electrode array shown in FIG. 69A.
Figure 69C:
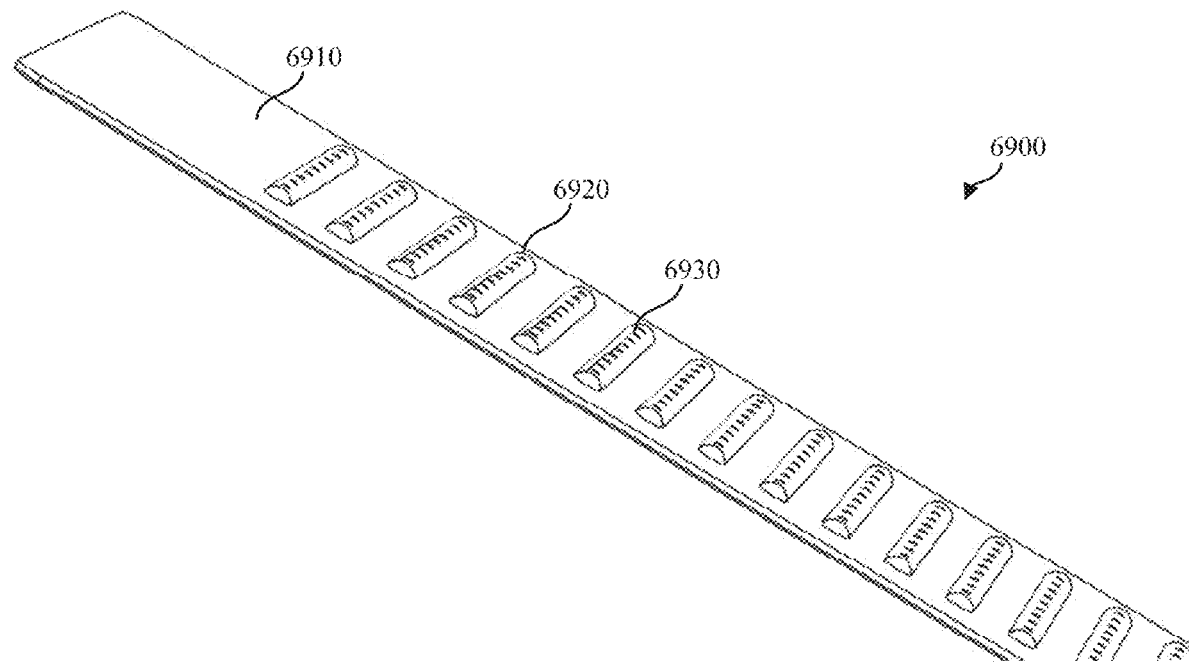

In some variations, the pulsed electric field devices described herein may be configured to output fluid to irrigate tissue, such as duodenal tissue, of a patient. For example, an electrode array of a pulsed electric field device may engage the duodenum and may be configured to output fluid (e.g., saline), for example, where the electrodes contact tissue. The electrode array, for example, one or more electrodes of the electrode array, may output fluid between the electrode and tissue, which may directly target the electrodes and may allow a reduction in fluid volume. The electrode array may be energized to treat a predetermined portion of tissue to resurface the duodenum. Utilizing an electrode array that is configured to deliver fluid may eliminate the need for a separate irrigation device and/or system. FIGS. 69A and 69B are respective plan and perspective views of an illustrative variation of an electrode array (6900) comprising a substrate (6910) (e.g., flex circuit) and a plurality of electrodes (6920). For example, the plurality of electrodes (6920) may comprise a plurality of substantially elongate electrodes disposed on the substrate (6910). In some variations, one or more of the electrodes (6920) (e.g., all, half, one third, two third) may comprise one or more fluid openings (6930) (e.g., one, two, three, four or more) configured to output fluid such as saline for irrigation. For example, the openings (6930) may be spaced apart along a length of an electrode (6920). As shown in FIG. 69C, the one or more openings (6930) may be disposed at an apex of each electrode (6920), although an opening (6930) may be disposed at any part of the electrode (6920) (e.g., base, sidewall, edges). Additionally or alternatively, the substrate (6910) may comprise one or more fluid openings (not shown) such as between proximate electrodes (6920). The electrode array (6900) may be in fluid communication with (e.g., fluidically coupled to) a fluid source (not shown) for fluid irrigation.

Figure 69D:
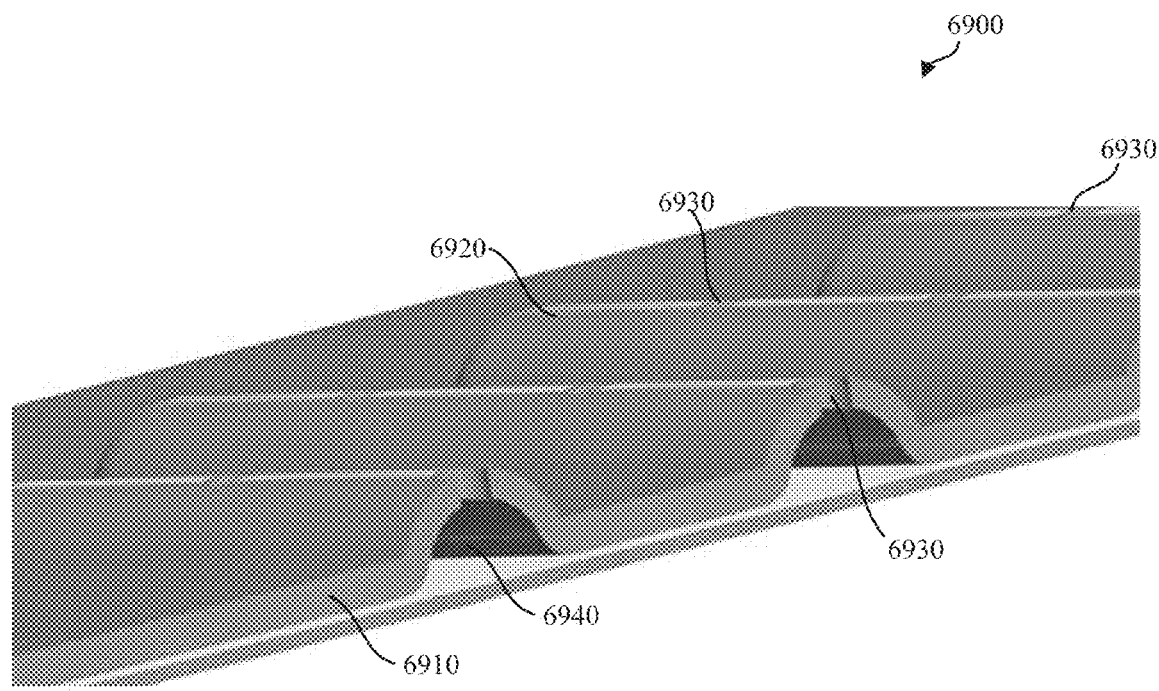
FIG. 69D is a perspective cross-sectional view of the electrode array shown in FIG. 69A.

FIG. 69D is a perspective cross-sectional view of the electrode array (6900) depicting an electrode (6920) comprising a fluid channel (6940). The fluid channel (6940) of the electrode (6920) may be in fluid communication with the fluid openings (6930) of that electrode (6920). One or more of the fluid channels (6940) may be in fluid communication with a fluid source such that fluid flows through the electrode array (6900). In some variations, the electrode array (6900) may output fluid at a predetermined rate between about 0.001 cc/(s·cm$^2$) and about 1 cc/(s·cm$^2$). For example, the electrode array (6900) may be configured to weep when in an expanded configuration. The fluid between the electrode array (6900) and tissue may function in a similar manner to the tissue contact layer described herein.

In some variations, the expandable member may comprise one or more fluid channels. In some variations, the fluid channels may be configured to facilitate fluid flow for conduction (e.g., ionic fluid) and heat transfer (e.g., temperature control during treatment). In some variations, the fluid channels may be configured to remove fluid (e.g., via suction or negative pressure) used, for example, for conduction. The use of suction or negative pressure applied through the fluid channels may draw the tissue toward the expandable member (e.g., the electrodes) and may facilitate contact between the tissue and the electrode array (e.g., may increase a contact area between the surface of the tissue and the electrode surface). In some variations, the fluid opening may be disposed at an apex of one or more of the plurality of electrodes (6920). In some of these variations, the fluid opening may be disposed between electrodes, for example, at a nadir (e.g., recess, valley) between a pair of electrodes (6920). In some variations, a fluid source may be in fluid communication with the electrode array (6900). In some variations, removal of the fluid may facilitate apposition and/or contact between the tissue and the electrode array (6900).

Sensor

In some variations, the pulsed electric field devices and systems described here may comprise one or more sensors. Generally, the sensors may be configured to receive and/or transmit a signal corresponding to one or more parameters. In some variations, the sensor may comprise one or more of a temperature sensor, imaging sensor (e.g., CCD), pressure sensor, electrical sensor (e.g., impedance sensors, electrical voltage sensor, magnetic sensor (e.g., RF coil), electromagnetic sensor (e.g., infrared photodiode, optical photodiode, RF antenna), force sensor (e.g., a strain gauge), flow or velocity sensor (e.g., hot wire anemometer, vortex flowmeter), acceleration sensor (e.g., accelerometer), chemical sensor (e.g., pH sensors, protein sensor, glucose sensor), oxygen sensor (e.g., pulse oximetry sensor), audio sensor, sensor for sensing other physiological parameters, combinations thereof, and the like. In some variations, the electrical properties of cells can also be determined by applying an alternating current signal at a specific frequency to measure voltage.

Temperature measurements performed during a tissue treatment procedure may be used to determine one or more of tissue contact (e.g., complete contact, partial contact, no contact) with a pulsed field device and successful energy delivery to tissue. Thus, the safety of the tissue treatment procedures described herein may be enhanced through temperature measurement and monitoring. In some variations, temperature monitoring of the tissue may be used to prevent excess energy delivery to tissue that may otherwise lead to poor or suboptimal treatment outcomes. For example, energy delivery may be inhibited or delayed when tissue temperature measurements exceed a predetermined threshold.

Figure 51A:
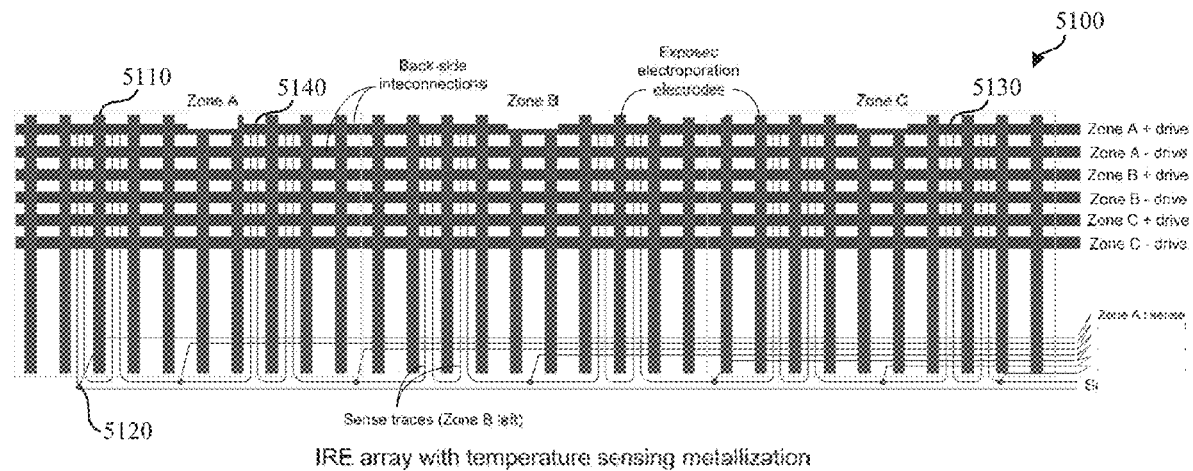
FIGS. 51A-51B, and 51D, are schematic circuit diagrams of illustrative variations of an electrode array, temperature sensor array, and fiducial generator.

As described herein, pulsed or modulated electric field treatment of tissue necessarily heats tissue locally around the electrodes. Temperature feedback allows variability in conductivity and contact resistance to be considered so as to not overheat tissue into necrotic cell death (e.g., heat-induced ablation). In some variations, a four-point probe may be configured as interstitial sensor elements within an electrode array. For four-point-probe connections, a differential voltage generated through a sense line may be sensed by a first pair of conductors, and the current drive generating that differential voltage may be applied by a second pair of conductors. In some variations, the drive current or voltage may be pulsed. For example, FIG. 51A is a schematic circuit diagram of an illustrative variation of an expandable member (5100) and tissue temperature sensor array (5120). The electrode array (5110) may comprise a plurality of elongate electrodes parallel to and spaced apart from each other. The electrode array (5110) may further comprise a tissue temperature sensor array described herein. For example, in some variations, one or more tissue temperature sensors may be disposed between proximate electrodes of the array (5110). For example, a tissue temperature sensor may be configured to extend in parallel or be interdigitated between proximate elongate electrodes (5110). FIG. 51A depicts a plurality of groups of electrodes (e.g., zones A, B, C) comprising corresponding temperature sensors. The tissue temperature sensor array may comprise a common point (5120) where a 4 point prove drive current (e.g., sense current) begins passing through the temperature sensing trace (5140). A plurality of temperature sensors may be provided for each zone. For example, trace (5140) is between the Zone A and Zone B sense point, and trace (5140) is in series with trace (5130). The voltage difference between the sense current for each zone divided by the sense current driven through the entire trace may provide the resistance of the trace (5140). A measured change in resistance of the trace (5140) may correspond to a temperature change where the resistance change of copper due to temperature is known.

The temperature sensor may be configured to be thermally connected and in contact with the tissue such that the measured sensor temperature corresponds to the tissue temperature. The temperature sensor may be electrically isolated from the tissue, such that a sense current only passes through the temperature sensor and a high voltage drive for the electrodes does not damage the temperature sensor. In some variations, the electrode array may comprise one or more drive circuits for applying a voltage or current pulse to the temperature sensor and a sense circuit for measuring the voltage or current across the temperature sensor.

In some variations, the temperature sensor (5120) may comprise an insulator configured to sustain, without dielectric breakdown, a pulse waveform configured to generate a pulsed or modulated electric field for treating tissue. In some variations, the insulator may comprise a thickness of at least about 0.02 mm. In some variations, the temperature sensor (5120) may comprise a width of up to about 0.07 mm and a length of at least about 2 cm. In some variations, a distance between the temperature sensor (5120) and the electrode (5110) may be at least about 0.2 mm. In some variations, temperature the sensor (5120) may extend substantially parallel to the elongate electrodes (5110).

In some variations, each of the temperature sensors may comprise a temperature resolution of less than about 0.5° C. For example, a half-ounce copper electrode comprising a width of about 0.075 mm and a length of about 2 cm may comprise a resistance of about 0.267 ohms at 37° C., a resistance of about 0.273 ohms at 43° C., and provide about a 0.5° C. resolution for each 2 cm of the electrode. A longer electrode may provide proportionately better sensitivity. In some variations, the temperature sensor may comprise a thermal diffusion time constant of less than about 5 milliseconds.

In some variations, a measured temperature may be used to determine whether the electrode array is in contact with tissue. For example, a current pulse of r length may sample the material surrounding a sense line to a depth of approximately r=√κτ. A sensor comprising length $L_s$, resistance $R_s$, and drive current $I_s$ may dissipate $I_s^2 R_s/L_s$ watts per unit length during the pulse. The surrounding material has a heat capacity and density $C_v$, $\rho$. The temperature rise for well-contacted tissue is given by equation (5):

$$\Delta T = \frac{I_s^2 R_s}{C_v \rho \kappa \pi L_s} \quad \text{eqn. (5)}$$

Using $I_s$=0.5 A and $L_s$=2 cm and $R_s$=0.276 ohm, then $\Delta T$=1.6° C. This constant temperature difference is present in all measurements and will therefore cancel from temperature rise measurements. The temperature rise where no tissue is contacted is given by equation (6):

$$\Delta T = \sqrt{\frac{\tau}{\kappa}} \frac{I_s^2 R_s}{2 C_v \rho Z_f L_s} \quad \text{eqn. (6)}$$

$Z_f$ is a substrate thickness. For $Z_f$=0.135 mm and τ=1 ms, $\Delta T$=0.65° C. Pulses longer than about 6 ms may generate an increased measured temperature corresponding to tissue temperature due to line heating. The maximum pulse duration is given by equation (7):

$$\tau = s^2/\kappa \quad \text{eqn. (7)}$$

s is the temperature sensor spacing. For temperature sensors spaced apart by about 0.075 mm, a maximum pulse duration may be about 21 msec before the line starts to heat linearly with time. By monitoring a rate of temperature rise, a tissue contact status may be determined. Energy delivery may be modified (e.g., reduced, inhibited) if the measured temperature exceeds a predetermined threshold.

In some variations, a temperature sensor may be configured to operate in a second mode where one conductor of the temperature sensor carries current and voltage to each end of the fine trace. In the second mode, temperature may be calculated using V/I=R for the entire trace, assuming that a quickly changing resistance is at the temperature sensor.

Figure 51B:
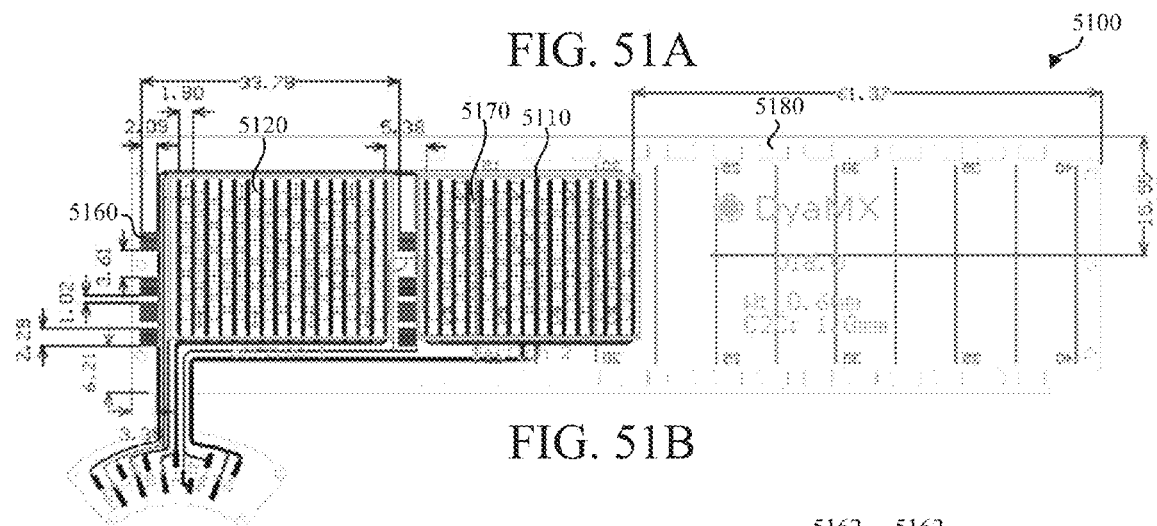
Figure 51C:
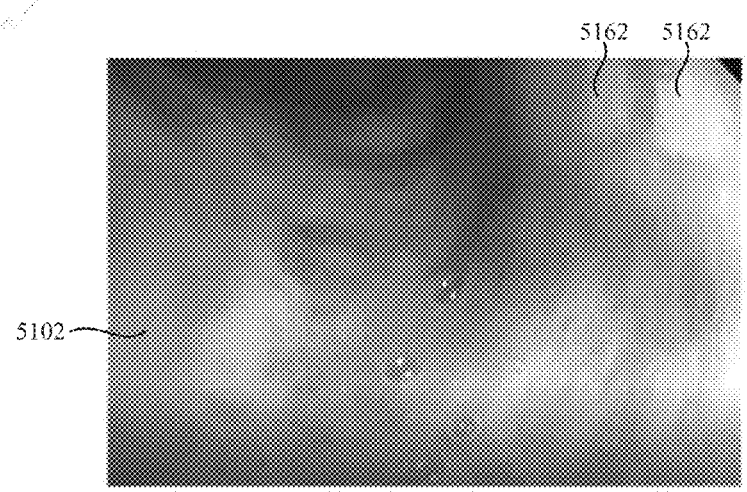
FIG. 51C is an image of a visual marker generated by a fiducial generator.
Figure 59:
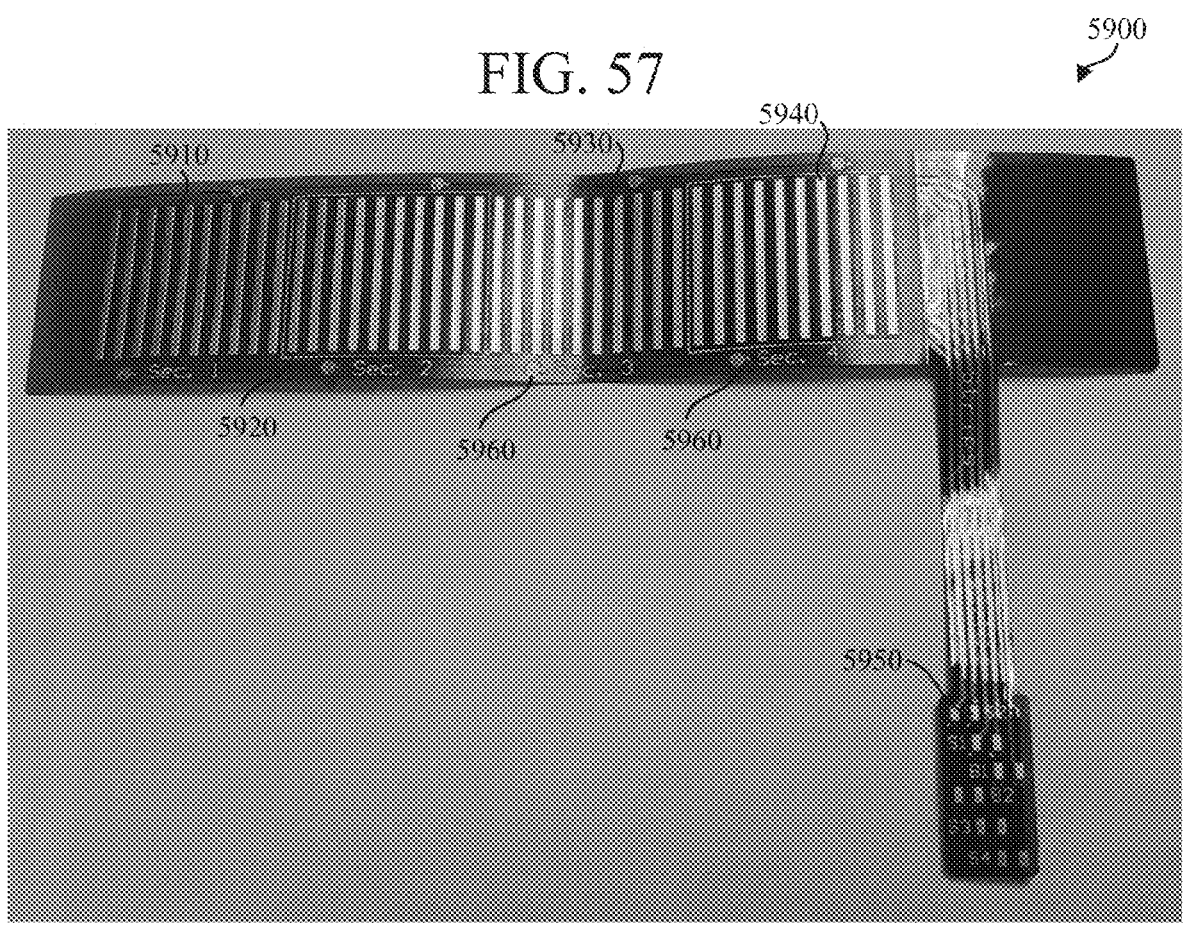
FIG. 59 is an image of an illustrative variation of an electrode array.

FIG. 51B is a schematic circuit diagram of an illustrative variation of an electrode array (5110) comprising a plurality of temperature sensors (5120) and fiducial generators (5160) (described in more detail with respect to FIGS. 52 and 59). FIG. 51C is an image of visual markers on duodenal tissue generated by the expandable member (5100) shown in FIG. 51B. The expandable member (5100) may define a plurality of openings (5170) (e.g., fluid openings, through holes) configured for one or more of suction and/or fluid irrigation, as described in detail herein. Furthermore, the expandable member (5100) may comprise one or more tracks (5180) configured to couple to one or more of a gear and friction roller. The tracks (5180) may comprise a plurality of spaced apart openings in the expandable member (5100) configured to aid expansion and contraction of the expandable member between compressed and expanded configurations. In some variations, the fiducial generators (5160) may comprise a length of about 2 mm and a width of about 2 mm. In some variations, one or more of the fiducial generators (5160) may comprise a shape having one or more vertices (e.g., corner, angular point, intersection) such as in a square, rectangle, triangle, polygon, etc. Visual markers generated on tissue may be easier to identify and visualize if formed with sharp corners rather than rounded edges. For example, a visual marker having a circular shape may be relatively difficult to discern from native tissue.

In some variations, one or more of the fiducial generators (5160) may comprise DC resistive heaters configured to mark tissue. The fiducial generators (5160) may be electrically isolated from the electrode array (5110). In some variations, one or more of the fiducial generators (5160) may be configured to raise the temperature of a top layer of mucosa tissue (e.g., less than 0.1 mm depth) to an average of about 49° C. for less than about 2.5 seconds. In this manner, one or more of the visual markers may fade and may not be visually visible after about one day. In some variations, histological evidence of the visual markers may not be present after about three days. The visual markers may be configured to identify treatment locations and aid repositioning of an ablation device. For example, an operator may advance the expandable member (5100) beyond the distal-most visual marker in the duodenum during an ablation procedure.

The duodenal tissue (5102) shown in FIG. 51C includes a pair of visual markers (5162) generated on the tissue (5102) by the fiducial generators (5160). In some variations, the visual markers may be identified based on one or more of color, shape, number, and size of the marker left on tissue. The visual marker may be visualized by using, for example, an endoscope. A set of repeated shapes may be easier to discern than a single visual marker. FIG. 51B depicts a set of 8 fiducial generators (5160).

Figure 51D:
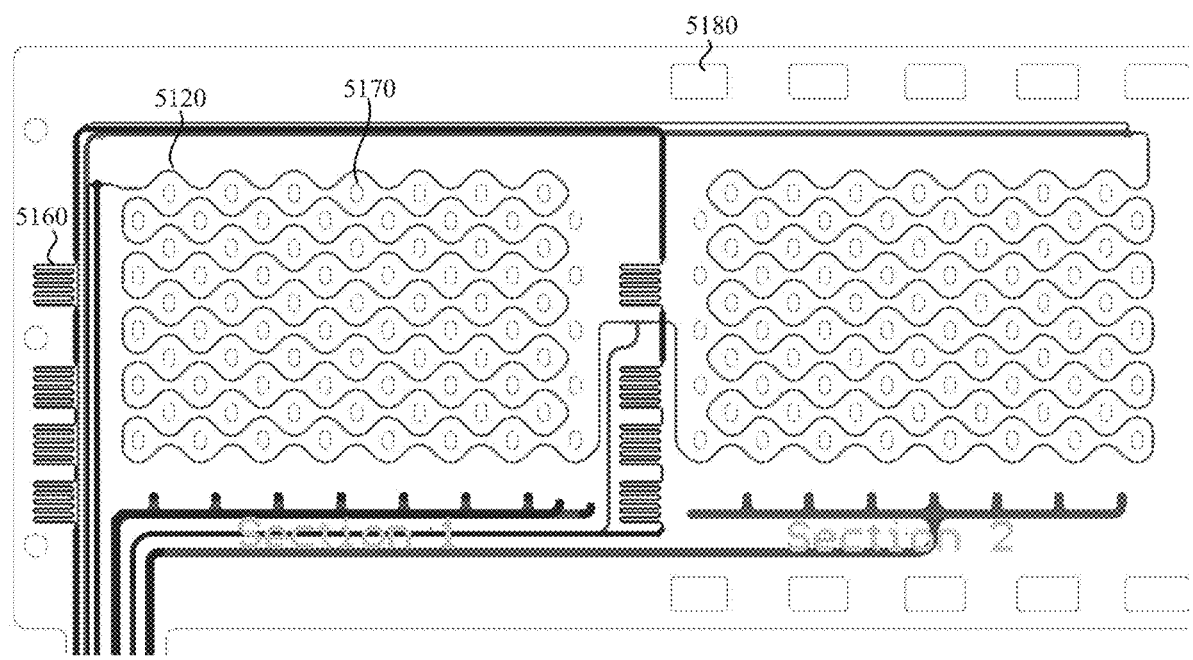

FIG. 51D is a detailed schematic circuit diagram of the expandable member (5100) showing a temperature sensor (5120) and openings (5170) without the electrode array (5110) for the sake of clarity. As shown in FIG. 51D, the temperature sensor (5120) may comprise a serpentine shape that may snake back and forth along a predetermined path. For example, the temperature sensor (5120) may curve around each opening (5170) of the expandable member (5100). As described herein, one or more openings (5170) may extend through the expandable member (5100) such that tissue may in contact with the expandable member (5100) may be suctioned into and through the openings (5170). In some variations, the fiducial generators (5160) may be spaced between adjacent electrode array (5110) sections (e.g., between Section 1 and Section 2).

In some variations, the electrode array (5110) may comprise a length of about 60 mm and a width of about 20 mm. Therefore, about a 20 mm length of the duodenum may be treated at a time. In some variations, the electrode array (5110) may be divided into two or more independently powered sections in order to reduce signal generator requirements. For example, an electrode array (5110) may have a circumferential length of about 60 mm. An electrode array (5110) comprising two sections may have each section comprise a circumferential length of about 27 mm. In some variations, the configuration and placement of the electrode array (5110) on the expandable member may facilitate one or more of manufacturing techniques and temperature measurement of tissue at a predetermined depth. In some variations, a set of fiducial generators may be disposed between sections of the electrode array where, for example, each fiducial generator may generate a visual marker having a length and width of about 2 mm. The expandable member (5100) depicted in FIG. 51B and as described herein may correspond to the expandable member (7600) depicted in FIG. 77.

In some variations, one or more of the temperature sensors (5120) (e.g., temperature traces) may extend generally across a plurality of the electrodes of the electrode array (5110). For example, one or more of the temperature sensors (5120) may comprise a generally serpentine shape which may be continuous. In some variations, a temperature sensor (5120) may measure an average temperature across a predetermined portion of the sensor (5120) that may be a better representation of tissue temperature. By contrast, a temperature measurement taken very close to an electrode edge may have a misleadingly high temperature, which is not representative of the overall tissue temperature. In some variations, the temperature trace lines may be disposed on an electrode side of the expandable member (5100) and/or along an opposite side of the expandable member (5100). In some variations, temperature measurements from the one or more temperature sensors (5120) may correspond to a temperature of tissue at a predetermined depth.

In some variations, one or more of the temperature sensors (5120) may comprise a thickness of between about 0.030 mm and about 0.040 mm and a width of between about 0.09 mm and about 0.12 mm. In some variations, a temperature sensor may be spaced apart from itself and/or other temperature sensors by between about 0.10 mm and about 0.17 mm. In some variations, one or more temperature sensors (5120) may be disposed on the expandable member (5100) using button plating.

Figure 52A:
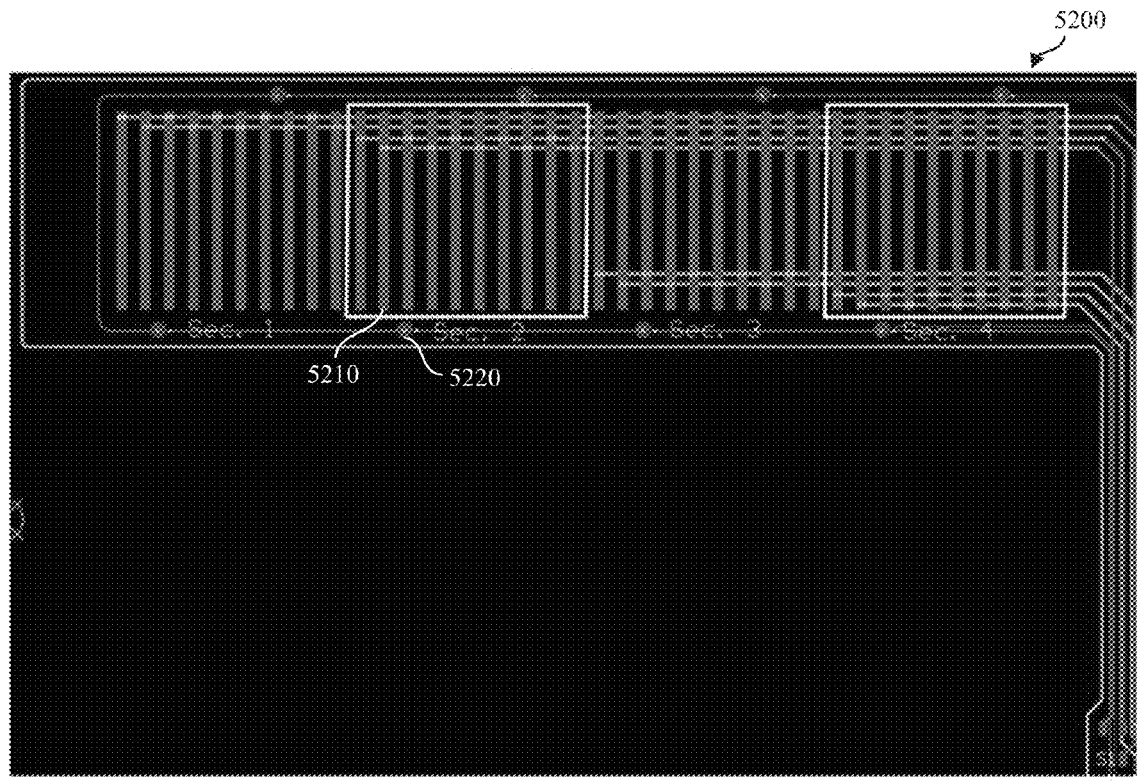
FIG. 52A is a schematic circuit diagram of an illustrative variation of an electrode array, temperature sensor array, and fiducial generator.
Figure 52B:
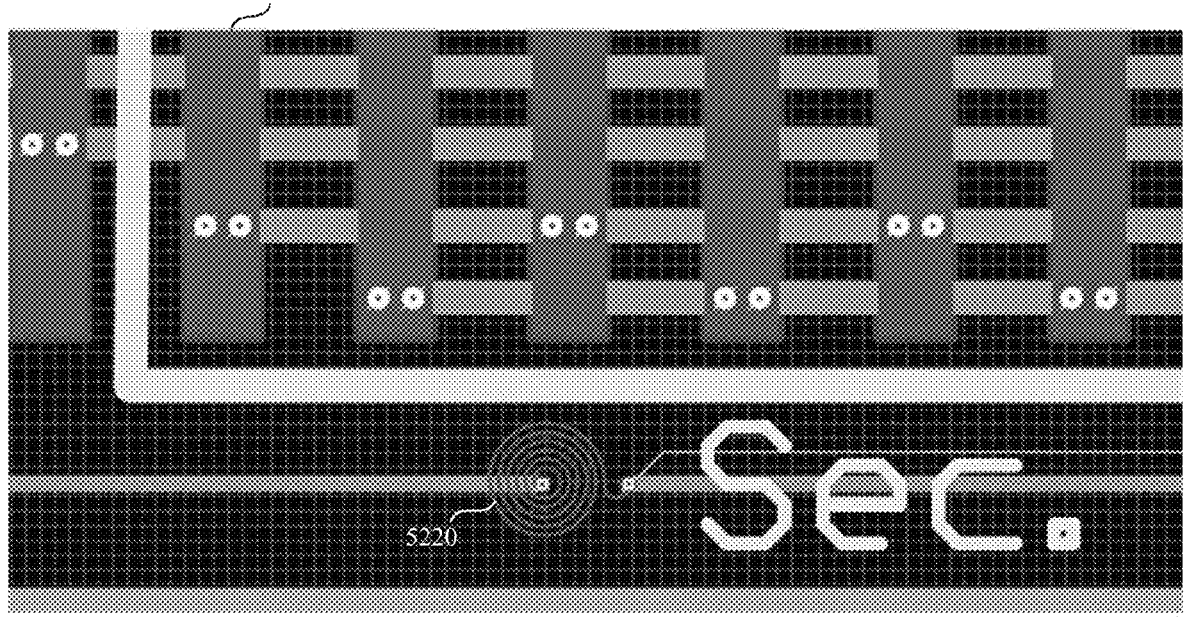
FIG. 52B is a detailed view of the schematic circuit diagram of the electrode array, temperature sensor, and fiducial generator shown in FIG. 52A.

In some variations, visually marking treated tissue may aid an operator in performing a tissue treatment procedure where discrete portions of tissue are treated sequentially. In some variations, a fiducial generator may be configured to generate a visual marker on tissue. This may allow treated portions of tissue to be visualized within a body cavity (e.g., duodenum). In some of these variations, the fiducial generator may be disposed on a substrate of an electrode array along a perimeter of the elongate electrodes. In some variations, the fiducial generator may comprise one or more temperature sensors as described herein. In some variations, the fiducial generator may comprise a spiral or serpentine shape. In some variations, high current pulses may be configured to heat one or more fiducial generators above 80° C., thus creating a visually discernable mark on tissue in contact with the fiducial generator. FIG. 52A is a schematic circuit diagram (5200) of an illustrative variation of an electrode array (5210) and a plurality (e.g., four) fiducial generators (5220). FIG. 52B is a detailed view of the schematic circuit diagram of the electrode array (5210) and one spiral fiducial generator (5220). FIG. 59 is an image of an illustrative variation of an electrode array (5900) comprising a plurality of electrodes grouped in different sections (5910, 5920, 5930, 5940), connector pad (5950), and a plurality of fiducial generators (5960). For example, the electrode array (5900) may be grouped into a first section (5910), second section (5920), third section (5930), and fourth section (5940). Each of the sections may be wired to a corresponding pad (S1, S2, S3, S4) of the connector pad (5950). In some variations, each section (5910, 5920, 5930, 5940), may comprise at least one fiducial generator (5960). The fiducial generators (5960) may be wired in series. In some variations, electrode array (5210) in tissue may unroll with different diameters based on a local diameter of the tissue (e.g., duodenum) to be treated. The electrode array (5210) may be configured such that only the sections of the electrode array (5900) in at least partial contact with the tissue may be energized by a signal generator. In some variations, the signal generator may be configured to sequentially drive each section of the electrode array (5900).

In some variations, one or more fiducial generators may be disposed between electrodes of an electrode array. For example, a fiducial generator may comprise an elongate shape between adjacent electrodes and disposed near an edge of the electrode array, which may reduce a length of one or more of the elongate electrodes.

Dilator

Generally, the dilators described here may be configured to assist advancement of one or more portions of a pulsed electric field device into and through a body cavity or lumen such as, for example, a duodenum. In some variations, a dilator may generally be configured to dilate a body cavity or lumen, such as a lumen of a duodenum. The dilator may be atraumatic in shape to minimize any inadvertent or unintended damage and may comprise any shape suitable to enlarge a tissue lumen (e.g., conical). For example, in some variations, a dilator may comprise a conical shape comprising a taper of between about 1 degree and about 45 degrees, which may facilitate PEF device advancement through the gastrointestinal tract. In some variations, the dilator may comprise PET, PEBA, PEEK, PTFE, silicone, PS, PEI, latex, sulphate, barium sulfate, a copolymer, combinations thereof, and the like. In some variations, the dilator may comprise a solid configuration. In some variations, the dilator may comprise a plurality of materials configured to provide a desired stiffness and compliance along a length of the dilator. In some variations, the dilator may comprise one or more components configured to facilitate advancement of a guidewire.

In some variations, the dilator may comprise a length of between about 2 mm and about 10 cm. In some variations, the dilator may comprise a taper of between about 5 degrees and about 30 degrees relative to a longitudinal axis of the dilator. In some variations, a distal end of the dilator may be atraumatic (e.g., rounded, blunted). In some variations, a pulsed electric field device may comprise a plurality of dilators (e.g., 2, 3, 4, 5, 6, or more). For example, respective dilators may be disposed proximal and distal to an expandable member. This allows smooth proximal and distal advancement of the pulsed electric field device.

In some variations, a dilator may comprise a recess configured to facilitate mating or coupling with another elongate member such as a visualization device (e.g., endoscope). For example, this may enable the dilator and expandable member to removably couple to a visualization device during a treatment procedure. The length and taper of a plurality of dilators of a pulsed electric field device may be the same or different. For example, a distal dilator may have a steeper taper than a proximal dilator.

Elongate Body

Generally, the elongate bodies (e.g., catheters) described here may be configured to deliver an electrode array to the duodenum for treating tissue such as duodenal tissue. In some variations, an elongate body may comprise a shaft composed of a flexible polymeric material such as Teflon, Nylon, Pebax, urethane, combinations thereof, and the like. In some variations, the pulsed electric field device may comprise one or more steerable or deflectable catheters (e.g., unidirectional, bidirectional, 4-way, omnidirectional). In some variations, the elongate body may comprise one or more pull wires configured to steer or deflect a portion of the elongate body. In some variations, the elongate body may have a bend radius between about 5 cm and about 23 cm and/or between about 45 degrees and about 270 degrees. In some variations, the elongate bodies described herein may comprise a lumen through which another elongate body and/or a guidewire may slide. In some variations, the elongate bodies may comprise a plurality of lumens. For example, the elongate body may comprise one or more of an inflation lumen, fluid lumen, guidewire lumen, and lead lumen.

In some variations, the elongate body may be woven and/or braided and/or coiled, and may be composed of a material (e.g., nylon, stainless steel, nitinol, polymer) configured to enhance pushability, torquabilty and flexibility. In some variations, one or more of the first and second elongate bodies may comprise a metal-based radiopaque marker comprising one or more of a ring, band, and ink (e.g. platinum, platinum-iridium, gold, nitinol, palladium) configured to permit fluoroscopic visualization. In some variations, one or more of the first and second elongate bodies may comprise magnetic members configured to attract and couple to the bodies to each other. In this manner, the first elongate body need not comprise a lumen for the second elongate body. In some variations, the elongate body may comprise from about 2 layers to about 15 layers of materials to achieve a predetermined set of characteristics.

Handle

Generally, the handles described here may be configured to allow an operator to grasp and control one or more of the position, orientation, and operation of a pulsed electric field device. In some variations, a handle may comprise an actuator to permit translation and/or rotation of the first and second elongate bodies in addition to steering by an optional delivery catheter. Control of an expandable member, in some variations, may be performed by an expansion member (e.g., screw/rotation actuator, inflation actuator) of the handle. In some variations, the handle may be configured to control PEF energy delivery to the electrode array of an expandable member, using, for example, a handheld switch, and/or footswitch.

Figure 84:
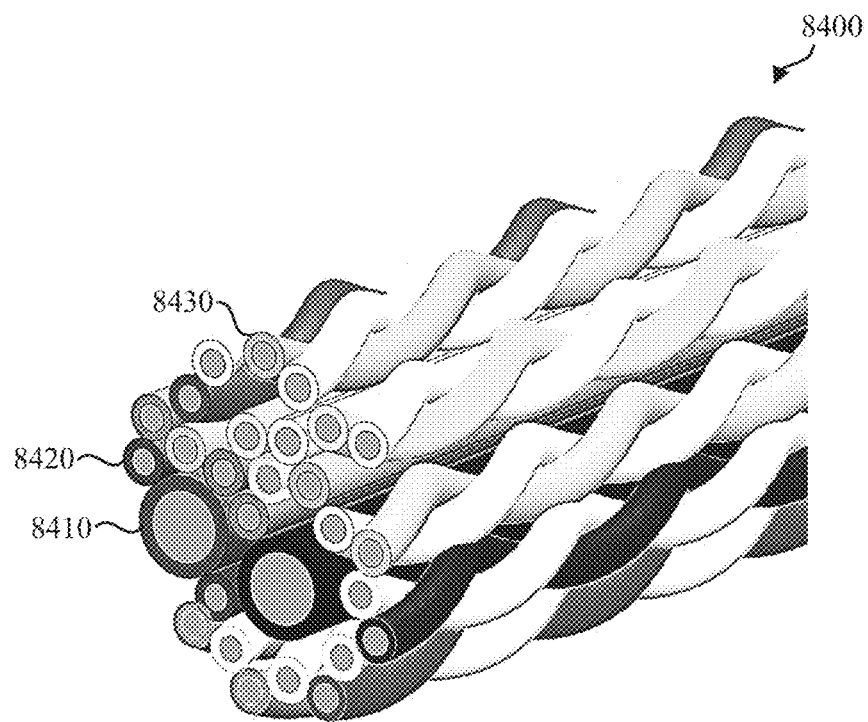
FIG. 84 is a cross-sectional perspective view of a set of twisted pair lead wires.

FIG. 84 is a cross-sectional perspective view of a set of lead wires (8400) (e.g., power transmission wire, wiring harness). In some variations, a set of lead wires (8400) may couple a signal generator and/or handle to one or more distal components (e.g., electrode, fiducial generator, temperature sensor) of a pulsed electric field device (not shown for the sake of clarity). The lead wires (8400) may be configured for one or more of power delivery, temperature sensing, and fiducial generation. In some variations, a power transmission wire (8430) may comprise a plurality of twisted pair wires. In some variations, the set of twisted pair wires (8430) may comprise between about 1 and about 20 twisted pairs based on the frequency and current of the energy delivered. In some variations, the set of twisted pair lead wires (8430) may facilitates high amperage and frequency transmission while minimizing loss. The set of twisted pair wires (8430) may have the same or different diameters. For example, the wire size and insulation thickness may be configured to minimize one or more of inductance between the wires, resistance of the wires, temperature increase of the wires, and a skin effect of the wires. Additionally or alternatively, specially woven litz wire and/or tubular conductors (e.g., coaxial cable) may be used to minimize these variable (e.g., inductance, resistance, temperature, skin effect) and mitigate loss. In some variations, a fiducial generation wire (8410) may be configured to deliver energy to one or more fiducial generators as described herein. In some variations, the fiducial generation wire (8410) may be non-twisted. In some variations, a temperature sensing wire (8420) may be configured to measure temperature from one or more temperature sensors of a pulsed electric field device. In some variations, the fiducial generation wire (8410) may be non-twisted and may have a larger diameter than the power transmission wire (8430) and the fiducial generation wire (8410).

Insulator

Generally, the insulators described here may be configured to electrically isolate one more portions of the electrode array, expandable member, inflatable member, dilator, and/or elongate body of the pulsed electric field device from each other. In some variations, the insulator may comprise one or more of a poly(p-xylylene) polymer such (e.g. parylene C, parylene N), polyurethane (PU), polytetrafluoroethylene (PTFE), expanded PTFE (ePTFE), polyimide (PI), polyester, polyethylene terephthalate (PET), PEEK, polyolefin, silicone, copolymer, a ceramic, combinations thereof, and the like.

Guidewire

In some variations, a guidewire may be slidably disposed within a lumen of an elongate body of a pulsed electric field device. The guidewire may be configured to assist in advancement of the pulsed electric field device through a gastrointestinal tract. In some variations, first and second elongate bodies of the pulsed electric field device may be translated along the guidewire relative to one another and/or the duodenum. In some variations, the guidewire may comprise one or more of stainless steel, nitinol, platinum, and other suitable biocompatible materials. In some variations, the guidewire may comprise a variable stiffness along its length. For example, a distal tip may be configured to be compliant (e.g., floppy) and an elongate body of the guidewire may be relatively stiff to aid pushability through patient anatomy. In some variations, a guidewire may comprise a diameter between about 0.014 inches to about 0.060 inches, and a length between about 180 cm and about 360 cm.

Signal Generator

Generally, the signal generators described here may be configured to provide energy (e.g., PEF energy waveforms) to a pulsed electric field device to treat predetermined portions of tissue such as duodenal tissue. In some variations, a PEF system as described herein may include a signal generator having an energy source and a processor configured to deliver a waveform to deliver energy to tissue. The waveforms disclosed herein may aid in treating diabetes. In some variations, the signal generator may be configured to control waveform generation and delivery in response to received sensor data. For example, energy delivery may be inhibited when a temperature sensor measurement confirms tissue temperature exceeding a predetermined threshold or ranges (e.g., above a predetermined maximum temperature).

The signal generator may generate and deliver several types of signals including, but not limited to, AC current, square wave AC current, sine wave AC current, AC current interrupted at predetermined time intervals, multiple profile current pulses trains of various power intensities, direct current (DC) impulses, stimulus range impulses, and/or hybrid electrical impulses. For example, the signal generator may generate monophasic (DC) pulses and biphasic (DC and AC) pulses. In some variations, a signal generator may be configured to generate between about 1 V and about 3,000 V, and between about 1 A and about 200 A of current delivered into a system resistance of between about 2Ω and about 30Ω, at frequencies of between about 50 kHz and about 950 kHz. The signal generator may comprise a processor, memory, energy source (e.g., current source), and user interface. The processor may incorporate data received from one or more of the memory, the energy source, the user interface, and the pulsed electric field device. The memory may further store instructions to cause the processor to execute modules, processes and/or functions associated with the system, such as waveform generation and delivery. For example, the memory may be configured to store patient data, clinical data, procedure data, safety data, and/or the like.

Generally, more than about 1,000 V/cm to about 2,500 V/cm is required at a treatment depth of tissue to induce electric fields across cell membranes greater than about 0.5 V in the duodenum. In some variations, more than about 1,500 to about 4,500 V/cm, including all ranges and sub-values in-between, is required at a treatment depth of tissue to induce electric fields across cell membranes greater than about 0.5 V in the duodenum Even relatively low tissue conductivity (e.g., about 0.3 S/m) may generate bulk tissue heating rates of at least about 800° C./s. The maximum temperature rise that should occur may be about 8° C. such that a maximum continuous on-time (100% duty cycle of alternating polarity pulses) may be about 10 msec. For example, the pulse waveform may comprise pairs of unipolar pulses of about 1 µs in groups between about 5 and about 500, with a delay between each group. In some variations, a series of these groups may be repetitively applied with increasingly longer delays between series. In some variations, a sequence of series may be applied with longer delays between sequences. In some variations, about 15 milliseconds of cumulative ON time may be distributed across about 10 seconds.

In some variations, the signal generator may be configured to generate current, voltage, and power in the pulsed or modulated electric field spectrum between about 250 kHz and about 950 MHz, a pulse width between about 0.5 µs and about 4 µs, a voltage applied by the electrode array of between about 100 V and about 2 kV, and a current density between about 0.6 A and about 100 A from the electrode array per square centimeter of tissue. In some variations, the signal generator may be configured to drive into tissue resistance of from about 5 ohms to about 30 ohms of load. For example, the current density may be between about 0.6 A and about 100 A from the electrode array per square centimeter of tissue. In some variations, the pulse waveform may comprise a pulse group of between about 1 and about 50 with between about 1 and about 100 pulses per group. In some of these variations, the pulse waveform may comprise a group delay between about 10 µs and about 4000 µs, and a replenish rate of between about 50 ms and about 4000 ms. For example, a balanced bipolar pulse waveform (e.g., within 10%) may reduce sympathetic nerve excitation, which may reduce perceived pain and spontaneous muscle contraction. Microsecond pulsing between about 1 µs and about 10 µs may generate cell lysis while minimizing nerve stimulation. An electric field distribution produced by short bipolar pulses does not depend as strongly on tissue homogeneity especially in anisotropic areas.

In some variations, a set of bipolar pulses may be divided into bursts of bipolar pairs with a time delay between the bursts. This may allow the heat generated at the cell membranes to disperse, allowing more treatment before the transition from cell lysis to necrosis. The total time that pulsed or modulated electric field is applied to the tissue determines the density and size of the membrane pores, and the extent that ion flow has altered the contents of a cell. For example, given a tissue thermal diffusivity κ of 0.13 mm²/s and a cell diameter $D_{cell}$ of 10 micron, the thermal diffusion time is roughly $D_{cell}^2/K$=0.8 msec. Thus, applying a pulse burst and then waiting a millisecond allows the temperature to equilibrate across the cell.

Figure 53:
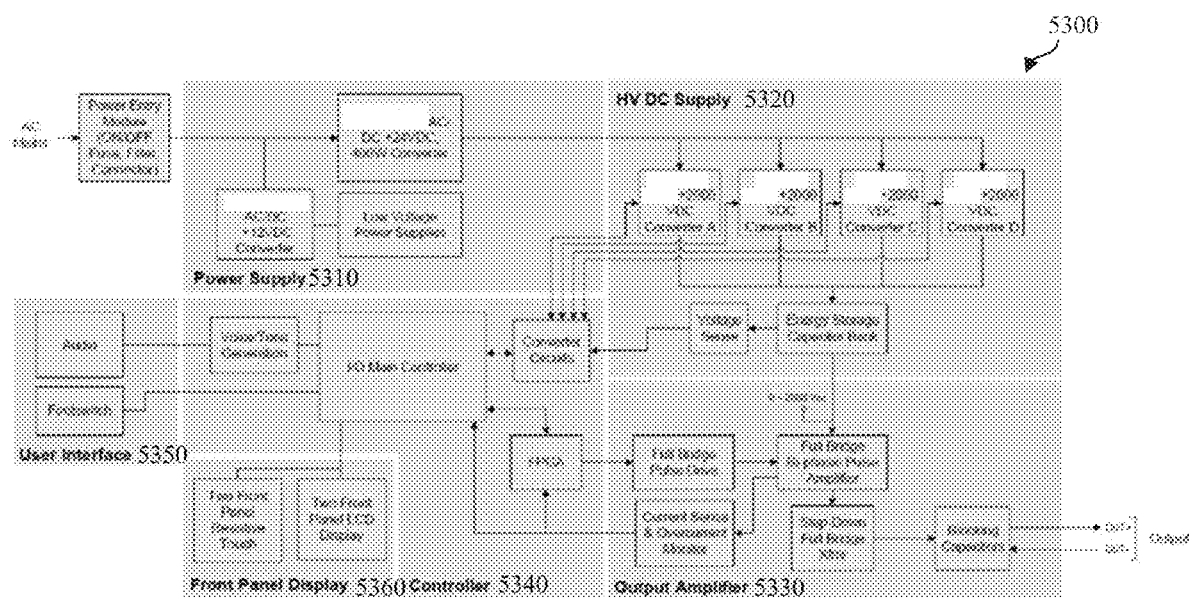
FIG. 53 is a schematic circuit block diagram of an illustrative variation of a signal generator.

FIG. 53 is a circuit block of a signal generator (5300) comprising a power supply (5310), high voltage DC supply (5320), output amplifier (5330), controller (5340), user interface (5350), and display (5360). The controller (5340) may comprise a processor. Generally, the processor (e.g., CPU) described here may process data and/or other signals to control one or more components of the system. The processor may be configured to receive, process, compile, compute, store, access, read, write, and/or transmit data and/or other signals. In some variations, the processor may be configured to access or receive data and/or other signals from one or more of a sensor (e.g., temperature sensor) and a storage medium (e.g., memory, flash drive, memory card). In some variations, the processor may be any suitable processing device configured to run and/or execute a set of instructions or code and may include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data and/or power transfer), and/or central processing units (CPU). The processor may be, for example, a general purpose processor, Field Programmable Gate Array (FPGA), an Application Specific Integrated Circuit (ASIC), a processor board, and/or the like. The processor may be configured to run and/or execute application processes and/or other modules, processes and/or functions associated with the system. The underlying device technologies may be provided in a variety of component types (e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Generally, the pulsed electric field device described here may comprise a memory configured to store data and/or information. In some variations, the memory may comprise one or more of a random access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and the like. In some variations, the memory may store instructions to cause the processor to execute modules, processes, and/or functions associated with a pulsed electric field device, such as signal waveform generation, pulsed electric field device control, data and/or signal transmission, data and/or signal reception, and/or communication. Some variations described herein may relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes.

In some variations, the pulsed electric field device may further comprise a communication device configured to permit an operator to control one or more of the devices of the PEF system. The communication device may comprise a network interface configured to connect the pulsed electric field device to another system (e.g., Internet, remote server, database) by wired or wireless connection. In some variations, the pulsed electric field device may be in communication with other devices (e.g., cell phone, tablet, computer, smart watch, and the like) via one or more wired and/or wireless networks. In some variations, the network interface may comprise one or more of a radiofrequency receiver/transmitter, an optical (e.g., infrared) receiver/transmitter, and the like, configured to communicate with one or more devices and/or networks. The network interface may communicate by wires and/or wirelessly with one or more of the pulsed electric field device, network, database, and server.

The network interface may comprise RF circuitry configured to receive and/or transmit RF signals. The RF circuitry may convert electrical signals to/from electromagnetic signals and communicate with communications networks and other communications devices via the electromagnetic signals. The RF circuitry may comprise well-known circuitry for performing these functions, including but not limited to an antenna system, an RF transceiver, one or more amplifiers, a tuner, one or more oscillators, a mixer, a digital signal processor, a CODEC chipset, a subscriber identity module (SIM) card, memory, and so forth.

Wireless communication through any of the devices may use any of plurality of communication standards, protocols and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol. In some variations, the devices herein may directly communicate with each other without transmitting data through a network (e.g., through NFC, Bluetooth, WiFi, RFID, and the like).

In some variations, the user interface may comprise an input device (e.g., touch screen) and output device (e.g., display device) and be configured to receive input data from one or more of the pulsed electric field device, network, database, and server. For example, operator control of an input device (e.g., keyboard, buttons, touch screen) may be received by the user interface and may then be processed by processor and memory for the user interface to output a control signal to the pulsed electric field device. Some variations of an input device may comprise at least one switch configured to generate a control signal. For example, an input device may comprise a touch surface for an operator to provide input (e.g., finger contact to the touch surface) corresponding to a control signal. An input device comprising a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In variations of an input device comprising at least one switch, a switch may comprise, for example, at least one of a button (e.g., hard key, soft key), touch surface, keyboard, analog stick (e.g., joystick), directional pad, mouse, trackball, jog dial, step switch, rocker switch, pointer device (e.g., stylus), motion sensor, image sensor, and microphone. A motion sensor may receive operator movement data from an optical sensor and classify an operator gesture as a control signal. A microphone may receive audio data and recognize an operator voice as a control signal.

A haptic device may be incorporated into one or more of the input and output devices to provide additional sensory output (e.g., force feedback) to the operator. For example, a haptic device may generate a tactile response (e.g., vibration) to confirm operator input to an input device (e.g., touch surface). As another example, haptic feedback may notify that operator input is overridden by the pulsed electric field device.

II. Methods

Also described here are methods of treating tissue. In some variations, methods may comprise treating diabetes of a patient using the systems and devices described herein. In particular, the systems, devices, and methods described herein may resurface a predetermined portion of tissue, for example, duodenal tissue, for the treatment of, for example, diabetes using a pulsed or modulated (e.g., sine wave) electric field. In some variations, the generated pulsed or modulated electric field may be substantially uniform such that pulsed or modulated electric field energy for tissue treatment may be delivered to a predetermined portion of the duodenum (e.g., mucosal layer) without significant energy delivery to deeper layers of the duodenum. Thus, the methods may improve the efficiency and effectiveness of energy delivery to duodenal tissue. Moreover, the methods described here may also avoid the excess thermal tissue heating necessarily generated by application of one or more other thermal energy modalities to tissue.

In some variations, methods may include using a pulsed electric field system comprising a closed-loop temperature feedback system. The temperature feedback system may comprise a temperature sensor configured to monitor tissue temperature. In these variations, the methods may inhibit pulse waveform delivery by a signal generator based on sensor measurements. In some variations, a temperature rise in the tissue may be limited to from about 3° C. to about 10° C., from about 2° C. to about 5° C., or from about 3° C. to about 8° C., including all sub-values and ranges in-between. In some of these variations, a fiducial generator may be configured to thermally generate a visual marker (e.g., fiducial) on tissue. The visual marker may aid in identification of a tissue treatment area during and after a procedure.

Method of Treating Diabetes

Generally, methods of treating diabetes may comprise generating a pulsed or modulated electric field to cause a change in (e.g., treat) duodenal tissue. Normally, the small intestine sends signals to the brain, pancreas, and liver to promote glycemic hemostasis. For example, enteroendocrine cells of the mucosal villa may generate these signals. Duodenal mucosal resurfacing using the systems, methods, and devices described herein may be used to treat, for example, type 2 diabetes. Clinical studies have demonstrated that duodenal mucosal resurfacing of the mucosal layer of the duodenum is a safe procedure that may have a positive impact on glycemic hemostasis in patients with type 2 diabetes.

In some variations, the pulsed or modulated electric field may cause cell lysis in tissue that is at least 50% pore-induced and less than 50% heat-induced. In some variations, a method of treating diabetes may include advancing a pulsed electric field device towards a duodenum of a patient. In some of these variations, a patient may be positioned on their left lateral side during the procedure, and the duodenum may optionally be insufflated (e.g., using $CO_2$ or saline). The pulsed electric field device may comprise an elongate body and an expandable member comprising an electrode array. Once in the duodenum, the expandable member may be transitioned into an expanded configuration. In some variations, one or more turns of the expandable member may be unrolled to contact the duodenum. In some variations, a visualization device (e.g., endoscope) may be advanced into the duodenum to visualize, inspect, and/or confirm a treatment area during a procedure. For example, one or more transparent portions of a pulsed electric field device may allow the visualization device to identify an ampulla of the duodenum. Once the device is located at a desired position within the duodenum, a pulse waveform may be delivered to the electrodes to generate a pulsed electric field to treat a portion of the duodenum. It should be appreciated that any of systems and devices described herein may be used in the methods described here.

In some variations, a method of treating diabetes may include one or more of application of a radially outward force to the tissue resulting in tissue stretching (e.g., dilating) tissue and applying negative pressure (e.g., suction) to the tissue to facilitate a consistent tissue-electrode interface. For example, tissue stretched or dilated by an expandable member of a pulsed electric field device in the expanded configuration, whether through the application of a radial force and/or negative pressure, may have a more uniform tissue thickness, which may aid in a consistent energy delivery and treatment. In some variations, tissue may be in contact with the expandable member in the expanded configuration within the duodenum. A visualization device (e.g., endoscope) may be advanced into and disposed within a lumen of the expandable member in the expanded configuration. Then, the visualization device may be configured to generate a negative pressure sufficient to pull tissue into and/or through one or more openings (e.g., fluid openings) of the expandable member. This may reduce tissue tenting and/or air pockets over the electrodes and ensure a consistent tissue-electrode interface tissue around a circumference of the duodenum. Furthermore, suction may enable a reduction in the radial force applied by the expandable member. In some variations, the negative pressure (e.g., suction) applied to the tissue may be between about 50 mmHg and about 75 mmHg. In some variations, the negative pressure (e.g., suction) applied to the tissue may be applied intermittently or in relatively short time periods at a pressure of between about 100 mmHg and about 250 mmHg. For example, higher negative pressure may be applied in spurts or feathered so as to ensure contact between the tissue and the electrodes without tissue pressure necrosis.

Figure 71A:
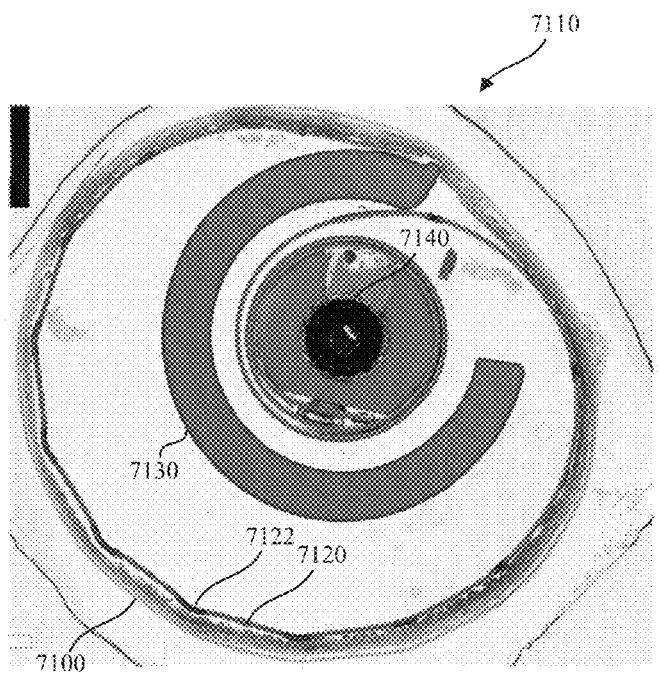
FIG. 71A is a cross-sectional image of a pulsed electric field device in an expanded configuration that dilates a duodenum.
Figure 71B:
FIG. 71B is a cross-sectional image of an undilated duodenum.

FIG. 71B is a cross-sectional image of an undilated duodenum (7100) that has varying thicknesses around its circumference. As shown there, in a natural state (e.g., without external force applied, undilated), the duodenal tissue has a variable thickness around the circumference of the duodenum. FIG. 71A is a cross-sectional image of a pulsed electric field device (7110) in an expanded configuration in the duodenum (7100). The pulsed electric field device (7110) comprises an expandable member (7120), electrode array (7122), dilator (7130), and elongate body (7140). The expanded pulsed electric field device (7110) expands to apply a radial force to the duodenal tissue to dilate the duodenum (7110), reduce the thickness of the duodenal tissue, and/or create a more uniform duodenal tissue thickness around the circumference of the duodenum as compared with an undilated duodenum. Stretched or dilated tissue may comprise a smaller range of tissue thicknesses than unstretched tissue. In some variations, about 1 inch to about 15 inches of water ($inH_2O$) may be applied to dilate but not damage the tissue through pressure necrosis. For example, an expandable member may be configured to generate about 2 inches to about 6 inches of water ($inH_2O$) to slightly dilate tissue such as duodenum tissue. Stretched tissue dilated by the expandable member in the expanded configuration may reduce a wall thickness of the tissue, thereby allowing for a lower dose of energy to treat a predetermined depth of tissue. Stretched tissue may comprise realign (e.g., reoriented) cellular structures that increase tissue circumference. Reducing total energy delivery may correspond to a lower overall temperature increase of the tissue, which may increases the safety profile of the treatment procedure as well as promote a faster and safer healing cascade.

In some variations, negative pressure may be applied to the tissue to ensure even contact between tissue and an electrode array during treatment. For example, negative pressure or suction may be applied by an expandable member to a tissue lumen (e.g., duodenum, duodenal tissue) to facilitate tissue apposition with an electrode array of the expandable member. Higher tissue apposition may further enable a reduction in total energy delivery and improved treatment outcomes.

In some variations, stretching the tissue by applying a radially outward force using the expandable member and/or application of negative pressure to the tissue from the expandable member may reduce a range of tissue thicknesses as shown in FIG. 71A. For example, the expandable member may stretch tissue such that a ratio of manipulated (e.g., compressed/stretched/dilated) tissue thickness to unmanipulated tissue thickness is about 0.5.

Figure 71C:
FIG. 71C is a cross-sectional image of an undilated duodenum.
Figure 71D:
FIG. 71D is a detailed cross-sectional image of the undilated duodenum shown in FIG. 71C.
Figure 71E:
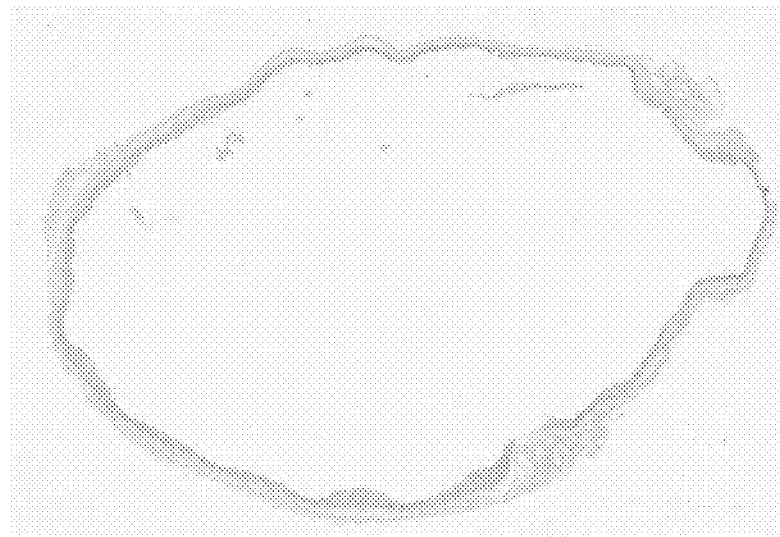
FIG. 71E is a cross-sectional image of a dilated duodenum.
Figure 71F:
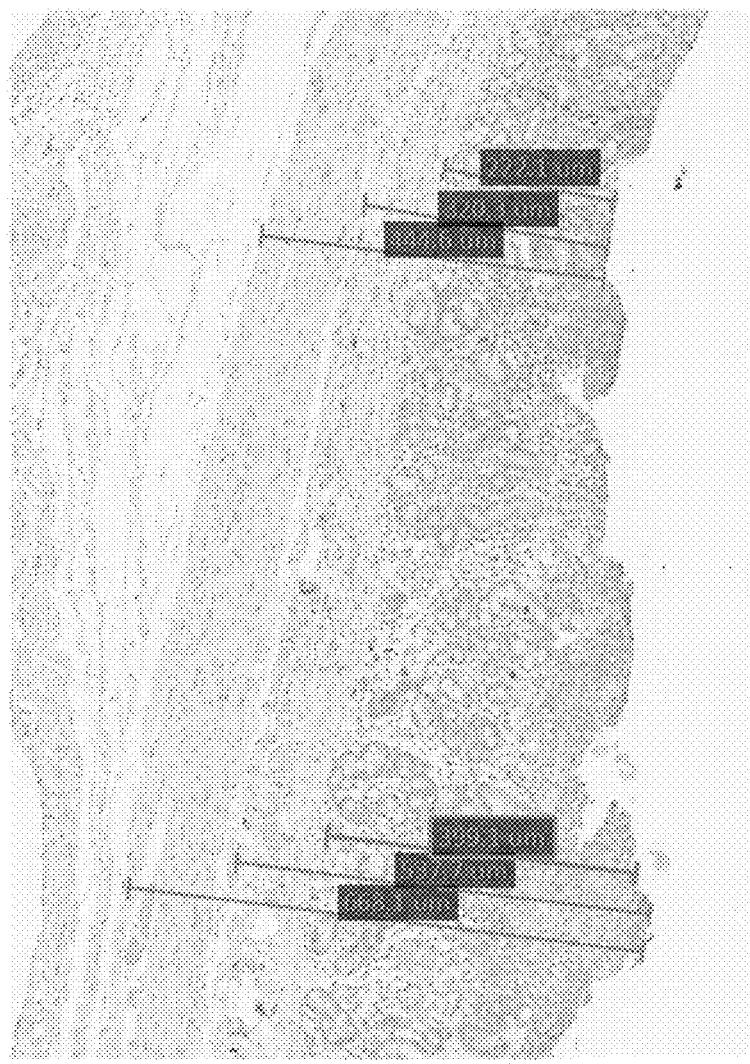
FIG. 71F is a detailed cross-sectional image of the dilated duodenum depicted in FIG. 71E.

FIGS. 71C and 71D are cross-sectional images of an undilated (e.g., unstretched) duodenum. FIGS. 71E and 71F are cross-sectional images of a dilated (e.g., stretched) duodenum. In some variations, an ablation device as described herein may transition to an expanded configuration to dilate (e.g., stretch, extend) the tissue during a treatment procedure. In some variations, tissue may be treated within a predetermined range of dilation ratios. In some variations, a ratio of dilated to undilated mucosa tissue may be between about 0.40 and about 0.60, between about 0.45 and about 0.55, and about 0.50, including all ranges and sub-values in-between. In some variations, a ratio of dilated to undilated submucosa tissue may be between about 0.15 and about 0.35, between about 0.20 and about 0.30, and about 0.26, including all ranges and sub-values in-between. In some variations, a ratio of dilated duodenum diameter to undilated duodenum diameter may be between about 1.5 and about 2.3, between about 1.7 and about 2.1, and about 1.91, including all ranges and sub-values in-between. In some variations, a ratio of a dilated duodenum diameter to an undilated duodenum diameter may be between about 1.5 and about 2.3, between about 1.7 and about 2.1, and about 1.91, including all ranges and sub-values in-between.

In some variations, an ablation device may be configured to simultaneously dilate and suction tissue to the ablation device. In some variations, a ratio of suction and dilated to undilated mucosa tissue may be between about 0.40 and about 0.60, between about 0.45 and about 0.55, and about 0.47, including all ranges and sub-values in-between. In some variations, a ratio of suction and dilated to undilated submucosa tissue may be between about 0.20 and about 0.50, between about 0.30 and about 0.40, and about 0.33, including all ranges and sub-values in-between.

In some variations, the suction may be generated by the device itself while in the expanded configuration. Additionally or alternatively, the suction may be generated by a visualization device such as an endoscope. An amount of suction may be configured to secure apposition of tissue to the surface of the expandable member (e.g., electrode surfaces). However, the amount of suction should not exceed a predetermined threshold corresponding to pressure necrosis. In some variations, the negative pressure (e.g., suction) applied to the tissue may be between about 50 mmHg and about 75 mmHg for less than about one minute. In some variations, the negative pressure (e.g., suction) applied to the tissue may be between about 10 mmHg and about 200 mmHg. The amount of suction may be a function of one or more of total surface area of the expandable member, number and size of the openings, time that suction is applied, edge condition of the openings, compliance of tissue, vascularization of tissue, and friability of tissue.

In some variations, an amount of tissue compliance may correspond to an amount of dilation and suction needed to ensure uniform surface contact of the electrodes and the desired tissue treatment. In some variations, the tissue may respond better to less dilation and more suction (or vice versa) depending on compliance and structure. In some variations, apposition may be assessed visually and/or through impedance measurement. In some variations, apposition may be measured using one or more temperature sensors and/or pressure sensors.

Figure 55A:
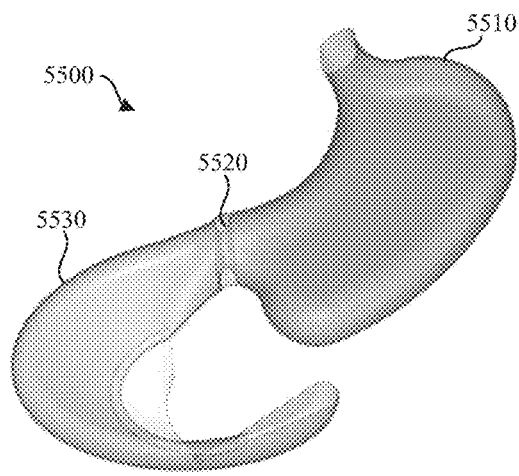
FIGS. 55A-55F are schematic views of an illustrative variation of a method of treating diabetes.
Figure 55B:
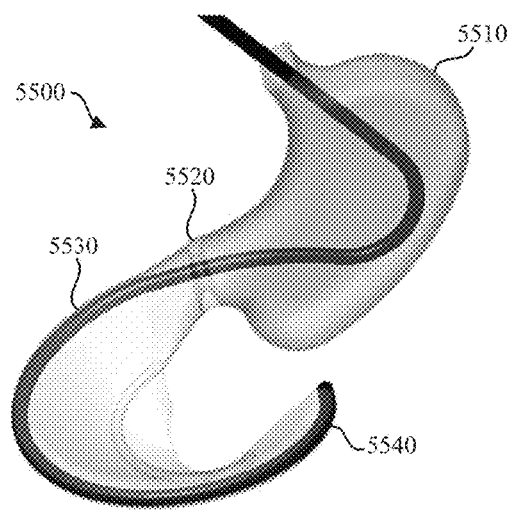
Figure 55C:
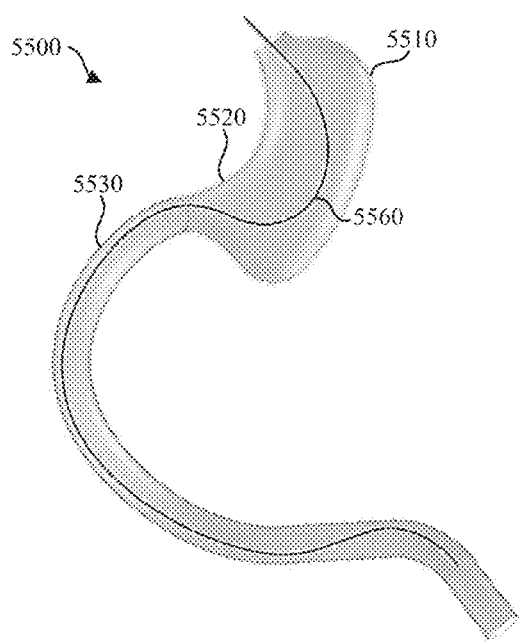
Figure 55D:
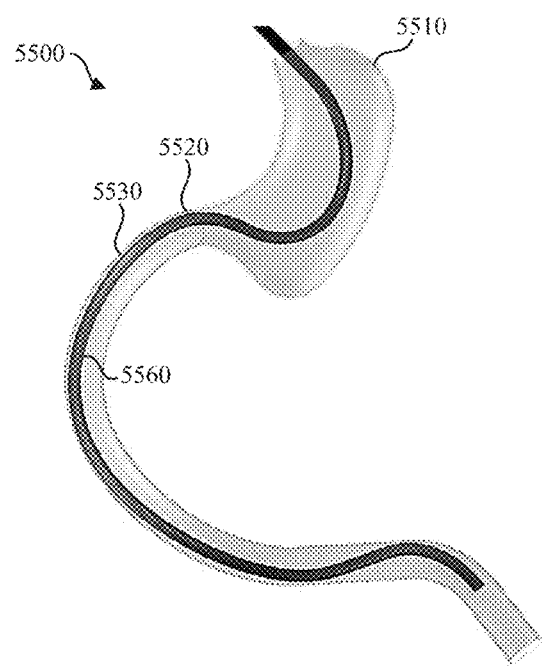
Figure 81A:
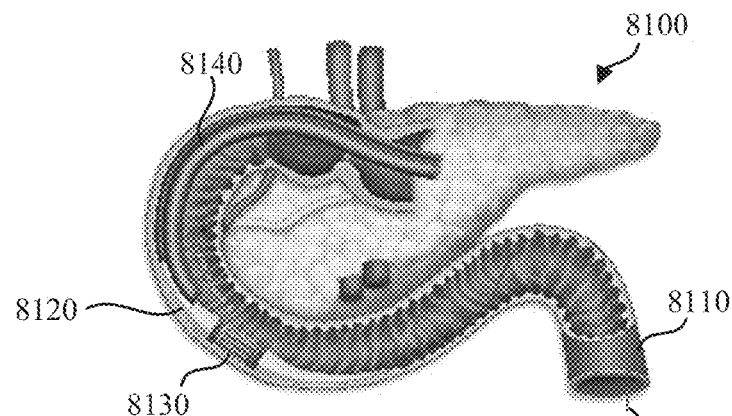
FIGS. 81A-81C are schematic views of an illustrative variation of a method of treating diabetes.
Figure 81B:
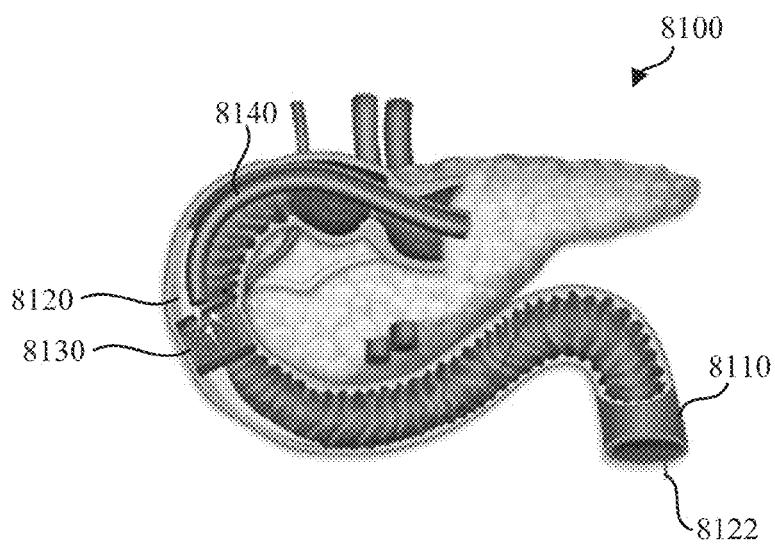
Figure 81C:
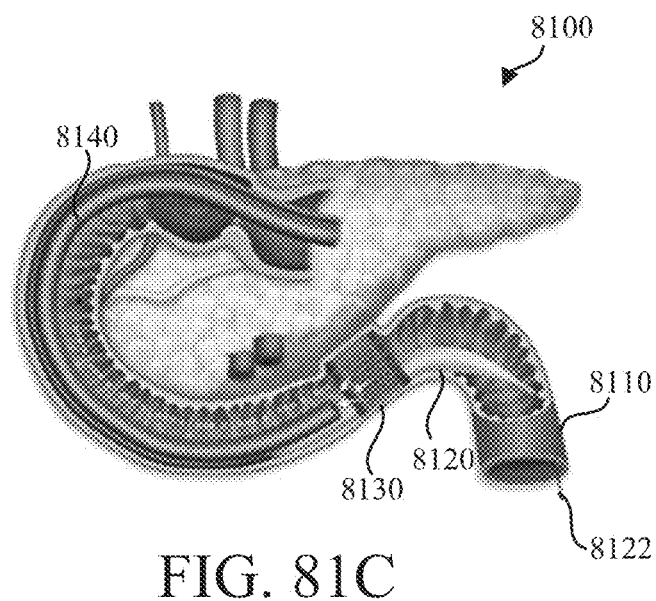

The introduction and advancement of various devices into the duodenum is illustrated in the schematic views of FIGS. 55A-55F where the gastrointestinal tract (5500) comprises the stomach (5510), the pylorus (5520), and the duodenum (5530). FIG. 55B depicts a visualization device (e.g., endoscope) (5540) advanced through the stomach (5510) and into the duodenum (5530). The visualization device (5540) may be configured to image tissue, pulsed electric field devices, and visual markers (e.g., anatomical landmarks, thermal markers, fiducials), and aid positional determination. For example, the imaged tissue may be used to identify tissue as one or more of treated, marked, affected, untreated, and the like. FIG. 55C depicts a guidewire (5560) advanced through the stomach (5510) and into the duodenum (5530). In some variations, as shown in FIG. 55D, a visualization device (5540) may be advanced over the guidewire (5530) and into the duodenum (5530). In some variations, as shown in FIG. 55D, a therapeutic device (5560) may be advanced over the guidewire (5560) that was placed with a visualization device (5540) and into the duodenum (5530). FIGS. 56A-56H are detailed perspective views of the pulsed electric field device (5650) and the visualization device (5640) in the duodenum (5630) and are described with respect to the methods for treating diabetes in more detail herein. FIGS. 81A-81C are schematic views of another variation of a method of treating diabetes as described in more detail herein. FIGS. 82A-82D are images corresponding to the method shown in FIGS. 81A-81C.

Figure 54:
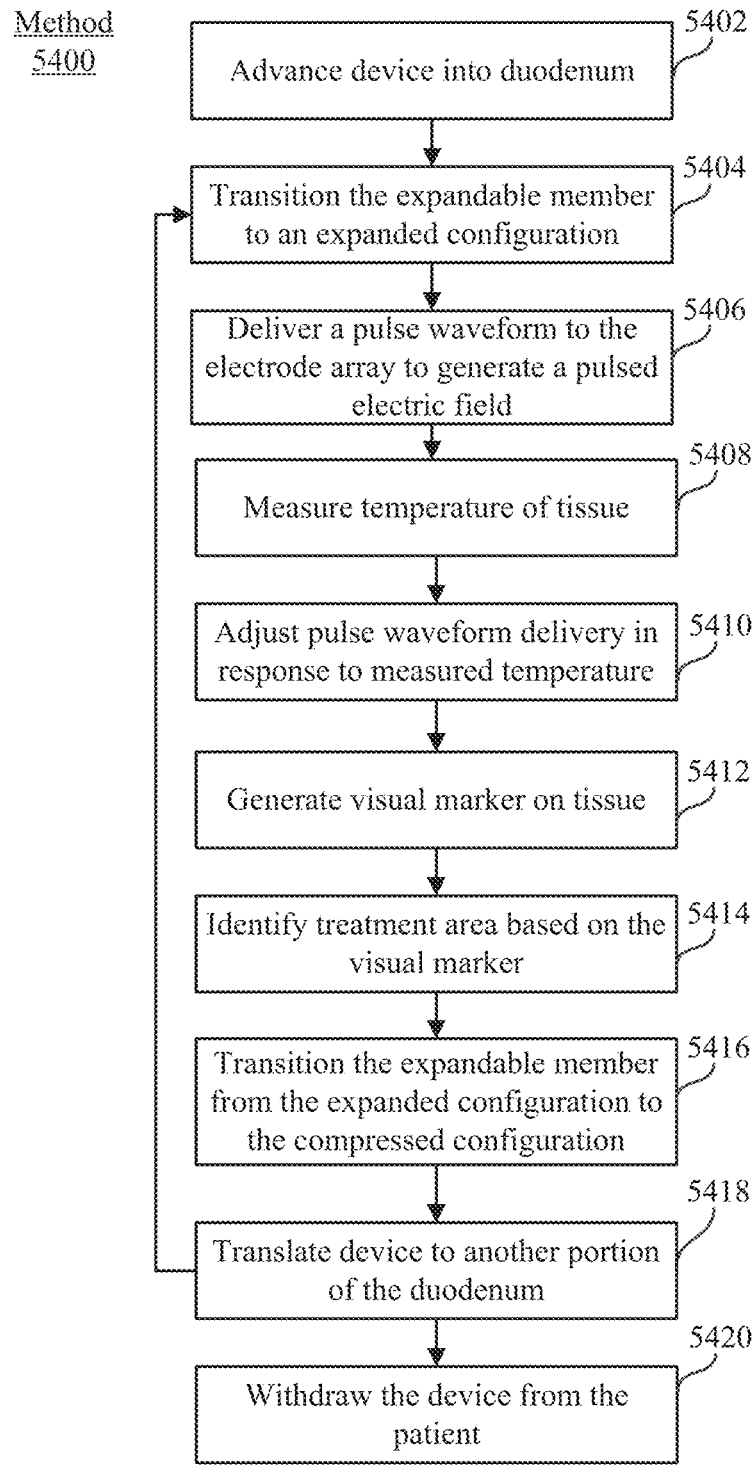
FIG. 54 is a flowchart describing an illustrative variation of a method of treating diabetes.
Figure 55E:
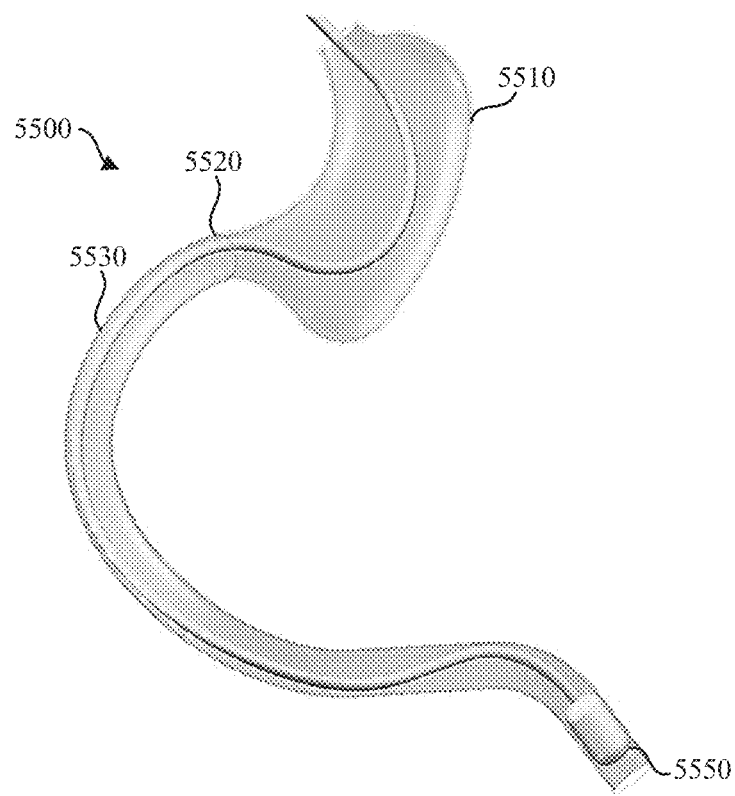
Figure 55F:
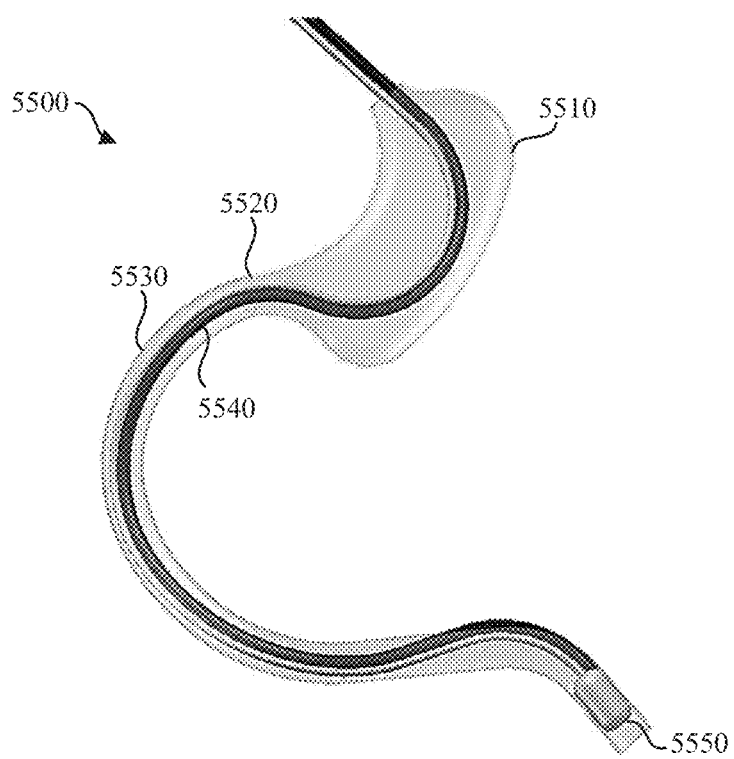
Figure 56A:
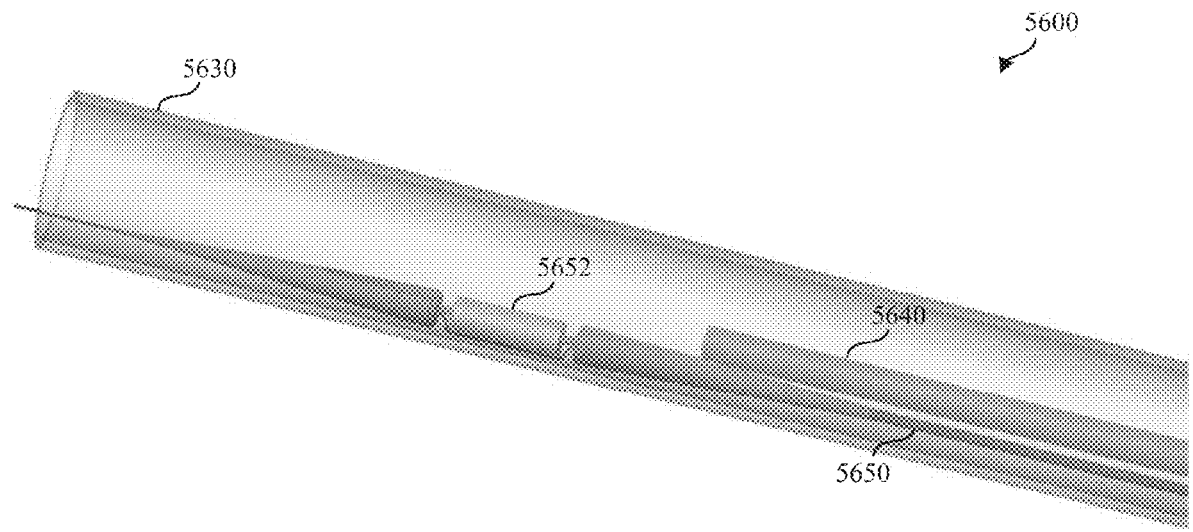
FIGS. 56A-56H are perspective views of an illustrative variation of a method of treating diabetes using a pulsed electric field device and visualization device.
Figure 82A:
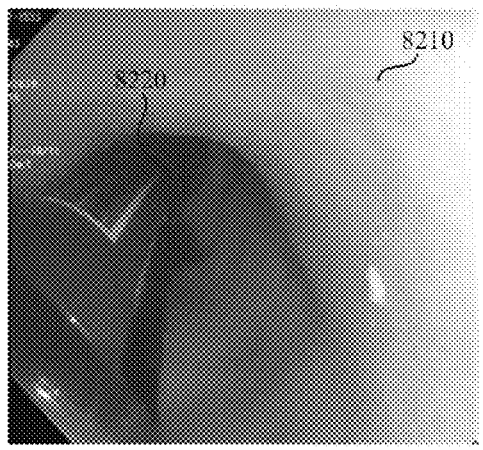
FIGS. 82A-82D are images of an illustrative variation of a method of treating diabetes using a pulsed electric field device and visualization device.

FIG. 54 is a flowchart that generally describes a variation of a method of treating diabetes (5400). The method (5400) may include advancing a pulsed electric field device comprising an expandable member comprising an electrode array toward a first portion of the duodenum (5402). For example, FIG. 55E depicts a pulsed electric field device (5550) advanced through the stomach (5510) and into the duodenum (5530) over a guidewire. Similarly, a visualization device may be advanced into the duodenum. FIG. 55F depicts a visualization device (5540) (e.g., endoscope) advanced into the duodenum (5530) alongside (e.g., substantially parallel to) the pulsed electric field device (5550). In FIG. 56A, the pulsed electric field device (5650) comprises the expandable member (5652) in a compressed configuration within the duodenum (5630). For example, the expandable member (5652) is in a rolled configuration comprising a plurality of turns about a longitudinal axis of the pulsed electric field device (5650). In the compressed configuration, the expandable member (5652) may comprise a lumen having a first inner diameter. The visualization device (5640) may be manipulated independently of the pulsed electric field device (5650). Likewise, FIG. 81A depicts a method of treating diabetes (8100) including a pulsed electric field device (8120) comprising an expandable member (8130) and a visualization device (8140) advanced into a duodenum (8110) along a guidewire (8122). In some variations, one or more of the device (8120) and the visualization device (8140) may be disposed distal to the papilla. FIG. 82A is an image of an expandable member (8220) of a pulsed electric field device from the perspective of a distal end of a visualization device (e.g., endoscope). The expandable member (8220) may be in a compressed configuration as it is advanced through the duodenum (8210).

In step S404, the expandable member of the pulsed or modulated electric field device may transition from a compressed configuration to an expanded configuration to, for example, engage tissue and/or allow a visualization device to advance through a lumen of the expandable member. As shown in the expanded configuration of FIG. 56B, the expandable member (5652) may comprise a lumen having a second inner diameter larger than the first inner diameter. In some of these variations, the visualization device (5640) may be advanced through the lumen of the expandable member (5652) in the expanded configuration to allow the visualization device (5640) to visualize, for example, tissue (5600) and a distal portion of the pulsed electric field device (5650). Additionally or alternatively, the pulsed electric field device (5650) may comprise a second expandable member (e.g., inflatable member, balloon) (not shown) disposed distal to the expandable member (5652). In some of these variations, the second expandable member may be inflated to aid in one or more of advancement, positioning, and visualization of the pulsed electric field device (5650) and tissue (5630). For example, one or more portions of the second expandable member may be transparent to allow a visualization device to see through the second expandable member.

Figure 56B:
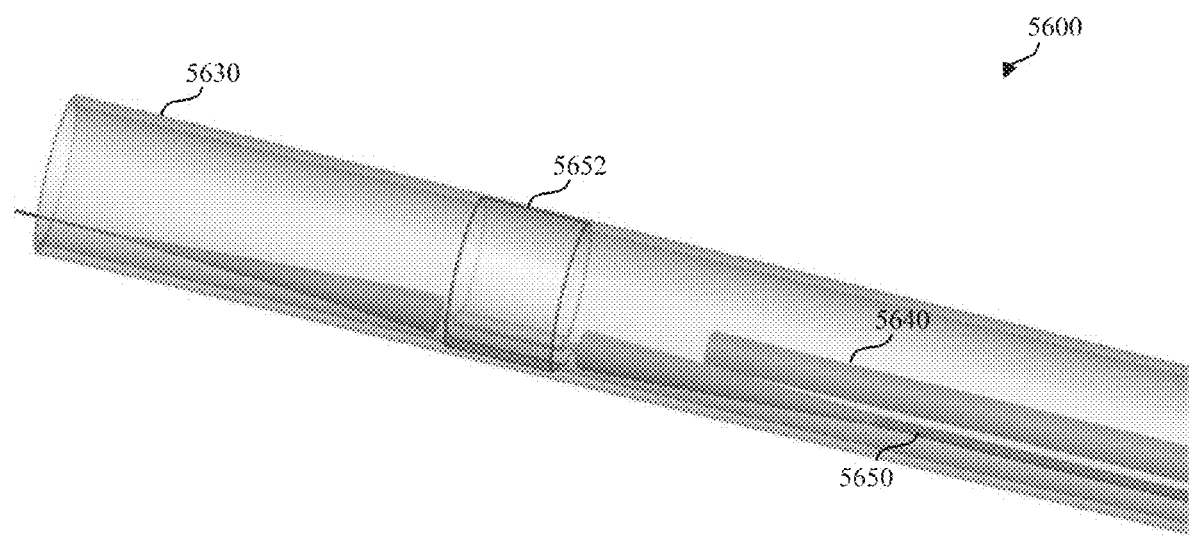
Figure 56C:
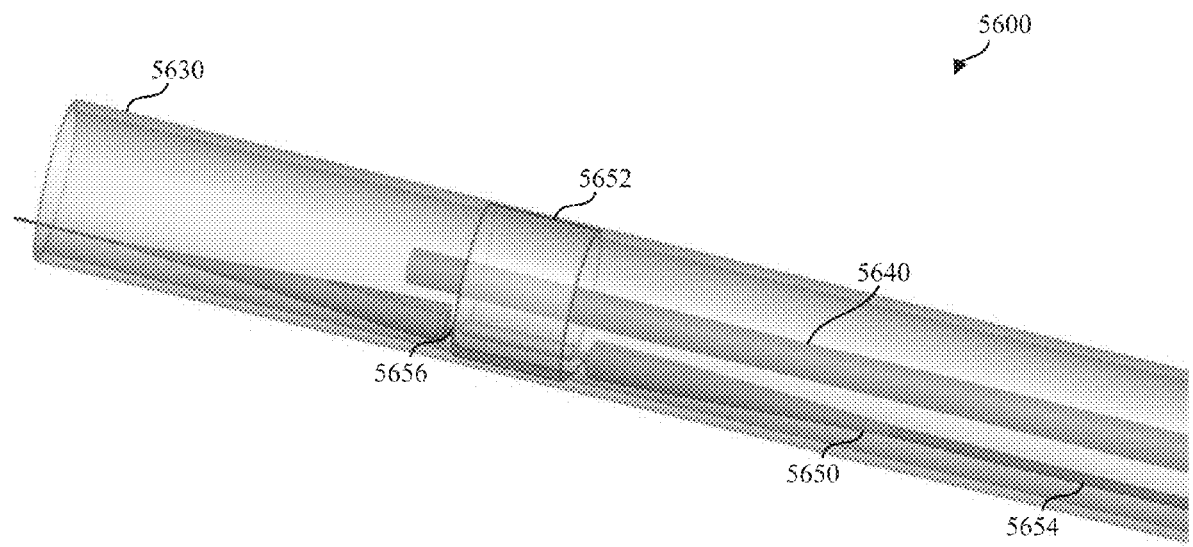
Figure 64A:
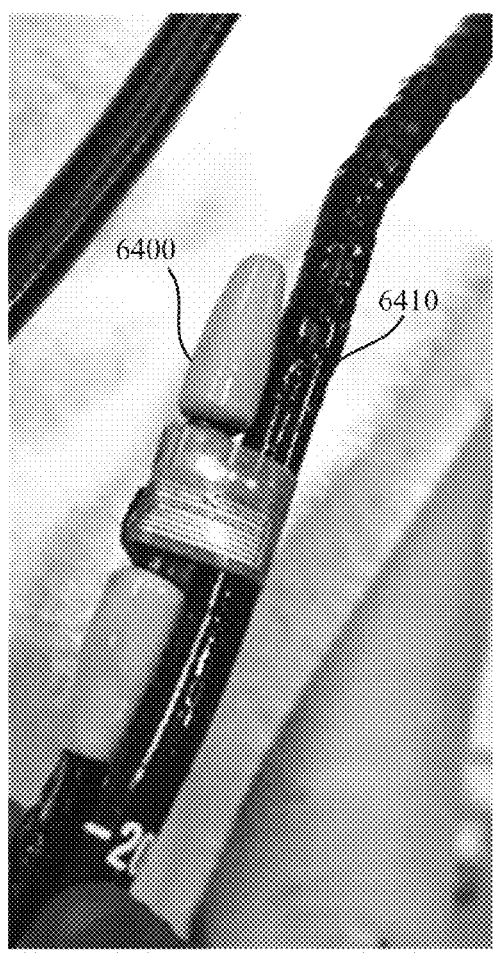
FIG. 64A is an image of an illustrative variation of a pulsed electric field device and visualization device.
Figure 64B:
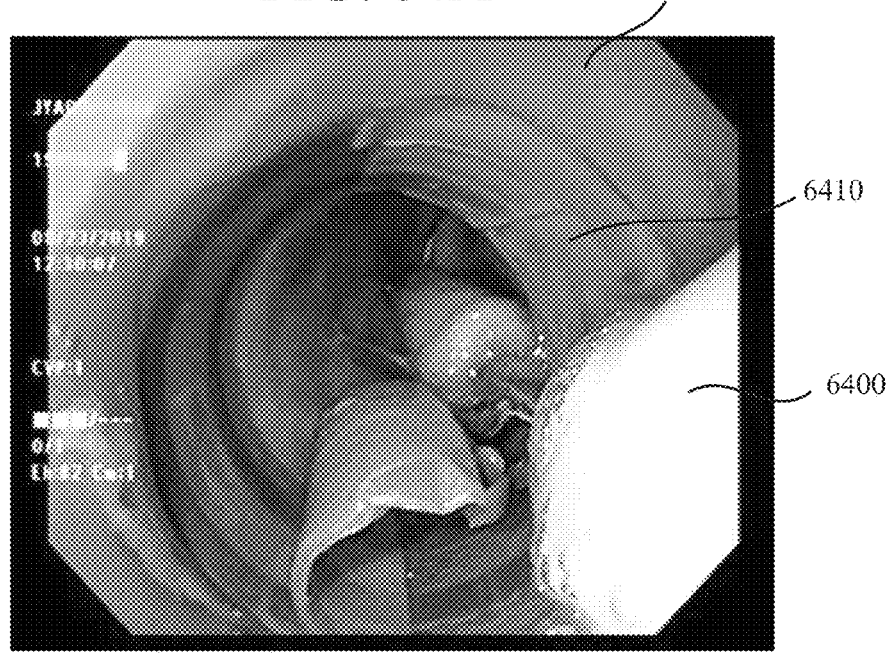
FIG. 64B is an image of an illustrative variation of a pulsed electric field device in an unrolled configuration within a tissue lumen.

As shown in FIG. 56B, the expandable member (5652) may unroll by one or more turns to transition the expandable member (5652) to an expanded configuration (e.g., unrolled configuration). As shown in FIG. 56C, the pulsed electric field device (5650) may comprise a first elongate body (5654) and a second elongate body (5656) positioned within the first elongate body (5654). The expandable member (5652) may be rolled about the second elongate body (5656) a predetermined number of turns. In some of these variations, the second elongate body (5656) may be rotated relative to the first elongate body (5654) to unroll the expandable member (5652), causing the expandable member to contact the duodenum (5630). Complete circumferential contact between the expandable member (5652) and duodenum (5630) may improve energy delivery and treatment outcomes. For example, FIG. 64B is an image of a variation of a pulsed electric field device (6400) in an unrolled configuration within a tissue lumen (6430) imaged by a visualization device retracted relative to the pulsed electric field device (6400) to allow visualization of a proximal end of the expandable member (6410) and tissue (6430).

In some variations, as shown in FIG. 81B, the expandable member (8130) of device (8120) may transition to the expanded configuration to contact tissue. In some variations, a distal end of the visualization device (8120) may be disposed either within a lumen of the expandable member (8130), proximal to a proximal end of the expandable member (8130), or distal to a distal end of the expandable member (8130). As shown in FIG. 81B, the visualization device (8120) may be configured to generate a negative pressure (e.g., suction) within a lumen of the expandable member (8130) that suctions tissue (8110) to a surface of the expandable member (8130). Additionally or alternatively, the device (8120) may be configured to generate negative pressure to suction tissue (8110) to the surface of the surface of the expandable member (8130). In some variations, suction may be applied during delivery of a pulse waveform and reduced during time periods when pulsed electric field energy is not delivered. For example, suction may be reduced (or halted) during a time period when tissue is cooling after energy delivery, and when one or more of the device (8130) and visualization device are advanced within tissue (8110). Thus, suction may be generated intermittently throughout a treatment process. An amount of suction applied to one or more portions of tissue may be as described herein.

Figure 82B:
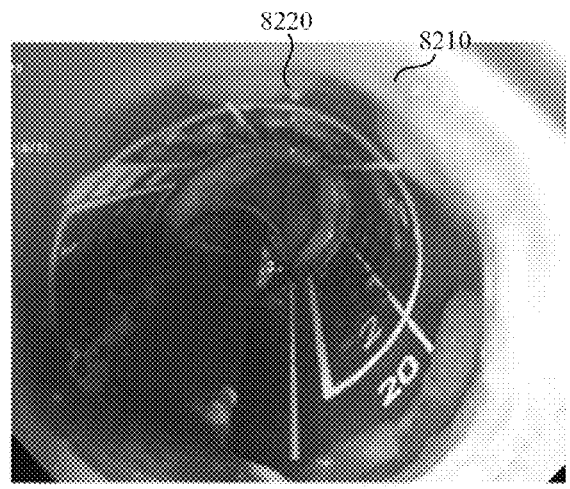
Figure 82C:
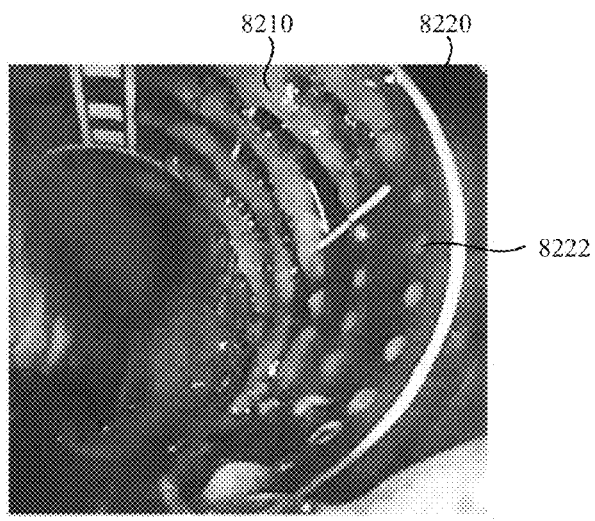

FIG. 82B is an image of the expandable member (8220) in an expanded configuration where the expandable member (8220) contacts the duodenum (8210). FIG. 82C is an image of the of the tissue (8210) in contact with the expandable member (8220) after applying negative pressure as described herein. In FIG. 82C, tissue is pulled through a plurality of openings (8222) that extend through a thickness of the expandable member (8220). The close contact between the tissue (8210) and the expandable member (8220) may improve energy delivery and treatment outcomes. One or more pulse waveforms may be delivered while suction is being applied.

In step S406, one or more pulse waveforms may be delivered to an electrode array of an expandable member to generate a pulsed or modulated electric field. For example, FIG. 56C depicts the expandable member (5652) in the expanded configuration comprising electrodes (not depicted) configured to receive the pulse waveform to generate a pulsed or modulated electric field for treating the duodenum (5630). In some variations, one or more of the visualization member (5640) and pulsed electric field device (5650) may be configured to apply suction or negative pressure to tissue in order to increase the apposition of tissue (5630) to an electrode array of the expandable member (5652). In some variations, fluid may be drawn or suctioned between the pulsed electric field device and the duodenum from the expandable member. For example, suction or negative pressure may be applied by the visualization device.

In some variations, the pulse waveform may comprise a frequency between about 250 kHz and about 950 kHz, between about 250 kHz and about 950 kHz, about 350 kHz, a pulse width between about 0.5 µs and about 4 µs, a voltage applied by the electrode array of between about 100 V and about 2 kV, and a current density between about 0.6 A and about 100 A or between about 0.6 A and about 65 A from the electrode array per square centimeter of tissue, including all ranges and sub-values in-between. For example, the current density may be between about 0.6 A and about 100 A or between about 0.6 A and about 65 A from the electrode array per square centimeter of tissue.

In some variations, the pulse waveform may comprise a pulse group of between about 1 and about 100 with between about 1 and about 100 pulses per group. In some of these variations, the pulse waveform may comprise a group delay between about 10 µs and about 2000 µs or between about 10 µs and about 500 µs, and a replenish rate of between about 50 ms and about 4000 ms or between about 50 ms and about 500 ms. In some variations, the pulsed or modulated electric field generated by the pulsed electric field device (5650) spatially varies up to about 20% within tissue (5360) at a predetermined treatment distance from the expandable member (5652). For example, treatment of a 4 cm$^2$ treatment area of the duodenum may comprise delivering about 900 V applied into 10 S2 or about 600 V applied into 50 S2 for an instantaneous power of about 81,000 watts or about 20,250 watts/cm$^2$, or about 1,800 watts/cm$^2$, respectively. Voltage may be applied for about 2 µs for a corresponding dose of about 0.04 joules/cm$^2$ or for about 0.015 s for a corresponding dose of about 27 joules/cm$^2$. In some variations, a treatment pulse may be repeated about 1000 times to equal about 40.5 Joules of total energy. For example, a treatment area of the duodenum of about 400 cm² may comprise a dose of about 16,200 J. As another example, a treatment area of the duodenum of about 100 cm² may comprise a dose of about 27 kJ.

In some variations, the pulse waveform delivered to a portion (e.g., section) of tissue may comprise a plurality of pulse waveforms. That is, a portion may be treated a plurality of times (e.g., two times, three times, four times).

In some variations, a temperature sensor may measure a temperature of the tissue and the temperature may be used to inhibit pulse waveform delivery, thereby adding a margin of safety to the procedure. In step S408, a temperature of the tissue may be measured using a temperature sensor. For example, temperature may be measured at least during pulse waveform delivery or immediately after each packet of energy. In step S410, pulse waveform delivery may be adjusted in response to the measured temperature. For example, pulse waveform delivery may be inhibited when the measured temperature exceeds a predetermined threshold. This may prevent unintended damage to tissue due to thermal heating.

Figure 57:
FIG. 57 is an image of an illustrative variation of a thermal marking on tissue.

In some variations, a visual marker may be generated on the duodenal tissue using a fiducial generator. The visual marker may be visualized using, for example, the visualization devices described herein, to identify a treatment area to aid complete treatment coverage of the duodenum. In step S412, one or more visual markers may be generated on the tissue using a fiducial generator (e.g., temperature sensor). As shown in FIG. 57, one or more visual markers (5710) may be generated along an inner circumference of the duodenum (5700).

Figure 82D:
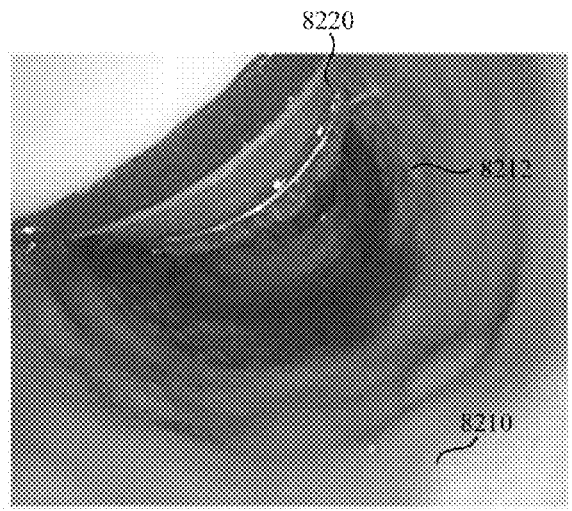

In step S414, a treatment area may be identified based on one or more of the visual marker and suctioned tissue. For example, a visualization device in the duodenum may image one or more visual markers. The area between visual markers (5710) may correspond to a treated area having undergone PEF-induced cell death. FIGS. 56D-56H illustrate visual markers (5634) generated on tissue. Moreover, retreatment of the duodenum in another procedure may be guided by one or more of the visual markers generated by the fiducial generator. FIG. 82D depicts an image of tissue (8210) comprising suctioned tissue (8212) that may be visually identified by a visualization device. The visual markers may be used to identify the treated portions of tissue and align the pulsed electric field device to non-treated portions of tissue to be treated.

Figure 56D:
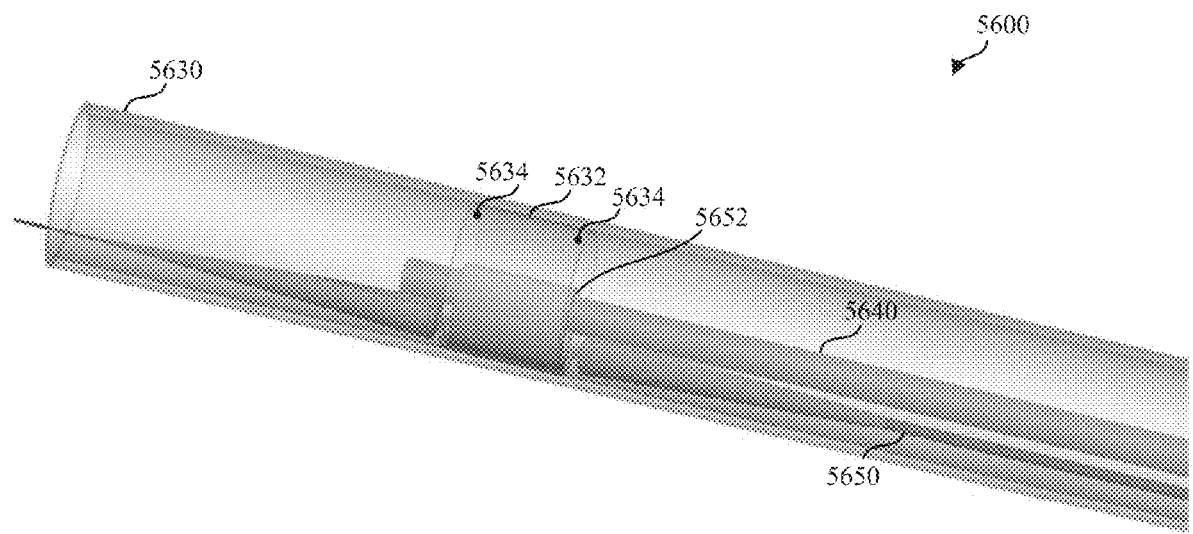

In some variations, the pulsed electric field device may be retracted proximally through the duodenum to treat the entire duodenum with a pulsed or modulated electric field. Generally, the duodenum comprises an area of about 260 cm². In step S416, the expandable member may transition from the expanded configuration to the compressed configuration (or the partially or semi-expanded configuration in which the expandable member is collapsed to the outer diameter of the visualization device) to aid translation of the pulsed electric field device through the duodenum. FIG. 56D depicts the expandable member (5652) in a partially expanded configuration such that the expandable member (5652) disengages from the treated portion (5632) of the duodenum (5630) and engages an outer surface of the visualization device (5640). This allows the pulsed electric field device (5650) and the visualization device (5640) to be slidably translated together relative to the duodenum (5630).

Figure 56E:
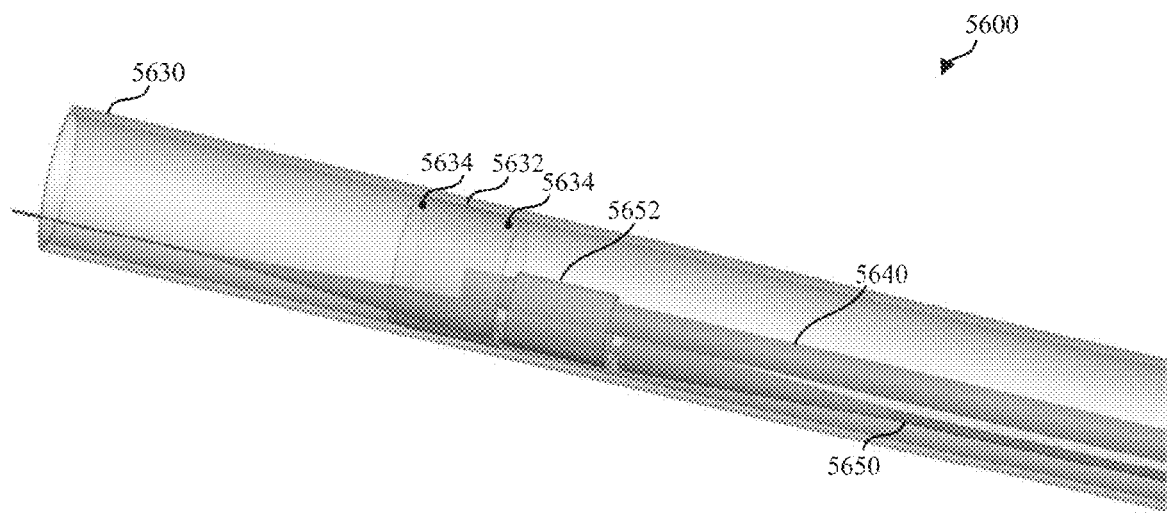

In step S418, the pulsed electric field device may be translated to another portion of the duodenum. In some variations, the duodenum may be treated over about 2 portions to about 20 portions, about 6 portions to about 15 portions, about 10 portions to about 12 portions, including all ranges and sub-values in-between. For example, FIG. 56E depicts the pulsed electric field device (5650) retracted proximally relative to the treated portion (5632). In some of these variations, retraction may be guided by a position of the visual marker visualized by a visualization device. For example, the visualization device (5640) may be retracted to view duodenal tissue (5630) proximal of the expandable member (5652) in FIG. 56F. Similarly, as shown in FIG. 81C, the device (8120) and/or visualization device (8140) may be advanced through the duodenum (8110) multiple times to repeat the energy delivery process described herein. In some variations, a total treatment length of tissue may be between about 6 cm and about 20 cm. In some variations, a portion of the tissue may have a circumference between about 22 mm and an average of about 25 mm. In some variations, more than about 60 percent of a circumference of a portion of the duodenum may be treated.

Figure 56F:
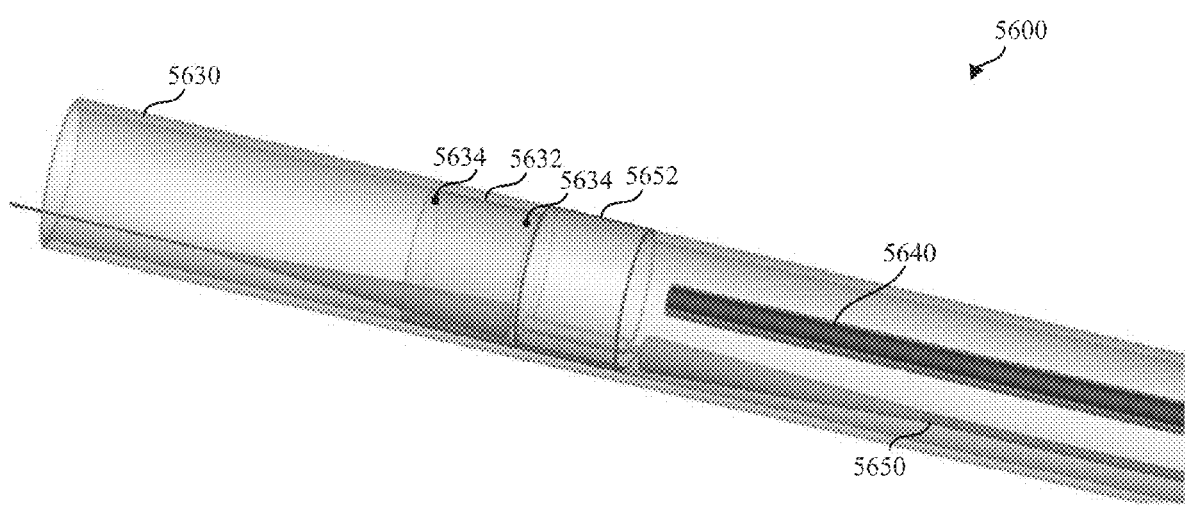
Figure 56G:
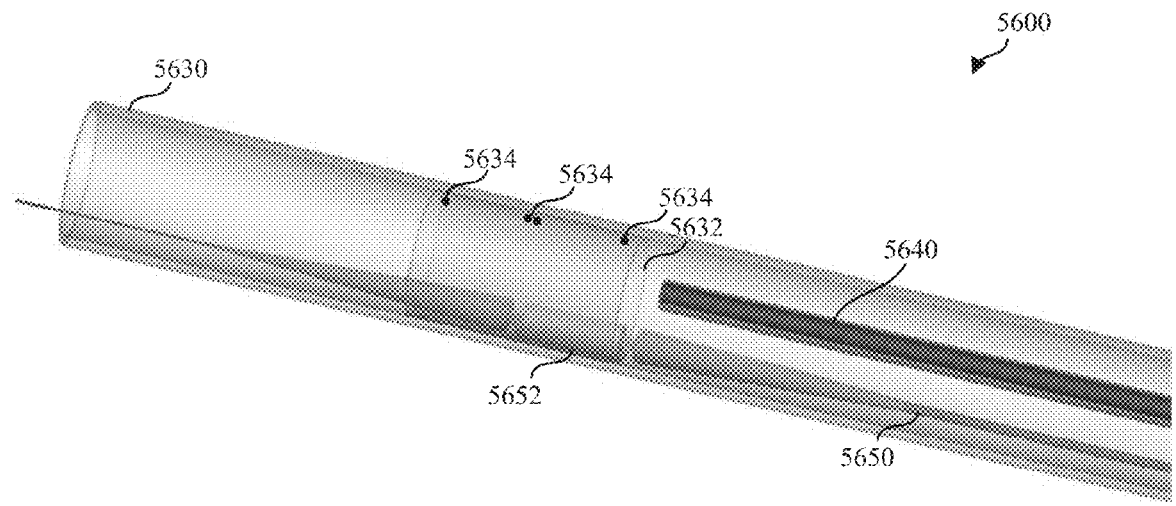

In some variations, steps S404 to S418 may be repeated until a predetermined length of the duodenum has been treated. For example, FIG. 56F depicts the expandable member (5652) transitioned to the expanded configuration just proximal to the treated portion (5632). The visualization device (5640) is retracted proximally relative to the expandable member (5652) such that the expandable member (5652) and treated portion (5632) may be visualized. The expandable member (5652) may be positioned proximal to the visual markers (5634). FIG. 56G depicts the duodenum (5630) and pulsed electric field device (5650) after delivering a second pulse waveform. In particular, an area of the treated portion (5632) has increased and the expandable member (5652) has transitioned to the compressed configuration. For example, the second elongate body (5656) may be rotated relative to the first elongate body (5654) to turn the expandable member (5652) about a longitudinal axis of the second elongate body (5656) to reduce a diameter of the expandable member (5652). In some variations, the pulse waveform and generated pulsed or modulated electric field may be the same or different for each portion of the duodenum.

In some variations, the electrode array may be configured such that a total surface area of electrodes in contact with the tissue may comprise resistance of the system or impedance that matches a voltage and current output of a signal generator. For example, the number of electrodes arrays may be independently matched to a desired treatment area, thereby controlling the amount of voltage and current generated by a signal generator. This multiplexing technique may significantly reduce the cost and complexity of a signal generator.

Figure 56H:
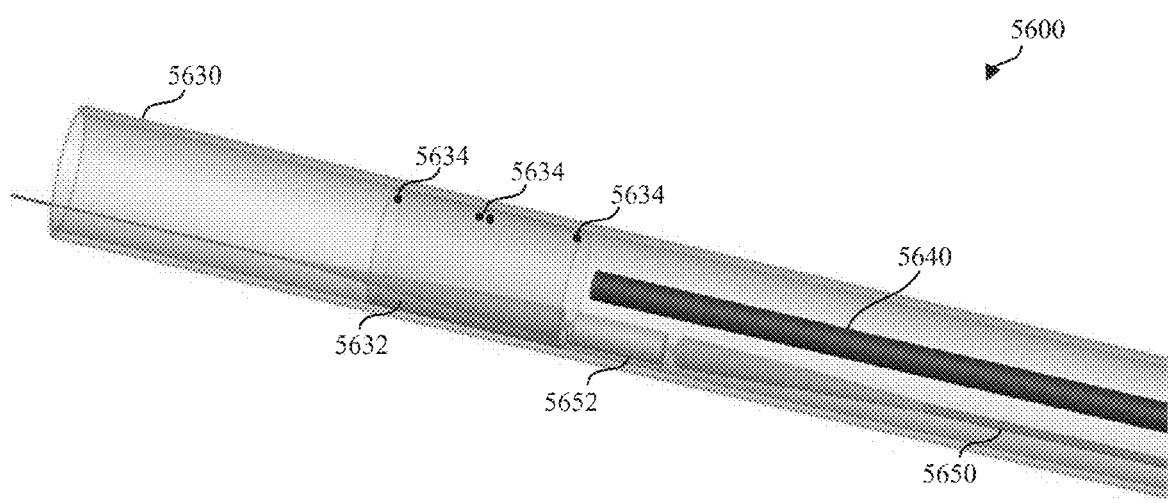

In step S420, the pulsed electric field device and the visualization device may be withdrawn from the patient. The pulsed electric field device and the visualization device may be withdrawn from the patient sequentially or simultaneously. FIG. 56H depicts the pulsed electric field device (5650) being withdrawn out of the duodenum (5630) after treating a predetermined area of tissue (e.g., the treated portion (5632)). For example, FIG. 64A is a plan view image of a variation of a pulsed electric field device (6400) engaged to a visualization device (6410) and withdrawn from the patient. In FIG. 64A, an expandable member of the pulsed electric field device (6400) is in the semi-expanded configuration to hold the pulsed electric field device to the visualization device (6410).

Figure 58A:
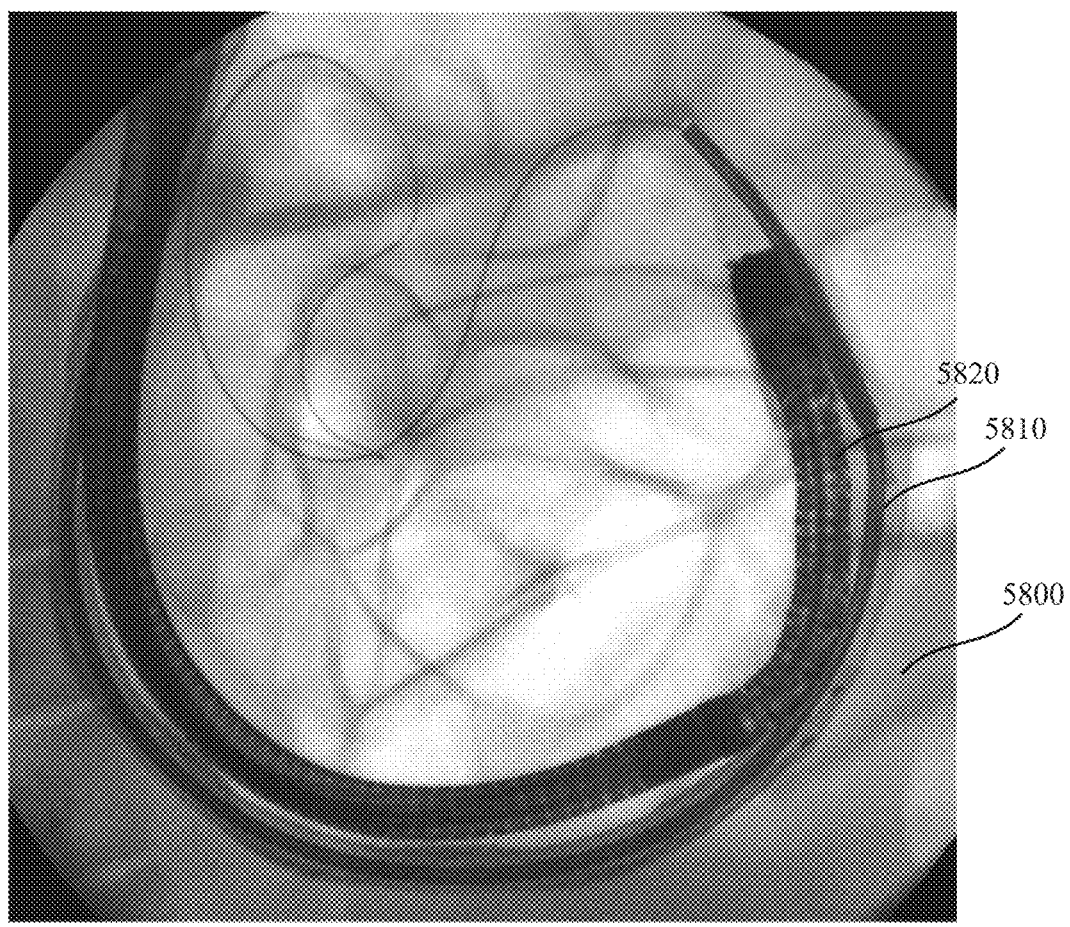
FIGS. 58A-58E are images of an illustrative variation of a treatment procedure in a patient using a pulsed electric field device and visualization device.
Figure 58B:
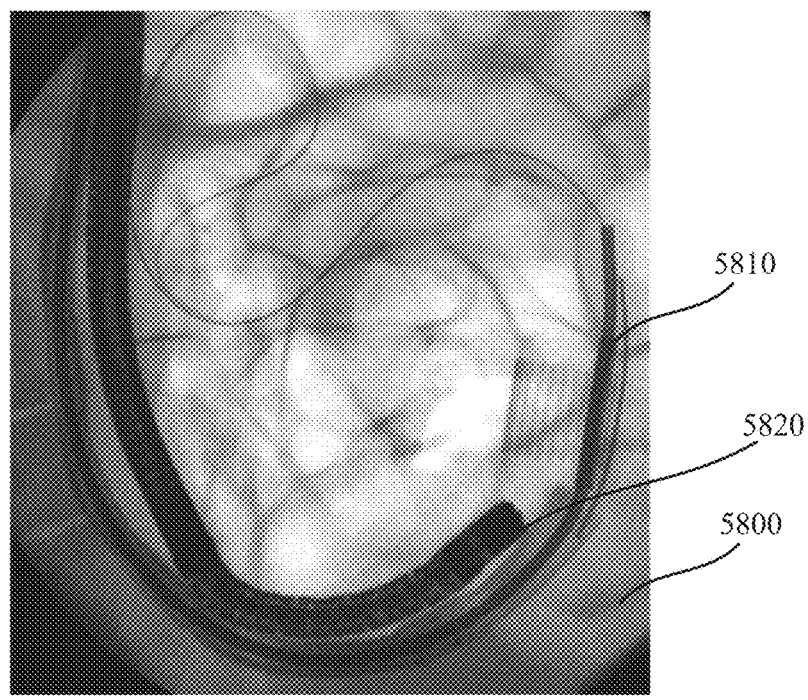
Figure 58C:
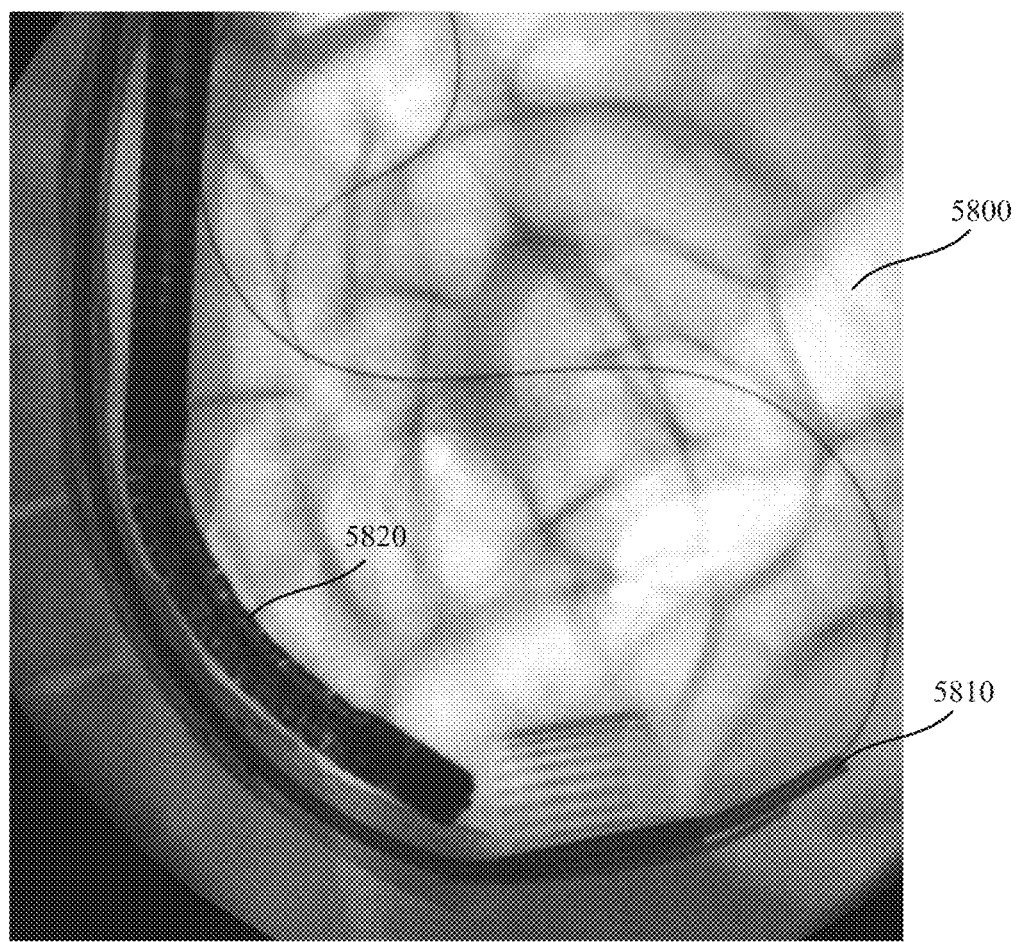
Figure 58D:
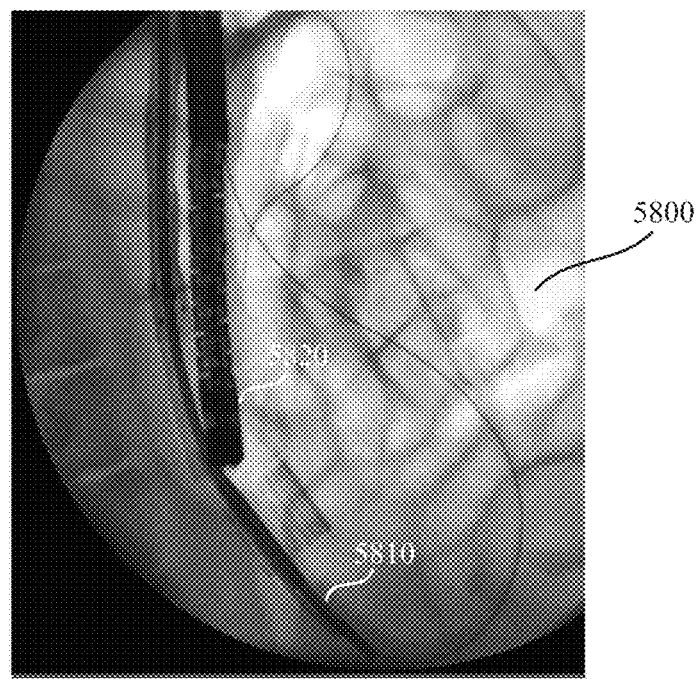
Figure 58E:
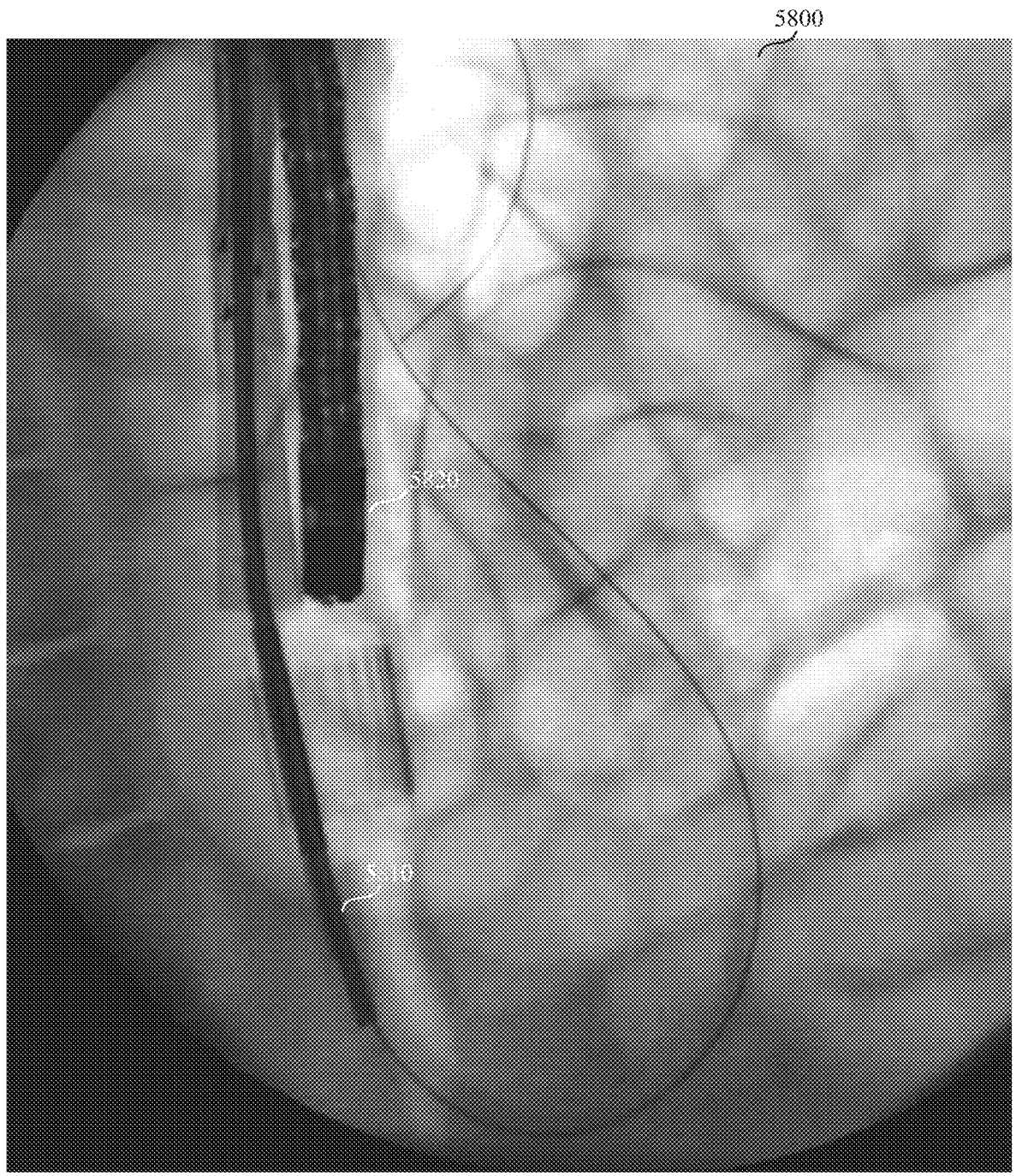

An example of a treatment procedure in a patient using a pulsed electric field device is shown in the fluoroscopic images of FIGS. 58A-58E. FIG. 58A depicts a pulsed electric field device (5810) and visualization device (5820) (e.g., endoscope) advanced into a distal portion of a duodenum (5800). FIG. 58B depicts the pulsed electric field device (5810) in an expanded configuration with an endoscope (5820) proximal to the expandable member (5812). FIGS. 58C, 58D, and 58E depict the pulsed electric field device being translated proximally through the duodenum (5800). Although depicted here as being translated proximally through the duodenum (5800) during a treatment procedure, the pulsed electric field device (5810) may be advanced distally through the duodenum (5800) instead (e.g., a proximal portion of the duodenum (5800) may be treated prior to one or more portions distal of the proximal portion). In some variations, the treatment procedures performed herein may utilize fluoroscopic guidance without a visualization device.

In some variations, pulsed electric field energy may be delivered while safely controlling tissue temperature. For example, energy delivery may be pulsed such that sufficient delay is given for a tissue temperature to fall before another energy burst is delivered. Furthermore, delivery may be inhibited when a predetermined tissue temperature is exceeded (e.g., relative change in temperature, absolute temperature). For example, tissue temperature rise may be limited to about 6° C. and/or about 43° C. as an absolute temperature. In the methods described herein, heat is a byproduct of energy delivery and not the desired mode of action.

Figure 83A:
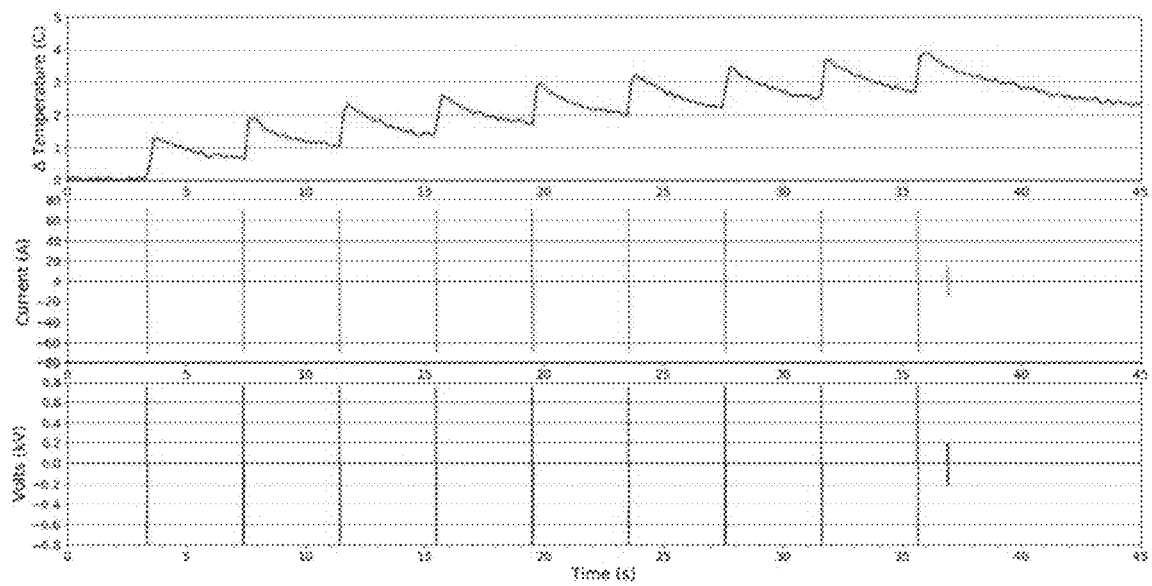
FIGS. 83A and 83B are tissue temperature, voltage, and current plots over time for illustrative variations of methods of treating tissue.
Figure 83B:
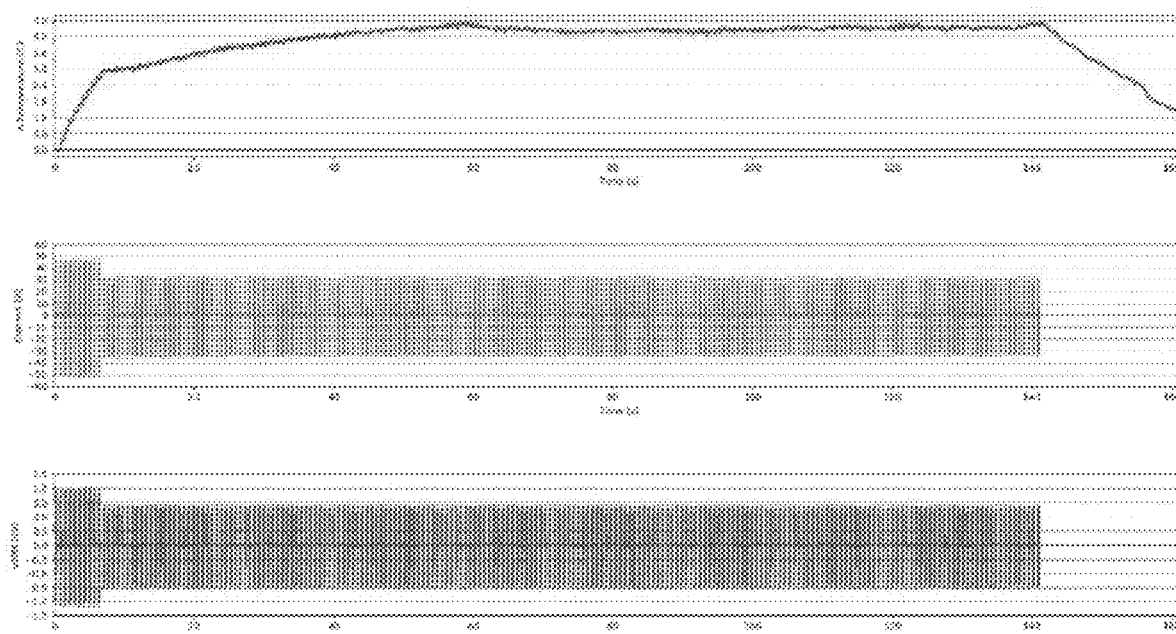

FIGS. 83A and 83B are tissue temperature, voltage, and current plots over time corresponding to methods of treating tissue described herein. FIG. 83A depicts a temperature rise of about 4° C. where temperature is measured at, for example, the expandable member of the pulsed electric field device.

Alternatively, one or more pulse waveforms may be delivered in a manner in which the tissue is first heated to about 41° C. and then the pulse waveforms delivered in a manner to prevent tissue from exceeding a predetermined tissue temperature (e.g., 45° C.). For example, the initial heating of the tissue could be done with a low power energy application to control the time and depth of tissue brought up to temperature. This method may decrease the tissue critical threshold value for the pulsed electric field to affect the cell structure.

EXAMPLES

FIGS. 72A-75 are images of duodenal tissue healing (e.g., healing cascade) after treatment using the systems, device, and methods described herein. Advantageously, the healing processes described herein may reduce a necrotic response (e.g., macrophage response) that may otherwise create a large areas of inflammation within the duodenal tissue.

Figure 72A:
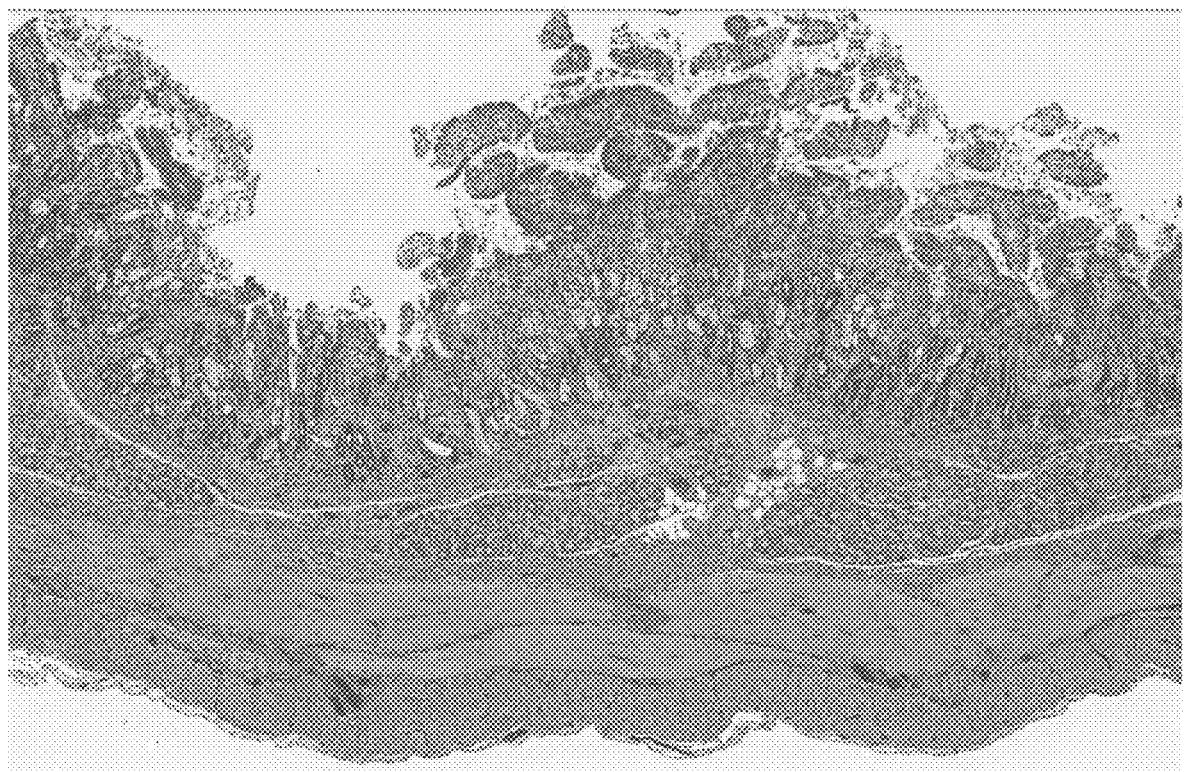
FIGS. 72A and 72B are detailed cross-sectional images of duodenal tissue about a day after treatment.
Figure 72B:
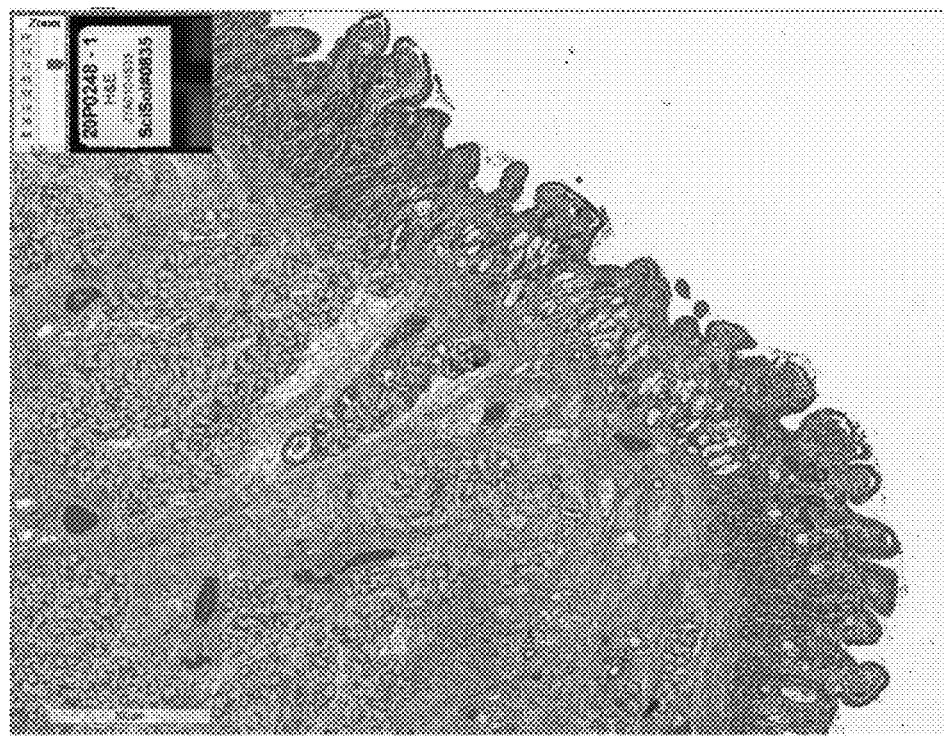
Figure 73:
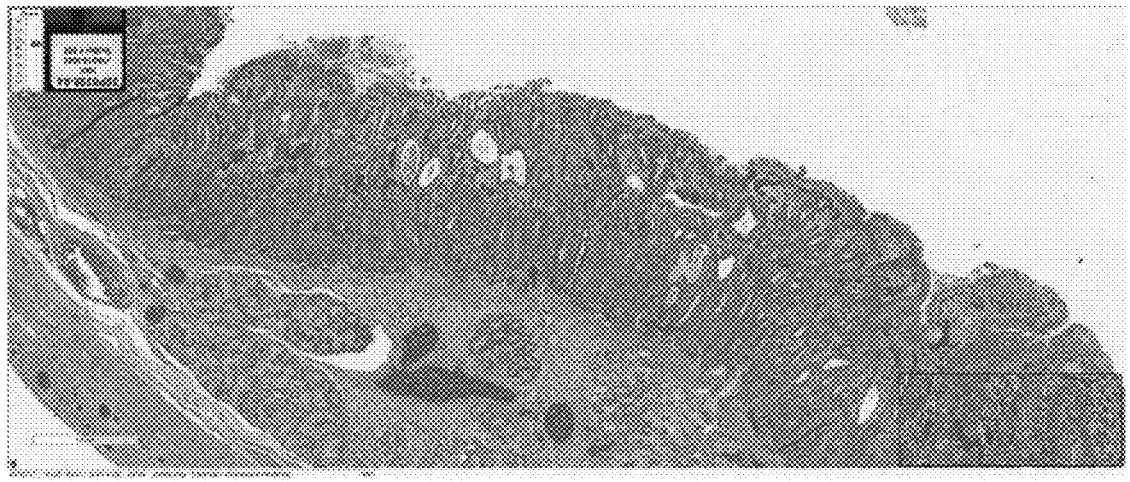
FIG. 73 is a detailed cross-sectional image of duodenal tissue about three days after treatment.
Figure 74A:
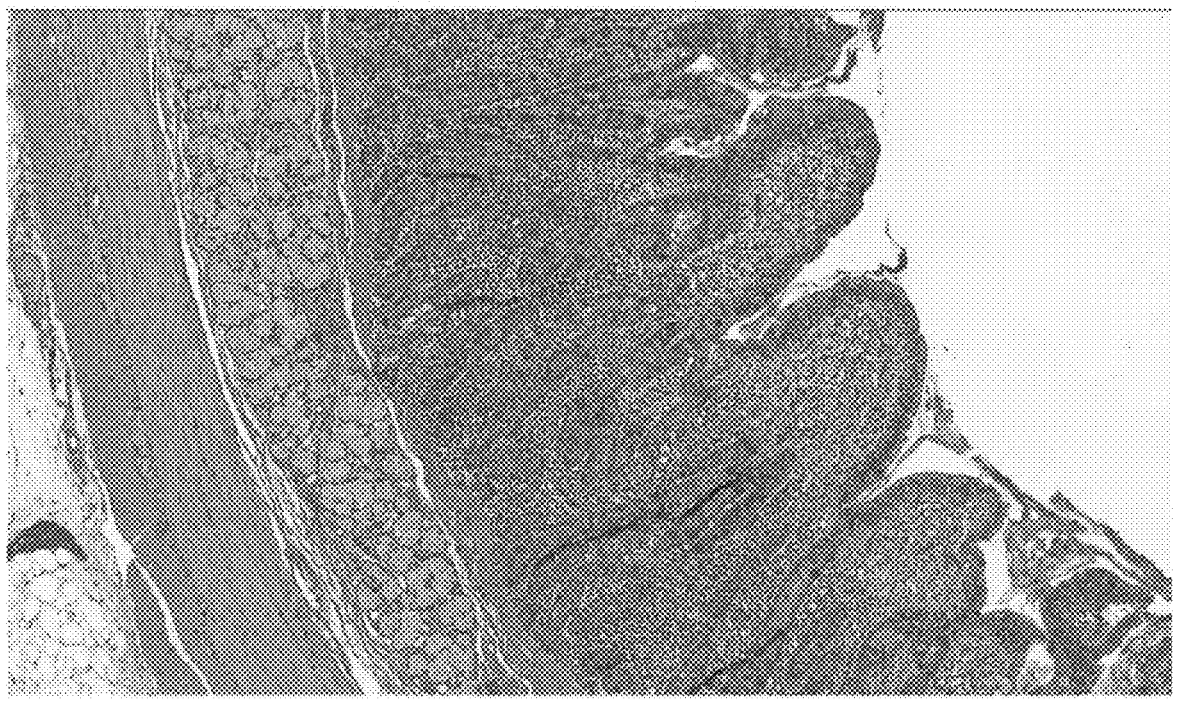
FIGS. 74A and 74B are detailed cross-sectional images of duodenal tissue about seven days after treatment.
Figure 74B:
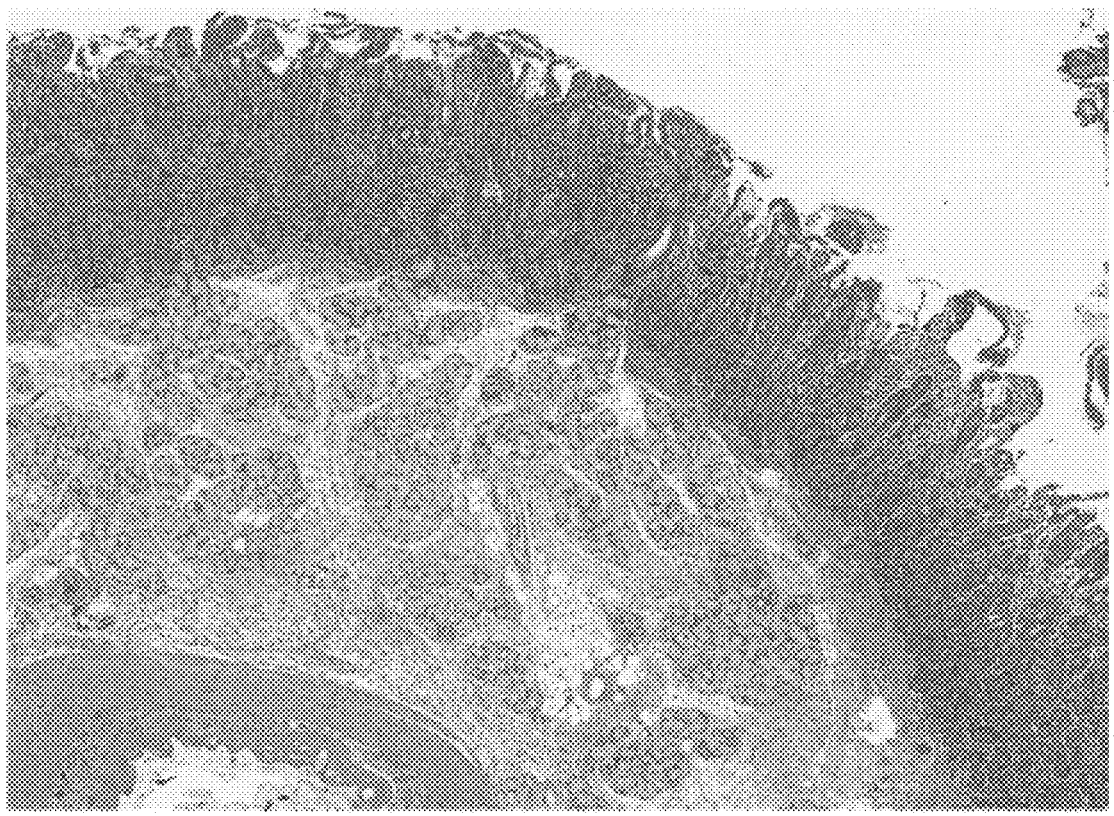

FIGS. 72A and 72B are detailed cross-sectional images of duodenal tissue about a day after treatment. The tissue depicted in FIGS. 72A and 72B may include increased vascularization. FIG. 73 is a detailed cross-sectional image of duodenal tissue about three days after treatment having an increased blood supply for new cells and without a significant macrophage response. FIGS. 74A and 74B are detailed cross-sectional images of duodenal tissue about seven days after treatment. The tissue viewed through an endoscope at about seven days may be indistinguishable from native tissue. For example, the blood supply in FIGS. 74A and 7B may be indistinguishable from native (e.g., untreated) tissue and the dimensions of the new villi will have about the same dimensions as natural villi. FIG. 75 is a detailed cross-sectional image of duodenal tissue about fourteen days after treatment where the treated tissue may be histologically indistinguishable from native tissue.

Figure 60:
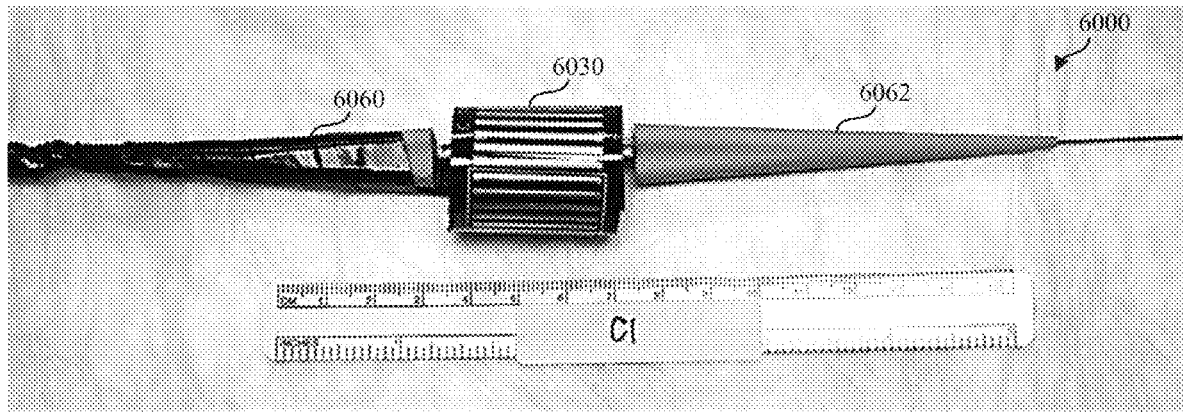
FIG. 60 is an image of an illustrative variation of a pulsed electric field device.

FIG. 60 is an image of a variation of a pulsed electric field device (6000) comprising an expandable member (6030), a proximal dilator (6060), and a distal dilator (6062). The expandable member (6030) may comprise a plurality of turns about a longitudinal axis of the device (6000). The expandable member (6030) comprise an electrode array such as shown in FIG. 59. The dilators (6060, 6062) may assist in smoothly advancing and/or retracting the pulsed electric field device (6000) through one or more body cavities and may assist in preventing the expandable member (6030) from catching on tissue. For example, dilators (6060, 6062) may be configured to protect an edge of the expandable member (6030) from contacting tissue as it is being translated (e.g., advanced, retracted) through a body cavity. The expandable member (6030) is disposed between the distal dilator (6062) and the proximal dilator (6060).

Figure 61A:
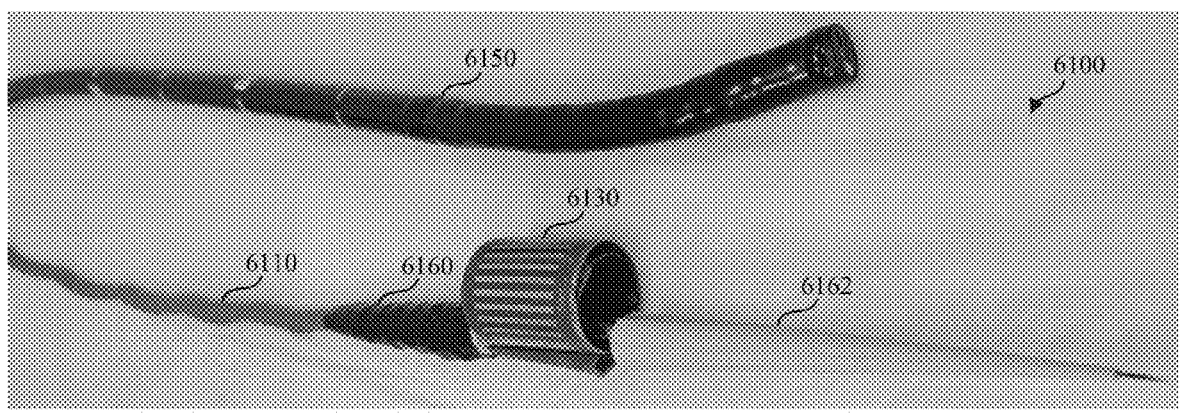
FIG. 61A is a perspective view of an image of an illustrative variation of a pulsed electric field device and visualization device.
Figure 61B:
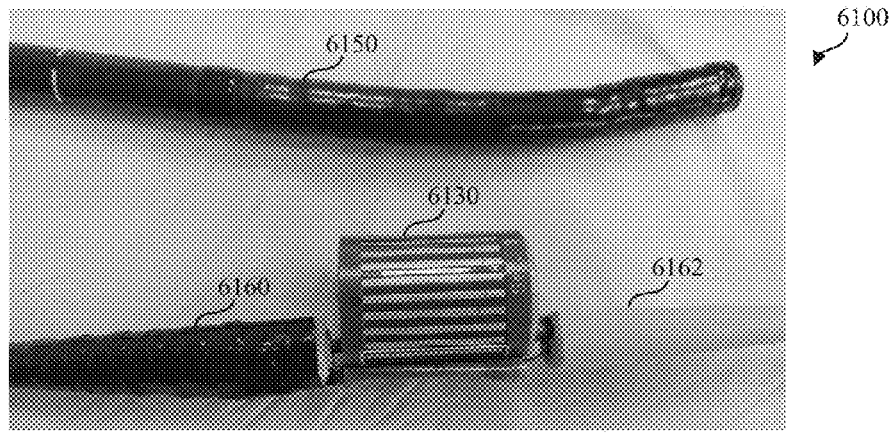
FIG. 61B is a detailed image of the pulsed electric field device and visualization device shown in FIG. 61A.

FIG. 61A is an image showing a perspective view of a pulsed electric field device (6100) and a visualization device (6150). FIG. 61B is a detailed image of the pulsed electric field device (6100) and the visualization device (6150). The pulsed electric field device (6100) shown in FIGS. 61A-61B is similar to the pulsed electric field device (6000) shown in FIG. 60 and comprises an elongate body (6110), an expandable member (6030), a proximal dilator (6060), and a distal dilator (6062). The visualization device (6150) may comprise a diameter sufficient to be advanced through a lumen of the expandable member (6130) when in a semi-expanded or expanded configuration.

Figure 62A:
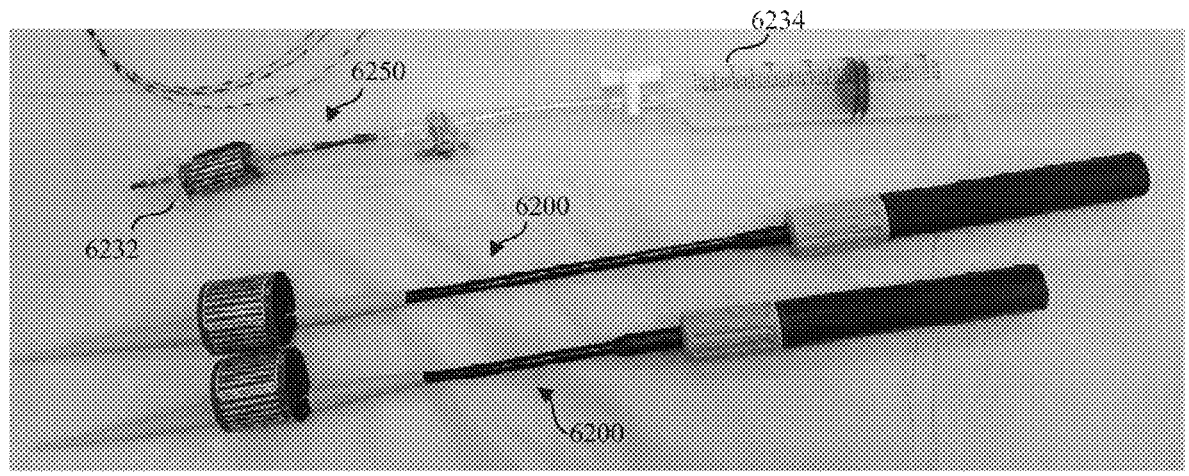
FIG. 62A is an image of illustrative variations of pulsed electric field devices.
Figure 62B:
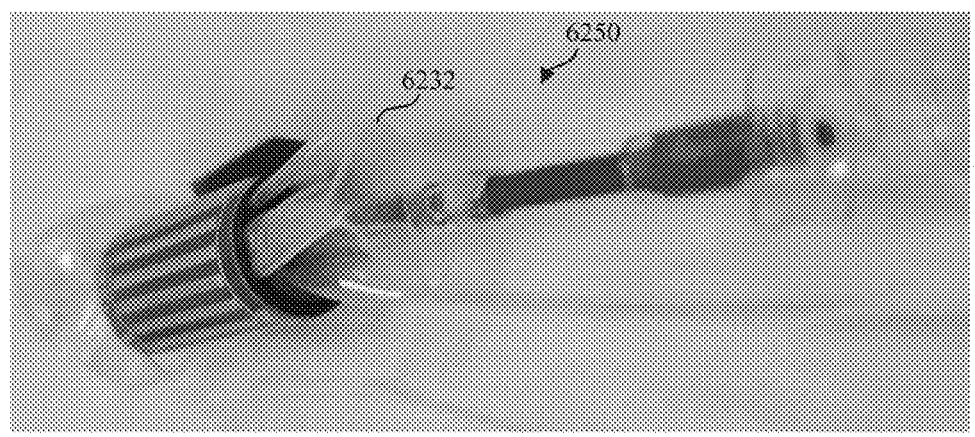
FIG. 62B is an image of an illustrative variation of a pulsed electric field device comprising a balloon.
Figure 62C:
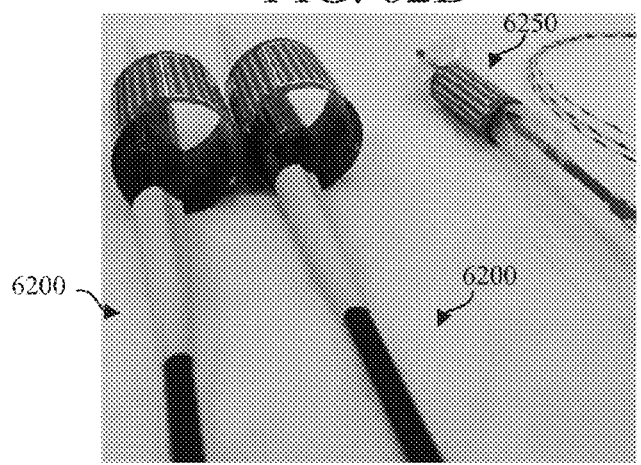
FIG. 62C is a perspective view of the pulsed electric field devices shown in FIG. 62A.

FIG. 62A is an image of illustrative variations of pulsed electric field devices (6200, 6250). The pulsed electric field devices (6200, 6250) shown in FIGS. 62A-62C are similar to the pulsed electric field device (6000) shown and described with respect to FIGS. 60 and 61A-61B. Furthermore, the pulsed electric field device (6250) may comprise an inflatable member (6232) (e.g., balloon). As shown in FIG. 62A, an inflation actuator (6234) may be fluidically coupled to the balloon (6232) of the pulsed electric field device (6250). FIG. 62B is an image of an illustrative variation of a pulsed electric field device (6250) comprising the inflatable member (6232) in a compressed configuration (e.g., uninflated, deflated). FIG. 62C is a perspective view of the pulsed electric field devices (6200, 6250) shown in FIG. 62A.

Figure 63A:
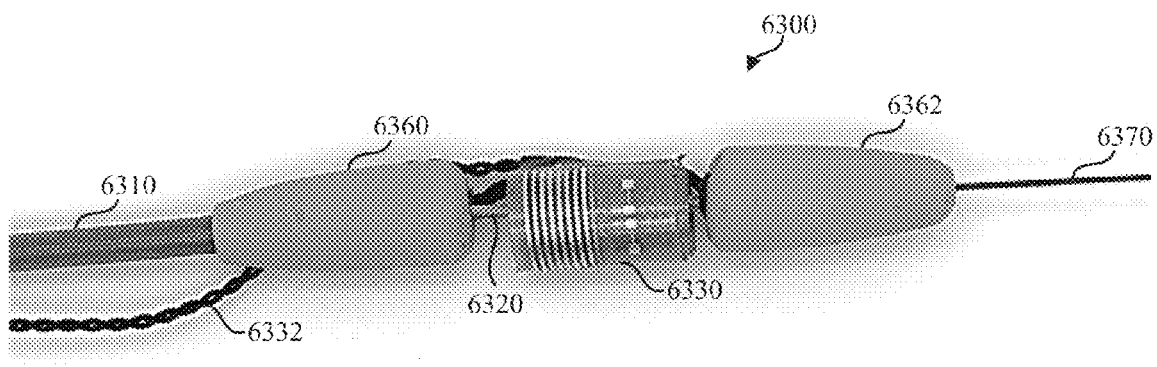
FIG. 63A is an image of an illustrative variation of a pulsed electric field device in a rolled configuration.
Figure 63B:
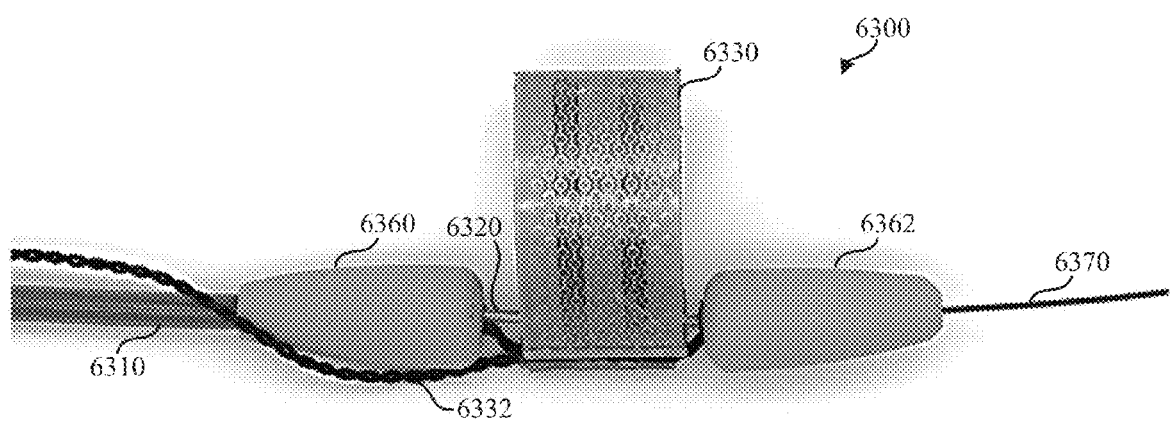
FIG. 63B is an image of an illustrative variation of a pulsed electric field device in an unrolled configuration.
Figure 63C:
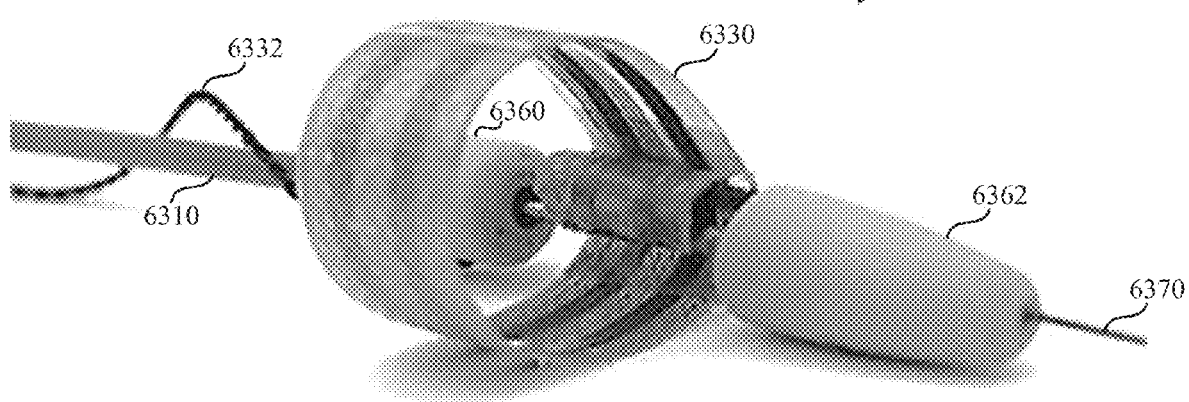
FIG. 63C is a perspective view of the pulsed electric field device shown in FIG. 63B.
Figure 66:
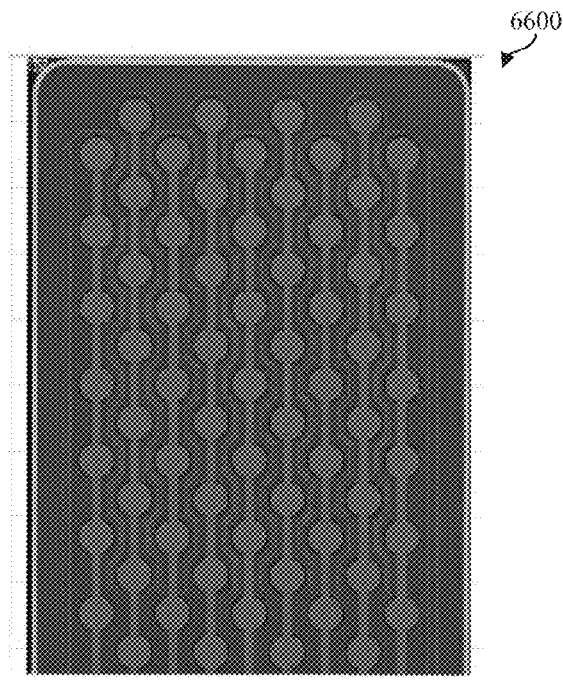
FIG. 66 is a schematic circuit diagram of an illustrative variation of an electrode array.

FIGS. 63A-63C are additional variations of a pulsed electric field device (6300) comprising a first elongate body (6310), second elongate body (6320), expandable member (6330), proximal dilator (6360), distal dilator (6362), leads (6332) coupled to the expandable member (6330), and guidewire (6370). The expandable member (6330) may comprise a plurality of turns about a longitudinal axis of the device (6300). The expandable member (6330) may comprise an electrode array such as shown in FIG. 66. The dilators (6360, 6362) may assist in smoothly advancing and/or retracting the pulsed electric field device (6300) through one or more body cavities and may assist in preventing the expandable member (6330) from catching on tissue. For example, dilators (6360, 6362) may be configured to protect an edge of the expandable member (6330) from contacting tissue as it is being translated (e.g., advanced, retracted) through a body cavity. The expandable member (6330) is disposed between the distal dilator (6362) and the proximal dilator (6360). FIG. 63A is an image of a pulsed electric field device (6300) with the expandable member (6330) in a rolled configuration. FIG. 63B is an image of the pulsed electric field device (6300) with the expandable member (6330) in an unrolled configuration. FIG. 63C is a perspective view of the pulsed electric field device (6300) with the expandable member (6330) in the unrolled configuration. The pulsed electric field device (6300) may be slidably translated along the guidewire (6370) that extends through the second elongate body (6320).

Figure 65:
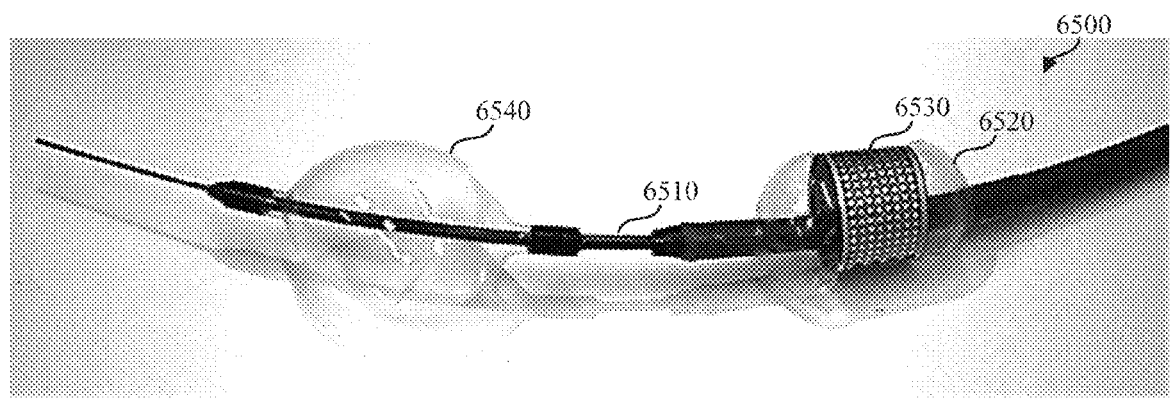
FIG. 65 is an image of an illustrative variation of a pulsed electric field device.
Figure 67:
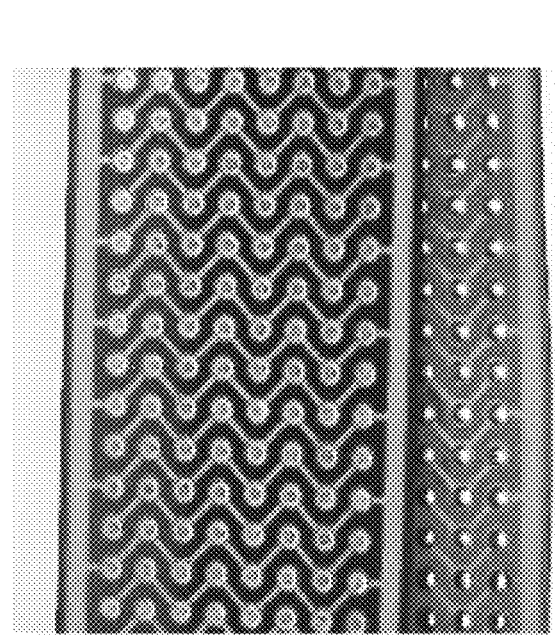
FIG. 67 is an image of an illustrative variation of an electrode array.

FIG. 65 is an image of a variation of a pulsed electric field device (6500) comprising an elongate body (6510), first expandable member (6520) comprising an electrode array (6530), and a second expandable member (6540) disposed distal to the first expandable member (6520). The first expandable member (6330) and second expandable member (6540) may comprise an inflatable member such as a balloon. The first expandable member (6530) may comprise an electrode array such as shown in FIG. 67. The second expandable member (6530) may assist in smoothly advancing and/or retracting the pulsed electric field device (6500) through one or more body cavities and may improve visualization of the tissue and first expandable member (6530). In some variations, at least a proximal and distal portions of the first and second expandable members (6530, 6540) may be transparent. The elongate body (6510) may comprise one or more inflation lumens configured to transition the first and second expandable members (6530, 6540) between compressed and expanded configurations.

Figure 68:
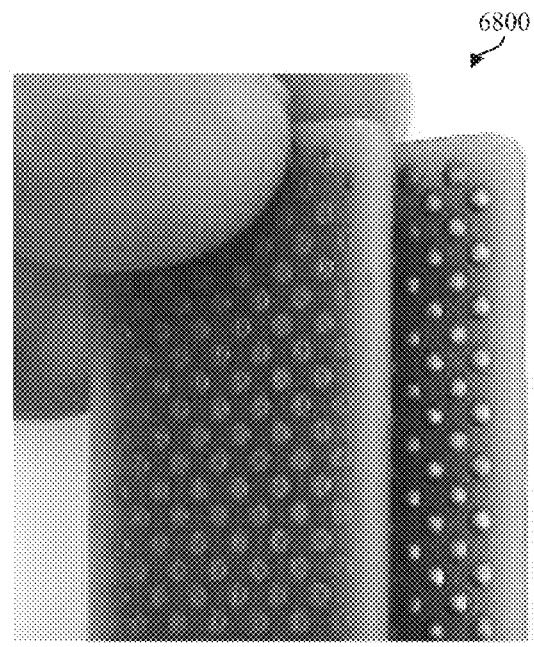
FIG. 68 is an image of an illustrative variation of an electrode array.

FIG. 66 is a schematic circuit diagram of a variation of an electrode array (6600) of the pulsed electric field devices described herein. FIGS. 67 and 68 are images of variations of an electrode array (6700, 6800) of the pulsed electric field devices described herein. FIG. 67 depicts a flexible circuit comprising raised (e.g., domed) electrodes. FIG. 68 depicts a rigid circuit board comprising raised (e.g., domed) electrodes.

Figure 79A:
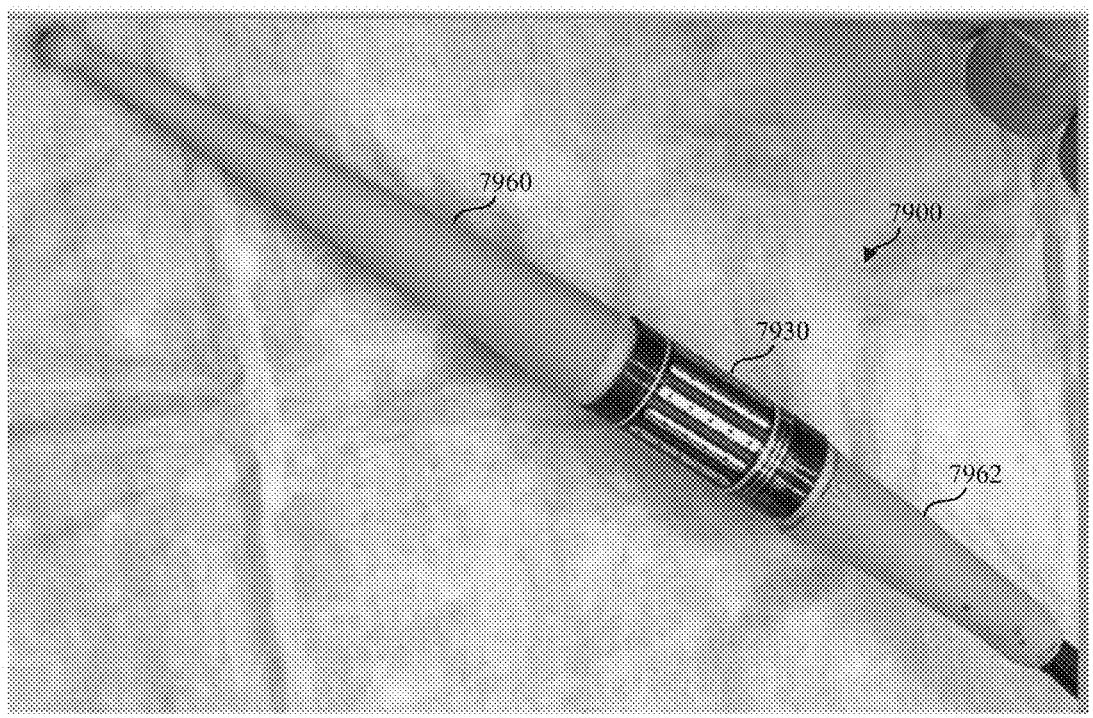
FIG. 79A is an image of an illustrative variation of a pulsed electric field device in a compressed configuration.
Figure 79B:
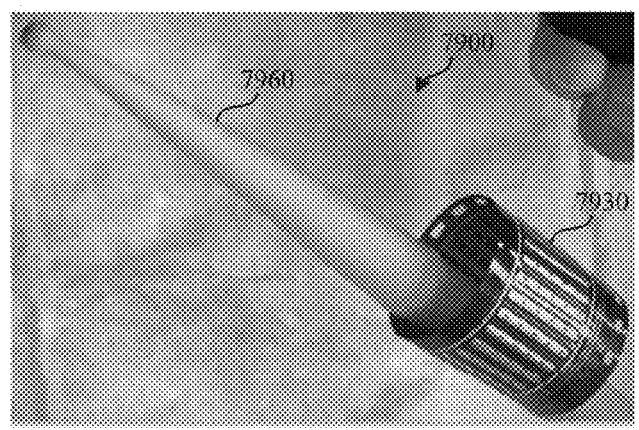
FIG. 79B is an image of an illustrative variation of a pulsed electric field device in an expanded configuration.
Figure 79C:
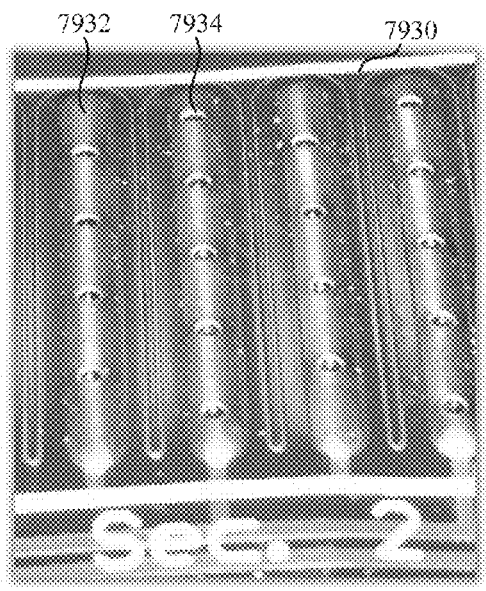
FIG. 79C is a detailed image of an unrolled electrode array of the pulsed electric field device depicted in FIGS. 79A and 79B.

FIG. 79A is an image of a variation of a pulsed electric field device (7900) in a compressed configuration. The pulsed electric field device (7900) may comprise an expandable member (7930), a distal dilator (7960), and a proximal dilator (7962). FIG. 79B is an image of the pulsed electric field device (7900) in an expanded configuration. The expandable member (7930) may comprise a plurality of turns about a longitudinal axis of the device (7900). The expandable member (7930) comprise an electrode array such as shown in FIG. 79C. The dilators (7960, 7962) may assist in smoothly advancing and/or retracting the pulsed electric field device (7900) through one or more body cavities and may assist in preventing the expandable member (7930) from catching on tissue. For example, dilators (7960, 7962) may be configured to protect an edge of the expandable member (7930) from contacting tissue as it is being translated (e.g., advanced, retracted) through a body cavity. The expandable member (7930) is disposed between the distal dilator (7962) and the proximal dilator (7960). FIG. 79C is a detailed image of an unrolled electrode array (7930) of the pulsed electric field device (7900) depicted in FIGS. 79A and 79B. The electrode array (7930) may comprise a plurality of electrodes (7932) defining one or more openings (7934) as described in more detail herein.

It should be understood that the examples and illustrations in this disclosure serve exemplary purposes and departures and variations such as the number of electrodes and devices, and so on can be built and deployed according to the teachings herein without departing from the scope of this invention.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

The specific examples and descriptions herein are exemplary in nature and variations may be developed by those skilled in the art based on the material taught herein without departing from the scope of the present invention, which is limited only by the attached claims.

The invention claimed is:

1. A device for treating tissue of a patient, comprising:
a first elongate body comprising a lumen;
a second elongate body at least partially positioned within the lumen;
an expandable member rolled about the second elongate body, wherein the expandable member comprises an inner end coupled to the second elongate body, an outer end coupled to the first elongate body, and an electrode array; and
a first gear and a second gear each coupled to the second elongate body, the first gear coupled to a proximal portion of the expandable member and the second gear coupled to a distal portion of the expandable member.

2. The device of claim 1, wherein the second elongate body is configured to rotate relative to the first elongate body to transition the expandable member between a rolled configuration and an unrolled configuration.

3. The device of claim 2, wherein the expandable member comprises a lumen of at least 10 mm in diameter in the unrolled configuration.

4. A system for treating tissue of a patient, comprising:
the device of claim 3; and
a third elongate body disposed within the lumen of the expandable member.

5. The system of claim 4, wherein the third elongate body is an endoscope.

6. The device of claim 1 further comprising a distal dilator and a proximal dilator coupled to one of the first elongate body and the second elongate body, the expandable member disposed between the distal dilator and the proximal dilator.

7. A system for treating tissue of a patient, comprising:
the device of claim 1; and
a signal generator operably coupled to the electrode array, the signal generator configured to generate a pulse waveform comprising a frequency between about 250 kHz and about 950 kHz, a pulse width between about 0.5 us and about 4 μs, a voltage applied by the electrode array of between about 100 V and about 2 kV, and a current density between about 0.6 A and about 100 A from the electrode array per square centimeter of tissue.

8. The system of claim 7, wherein the signal generator is configured to inhibit delivery of the pulse waveform based on a temperature of the tissue.

9. The device of claim 1, wherein the electrode array is configured to generate a therapeutic electric field at a first tissue depth of about 1 mm and a non-therapeutic electric field at a second tissue depth of at least about 1.5 mm.

10. The device of claim 1, wherein the expandable member defines one or more openings through the expandable member.

11. The device of claim 10, wherein the one or more openings are configured for one or more of fluid suction and tissue suction.

12. The device of claim 10, wherein the device is configured for application of suction between about 10 mmHg and about 200 mmHg through the expandable member.

13. The device of claim 1, wherein the electrode array is configured to generate a therapeutic electric field that treats a predetermined set of cell types and not muscularis tissue.

14. The device of claim 1, wherein the electrode array is configured to generate a therapeutic electric field that treats cells but leaves intact tissue scaffolding.

15. The device of claim 1, wherein the expandable member is rolled around the first gear and the second gear.

16. The device of claim 1, wherein rotation of the first gear in a first direction transitions the expandable member from a rolled configuration about the second elongate body to an unrolled configuration about the second elongate body.

17. The device of claim 16, wherein the expandable member comprises a track configured to couple to the first gear, and wherein rotation of the first gear in the first direction unrolls the track from the first gear.

18. The device of claim 17, wherein the track comprises a plurality of spaced apart openings in the expandable member.

19. The device of claim 18, wherein the openings of the plurality of spaced apart openings have one or more of: a) different sizes along a length of the expandable member; and b) different spacing between the openings along the length of the expandable member.

20. The device of claim 1, wherein rotation of the first gear in a second direction transitions the expandable member from an unrolled configuration about the second elongate body to a rolled configuration about the second elongate body.

21. The device of claim 20, wherein the expandable member comprises a track configured to couple to the first gear, and wherein rotation of the first gear in the second direction rolls the track around the first gear.

22. A system for electroporating tissue to treat a condition of a patient, comprising:
an elongate body;
a gear coupled to the elongate body;
an expandable member coupled to the gear and the elongate body, the gear directly engaging the expandable member and configured to transition the expandable member between a compressed configuration and an expanded configuration having a diameter greater than about 25 mm, wherein the expandable member further comprises an electrode array comprising a plurality of electrodes; and
a signal generator coupled to the electrode array, the signal generator configured to deliver a pulsed or modulated electric field waveform to the electrode array to perform electroporation thereby generating a therapeutic electric field at a first tissue depth of about 1 mm and a non-therapeutic electric field at a second tissue depth of at least about 1.5 mm.

23. The system of claim 22, wherein a ratio of a center-to-center distance between a plurality of proximate electrodes of the electrode array to a width of at least one electrode of the plurality of electrodes is between about 2.3:1 and about 3.3:1.

24. The system of claim 22, wherein the pulsed electric field waveform comprises a frequency of about 350 kHz to about 500 kHz, a pulse width of about 0.5 us to about 4 μs, and a voltage applied by the electrode array of about 400 V to about 750 V.

25. The system of claim 24, wherein the signal generator generates a drive voltage of between about 500 V and about 750 V delivered to the electrode array.

26. A device for treating tissue of a patient, comprising:
a first elongate body comprising a lumen;
a second elongate body at least partially positioned within the lumen;
an expandable member rolled about the second elongate body, wherein the expandable member comprises an inner end coupled to the second elongate body, an outer end coupled to the first elongate body, and an electrode array;
a gear coupled to the second elongate body and directly engaging the expandable member, wherein rotation of the gear rolls and unrolls the expandable member about the second elongate body.

27. The device of claim 26, wherein the electrode array comprises a plurality of parallel and/or interdigitated elongate electrodes.

28. The device of claim 27, wherein the expandable member defines one or more openings through the expandable member disposed between the parallel and/or interdigitated elongate electrodes.

* * * * *